US006521454B1

(12) United States Patent
Becnel et al.

(10) Patent No.: US 6,521,454 B1
(45) Date of Patent: Feb. 18, 2003

(54) BACULOVIRUSES, INSECTICIDAL COMPOSITIONS, AND METHODS FOR CONTROL OF INVERTEBRATES

(75) Inventors: James J. Becnel, Gainesville, FL (US); Fukuda Tukuo, Gainesville, FL (US); Bettina Moser, Gainesville, FL (US); Andrew Cockburn, Morgantown, WV (US); Susan E. White, Gainesville, FL (US); Albert H. Undeen, Whittier, NC (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 09/345,236

(22) Filed: Jun. 30, 1999

(51) Int. Cl.[7] .......................... C12N 15/63; C12Q 1/68; C12P 19/34; C07H 21/02; C07H 21/04
(52) U.S. Cl. .......................... 435/455; 435/6; 435/91.1; 536/23.1; 536/23.72; 536/25.3
(58) Field of Search .......................... 436/6, 91.1, 91.4, 436/455; 536/23.1, 23.71, 23.72

(56) References Cited

U.S. PATENT DOCUMENTS

| 4,911,913 A | | 3/1990 | Hostetter et al. | |
| 5,004,687 A | | 4/1991 | Miller | |
| 5,141,744 A | * | 8/1992 | Chang et al. | 424/93 |
| 5,275,815 A | * | 1/1994 | Payne | 424/93 |
| 6,017,734 A | * | 1/2000 | Summers et al. | 435/69.7 |

OTHER PUBLICATIONS

Journal of Invertebrate Pathology, 14, pp. 284–286 (1969).*
Yi Pang et al., Synthesis and toxicity of full–length and truncated bacterial CryIVD mosquitocidal proteins expressed in lepidopteran cells using a baculovirus vector, Journal of General Virology (1992), 73, pp. 89–101.*
Asian Journal of Chemistry, vol. 12, No. 4 (2000), pp. 1199–1208.*
Brad Stiles et al., Midgut pH in Different Instars of Three Aedes Mosquito Species and the Relation between pH and Susceptibility of Llarvae to a Nuclear Polyhedrosis Virus, Journal of Invertebrate Pathology, 35, pp. 58–64.*

Chapman et al., "Protozoans, Nematodes, and Viruses of Anophelines[1]", *Miscellaneous Publications*, vol. 7(1), pp. 134–139, 1970.

Clark et al., "A Polyhedrosis in *Culex salinarius* of Louisiana", *Journal of Invertebrate Pathology*, vol. 13, p. 312, 1969.

Clark et al., "Nuclear–Polyhedrosis and Cytoplasmic–Polyhedrosis Virus Infections in Louisiana Mosquitoes[1]", *Journal of Invertebrate Pathology*, vol. 14, pp. 284–286, 1969.

Kellen et al., "A Possible Polyhedrosis in *Culex tarsalis* Coquillett (Diptera: Culicidae)[1]", *Journal of Insect Pathology*, vol. 5, pp. 98–103, 1963.

Stiles et al., "Midgut pH in Different Instars of Three Aedes Mosquito Species and the Relation between pH and Susceptibility of Larvae to a Nuclear Polyhedrosis Virus[1,2]", *Journal of Invertebrate Pathology*, vol. 35, pp. 58–64, 1980.

Brian A. Federici, "Biological Control of Mosquitoes", *American Mosquito Control Association, Inc.*, Bulletin No. 6, pp. 59–74, 1985.

Federici et al., "Studies of the Pathology of a Baculovirus in *Aedes Triseriatus*", vol. 20, pp. 14–21, 1972.

Federici et al., "Formation of Virion–Occluding Proteinic Spindles in a Baculovirus Disease of *Aedes triseriatus*[1]", vol. 20, pp. 129–138, 1972.

Brian A. Federici, "Mosquito Baculovirus: Sequence of Morphogenesis and Ultrastructure of the Virion", *Virology*, vol. 100, pp. 1–9, 1980.

Sherman et al., "Baculovirus Replication in a Mosquito (Dipteran) Cell Line", *Infection and Immunity*, vol. 26(1), pp. 232–234, 1979.

* cited by examiner

Primary Examiner—Sean McGarry
Assistant Examiner—Jane Zara
(74) Attorney, Agent, or Firm—M. Howard Silverstein; John D. Fado; Gail E. Poulos

(57) ABSTRACT

Although the present invention has been described with reference to specific details of certain embodiments thereof, it is not intended that such details should be regarded as limitations upon the scope of the invention except as and to the extent that they are included in the accompanying claims.

29 Claims, No Drawings

SEQUENCE LISTING

<160> NUMBER OF SEQ ID NOS: 148

<210> SEQ ID NO 1
<211> LENGTH: 2446
<212> TYPE: DNA
<213> ORGANISM: mosquito baculovirus
<220> FEATURE:
<221> NAME/KEY: CDS
<222> LOCATION: (8)...(1396)
<221> NAME/KEY: CDS
<222> LOCATION: (1522)...(2247)

<400> SEQUENCE: 1

```
gaattcg atg aac gag atg cca att ttg cca cct tcg ttt ccg gac gtg       49
        Met Asn Glu Met Pro Ile Leu Pro Pro Ser Phe Pro Asp Val
          1               5                  10 ggg gat gtg tac acg acc gtt tgg gtc gcc acg aac gtt ggc tgt gag       97
Gly Asp Val Tyr Thr Thr Val Trp Val Ala Thr Asn Val Gly Cys Glu
 15                  20                  25                  30 gcg tgg acc aac gaa att aaa gcg aag gct gca cca aac agt cga cag      145
Ala Trp Thr Asn Glu Ile Lys Ala Lys Ala Ala Pro Asn Ser Arg Gln
                 35                  40                  45
```

-continued

```
att gta att gag gtc gag tac ggc gcc cag cgt agc act ctt ccc ttc    193
Ile Val Ile Glu Val Glu Tyr Gly Ala Gln Arg Ser Thr Leu Pro Phe
         50                  55                  60 aac ctc gtg gtg cag agc gtg ttt gct gcg gtt cac ggt gga ctc aac    241
Asn Leu Val Val Gln Ser Val Phe Ala Ala Val His Gly Gly Leu Asn
             65                  70                  75 ccc ggc ttt atg agc gga cac cgg gac ctg ttg aga att tta aaa atc    289
Pro Gly Phe Met Ser Gly His Arg Asp Leu Leu Arg Ile Leu Lys Ile
         80                  85                  90 gag caa gtg ttt acc gat ccc att tcg gac aac gtt acg tac acc att    337
Glu Gln Val Phe Thr Asp Pro Ile Ser Asp Asn Val Thr Tyr Thr Ile
 95                 100                 105                 110 acg gat agc att gtg acg cgg gtg cac gta ttc acc gac tct ggg ctc    385
Thr Asp Ser Ile Val Thr Arg Val His Val Phe Thr Asp Ser Gly Leu
                115                 120                 125 aat aat atg cgc gcg gtt gtg ccc tcc gag tat ccg gaa acg ttt acg    433
Asn Asn Met Arg Ala Val Val Pro Ser Glu Tyr Pro Glu Thr Phe Thr
            130                 135                 140 atg atg ttg gcg cgc cgc aaa tcc cag tac atg atc gag gag tct atc    481
Met Met Leu Ala Arg Arg Lys Ser Gln Tyr Met Ile Glu Glu Ser Ile
        145                 150                 155 agg ctt tcc aag tcg gga atg ggg tcg ggc tcg ggc gac aag gct atc    529
Arg Leu Ser Lys Ser Gly Met Gly Ser Gly Ser Gly Asp Lys Ala Ile
160                 165                 170 gtt att cgt gcg caa gat tta ccc ccc gat gag tac aag gat ttg ctc    577
Val Ile Arg Ala Gln Asp Leu Pro Pro Asp Glu Tyr Lys Asp Leu Leu
175                 180                 185                 190 aag gag tac gaa att cgc aat cgt gga aac ccc gac tgt cca cgg cac    625
Lys Glu Tyr Glu Ile Arg Asn Arg Gly Asn Pro Asp Cys Pro Arg His
                195                 200                 205 atg tac gga ccg tac gag gac tac gat gag gat att atg cgc cgt aaa    673
Met Tyr Gly Pro Tyr Glu Asp Tyr Asp Glu Asp Ile Met Arg Arg Lys
            210                 215                 220 act acg ctg agc gat tac aat ttg act gcg gaa gat ttg cgc ggg att    721
Thr Thr Leu Ser Asp Tyr Asn Leu Thr Ala Glu Asp Leu Arg Gly Ile
        225                 230                 235 gcg ggt tct tcg gat att ggc gat gcg ggt gag acg att agt acg gtg    769
Ala Gly Ser Ser Asp Ile Gly Asp Ala Gly Glu Thr Ile Ser Thr Val
240                 245                 250 gct aag cgc aaa tct gcc ggt caa cgg aag gtg ccc aag ttt aag ggt    817
Ala Lys Arg Lys Ser Ala Gly Gln Arg Lys Val Pro Lys Phe Lys Gly
255                 260                 265                 270 aaa aat atg gag ata ttg gcc aga agt gtt caa caa att ggg gac gag    865
Lys Asn Met Glu Ile Leu Ala Arg Ser Val Gln Gln Ile Gly Asp Glu
                275                 280                 285 aac act gcc gat ttg att caa gaa ctt gaa aac ttt aaa gat gac aac    913
Asn Thr Ala Asp Leu Ile Gln Glu Leu Glu Asn Phe Lys Asp Asp Asn
            290                 295                 300 gaa cag ccc gtg gac gtg gaa ccg gcc gtg tcg cag gaa atc gta aag    961
Glu Gln Pro Val Asp Val Glu Pro Ala Val Ser Gln Glu Ile Val Lys
        305                 310                 315 aat gaa tac atc gaa gtt ttg gtc aac gtg gat gaa atg cca caa cgt   1009
Asn Glu Tyr Ile Glu Val Leu Val Asn Val Asp Glu Met Pro Gln Arg
320                 325                 330 tcg cgc acc tgt tca cgg tct agc agc agc tcc agt tcg agc tcg gaa   1057
Ser Arg Thr Cys Ser Arg Ser Ser Ser Ser Ser Ser Ser Ser Ser Glu
335                 340                 345                 350 tcc gat agt gaa agt gag gat gaa tcg acc cca acc cca gct cca gat   1105
Ser Asp Ser Glu Ser Glu Asp Glu Ser Thr Pro Thr Pro Ala Pro Asp
```

-continued

```
                      355                 360                 365
cca gct ccg gcg aag gtg aag gta tcg agc cca acc cgg gcc cca gct        1153
Pro Ala Pro Ala Lys Val Lys Val Ser Ser Pro Thr Arg Ala Pro Ala
            370                 375                 380 gtg gcc gaa gtc aca tca tcc acc ccg acc cgg gct caa acg cca ccc        1201
Val Ala Glu Val Thr Ser Ser Thr Pro Thr Arg Ala Gln Thr Pro Pro
        385                 390                 395 gaa agt gtg gca cca act gtg gcc aaa gtt aaa ggt ggt ccg ccc aag        1249
Glu Ser Val Ala Pro Thr Val Ala Lys Val Lys Gly Gly Pro Pro Lys
    400                 405                 410 gtg aag caa agt ttg cct cca cgc aag cgc gcc tac aat aaa gtg gtt        1297
Val Lys Gln Ser Leu Pro Pro Arg Lys Arg Ala Tyr Asn Lys Val Val
415                 420                 425                 430 gaa gat gag gaa caa ccg caa cca cca cct cag ccc gct aaa cgt gcg        1345
Glu Asp Glu Glu Gln Pro Gln Pro Pro Gln Pro Ala Lys Arg Ala
            435                 440                 445 cga aag tct cgc aat gcc aag gaa agt gag cgg gtt aat aaa cgt aaa        1393
Arg Lys Ser Arg Asn Ala Lys Glu Ser Glu Arg Val Asn Lys Arg Lys
        450                 455                 460 cgt taaagaaaaa aaaaaatata cacacacact ataaatatat aatcttgata            1446
Arg ttaaattta acggtgatat aaacggtgat ctggggtggt gggtgcacat ttgtaataaa      1506
atagggatca ataca atg tcg tgt ctt ctt gct acg tgt cac aag ccc tgt      1557
              Met Ser Cys Leu Leu Ala Thr Cys His Lys Pro Cys
                  465                 470                 475 atc tgc agc cca acc gtg cag tcc att gag tcg tgt gac gct gag ctg        1605
Ile Cys Ser Pro Thr Val Gln Ser Ile Glu Ser Cys Asp Ala Glu Leu
            480                 485                 490 aaa att gcc caa gct tgg gag cta cac gat gga acc ttt gtg ctg ttg        1653
Lys Ile Ala Gln Ala Trp Glu Leu His Asp Gly Thr Phe Val Leu Leu
        495                 500                 505 gag cgc agg gac gac tcc tcg gtg gac acg agc tac att ggt gca cct        1701
Glu Arg Arg Asp Asp Ser Ser Val Asp Thr Ser Tyr Ile Gly Ala Pro
    510                 515                 520 tcg tcg agg cta acc gtg gtg caa acc gag gcg gtg ctg aaa aag ttg        1749
Ser Ser Arg Leu Thr Val Val Gln Thr Glu Ala Val Leu Lys Lys Leu
525                 530                 535 aat gtt cta gac tgg tcg tgg gct caa att gtg ctg ctc gac aat ccg        1797
Asn Val Leu Asp Trp Ser Trp Ala Gln Ile Val Leu Leu Asp Asn Pro
540                 545                 550                 555 gtc aag tac ccg cag tac tcg agg cca acc atc tac ttc aac tac gtc        1845
Val Lys Tyr Pro Gln Tyr Ser Arg Pro Thr Ile Tyr Phe Asn Tyr Val
            560                 565                 570 aag atg cgc aac tgt acc cta tac ggt gga cac gtg cgc aca ctg ggc        1893
Lys Met Arg Asn Cys Thr Leu Tyr Gly Gly His Val Arg Thr Leu Gly
        575                 580                 585 gac ccc gta ctc tac ttg gaa aat tgt agc ggc gag gag gtc cgc gcg        1941
Asp Pro Val Leu Tyr Leu Glu Asn Cys Ser Gly Glu Glu Val Arg Ala
    590                 595                 600 ctg cac tct agc tta tcg agc cgc agg tac tgc gtc gga ttt gcc ata        1989
Leu His Ser Ser Leu Ser Ser Arg Arg Tyr Cys Val Gly Phe Ala Ile
605                 610                 615 ctc acc acc acc ggt gag ctc agg tgg tgc gta tcg gat caa agt ttg        2037
Leu Thr Thr Thr Gly Glu Leu Arg Trp Cys Val Ser Asp Gln Ser Leu
620                 625                 630                 635 gtt aaa ctg ttc aaa acc gtt gac acc acc gcc gga tac tgc ccc aag        2085
Val Lys Leu Phe Lys Thr Val Asp Thr Thr Ala Gly Tyr Cys Pro Lys
            640                 645                 650
```

```
atg tac att tcc tac acg acc aag cgc att ttg tgg cat ctg tgg aac    2133
Met Tyr Ile Ser Tyr Thr Thr Lys Arg Ile Leu Trp His Leu Trp Asn
            655                 660                 665 tcg agt tcg gaa ttt gcg ctg caa cgt ttg gga gga tca cac gtc gct    2181
Ser Ser Ser Glu Phe Ala Leu Gln Arg Leu Gly Gly Ser His Val Ala
        670                 675                 680 gca ctc tgc ctg cgg gag tgc tcg gac cag gga att gtt cgc gct atc    2229
Ala Leu Cys Leu Arg Glu Cys Ser Asp Gln Gly Ile Val Arg Ala Ile
    685                 690                 695 aaa ggt tca aaa caa ttc tagtgtttag atttacattt atttattttt           2277
Lys Gly Ser Lys Gln Phe
700                 705 ctattataca ataaaaaata tttttataaa ctaaatctca ccaactttt cccctacata   2337 tcacggccct tagcacgaga tgaacggcgg ttgggtggta cattggtaaa tgggtaacga  2397
taggccaaga cttttctgaa attcggtcac caagtttgag tttgaattc              2446
```

<210> SEQ ID NO 2
<211> LENGTH: 463
<212> TYPE: PRT
<213> ORGANISM: mosquito baculovirus

<400> SEQUENCE: 2

```
Met Asn Glu Met Pro Ile Leu Pro Pro Ser Phe Pro Asp Val Gly Asp
 1               5                  10                  15

Val Tyr Thr Thr Val Trp Val Ala Thr Asn Val Gly Cys Glu Ala Trp
                20                  25                  30

Thr Asn Glu Ile Lys Ala Lys Ala Ala Pro Asn Ser Arg Gln Ile Val
            35                  40                  45

Ile Glu Val Glu Tyr Gly Ala Gln Arg Ser Thr Leu Pro Phe Asn Leu
        50                  55                  60

Val Val Gln Ser Val Phe Ala Ala Val His Gly Gly Leu Asn Pro Gly
65                  70                  75                  80

Phe Met Ser Gly His Arg Asp Leu Leu Arg Ile Leu Lys Ile Glu Gln
                85                  90                  95

Val Phe Thr Asp Pro Ile Ser Asp Asn Val Thr Tyr Thr Ile Thr Asp
            100                 105                 110

Ser Ile Val Thr Arg Val His Val Phe Thr Asp Ser Gly Leu Asn Asn
        115                 120                 125

Met Arg Ala Val Val Pro Ser Glu Tyr Pro Glu Thr Phe Thr Met Met
    130                 135                 140

Leu Ala Arg Arg Lys Ser Gln Tyr Met Ile Glu Glu Ser Ile Arg Leu
145                 150                 155                 160

Ser Lys Ser Gly Met Gly Ser Gly Ser Asp Lys Ala Ile Val Ile
                165                 170                 175

Arg Ala Gln Asp Leu Pro Pro Asp Glu Tyr Lys Asp Leu Leu Lys Glu
            180                 185                 190

Tyr Glu Ile Arg Asn Arg Gly Asn Pro Asp Cys Pro Arg His Met Tyr
        195                 200                 205

Gly Pro Tyr Glu Asp Tyr Asp Glu Asp Ile Met Arg Arg Lys Thr Thr
    210                 215                 220

Leu Ser Asp Tyr Asn Leu Thr Ala Glu Asp Leu Arg Gly Ile Ala Gly
225                 230                 235                 240

Ser Ser Asp Ile Gly Asp Ala Gly Glu Thr Ile Ser Thr Val Ala Lys
                245                 250                 255

Arg Lys Ser Ala Gly Gln Arg Lys Val Pro Lys Phe Lys Gly Lys Asn
```

-continued

```
            260                 265                 270

Met Glu Ile Leu Ala Arg Ser Val Gln Gln Ile Gly Asp Glu Asn Thr
        275                 280                 285

Ala Asp Leu Ile Gln Glu Leu Glu Asn Phe Lys Asp Asp Asn Glu Gln
    290                 295                 300

Pro Val Asp Val Glu Pro Ala Val Ser Gln Glu Ile Val Lys Asn Glu
305                 310                 315                 320

Tyr Ile Glu Val Leu Val Asn Val Asp Glu Met Pro Gln Arg Ser Arg
                325                 330                 335

Thr Cys Ser Arg Ser Ser Ser Ser Ser Ser Ser Ser Ser Glu Ser Asp
            340                 345                 350

Ser Glu Ser Glu Asp Glu Ser Thr Pro Thr Pro Ala Pro Asp Pro Ala
        355                 360                 365

Pro Ala Lys Val Lys Val Ser Ser Pro Thr Arg Ala Pro Ala Val Ala
    370                 375                 380

Glu Val Thr Ser Ser Thr Pro Thr Arg Ala Gln Thr Pro Pro Glu Ser
385                 390                 395                 400

Val Ala Pro Thr Val Ala Lys Val Lys Gly Gly Pro Pro Lys Val Lys
                405                 410                 415

Gln Ser Leu Pro Pro Arg Lys Arg Ala Tyr Asn Lys Val Val Glu Asp
            420                 425                 430

Glu Glu Gln Pro Gln Pro Pro Pro Gln Pro Ala Lys Arg Ala Arg Lys
        435                 440                 445

Ser Arg Asn Ala Lys Glu Ser Glu Arg Val Asn Lys Arg Lys Arg
    450                 455                 460

<210> SEQ ID NO 3
<211> LENGTH: 242
<212> TYPE: PRT
<213> ORGANISM: mosquito baculovirus

<400> SEQUENCE: 3

Met Ser Cys Leu Leu Ala Thr Cys His Lys Pro Cys Ile Cys Ser Pro
 1               5                  10                  15

Thr Val Gln Ser Ile Glu Ser Cys Asp Ala Glu Leu Lys Ile Ala Gln
            20                  25                  30

Ala Trp Glu Leu His Asp Gly Thr Phe Val Leu Leu Glu Arg Arg Asp
        35                  40                  45

Asp Ser Ser Val Asp Thr Ser Tyr Ile Gly Ala Pro Ser Ser Arg Leu
    50                  55                  60

Thr Val Val Gln Thr Glu Ala Val Leu Lys Lys Leu Asn Val Leu Asp
65                  70                  75                  80

Trp Ser Trp Ala Gln Ile Val Leu Leu Asp Asn Pro Val Lys Tyr Pro
                85                  90                  95

Gln Tyr Ser Arg Pro Thr Ile Tyr Phe Asn Tyr Val Lys Met Arg Asn
            100                 105                 110

Cys Thr Leu Tyr Gly Gly His Val Arg Thr Leu Gly Asp Pro Val Leu
        115                 120                 125

Tyr Leu Glu Asn Cys Ser Gly Glu Glu Val Arg Ala Leu His Ser Ser
    130                 135                 140

Leu Ser Ser Arg Arg Tyr Cys Val Gly Phe Ala Ile Leu Thr Thr Thr
145                 150                 155                 160

Gly Glu Leu Arg Trp Cys Val Ser Asp Gln Ser Leu Val Lys Leu Phe
                165                 170                 175
```

```
Lys Thr Val Asp Thr Thr Ala Gly Tyr Cys Pro Lys Met Tyr Ile Ser
        180                 185                 190

Tyr Thr Thr Lys Arg Ile Leu Trp His Leu Trp Asn Ser Ser Ser Glu
        195                 200                 205

Phe Ala Leu Gln Arg Leu Gly Gly Ser His Val Ala Ala Leu Cys Leu
        210                 215                 220

Arg Glu Cys Ser Asp Gln Gly Ile Val Arg Ala Ile Lys Gly Ser Lys
225                 230                 235                 240

Gln Phe

<210> SEQ ID NO 4
<211> LENGTH: 2446
<212> TYPE: DNA
<213> ORGANISM: mosquito baculovirus
<220> FEATURE:
<221> NAME/KEY: CDS
<222> LOCATION: (1820)...(2218)
<221> NAME/KEY: CDS
<222> LOCATION: (2239)...(2445)
<221> NAME/KEY: CDS
<222> LOCATION: (323)...(490)

<400> SEQUENCE: 4
gaattcaaac tcaaacttgg tgaccgaatt tcagaaaagt cttggcctat cgttacccat      60
ttaccaatgt accacccaac cgccgttcat ctcgtgctaa gggccgtgat atgtagggg      120 aaaagttggt gagatttagt ttataaaaat attttttatt gtaatataga aaataaata      180 aatgtaaatc taaacactag aattgttttg aacctttgat agcgcgaaca attccctggt      240
ccgagcactc ccgcaggcag agtgcagcga cgtgtgatcc tcccaaacgt tgcagcgcaa      300
attccgaact cgagttccac ag atg cca caa aat gcg ctt ggt cgt gta gga      352
                         Met Pro Gln Asn Ala Leu Gly Arg Val Gly
                          1               5                  10 aat gta cat ctt ggg gca gta tcc ggc ggt ggt gtc aac ggt ttt gaa      400
Asn Val His Leu Gly Ala Val Ser Gly Gly Gly Val Asn Gly Phe Glu
             15                  20                  25 cag ttt aac caa act ttg atc cga tac gca cca cct gag ctc acc ggt      448
Gln Phe Asn Gln Thr Leu Ile Arg Tyr Ala Pro Pro Glu Leu Thr Gly
         30                  35                  40 ggt ggt gag tat ggc aaa tcc gac gca gta cct gcg gct cga              490
Gly Gly Glu Tyr Gly Lys Ser Asp Ala Val Pro Ala Ala Arg
         45                  50                  55 taagctagag tgcagcgcgc ggacctcctc gccgctacaa ttttccaagt agagtacggg      550
gtcgcccagt gtgcgcacgt gtccaccgta tagggtacag ttgcgcatct tgacgtagtt      610
gaagtagatg gttggcctcg agtactgcgg gtacttgacc ggattgtcga gcagcacaat      670
ttgagcccac gaccagtcta gaacattcaa cttttttcagc accgcctcgg tttgcaccac      730
ggttagcctc gacgaaggtg caccaatgta gctcgtgtcc accgaggagt cgtccctgcg      790
ctccaacagc acaaggttc catcgtgtag ctcccaagct gggcaattt tcagctcagc      850 gtcacacgac tcaatggact gcacggttgg gctgcagata cagggcttgt gacacgtagc      910
aagaagacac gacattgtat tgatccctat tttattacaa atgtgcaccc accaccccag      970
atcaccgttt atatccacgt taaaattta atatcaagatt atatatttat agtgtgtgtg     1030
tatatttttt ttttctttta acgtttacgt ttattaaccc gctcactttc cttggcattg     1090
cgagactttc gcgcacgttt agcgggctga ggtggtggtt gcggttgttc ctcatcttca     1150
accactttat tgtaggcgcg cttgcgtgga ggcaaacttt gcttcacctt gggcggacca     1210
```

-continued

```
cctttaactt tggccacagt tggtgccaca ctttcgggtg gcgtttgagc ccgggtcggg    1270
gtggatgatg tgacttcggc cacagctggg gcccggggttg ggctcgatac cttcaccttc   1330
gccggagctg gatctggagc tggggttggg gtcgattcat cctcactttc actatcggat    1390
tccgagctcg aactggagct gctgctagac cgtgaacagg tgcgcgaacg ttgtggcatt    1450
tcatccacgt tgaccaaaac ttcgatgtat tcattcttta cgatttcctg cgacacggcc    1510
ggttccacgt ccacgggctg ttcgttgtca tctttaaagt tttcaagttc ttgaatcaaa    1570
tcggcagtgt tctcgtcccc aatttgttga acacttctgg ccaatatctc catattttta   1630
cccttaaact tgggcacsct ccgttgaccg gcagatttgc gcttagccac cgtactaatc    1690
gtctcacccg catcgccaat atccgaagaa cccgcaatcc cgcgcaaatc ttccgcagtc    1750
aaattgtaat cgctcagcgt agttttacgg cgcataatat cctcatcgta gtcctcgtac    1810 ggtccgtac atg tgc cgt gga cag tcg ggg ttt cca cga ttg cga att tcg   1861
         Met Cys Arg Gly Gln Ser Gly Phe Pro Arg Leu Arg Ile Ser
              60                  65                  70 tac tcc ttg agc aaa tcc ttg tac tca tcg ggg ggt aaa tct tgc gca    1909
Tyr Ser Leu Ser Lys Ser Leu Tyr Ser Ser Gly Gly Lys Ser Cys Ala
         75                  80                  85 cga ata acg ata gcc ttg tcg ccc gag ccc gac ccc att ccc gac ttg    1957
Arg Ile Thr Ile Ala Leu Ser Pro Glu Pro Asp Pro Ile Pro Asp Leu
         90                  95                 100 gaa agc ctg ata gac tcc tcg atc atg tac tgg gat ttg cgg cgc gcc    2005
Glu Ser Leu Ile Asp Ser Ser Ile Met Tyr Trp Asp Leu Arg Arg Ala
        105                 110                 115 aac atc atc gta aac gtt tcc gga tac tcg gag ggc aca acc gcg cgc    2053
Asn Ile Ile Val Asn Val Ser Gly Tyr Ser Glu Gly Thr Thr Ala Arg
        120                 125                 130 ata tta ttg agc cca gag tcg gtg aat acg tgc acc cgc gtc aca atg    2101
Ile Leu Leu Ser Pro Glu Ser Val Asn Thr Cys Thr Arg Val Thr Met
135                 140                 145                 150 cta tcc gta atg gtg tac gta acg ttg tcc gaa atg gga tcg gta aac    2149
Leu Ser Val Met Val Tyr Val Thr Leu Ser Glu Met Gly Ser Val Asn
                155                 160                 165 act tgc tcg att ttt aaa att ctc aac agg tcc cgg tgt ccg ctc ata    2197
Thr Cys Ser Ile Phe Lys Ile Leu Asn Arg Ser Arg Cys Pro Leu Ile
                170                 175                 180 aag ccg ggg ttg agt cca ccg tgaaccgcag caaacacgct ctg cac cac gag  2250
Lys Pro Gly Leu Ser Pro Pro                      Leu His His Glu
                185                                        190 gtt gaa ggg aag agt gct acg ctg ggc gcc gta ctc gac ctc aat tac    2298
Val Glu Gly Lys Ser Ala Thr Leu Gly Ala Val Leu Asp Leu Asn Tyr
        195                 200                 205 aat ctg tcg act gtt tgg tgc agc ctt cgc ttt aat ttc gtt ggt cca    2346
Asn Leu Ser Thr Val Trp Cys Ser Leu Arg Phe Asn Phe Val Gly Pro
210                 215                 220                 225 cgc ctc aca gcc aac gtt cgt ggc gac cca aac ggt cgt gta cac atc    2394
Arg Leu Thr Ala Asn Val Arg Gly Asp Pro Asn Gly Arg Val His Ile
                230                 235                 240 ccc cac gtc cgg aaa cga agg tgg caa aat tgg cat ctc gtt cat cga    2442
Pro His Val Arg Lys Arg Arg Trp Gln Asn Trp His Leu Val His Arg
                245                 250                 255 att c                                                              2446
Ile

<210> SEQ ID NO 5
<211> LENGTH: 56
<212> TYPE: PRT
```

-continued

<213> ORGANISM: mosquito baculovirus

<400> SEQUENCE: 5

```
Met Pro Gln Asn Ala Leu Gly Arg Val Gly Asn Val His Leu Gly Ala
 1               5                  10                  15

Val Ser Gly Gly Gly Val Asn Gly Phe Glu Gln Phe Asn Gln Thr Leu
            20                  25                  30

Ile Arg Tyr Ala Pro Pro Glu Leu Thr Gly Gly Gly Glu Tyr Gly Lys
        35                  40                  45

Ser Asp Ala Val Pro Ala Ala Arg
    50                  55
```

<210> SEQ ID NO 6
<211> LENGTH: 133
<212> TYPE: PRT
<213> ORGANISM: mosquito baculovirus

<400> SEQUENCE: 6

```
Met Cys Arg Gly Gln Ser Gly Phe Pro Arg Leu Arg Ile Ser Tyr Ser
 1               5                  10                  15

Leu Ser Lys Ser Leu Tyr Ser Ser Gly Gly Lys Ser Cys Ala Arg Ile
            20                  25                  30

Thr Ile Ala Leu Ser Pro Glu Pro Asp Pro Ile Pro Asp Leu Glu Ser
        35                  40                  45

Leu Ile Asp Ser Ser Ile Met Tyr Trp Asp Leu Arg Arg Ala Asn Ile
    50                  55                  60

Ile Val Asn Val Ser Gly Tyr Ser Glu Gly Thr Thr Ala Arg Ile Leu
65                  70                  75                  80

Leu Ser Pro Glu Ser Val Asn Thr Cys Thr Arg Val Thr Met Leu Ser
                85                  90                  95

Val Met Val Tyr Val Thr Leu Ser Glu Met Gly Ser Val Asn Thr Cys
            100                 105                 110

Ser Ile Phe Lys Ile Leu Asn Arg Ser Arg Cys Pro Leu Ile Lys Pro
        115                 120                 125

Gly Leu Ser Pro Pro
    130
```

<210> SEQ ID NO 7
<211> LENGTH: 69
<212> TYPE: PRT
<213> ORGANISM: mosquito baculovirus

<400> SEQUENCE: 7

```
Leu His His Glu Val Glu Gly Lys Ser Ala Thr Leu Gly Ala Val Leu
 1               5                  10                  15

Asp Leu Asn Tyr Asn Leu Ser Thr Val Trp Cys Ser Leu Arg Phe Asn
            20                  25                  30

Phe Val Gly Pro Arg Leu Thr Ala Asn Val Arg Gly Asp Pro Asn Gly
        35                  40                  45

Arg Val His Ile Pro His Val Arg Lys Arg Arg Trp Gln Asn Trp His
    50                  55                  60

Leu Val His Arg Ile
65
```

<210> SEQ ID NO 8
<211> LENGTH: 53
<212> TYPE: PRT
<213> ORGANISM: mosquito baculovirus -continued

<400> SEQUENCE: 8

```
Met Asn Thr Ser Lys Phe Trp Ser Thr Trp Met Lys Cys His Asn Val
 1               5                  10                  15

Arg Ala Pro Val His Gly Leu Ala Ala Ala Pro Val Arg Ala Arg Asn
            20                  25                  30

Pro Ile Val Lys Val Arg Met Asn Arg Pro Gln Pro Gln Leu Gln Ile
        35                  40                  45

Gln Leu Arg Arg Arg
    50
```

<210> SEQ ID NO 9
<211> LENGTH: 64
<212> TYPE: PRT
<213> ORGANISM: mosquito baculovirus

<400> SEQUENCE: 9

```
Lys Gly Arg Val Leu Arg Trp Ala Pro Tyr Ser Thr Ser Ile Thr Ile
 1               5                  10                  15

Cys Arg Leu Phe Gly Ala Ala Phe Ala Leu Ile Ser Leu Val His Ala
            20                  25                  30

Ser Gln Pro Thr Phe Val Ala Thr Gln Thr Val Val Tyr Thr Ser Pro
        35                  40                  45

Thr Ser Gly Asn Glu Gly Gly Lys Ile Gly Ile Ser Phe Ile Glu Phe
    50                  55                  60
```

<210> SEQ ID NO 10
<211> LENGTH: 6624
<212> TYPE: DNA
<213> ORGANISM: mosquito baculovirus
<220> FEATURE:
<221> NAME/KEY: CDS
<222> LOCATION: (2630)...(3334)
<221> NAME/KEY: CDS
<222> LOCATION: (11)...(541)
<221> NAME/KEY: CDS
<222> LOCATION: (5333)...(5848)
<221> NAME/KEY: CDS
<222> LOCATION: (5892)...(6188)
<221> NAME/KEY: CDS
<222> LOCATION: (4458)...(4739)
<221> NAME/KEY: CDS
<222> LOCATION: (2243)...(2473)
<221> NAME/KEY: CDS
<222> LOCATION: (6432)...(6620)
<221> NAME/KEY: CDS
<222> LOCATION: (3865)...(4044)

<400> SEQUENCE: 10

```
gaattctctc atg ata acg ggg tat ata aag gtt ggt ttc ggg gct cgg        49
            Met Ile Thr Gly Tyr Ile Lys Val Gly Phe Gly Ala Arg
             1               5                  10 ctg gaa cct agc agc atg aat cga aag cgg cta act aaa ttc gtg cgc       97
Leu Glu Pro Ser Ser Met Asn Arg Lys Arg Leu Thr Lys Phe Val Arg
     15                  20                  25 gac ttg tat cgc gag ttt aat gag gtt cac tgc gaa cag aga ctg gaa      145
Asp Leu Tyr Arg Glu Phe Asn Glu Val His Cys Glu Gln Arg Leu Glu
 30                  35                  40                  45 gcg tta gac cgc gct gtg gac gcc gaa acg gag ggt att tat ctt ggg      193
Ala Leu Asp Arg Ala Val Asp Ala Glu Thr Glu Gly Ile Tyr Leu Gly
                 50                  55                  60 ctt agt gtg cgc aat cgt tac agt cat cgg gtg gtt tac cgg gca tgg      241
Leu Ser Val Arg Asn Arg Tyr Ser His Arg Val Val Tyr Arg Ala Trp
            65                  70                  75
```

-continued

| | | |
|---|---|---|
| atc gag cgt ggg gtc gcg cag cgg aac tgg ttt tgt gaa att gaa tta<br>Ile Glu Arg Gly Val Ala Gln Arg Asn Trp Phe Cys Glu Ile Glu Leu<br>      80                         85                      90 | 289 |
| cca caa gcg gtg ctc gac gct aac cat tac att tta att tat ttc ggc<br>Pro Gln Ala Val Leu Asp Ala Asn His Tyr Ile Leu Ile Tyr Phe Gly<br>    95                        100                      105 | 337 |
| aca cga gtc tat tgc caa cag ccg tgg cta acg tac ctg gac aaa acg<br>Thr Arg Val Tyr Cys Gln Gln Pro Trp Leu Thr Tyr Leu Asp Lys Thr<br>110                    115                    120                    125 | 385 |
| tac aag tgt tgg ggt aat agt gca cga caa cca act cgg tcg gaa ctg<br>Tyr Lys Cys Trp Gly Asn Ser Ala Arg Gln Pro Thr Arg Ser Glu Leu<br>                      130                    135                    140 | 433 |
| aag cgc gta cct agc acc tac tgg cgc cac aac acc acc tat ata acg<br>Lys Arg Val Pro Ser Thr Tyr Trp Arg His Asn Thr Thr Tyr Ile Thr<br>                145                    150                    155 | 481 |
| atg gac gcg cga tca ttt cga cca ctt gtc cgc ttc atg atc gac gtc<br>Met Asp Ala Arg Ser Phe Arg Pro Leu Val Arg Phe Met Ile Asp Val<br>          160                    165                    170 | 529 |
| cac gat gaa cgc tgactgtttc tgcccacccg gaccctgcta ccatgcactc<br>His Asp Glu Arg<br>    175 | 581 |
| ttcagccact gcggaggtat ctgccagtcc tgtggaaccc actacgaaga cctagacgag | 641 |
| ttcgtgcgct gtatgagggg ccagaccacc cacaaaccga accccatcgc cataacaatg | 701 |
| gggctctgcg aatactgtcc gagaaggcac ccggtcggcg tgtcctgcca aggctatcca | 761 |
| gcgtgcgaaa atgttccct gtcgcacgcc ccactccccc aatgtcccca ccgattaagc | 821 |
| ctatatttct ttcttttcaa gaaaaataat aaaaaatgat aaaatttata cacctcgttt | 881 |
| tattgcagca gtaaatatat cactctccct ccagcacctt caagcgttgg tccatcgttt | 941 |
| tgatactgtc ggccagctca ttgatggcga cgtttatgta tgaaaattta tcatcactgg | 1001 |
| agctggacag ctccgacagg tcgtcgttca gtttgcccaa ggtggtgttc atggggccaa | 1061 |
| gcttttgctc gagctcgtcc actctagccg tgagtttggt gaggtccacc ccgagccct | 1121 |
| cctcgcactt gcactcggga ggttgggctg gtagcgcat gatgagcacg gccaccattg | 1181 |
| tgaccagtag tagtagaatt agaaatagta agtttggggg catcgttggc tcttacttgc | 1241 |
| agctaccgtc aaaccactgg tactgaattt cggcactcac tctagcgact ggacgcgcag | 1301 |
| atccaggttc accagctcgt tgccaatttc gtaaaacttt gacgaggtcg agttttgcag | 1361 |
| ctccaccagc tcgcccgata tattctccaa tgtttcgccg attgcgctaa aattttccac | 1421 |
| acccgaccgt tcgacctcgt caatgcgctg ctccgtgtcg ctcaactgtt gctccgtggc | 1481 |
| ggtaacgcgc tccttcaatg gggacaggtc cggcaaatgg tcgtcccac attcacgctt | 1541 |
| ggcacccttg acggtgaaga ttgtgatcgc ggtcattatc gttaacattg tcagtataaa | 1601 |
| aattaaaaat attacaaggg gtgacgacat cgtgaggctt atggcgggga acaggtgcac | 1661 |
| cgtgagacca accgcagcgg accgaaaccc tccagggtgt cctcgagtaa ccggccgtca | 1721 |
| acggtcacca ccgcccggcc cgttcgtgac accaaataca ctccgtactc acaggcaccc | 1781 |
| atataactga tctcgctgtg cccctctggt agcacaaaat tccgccggta gaagcgccgt | 1841 |
| ttgcgcaggt tccgcaccac aatatcaacc gagactcgac acattttacg cccgctcgta | 1901 |
| aactcgtcct agcagcgcag cttgctgctt ggtcaagcac accggaatgg ggcgattata | 1961 |
| cggcccggg cggtaaatgt atttcgttgt accagtcccg cacacacaag cgtccggagt | 2021 |
| gaacgcttgc tcgagcaagt ttatctccaa ttgaccgccg gtacacacat acggttgcag | 2081 |

-continued

```
tttgttatcg tcggtgaaaa tgtcgcgata ggttgaaagg caggattgat ttataacgaa    2141
ttcgtctgca gtgaataccc gtaaaattcc atgctcttcg acacaatttc gcttctcggg    2201
aatagattta tgatccgtgc tgcagaaccc gcctatgcac g atg aaa ctc ctc cgt    2257
                                             Met Lys Leu Leu Arg
                                                     180
```

| | | | | | | | | | | | | | | | | |
|---|---|---|---|---|---|---|---|---|---|---|---|---|---|---|---|---|
| ctc | tgg | tca | aag | cgc | agt | tac | gtt | gac | agt | ccg | cat | tat | caa | tac | acg | 2305 |
| Leu | Trp | Ser | Lys | Arg | Ser | Tyr | Val | Asp | Ser | Pro | His | Tyr | Gln | Tyr | Thr | |
| | 185 | | | | 190 | | | | | 195 | | | | | | |
| gta | att | tgg | tgt | tgt | ggc | aat | cta | cgt | gct | gag | agc | cgg | cga | aat | gaa | 2353 |
| Val | Ile | Trp | Cys | Cys | Gly | Asn | Leu | Arg | Ala | Glu | Ser | Arg | Arg | Asn | Glu | |
| 200 | | | | | 205 | | | | | 210 | | | | | | |
| tct | ctg | gca | gca | ccg | att | cac | ccc | gag | ctc | gtg | cgg | ccc | gtt | ccc | gcg | 2401 |
| Ser | Leu | Ala | Ala | Pro | Ile | His | Pro | Glu | Leu | Val | Arg | Pro | Val | Pro | Ala | |
| 215 | | | | 220 | | | | | 225 | | | | | | 230 | |
| act | ctt | ggg | cgt | gtt | tgg | cta | gaa | att | ttg | cac | ccg | aag | tta | aaa | tca | 2449 |
| Thr | Leu | Gly | Arg | Val | Trp | Leu | Glu | Ile | Leu | His | Pro | Lys | Leu | Lys | Ser | |
| | | | | 235 | | | | | 240 | | | | | 245 | | |
| act | gaa | tca | tta | cga | gca | cca | gta | tgagcaccac taaaccgtac aacatttctt | | | | | | | | 2503 |
| Thr | Glu | Ser | Leu | Arg | Ala | Pro | Val | | | | | | | | | |
| | | | 250 | | | | | | | | | | | | | |

```
ccctttctat ttccacagga atcccaactt aaagacattt ggaacacttt cgagaagccc    2563
gaggagcgca aatgggccct tcagctaagc gacaaggtgt ggttgccacc ggaagaattc    2623
```

| | | | | | | | | | | | | | | | | |
|---|---|---|---|---|---|---|---|---|---|---|---|---|---|---|---|---|
| gacaca | atg | agt | gaa | ttc | atc | gag | acc | gta | cac | tac | aac | acc | gac | ccg | | 2671 |
| | Met | Ser | Glu | Phe | Ile | Glu | Thr | Val | His | Tyr | Asn | Thr | Asp | Pro | | |
| | | 255 | | | | 260 | | | | | 265 | | | | | |
| atc | cgg | tcg | agc | tat | ggc | att | tgt | ggg | ctg | cac | acc | cgc | ggg | aac | cgg | 2719 |
| Ile | Arg | Ser | Ser | Tyr | Gly | Ile | Cys | Gly | Leu | His | Thr | Arg | Gly | Asn | Arg | |
| | 270 | | | | 275 | | | | | 280 | | | | | | |
| ggc | tgc | cga | gag | tgg | gtg | att | gat | atc | gat | ttg | aaa | act | gac | gac | ccc | 2767 |
| Gly | Cys | Arg | Glu | Trp | Val | Ile | Asp | Ile | Asp | Leu | Lys | Thr | Asp | Asp | Pro | |
| 285 | | | | 290 | | | | | 295 | | | | | | 300 | |
| gag | ttg | gcc | aac | ttt | gtg | ctc | aac | gtg | tcc | gtg | gtc | acc | tca | atg | ttc | 2815 |
| Glu | Leu | Ala | Asn | Phe | Val | Leu | Asn | Val | Ser | Val | Val | Thr | Ser | Met | Phe | |
| | | | | 305 | | | | | 310 | | | | | | 315 | |
| ttc | ttc | ggt | acc | gaa | aac | att | aaa | gtt | tac | cac | acg | ggc | aac | gac | ggc | 2863 |
| Phe | Phe | Gly | Thr | Glu | Asn | Ile | Lys | Val | Tyr | His | Thr | Gly | Asn | Asp | Gly | |
| | | | 320 | | | | | 325 | | | | | 330 | | | |
| atc | cac | att | tgg | ctc | aac | ccg | gcc | aac | ttc | ccg | gtg | gac | tcg | agc | gcc | 2911 |
| Ile | His | Ile | Trp | Leu | Asn | Pro | Ala | Asn | Phe | Pro | Val | Asp | Ser | Ser | Ala | |
| | | 335 | | | | | 340 | | | | | 345 | | | | |
| gaa | ttg | cgc | gga | ttc | tac | ctc | gcc | gcc | atg | cag | cta | ccc | aaa | ggt | gag | 2959 |
| Glu | Leu | Arg | Gly | Phe | Tyr | Leu | Ala | Ala | Met | Gln | Leu | Pro | Lys | Gly | Glu | |
| | 350 | | | | | 355 | | | | | 360 | | | | | |
| gag | gaa | cta | cac | gag | ctg | gtg | cgg | acc | acc | gag | tgc | agg | ttg | ttt | tgc | 3007 |
| Glu | Glu | Leu | His | Glu | Leu | Val | Arg | Thr | Thr | Glu | Cys | Arg | Leu | Phe | Cys | |
| 365 | | | | | 370 | | | | | 375 | | | | | 380 | |
| gac | gcc | gac | tgc | tgc | gga | atc | gat | tgc | aag | ccc | aag | atg | cgc | atc | atc | 3055 |
| Asp | Ala | Asp | Cys | Cys | Gly | Ile | Asp | Cys | Lys | Pro | Lys | Met | Arg | Ile | Ile | |
| | | | | 385 | | | | | 390 | | | | | | 395 | |
| gac | acc | cca | ccc | aat | ccc | acg | gaa | ccg | att | tcg | ttt | gcc | gag | tgc | ttt | 3103 |
| Asp | Thr | Pro | Pro | Asn | Pro | Thr | Glu | Pro | Ile | Ser | Phe | Ala | Glu | Cys | Phe | |
| | | | | 400 | | | | 405 | | | | | 410 | | | |
| gtg | cgc | gct | ctc | tgc | tgc | aac | gaa | acc | tat | atg | aac | gaa | atg | aca | tcg | 3151 |
| Val | Arg | Ala | Leu | Cys | Cys | Asn | Glu | Thr | Tyr | Met | Asn | Glu | Met | Thr | Ser | |
| | | 415 | | | | | 420 | | | | | 425 | | | | |
| att | ata | cgc | aac | aac | cgg | gac | gtg | gtg | agc | acc | gtc | acc | gac | gtg | tgg | 3199 |
| Ile | Ile | Arg | Asn | Asn | Arg | Asp | Val | Val | Ser | Thr | Val | Thr | Asp | Val | Trp | |
| | 430 | | | | | 435 | | | | | 440 | | | | | |

-continued

```
aga ctc ttt tgg ccg ccc ata gat gcg ggc ctg ttt caa tcg cca gct          3247
Arg Leu Phe Trp Pro Pro Ile Asp Ala Gly Leu Phe Gln Ser Pro Ala
445                 450                 455                 460 aga ctc tgc cgt gca ccc ctc agt tac cac ttg aag ggc ggt cgg ctt          3295
Arg Leu Cys Arg Ala Pro Leu Ser Tyr His Leu Lys Gly Gly Arg Leu
                465                 470                 475 tcg cgt cgt att gac ttg gat gaa tat ttt aaa aat gat tgaaataaaa           3344
Ser Arg Arg Ile Asp Leu Asp Glu Tyr Phe Lys Asn Asp
            480                 485 agttttatta caatgactc attgaagttt ttattccccc caacatcaca agttcaaccc         3404
cgactgcggc tccattaaat gaaaaatgtt catttgttag cacgacttta acgggtccac        3464
ttttgtgggg ccgccaaatg ttgggctcca tatggaaaag ttagcccaac caagacgggt       3524
ccacttttgt ggggcccaca tttgcggtgc taaaggggtt gggttttggt tgaaataaaa       3584
taaaaatttt ctaactctaa caggtattat tatatttgat cacatttttc atcacaacat       3644
tagcgcggtg tggtgcgttt atcacagata gaccaccgcc gaatcgtaca cactggccgc      3704
tctttaggtc gacgttcaca cagtgaccca agttgcaagc ctgtccagtt cggtgcagta     3764
ccaccatacg agcctcccaa taatgttcca gcagaatctt tgcaagatcg cgttgatttt     3824
taatatcgag caatagcacc accggaccgt tgaccgtaac atg gtt gag ctg acg        3879
                                              Met Val Glu Leu Thr
                                                              490 aat tgc agt gcc aaa gtc tcc agt ata gtg gta cca aca ttg gct aac         3927
Asn Cys Ser Ala Lys Val Ser Ser Ile Val Val Pro Thr Leu Ala Asn
495                 500                 505                 510 gtt att cac caa tac cat cca agt ttc gtg cag gcg tcg ggc gtc aac         3975
Val Ile His Gln Tyr His Pro Ser Phe Val Gln Ala Ser Gly Val Asn
                515                 520                 525 tat ggt gct aaa aag ttt caa atc tac cag caa att tgt gca ctc gtt         4023
Tyr Gly Ala Lys Lys Phe Gln Ile Tyr Gln Gln Ile Cys Ala Leu Val
                530                 535                 540 aac cag gtc cgg gtc gca tga aagtaacacc aagttgtggg cactagcggc            4074
Asn Gln Val Arg Val Ala *
            545 gcgtataatt tgctcccgca gtacctctcg cggatacgac gcgacaagca ttgaacagcg       4134 attccaacaa cttggctgcg aagcacctcg actcgataac ccagtggtcc gtagttggtg       4194 gatagaatcc gtcaaagcga ccttttctc tcagttccag cgccgtgagc ggtcgaaagg       4254 tataaaaatt ctcctgaact gtggcgtacc ataagagagg atcgttttta cgagcgacat      4314 tcataacctc cccgtttata ggcaaagtgt cgaggtgaaa ccagttagat tgagcgttat      4374 tacggccaaa cacgaccgcg cagtccgcat cacgaacata caaatccatc cttatcaccg      4434 cagaccggtg gagtcattga acc atg ccc ttg gtg cac att gaa cag cgc gga      4487
                            Met Pro Leu Val His Ile Glu Gln Arg Gly
                                              550                 555 ttg tcg tgc tat gtc gct ggt ttc gag gcc aac gtg gaa ccc gac ctg         4535
Leu Ser Cys Tyr Val Ala Gly Phe Glu Ala Asn Val Glu Pro Asp Leu
            560                 565                 570 tac cag tgt att gtc gat tgc aaa ccc cac ctt atg cgc tat ata gca         4583
Tyr Gln Cys Ile Val Asp Cys Lys Pro His Leu Met Arg Tyr Ile Ala
575                 580                 585                 590 ctt aac cat ccg gaa ttt ttc gca cag ctg agg cca atc gat ggg cac         4631
Leu Asn His Pro Glu Phe Phe Ala Gln Leu Arg Pro Ile Asp Gly His
                595                 600                 605 aac ctt tac agt tcc acc agt ggg gat tac atc gat cta tgg ctt gag         4679
Asn Leu Tyr Ser Ser Thr Ser Gly Asp Tyr Ile Asp Leu Trp Leu Glu
```

```
cta ctg aac gag gct gct atg aag tcg ggc ttg gat gaa gag ggt gga      4727
Leu Leu Asn Glu Ala Ala Met Lys Ser Gly Leu Asp Glu Glu Gly Gly
            625                 630                 635 tta ggg agc tgt tgagcaaaca ttttcgcttg aagaaaggg aagagaaata           4779
Leu Gly Ser Cys
    640 aacaaacaac tttagtttac atcatcaagt gttttatttt tctaaaactg ccctcgattt    4839 ctccaccaaa ccctccataa attgcagctc atcggggaag catttgccga ccaggtccag    4899 cagttgcttc gcgcttagat agcgcacatc gatgtttaaa cagtagccaa agtagtactc    4959 caaatctcga ctctcgtaca tcacttctgt accgtcgcac accactcgca tggagatgga    5019 ccgcaggtcc atgtcgtaat gtaaaactag aagaaacttt tccggtgcca atgaggtaac    5079 ttctccgtac tcgagcagct cttggggcag ctcgaagggg atcattttcg gtaaaccgtg    5139 cggcgtgatg aggaccgtat tttcgtgcca ctcccactcg gcgggcgaca ttagggccaa    5199 atcgtggccc gctgccgtta cgttgccaaa gctgctattt atgttgtagg cttcgtactg    5259 tacgaagccc cgcaccgcca actggtggtc cacgtataaa aatctcgtca acgggtggcg    5319 caggtaccga aag atg gtt cga cga ttt tca gct cca acg tgc aca aat      5368
            Met Val Arg Arg Phe Ser Ala Pro Thr Cys Thr Asn
                    645                 650 gta ccc gaa aag ctg tac atg ttt gcg gtg aag ttc agc tac tct tta      5416
Val Pro Glu Lys Leu Tyr Met Phe Ala Val Lys Phe Ser Tyr Ser Leu
655                 660                 665                 670 aaa tat cgt act ata aat cga ttc acg ctc acc aat cgt agc agt att      5464
Lys Tyr Arg Thr Ile Asn Arg Phe Thr Leu Thr Asn Arg Ser Ser Ile
                675                 680                 685 cac aca atg ttg tac tct gta gaa gtt cgc gta ttt agt acg gag att      5512
His Thr Met Leu Tyr Ser Val Glu Val Arg Val Phe Ser Thr Glu Ile
            690                 695                 700 ccg tcg cag tcg ctg cac cac tcc cac cat atc gcc ata ccg ttc gat      5560
Pro Ser Gln Ser Leu His His Ser His His Ile Ala Ile Pro Phe Asp
        705                 710                 715 aaa gat aga tgg acc gtc gat ggc att tta ccg aac gat ata ccg ctc      5608
Lys Asp Arg Trp Thr Val Asp Gly Ile Leu Pro Asn Asp Ile Pro Leu
    720                 725                 730 gac cac acg ata cgg ttg tgt gtt acc gtc agg ggt agt aaa aaa ttt      5656
Asp His Thr Ile Arg Leu Cys Val Thr Val Arg Gly Ser Lys Lys Phe
735                 740                 745                 750 tcc tgc gta tgg cga gag acc acc tac aag tgc gga aat gtg tac gat      5704
Ser Cys Val Trp Arg Glu Thr Thr Tyr Lys Cys Gly Asn Val Tyr Asp
                755                 760                 765 cca cca cta gag tac cag ttg gag aag ctg ccg ggc gtg cag tat agc      5752
Pro Pro Leu Glu Tyr Gln Leu Glu Lys Leu Pro Gly Val Gln Tyr Ser
            770                 775                 780 gat cta gcg tta agg ata atc gag aag ttt gag cgc gct atg aag tac      5800
Asp Leu Ala Leu Arg Ile Ile Glu Lys Phe Glu Arg Ala Met Lys Tyr
        785                 790                 795 acg ata gaa gtc gat ttc act gca aat aaa tct caa agt ttg gaa tta      5848
Thr Ile Glu Val Asp Phe Thr Ala Asn Lys Ser Gln Ser Leu Glu Leu
    800                 805                 810 taaaccaccc gtctttcatt gttaacccgc ccgcaaccca acg atg tta caa gtt      5903
                                              Met Leu Gln Val
                                                      815 tcc cta gta gga ccc cac ttc aca ctc gtg ctc gcc agt ggc gat ttg      5951
Ser Leu Val Gly Pro His Phe Thr Leu Val Leu Ala Ser Gly Asp Leu
        820                 825                 830
```

```
cgg tgc cag ttt cta tta cca ccg tgg gcc gca ctg gac aac agt ttg    5999
Arg Cys Gln Phe Leu Leu Pro Pro Trp Ala Ala Leu Asp Asn Ser Leu
835                 840                 845                 850 atg ctc gtc gtg cag tgg gat cag cgc aac tat acc ctc aac tgg gcg    6047
Met Leu Val Val Gln Trp Asp Gln Arg Asn Tyr Thr Leu Asn Trp Ala
                855                 860                 865 ggc gaa ata ttt tac ggt gga att gca gca cga ccg gtg aca ccg cac    6095
Gly Glu Ile Phe Tyr Gly Gly Ile Ala Ala Arg Pro Val Thr Pro His
        870                 875                 880 atg ctc aag tgg tgc tac cac ctc gcg gtc cac cct gag ccc aac ttt    6143
Met Leu Lys Trp Cys Tyr His Leu Ala Val His Pro Glu Pro Asn Phe
    885                 890                 895 acc gtg gaa gaa aaa caa cct ggc tgt gat tta cga cac cct tta        6188
Thr Val Glu Glu Lys Gln Pro Gly Cys Asp Leu Arg His Pro Leu
    900                 905                 910 taataaaaaa aaaatcgctt caaacaggga caataaaacc cacaagtgta tagagttttt    6248
tttttatttt attttcccaa gtatattgga actggaaaga aataataaca acaataataa    6308
caataataat atcaataaaa aaggtattcg atttatgact gtgcgcgcgc gcacaacagg    6368
gccggcttct tgtttacaaa ctcaacttcc tgattctcga ccgtagcgcc cgggagctca    6428 tgc ttg tgc act ggt aac ctg cac ggg ata gag gaa cgt ttc cac cct    6476
    Leu Cys Thr Gly Asn Leu His Gly Ile Glu Glu Arg Phe His Pro
        915                 920                 925 atc gag caa cac ccc act ttc acc gac caa ctc act caa cca tgg ccg    6524
Ile Glu Gln His Pro Thr Phe Thr Asp Gln Leu Thr Gln Pro Trp Pro
    930                 935                 940 att tgg aca cac agc tgg ggg act ttg tcg acc cgg gcc aac att tcg    6572
Ile Trp Thr His Ser Trp Gly Thr Leu Ser Thr Arg Ala Asn Ile Ser
945                 950                 955                 960 tcg ggc tcc agg tcg tgc ggt atc gta gaa tct cga aca cgg cgc caa    6620
Ser Gly Ser Arg Ser Cys Gly Ile Val Glu Ser Arg Thr Arg Arg Gln
                965                 970                 975 gctt                                                                 6624

<210> SEQ ID NO 11
<211> LENGTH: 177
<212> TYPE: PRT
<213> ORGANISM: mosquito baculovirus

<400> SEQUENCE: 11

Met Ile Thr Gly Tyr Ile Lys Val Gly Phe Gly Ala Arg Leu Glu Pro
1               5                   10                  15

Ser Ser Met Asn Arg Lys Arg Leu Thr Lys Phe Val Arg Asp Leu Tyr
            20                  25                  30

Arg Glu Phe Asn Glu Val His Cys Glu Gln Arg Leu Glu Ala Leu Asp
        35                  40                  45

Arg Ala Val Asp Ala Glu Thr Glu Gly Ile Tyr Leu Gly Leu Ser Val
    50                  55                  60

Arg Asn Arg Tyr Ser His Arg Val Tyr Arg Ala Trp Ile Glu Arg
65                  70                  75                  80

Gly Val Ala Gln Arg Asn Trp Phe Cys Glu Ile Glu Leu Pro Gln Ala
            85                  90                  95

Val Leu Asp Ala Asn His Tyr Ile Leu Ile Tyr Phe Gly Thr Arg Val
            100                 105                 110

Tyr Cys Gln Gln Pro Trp Leu Thr Tyr Leu Asp Lys Thr Tyr Lys Cys
        115                 120                 125
```

```
Trp Gly Asn Ser Ala Arg Gln Pro Thr Arg Ser Glu Leu Lys Arg Val
    130                 135                 140

Pro Ser Thr Tyr Trp Arg His Asn Thr Tyr Ile Thr Met Asp Ala
145                 150                 155                 160

Arg Ser Phe Arg Pro Leu Val Arg Phe Met Ile Asp Val His Asp Glu
                165                 170                 175

Arg

<210> SEQ ID NO 12
<211> LENGTH: 77
<212> TYPE: PRT
<213> ORGANISM: mosquito baculovirus

<400> SEQUENCE: 12

Met Lys Leu Leu Arg Leu Trp Ser Lys Arg Ser Tyr Val Asp Ser Pro
1               5                   10                  15

His Tyr Gln Tyr Thr Val Ile Trp Cys Cys Gly Asn Leu Arg Ala Glu
                20                  25                  30

Ser Arg Arg Asn Glu Ser Leu Ala Ala Pro Ile His Pro Glu Leu Val
            35                  40                  45

Arg Pro Val Pro Ala Thr Leu Gly Arg Val Trp Leu Glu Ile Leu His
        50                  55                  60

Pro Lys Leu Lys Ser Thr Glu Ser Leu Arg Ala Pro Val
65                  70                  75

<210> SEQ ID NO 13
<211> LENGTH: 235
<212> TYPE: PRT
<213> ORGANISM: mosquito baculovirus

<400> SEQUENCE: 13

Met Ser Glu Phe Ile Glu Thr Val His Tyr Asn Thr Asp Pro Ile Arg
1               5                   10                  15

Ser Ser Tyr Gly Ile Cys Gly Leu His Thr Arg Gly Asn Arg Gly Cys
                20                  25                  30

Arg Glu Trp Val Ile Asp Ile Asp Leu Lys Thr Asp Asp Pro Glu Leu
            35                  40                  45

Ala Asn Phe Val Leu Asn Val Ser Val Val Thr Ser Met Phe Phe Phe
        50                  55                  60

Gly Thr Glu Asn Ile Lys Val Tyr His Thr Gly Asn Asp Gly Ile His
65                  70                  75                  80

Ile Trp Leu Asn Pro Ala Asn Phe Pro Val Asp Ser Ser Ala Glu Leu
                85                  90                  95

Arg Gly Phe Tyr Leu Ala Ala Met Gln Leu Pro Lys Gly Glu Glu
                100                 105                 110

Leu His Glu Leu Val Arg Thr Thr Glu Cys Arg Leu Phe Cys Asp Ala
            115                 120                 125

Asp Cys Cys Gly Ile Asp Cys Lys Pro Lys Met Arg Ile Ile Asp Thr
        130                 135                 140

Pro Pro Asn Pro Thr Glu Pro Ile Ser Phe Ala Glu Cys Phe Val Arg
145                 150                 155                 160

Ala Leu Cys Cys Asn Glu Thr Tyr Met Asn Glu Met Thr Ser Ile Ile
                165                 170                 175

Arg Asn Asn Arg Asp Val Val Ser Thr Val Thr Asp Val Trp Arg Leu
            180                 185                 190

Phe Trp Pro Pro Ile Asp Ala Gly Leu Phe Gln Ser Pro Ala Arg Leu
```

```
                    195                 200                 205
Cys Arg Ala Pro Leu Ser Tyr His Leu Lys Gly Gly Arg Leu Ser Arg
    210                 215                 220

Arg Ile Asp Leu Asp Glu Tyr Phe Lys Asn Asp
225                 230                 235

<210> SEQ ID NO 14
<211> LENGTH: 59
<212> TYPE: PRT
<213> ORGANISM: mosquito baculovirus

<400> SEQUENCE: 14

Met Val Glu Leu Thr Asn Cys Ser Ala Lys Val Ser Ser Ile Val Val
  1               5                  10                  15

Pro Thr Leu Ala Asn Val Ile His Gln Tyr His Pro Ser Phe Val Gln
                 20                  25                  30

Ala Ser Gly Val Asn Tyr Gly Ala Lys Lys Phe Gln Ile Tyr Gln Gln
             35                  40                  45

Ile Cys Ala Leu Val Asn Gln Val Arg Val Ala
         50                  55

<210> SEQ ID NO 15
<211> LENGTH: 94
<212> TYPE: PRT
<213> ORGANISM: mosquito baculovirus

<400> SEQUENCE: 15

Met Pro Leu Val His Ile Glu Gln Arg Gly Leu Ser Cys Tyr Val Ala
  1               5                  10                  15

Gly Phe Gl

```
Arg Leu Cys Val Thr Val Arg Gly Ser Lys Lys Phe Ser Cys Val Trp
            100                 105                 110

Arg Glu Thr Thr Tyr Lys Cys Gly Asn Val Tyr Asp Pro Pro Leu Glu
            115                 120                 125

Tyr Gln Leu Glu Lys Leu Pro Gly Val Gln Tyr Ser Asp Leu Ala Leu
            130                 135                 140

Arg Ile Ile Glu Lys Phe Glu Arg Ala Met Lys Tyr Thr Ile Glu Val
145                 150                 155                 160

Asp Phe Thr Ala Asn Lys Ser Gln Ser Leu Glu Leu
                165                 170

<210> SEQ ID NO 17
<211> LENGTH: 99
<212> TYPE: PRT
<213> ORGANISM: mosquito baculovirus

<400> SEQUENCE: 17

Met Leu Gln Val Ser Leu Val Gly Pro His Phe Thr Leu Val Leu Ala
1               5                   10                  15

Ser Gly Asp Leu Arg Cys Gln Phe Leu Leu Pro Pro Trp Ala Ala Leu
            20                  25                  30

Asp Asn Ser Leu Met Leu Val Val Gln Trp Asp Gln Arg Asn Tyr Thr
        35                  40                  45

Leu Asn Trp Ala Gly Glu Ile Phe Tyr Gly Ile Ala Ala Arg Pro
    50                  55                  60

Val Thr Pro His Met Leu Lys Trp Cys Tyr His Leu Ala Val His Pro
65              70                  75                  80

Glu Pro Asn Phe Thr Val Glu Glu Lys Gln Pro Gly Cys Asp Leu Arg
                85                  90                  95

His Pro Leu

<210> SEQ ID NO 18
<211> LENGTH: 63
<212> TYPE: PRT
<213> ORGANISM: mosquito baculovirus

<400> SEQUENCE: 18

Leu Cys Thr Gly Asn Leu His Gly Ile Glu Glu Arg Phe His Pro Ile
1               5                   10                  15

Glu Gln His Pro Thr Phe Thr Asp Gln Leu Thr Gln Pro Trp Pro Ile
            20                  25                  30

Trp Thr His Ser Trp Gly Thr Leu Ser Thr Arg Ala Asn Ile Ser Ser
            35                  40                  45

Gly Ser Arg Ser Cys Gly Ile Val Glu Ser Arg Thr Arg Arg Gln
    50                  55                  60

<210> SEQ ID NO 19
<211> LENGTH: 6624
<212> TYPE: DNA
<213> ORGANISM: mosquito baculovirus
<220> FEATURE:
<221> NAME/KEY: CDS
<222> LOCATION: (4127)...(4735)
<221> NAME/KEY: CDS
<222> LOCATION: (1237)...(1809)
<221> NAME/KEY: CDS
<222> LOCATION: (2500)...(3021)
<221> NAME/KEY: CDS
<222> LOCATION: (4994)...(5344)
<221> NAME/KEY: CDS
```

-continued

```
<222> LOCATION: (5401)...(5721)
<221> NAME/KEY: CDS
<222> LOCATION: (4740)...(4982)
<221> NAME/KEY: CDS
<222> LOCATION: (2)...(196)
<221> NAME/KEY: CDS
<222> LOCATION: (3790)...(3939)

<400> SEQUENCE: 19
```

| | | | | | | | | | | | | | | | | |
|---|---|---|---|---|---|---|---|---|---|---|---|---|---|---|---|---|
| a | agc | ttg | gcg | ccg | tgt | tcg | aga | ttc | tac | gat | acc | gca | cga | cct | gga | gcc | 49 |
| | Ser | Leu | Ala | Pro | Cys | Ser | Arg | Phe | Tyr | Asp | Thr | Ala | Arg | Pro | Gly | Ala | |
| | 1 | | | 5 | | | | | 10 | | | | | 15 | | | |

```
cga cga aat gtt ggc ccg ggt cga caa agt ccc cca gct gtg tgt cca       97
Arg Arg Asn Val Gly Pro Gly Arg Gln Ser Pro Pro Ala Val Cys Pro
             20                  25                  30 aat cgg cca tgg ttg agt gag ttg gtc ggt gaa agt ggg gtg ttg ctc      145
Asn Arg Pro Trp Leu Ser Glu Leu Val Gly Glu Ser Gly Val Leu Leu
     35                  40                  45 gat agg gtg gaa acg ttc ctc tat ccc gtg cag gtt acc agt gca caa      193
Asp Arg Val Glu Thr Phe Leu Tyr Pro Val Gln Val Thr Ser Ala Gln
 50                  55                  60 gca tgagctcccg ggcgctacgg tcgagaatca ggaagttgag tttgtaaaca            246
Ala
 65 agaagccggc cctgttgtgc gcgcgcgcac agtcataaat cgaatacctt ttttattgat    306
attattattg ttattattgt tgttattatt tctttccagt tccaatatac ttgggaaaat    366
aaaataaaaa aaaaactcta tacacttgtg ggttttattg tccctgtttg aagcgatttt    426
tttttttatta taaagggtgt cgtaaatcac agccaggttg ttttttcttcc acggtaaagt   486
tgggctcagg gtggaccgcg aggtggtagc accacttgag catgtgcggt gtcaccggtc    546
gtgctgcaat tccaccgtaa aatatttcgc ccgcccagtt gagggtatag ttgcgctgat    606
cccactgcac gacgagcatc aaactgttgt ccagtgcggc ccacggtggt aatagaaact    666
ggcaccgcaa atcgccactg gcgagcacga gtgtgaagtg gggtcctact agggaaactt    726
gtaacatcgt tgggttgcgg gcgggttaac aatgaaagac gggtggttta taattccaaa    786
ctttgagatt tatttgcagt gaaatcgact tctatcgtgt acttcatagc gcgctcaaac    846
ttctcgatta tccttaacgc tagatcgcta tactgcacgc ccggcagctt ctccaactgg    906
tactctagtg gtggatcgta cacatttccg cacttgtagg tggtctctcg ccatacgcag    966
gaaaattttt tactaccct gacggtaaca cacaaccgta tcgtgtggtc gagcggtata    1026
tcgttcggta aaatgccatc gacggtccat ctatctttat cgaacggtat ggcgatatgg   1086
tgggagtggt gcagcgactg cgacggaatc tccgtactaa atacgcgaac ttctacagag   1146
tacaacattg tgtgaatact gctacgattg gtgagcgtga atcgatttat agtacgatat   1206
tttaaagagt agctgaactt caccgcaaac atg tac agc ttt tcg ggt aca ttt    1260
                                   Met Tyr Ser Phe Ser Gly Thr Phe
                                                                70
```

| | | | | | | | | | | | | | | | |
|---|---|---|---|---|---|---|---|---|---|---|---|---|---|---|---|
| gtg | cac | gtt | gga | gct | gaa | aat | cgt | cga | acc | atc | ttt | cgg | tac | ctg | cgc | 1308 |
| Val | His | Val | Gly | Ala | Glu | Asn | Arg | Arg | Thr | Ile | Phe | Arg | Tyr | Leu | Arg | |
| | 75 | | | | 80 | | | | | 85 | | | | | | |

```
cac ccg ttg acg aga ttt tta tac gtg gac cac cag ttg gcg gtg cgg    1356
His Pro Leu Thr Arg Phe Leu Tyr Val Asp His Gln Leu Ala Val Arg
 90                  95                 100                 105 ggc ttc gta cag tac gaa gcc tac aac ata aat agc agc ttt ggc aac    1404
Gly Phe Val Gln Tyr Glu Ala Tyr Asn Ile Asn Ser Ser Phe Gly Asn
             110                 115                 120 gta acg gca gcg ggc cac gat ttg gcc cta atg tcg ccc gcc gag tgg    1452
Val Thr Ala Ala Gly His Asp Leu Ala Leu Met Ser Pro Ala Glu Trp
```

```
                                                                          -continued Val Thr Ala Ala Gly His Asp Leu Ala Leu Met Ser Pro Ala Glu Trp
            125                 130                 135 gag tgg cac gaa aat acg gtc ctc atc acg ccg cac ggt tta ccg aaa        1500
Glu Trp His Glu Asn Thr Val Leu Ile Thr Pro His Gly Leu Pro Lys
            140                 145                 150 atg atc ccc ttc gag ctg ccc caa gag ctg ctc gag tac gga gaa gtt        1548
Met Ile Pro Phe Glu Leu Pro Gln Glu Leu Leu Glu Tyr Gly Glu Val
            155                 160                 165 acc tca ttg gca ccg gaa aag ttt ctt cta gtt tta cat tac gac atg        1596
Thr Ser Leu Ala Pro Glu Lys Phe Leu Leu Val Leu His Tyr Asp Met
170                 175                 180                 185 gac ctg cgg tcc atc tcc atg cga gtg gtg tgc gac ggt aca gaa gtg        1644
Asp Leu Arg Ser Ile Ser Met Arg Val Val Cys Asp Gly Thr Glu Val
                190                 195                 200 atg tac gag agt cga gat ttg gag tac tac ttt ggc tac tgt tta aac        1692
Met Tyr Glu Ser Arg Asp Leu Glu Tyr Tyr Phe Gly Tyr Cys Leu Asn
            205                 210                 215 atc gat gtg cgc tat cta agc gcg aag caa ctg ctg gac ctg gtc ggc        1740
Ile Asp Val Arg Tyr Leu Ser Ala Lys Gln Leu Leu Asp Leu Val Gly
            220                 225                 230 aaa tgc ttc ccc gat gag ctg caa ttt atg gag ggt ttg gtg gag aaa        1788
Lys Cys Phe Pro Asp Glu Leu Gln Phe Met Glu Gly Leu Val Glu Lys
235                 240                 245 tcg agg gca gtt tta gaa aaa taaaacactt gatgatgtaa actaaagttg           1839
Ser Arg Ala Val Leu Glu Lys
250                 255 tttgtttatt tctcttccct ttcttccaag cgaaaatgtt tgctcaacag ctccctaatc      1899
caccctcttc atccaagccc gacttcatag cagcctcgtt cagtagctca agccatagat      1959
cgatgtaatc cccactggtg gaactgtaaa ggttgtgccc atcgattggc ctcagctgtg      2019
cgaaaaattc cggatggtta agtgctatat agcgcataag gtggggtttg caatcgacaa      2079
tacactggta caggtcgggt tccacgttgg cctcgaaacc agcgacatag cacgacaatc      2139
cgcgctgttc aatgtgcacc aagggcatgg ttcaatgact ccaccggtct gcggtgataa      2199
ggatggattt gtatgttcgt gatgcggact gcgcggtcgt gtttggccgt aataacgctc      2259
aatctaactg gtttcacctc gacactttgc ctataaacgg ggaggttatg aatgtcgctc      2319
gtaaaaacga tcctctctta tggtacgcca cagttcagga gaatttttat accttttcgac    2379 cgctcacggc gctggaactg agagaaaaag gtcgctttga cggattctat ccaccaacta     2439
cggaccactg ggttatcgag tcgaggtgct tcgcagccaa gttgttggaa tcgctgttca     2499 atg ctt gtc gcg tcg tat ccg cga gag gta ctg cgg gag caa att ata        2547
Met Leu Val Ala Ser Tyr Pro Arg Glu Val Leu Arg Glu Gln Ile Ile
            260                 265                 270 cgc gcc gct agt gcc cac aac ttg gtg tta ctt tca tgc gac ccg gac        2595
Arg Ala Ala Ser Ala His Asn Leu Val Leu Leu Ser Cys Asp Pro Asp
            275                 280                 285 ctg gtt aac gag tgc aca aat ttg ctg gta gat ttg aaa ctt ttt agc        2643
Leu Val Asn Glu Cys Thr Asn Leu Leu Val Asp Leu Lys Leu Phe Ser
            290                 295                 300 acc ata gtt gac gcc cga cgc ctg cac gaa act tgg atg gta ttg gtg        2691
Thr Ile Val Asp Ala Arg Arg Leu His Glu Thr Trp Met Val Leu Val
305                 310                 315                 320 aat aac gtt agc caa tgt tgg tac cac tat act gga gac ttt ggc act        2739
Asn Asn Val Ser Gln Cys Trp Tyr His Tyr Thr Gly Asp Phe Gly Thr
                325                 330                 335 gca att cgt cag ctc aac cat gtt acg gtc aac ggt ccg gtg gtg cta        2787
Ala Ile Arg Gln Leu Asn His Val Thr Val Asn Gly Pro Val Val Leu
```

-continued

```
                340                 345                 350
ttg ctc gat att aaa aat caa cgc gat ctt gca aag att ctg ctg gaa      2835
Leu Leu Asp Ile Lys Asn Gln Arg Asp Leu Ala Lys Ile Leu Leu Glu
            355                 360                 365 cat tat tgg gag gct cgt atg gtg gta ctg cac cga act gga cag gct      2883
His Tyr Trp Glu Ala Arg Met Val Val Leu His Arg Thr Gly Gln Ala
        370                 375                 380 tgc aac ttg ggt cac tgt gtg aac gtc gac cta aag agc ggc cag tgt      2931
Cys Asn Leu Gly His Cys Val Asn Val Asp Leu Lys Ser Gly Gln Cys
385                 390                 395                 400 gta cga ttc ggc ggt ggt cta tct gtg ata aac gca cca cac cgc gct      2979
Val Arg Phe Gly Gly Gly Leu Ser Val Ile Asn Ala Pro His Arg Ala
                405                 410                 415 aat gtt gtg atg aaa aat gtg atc aaa tat aat aat acc tgt              3021
Asn Val Val Met Lys Asn Val Ile Lys Tyr Asn Asn Thr Cys
            420                 425                 430 tagagttaga aaattttat tttatttcaa ccaaaaccca accccttag caccgcaaat      3081 gtgggcccca caaagtgga cccgtcttgg ttgggctaac ttttccatat ggagcccaac     3141
atttggcggc cccacaaaag tggacccgtt aaagtcgtgc taacaaatga acattttca    3201 tttaatggag ccgcagtcgg ggttgaactt gtgatgttgg ggggaataaa aacttcaatg   3261
agtcattgtt aataaaactt tttatttcaa tcatttttaa aatattcatc caagtcaata   3321
cgacgcgaaa gccgaccgcc cttcaagtgg taactgaggg gtgcacggca gagtctagct   3381
ggcgattgaa acaggcccgc atctatgggc ggccaaaaga gtctccacac gtcggtgacg   3441
gtgctcacca cgtcccggtt gttgcgtata atcgatgtca tttcgttcat ataggtttcg   3501
ttgcagcaga gagcgcgcac aaagcactcg gcaaacgaaa tcggttccgt gggattgggt   3561
ggggtgtcga tgatgcgcat cttgggcttg caatcgattc cgcagcagtc ggcgtcgcaa   3621
aacaacctgc actcggtggt ccgcaccagc tcgtgtagtt cctcctcacc tttgggtagc   3681
tgcatggcgg cgaggtagaa tccgcgcaat tcggcgctcg agtccaccgg gaagttggcc   3741
gggttgagcc aaatgtggat gccgtcgttg cccgtgtggt aaacttta atg ttt tcg    3798
                                                    Met Phe Ser gta ccg aag aag aac att gag gtg acc acg gac acg ttg agc aca aag    3846
Val Pro Lys Lys Asn Ile Glu Val Thr Thr Asp Thr Leu Ser Thr Lys
            435                 440                 445 ttg gcc aac tcg ggg tcg tca gtt ttc aaa tcg ata tca atc acc cac    3894
Leu Ala Asn Ser Gly Ser Ser Val Phe Lys Ser Ile Ser Ile Thr His
450                 455                 460                 465 tct cgg cag ccc cgg ttc ccg cgg gtg tgc agc cca caa atg cca        3939
Ser Arg Gln Pro Arg Phe Pro Arg Val Cys Ser Pro Gln Met Pro
                470                 475                 480 tagctcgacc ggatcgggtc ggtgttgtag tgtacggtct cgatgaattc actcattgtg   3999
tcgaattctt ccggtggcaa ccacaccttg tcgcttagct gaagggccca tttgcgctcc   4059
tcgggcttct cgaaagtgtt ccaaatgtct ttaagttggg attcctgtgg aaatagaaag   4119 ggaagaa atg ttg tac ggt tta gtg gtg ctc ata ctg gtg ctc gta atg    4168
        Met Leu Tyr Gly Leu Val Val Leu Ile Leu Val Leu Val Met
                            485                 490 att cag ttg att tta act tcg ggt gca aaa ttt cta gcc aaa cac gcc    4216
Ile Gln Leu Ile Leu Thr Ser Gly Ala Lys Phe Leu Ala Lys His Ala
495                 500                 505                 510 caa gag tcg cgg gaa cgg gcc gca cga gct cgg ggt gaa tcg gtg ctg    4264
Gln Glu Ser Arg Glu Arg Ala Ala Arg Ala Arg Gly Glu Ser Val Leu
                515                 520                 525
```

```
cca gag att cat ttc gcc ggc tct cag cac gta gat tgc cac aac acc      4312
Pro Glu Ile His Phe Ala Gly Ser Gln His Val Asp Cys His Asn Thr
        530                 535                 540 aaa tta ccg tgt att gat aat gcg gac tgt caa cgt aac tgc gct ttg      4360
Lys Leu Pro Cys Ile Asp Asn Ala Asp Cys Gln Arg Asn Cys Ala Leu
            545                 550                 555 acc aga gac gga gga gtt tca tcg tgc ata ggc ggg ttc tgc agc acg      4408
Thr Arg Asp Gly Gly Val Ser Ser Cys Ile Gly Gly Phe Cys Ser Thr
    560                 565                 570 gat cat aaa tct att ccc gag aag cga aat tgt gtc gaa gag cat gga      4456
Asp His Lys Ser Ile Pro Glu Lys Arg Asn Cys Val Glu Glu His Gly
575                 580                 585                 590 att tta cgg gta ttc act gca gac gaa ttc gtt ata aat caa tcc tgc      4504
Ile Leu Arg Val Phe Thr Ala Asp Glu Phe Val Ile Asn Gln Ser Cys
                595                 600                 605 ctt tca acc tat cgc gac att ttc acc gac gat aac aaa ctg caa ccg      4552
Leu Ser Thr Tyr Arg Asp Ile Phe Thr Asp Asp Asn Lys Leu Gln Pro
            610                 615                 620 tat gtg tgt acc ggc ggt caa ttg gag ata aac ttg ctc gag caa gcg      4600
Tyr Val Cys Thr Gly Gly Gln Leu Glu Ile Asn Leu Leu Glu Gln Ala
        625                 630                 635 ttc act ccg gac gct tgt gtg tgc ggg act ggt aca acg aaa tac att      4648
Phe Thr Pro Asp Ala Cys Val Cys Gly Thr Gly Thr Thr Lys Tyr Ile
    640                 645                 650 tac cgc ccg ggg ccg tat aat cgc ccc att ccg gtg tgc ttg acc aag      4696
Tyr Arg Pro Gly Pro Tyr Asn Arg Pro Ile Pro Val Cys Leu Thr Lys
655                 660                 665                 670 cag caa gct gcg ctg cta gga cga gtt tac gag cgg gcg taaa atg tgt    4745
Gln Gln Ala Ala Leu Leu Gly Arg Val Tyr Glu Arg Ala      Met Cys
                675                 680                     685 cga gtc tcg gtt gat att gtg gtg cgg aac ctg cgc aaa cgg cgc ttc      4793
Arg Val Ser Val Asp Ile Val Val Arg Asn Leu Arg Lys Arg Arg Phe
            690                 695                 700 tac cgg cgg aat ttt gtg cta cca gag ggg cac agc gag atc agt tat      4841
Tyr Arg Arg Asn Phe Val Leu Pro Glu Gly His Ser Glu Ile Ser Tyr
        705                 710                 715 atg ggt gcc tgt gag tac gga gtg tat ttg gtg tca cga acg ggc cgg      4889
Met Gly Ala Cys Glu Tyr Gly Val Tyr Leu Val Ser Arg Thr Gly Arg
    720                 725                 730 gcg gtg gtg acc gtt gac ggc cgg tta ctc gag gac acc ctg gag ggt      4937
Ala Val Val Thr Val Asp Gly Arg Leu Leu Glu Asp Thr Leu Glu Gly
735                 740                 745 ttc ggt ccg ctg cgg ttg gtc tca cgg tgc acc tgt tcc ccg cca           4982
Phe Gly Pro Leu Arg Leu Val Ser Arg Cys Thr Cys Ser Pro Pro
    750                 755                 760 taagcctcac g atg tcg tca ccc ctt gta ata ttt tta att ttt ata ctg     5032
             Met Ser Ser Pro Leu Val Ile Phe Leu Ile Phe Ile Leu
                 765                 770                 775 aca atg tta acg ata atg acc gcg atc aca atc ttc acc gtc aag ggt      5080
Thr Met Leu Thr Ile Met Thr Ala Ile Thr Ile Phe Thr Val Lys Gly
            780                 785                 790 gcc aag cgt gaa tgt ggg gac gac cat ttg ccg gac ctg tcc cca ttg      5128
Ala Lys Arg Glu Cys Gly Asp Asp His Leu Pro Asp Leu Ser Pro Leu
795                 800                 805 aag gag cgc gtt acc gcc acg gag caa cag ttg agc gac acg gag cag      5176
Lys Glu Arg Val Thr Ala Thr Glu Gln Gln Leu Ser Asp Thr Glu Gln
810                 815                 820                 825 cgc att gac gag gtc gaa cgg tcg ggt gtg gaa aat ttt agc gca atc      5224
Arg Ile Asp Glu Val Glu Arg Ser Gly Val Glu Asn Phe Ser Ala Ile
        830                 835                 840
```

-continued

```
ggc gaa aca ttg gag aat ata tcg ggc gag ctg gtg gag ctg caa aac    5272
Gly Glu Thr Leu Glu Asn Ile Ser Gly Glu Leu Val Glu Leu Gln Asn
            845                 850                 855 tcg acc tcg tca aag ttt tac gaa att ggc aac gag ctg gtg aac ctg    5320
Ser Thr Ser Ser Lys Phe Tyr Glu Ile Gly Asn Glu Leu Val Asn Leu
        860                 865                 870 gat ctg cgc gtc cag tcg cta gag tgagtgccga aattcagtac cagtggtttg    5374
Asp Leu Arg Val Gln Ser Leu Glu
    875                 880 acggtagctg caagtaagag ccaacg atg ccc caa act tta cta ttt cta att    5427
                             Met Pro Gln Thr Leu Leu Phe Leu Ile
                                         885                 890 cta cta cta ctg gtc aca atg gtg gcc gtg ctc atc atg cgc tac cca    5475
Leu Leu Leu Leu Val Thr Met Val Ala Val Leu Ile Met Arg Tyr Pro
                895                 900                 905 gcc caa cct ccc gag tgc aag tgc gag gag ggc tcg ggg gtg gac ctc    5523
Ala Gln Pro Pro Glu Cys Lys Cys Glu Glu Gly Ser Gly Val Asp Leu
            910                 915                 920 acc aaa ctc acg gct aga gtg gac gag ctc gag caa aag ctt ggc ccc    5571
Thr Lys Leu Thr Ala Arg Val Asp Glu Leu Glu Gln Lys Leu Gly Pro
        925                 930                 935 atg aac acc acc ttg ggc aaa ctg aac gac gac ctg tcg gag ctg tcc    5619
Met Asn Thr Thr Leu Gly Lys Leu Asn Asp Asp Leu Ser Glu Leu Ser
    940                 945                 950 agc tcc agt gat gat aaa ttt tca tac ata aac gtc gcc atc aat gag    5667
Ser Ser Ser Asp Asp Lys Phe Ser Tyr Ile Asn Val Ala Ile Asn Glu
955                 960                 965                 970 ctg gcc gac agt atc aaa acg atg gac caa cgc ttg aag gtg ctg gag    5715
Leu Ala Asp Ser Ile Lys Thr Met Asp Gln Arg Leu Lys Val Leu Glu
                975                 980                 985 gga gag tgatatattt actgctgcaa taaaacgagg tgtataaatt ttatcatttt    5771
Gly Glu ttattatttt tcttgaaaag aaagaaatat aggcttaatc ggtgggaca ttgggggagt    5831 ggggcgtgcg acagggaaca tttttcgcac gctggatagc cttggcagga cacgccgacc    5891
gggtgccttc tcggacagta ttcgcagagc ccattgtta tggcgatggg gttcggtttg    5951
tgggtggtct ggcccctcat acagcgcacg aactcgtcta ggtcttcgta gtgggttcca    6011
caggactggc agatacctcc gcagtggctg aagagtgcat ggtagcaggg tccgggtggg    6071
cagaaacagt cagcgttcat cgtggacgtc gatcatgaag cggacaagtg gtcgaaatga    6131
tcgcgcgtcc atcgttatat aggtggtgtt gtggcgccag taggtgctag gtacgcgctt    6191
cagttccgac cgagttggtt gtcgtgcact attaccccaa cacttgtacg ttttgtccag    6251
gtacgttagc cacggctgtt ggcaatagac tcgtgtgccg aaataaatta aaatgtaatg    6311
gttagcgtcg agcaccgctt gtggtaattc aatttcacaa aaccagttcc gctgcgcgac    6371
cccacgctcg atccatgccc ggtaaaccac ccgatgactg taacgattgc gcacactaag    6431
cccaagataa atacgctccg tttcggcgtc cacagcgcgg tctaacgctt ccagtctctg    6491
ttcgcagtga acctcattaa actcgcgata caagtcgcgc acgaatttag ttagccgctt    6551
tcgattcatg ctgctaggtt ccagccgagc cccgaaacca acctttatat accccgttat    6611
catgagagaa ttc                                                       6624
```

<210> SEQ ID NO 20
<211> LENGTH: 65
<212> TYPE: PRT
<213> ORGANISM: mosquito baculovirus

```
<400> SEQUENCE: 20

Ser Leu Ala Pro Cys Ser Arg Phe Tyr Asp Thr Ala Arg Pro Gly Ala
 1               5                  10                  15

Arg Arg Asn Val Gly Pro Gly Arg Gln Ser Pro Ala Val Cys Pro
            20                  25                  30

Asn Arg Pro Trp Leu Ser Glu Leu Val Gly Glu Ser Gly Val Leu Leu
            35                  40                  45

Asp Arg Val Glu Thr Phe Leu Tyr Pro Val Gln Val Thr Ser Ala Gln
        50                  55                  60

Ala
65

<210> SEQ ID NO 21
<211> LENGTH: 191
<212> TYPE: PRT
<213> ORGANISM: mosquito baculovirus

<400> SEQUENCE: 21

Met Tyr Ser Phe Ser Gly Thr Phe Val His Val Gly Ala Glu Asn Arg
 1               5                  10                  15

Arg Thr Ile Phe Arg Tyr Leu Arg His Pro Leu Thr Arg Phe Leu Tyr
            20                  25                  30

Val Asp His Gln Leu Ala Val Arg Gly Phe Val Gln Tyr Glu Ala Tyr
        35                  40                  45

Asn Ile Asn Ser Ser Phe Gly Asn Val Thr Ala Ala Gly His Asp Leu
    50                  55                  60

Ala Leu Met Ser Pro Ala Glu Trp Glu Trp His Glu Asn Thr Val Leu
65                  70                  75                  80

Ile Thr Pro His Gly Leu Pro Lys Met Ile Pro Phe Glu Leu Pro Gln
                85                  90                  95

Glu Leu Glu Tyr Gly Glu Val Thr Ser Leu Ala Pro Glu Lys Phe
            100                 105                 110

Leu Leu Val Leu His Tyr Asp Met Asp Leu Arg Ser Ile Ser Met Arg
        115                 120                 125

Val Val Cys Asp Gly Thr Glu Val Met Tyr Glu Ser Arg Asp Leu Glu
    130                 135                 140

Tyr Tyr Phe Gly Tyr Cys Leu Asn Ile Asp Val Arg Tyr Leu Ser Ala
145                 150                 155                 160

Lys Gln Leu Leu Asp Leu Val Gly Lys Cys Phe Pro Asp Glu Leu Gln
                165                 170                 175

Phe Met Glu Gly Leu Val Glu Lys Ser Arg Ala Val Leu Glu Lys
            180                 185                 190

<210> SEQ ID NO 22
<211> LENGTH: 174
<212> TYPE: PRT
<213> ORGANISM: mosquito baculovirus

<400> SEQUENCE: 22

Met Leu Val Ala Ser Tyr Pro Arg Glu Val Leu Arg Glu Gln Ile Ile
 1               5                  10                  15

Arg Ala Ala Ser Ala His Asn Leu Val Leu Ser Cys Asp Pro Asp
            20                  25                  30

Leu Val Asn Glu Cys Thr Asn Leu Leu Val Asp Leu Lys Leu Phe Ser
        35                  40                  45
```

-continued

```
Thr Ile Val Asp Ala Arg Arg Leu His Glu Thr Trp Met Val Leu Val
    50                  55                  60

Asn Asn Val Ser Gln Cys Trp Tyr His Tyr Thr Gly Asp Phe Gly Thr
65                  70                  75                  80

Ala Ile Arg Gln Leu Asn His Val Thr Val Asn Gly Pro Val Val Leu
                85                  90                  95

Leu Leu Asp Ile Lys Asn Gln Arg Asp Leu Ala Lys Ile Leu Leu Glu
            100                 105                 110

His Tyr Trp Glu Ala Arg Met Val Val Leu His Arg Thr Gly Gln Ala
        115                 120                 125

Cys Asn Leu Gly His Cys Val Asn Val Asp Leu Lys Ser Gly Gln Cys
    130                 135                 140

Val Arg Phe Gly Gly Gly Leu Ser Val Ile Asn Ala Pro His Arg Ala
145                 150                 155                 160

Asn Val Val Met Lys Asn Val Ile Lys Tyr Asn Asn Thr Cys
                165                 170

<210> SEQ ID NO 23
<211> LENGTH: 50
<212> TYPE: PRT
<213> ORGANISM: mosquito baculovirus

<400> SEQUENCE: 23

Met Phe Ser Val Pro Lys Lys Asn Ile Glu Val Thr Thr Asp Thr Leu
 1               5                  10                  15

Ser Thr Lys Leu Ala Asn Ser Gly Ser Ser Val Phe Lys Ser Ile Ser
            20                  25                  30

Ile Thr His Ser Arg Gln Pro Arg Phe Pro Arg Val Cys Ser Pro Gln
        35                  40                  45

Met Pro
    50

<210> SEQ ID NO 24
<211> LENGTH: 203
<212> TYPE: PRT
<213> ORGANISM: mosquito baculovirus

<400> SEQUENCE: 24

Met Leu Tyr Gly Leu Val Val Leu Ile Leu Val Leu Val Met Ile Gln
 1               5                  10                  15

Leu Ile Leu Thr Ser Gly Ala Lys Phe Leu Ala Lys His Ala Gln Glu
            20                  25                  30

Ser Arg Glu Arg Ala Ala Arg Ala Arg Gly Glu Ser Val Leu Pro Glu
        35                  40                  45

Ile His Phe Ala Gly Ser Gln His Val Asp Cys His Asn Thr Lys Leu
    50                  55                  60

Pro Cys Ile Asp Asn Ala Asp Cys Gln Arg Asn Cys Ala Leu Thr Arg
65                  70                  75                  80

Asp Gly Gly Val Ser Ser Cys Ile Gly Gly Phe Cys Ser Thr Asp His
                85                  90                  95

Lys Ser Ile Pro Glu Lys Arg Asn Cys Val Glu Glu His Gly Ile Leu
            100                 105                 110

Arg Val Phe Thr Ala Asp Glu Phe Val Ile Asn Gln Ser Cys Leu Ser
        115                 120                 125

Thr Tyr Arg Asp Ile Phe Thr Asp Asp Asn Lys Leu Gln Pro Tyr Val
    130                 135                 140
```

-continued

```
Cys Thr Gly Gly Gln Leu Glu Ile Asn Leu Leu Glu Gln Ala Phe Thr
145                 150                 155                 160

Pro Asp Ala Cys Val Cys Gly Thr Gly Thr Thr Lys Tyr Ile Tyr Arg
                165                 170                 175

Pro Gly Pro Tyr Asn Arg Pro Ile Pro Val Cys Leu Thr Lys Gln Gln
                180                 185                 190

Ala Ala Leu Leu Gly Arg Val Tyr Glu Arg Ala
        195                 200

<210> SEQ ID NO 25
<211> LENGTH: 81
<212> TYPE: PRT
<213> ORGANISM: mosquito baculovirus

<400> SEQUENCE: 25

Met Cys Arg Val Ser Val Asp Ile Val Val Arg Asn Leu Arg Lys Arg
1               5                   10                  15

Arg Phe Tyr Arg Arg Asn Phe Val Leu Pro Glu Gly His Ser Glu Ile
            20                  25                  30

Ser Tyr Met Gly Ala Cys Glu Tyr Gly Val Tyr Leu Val Ser Arg Thr
        35                  40                  45

Gly Arg Ala Val Val Thr Val Asp Gly Arg Leu Leu Glu Asp Thr Leu
    50                  55                  60

Glu Gly Phe Gly Pro Leu Arg Leu Val Ser Arg Cys Thr Cys Ser Pro
65                  70                  75                  80

Pro

<210> SEQ ID NO 26
<211> LENGTH: 117
<212> TYPE: PRT
<213> ORGANISM: mosquito baculovirus

<400> SEQUENCE: 26

Met Ser Ser Pro Leu Val Ile Phe Leu Ile Phe Ile Leu Thr Met Leu
1               5                   10                  15

Thr Ile Met Thr Ala Ile Thr Ile Phe Thr Val Lys Gly Ala Lys Arg
            20                  25                  30

Glu Cys Gly Asp Asp His Leu Pro Asp Leu Ser Pro Leu Lys Glu Arg
        35                  40                  45

Val Thr Ala Thr Glu Gln Gln Leu Ser Asp Thr Glu Gln Arg Ile Asp
    50                  55                  60

Glu Val Glu Arg Ser Gly Val Glu Asn Phe Ser Ala Ile Gly Glu Thr
65                  70                  75                  80

Leu Glu Asn Ile Ser Gly Glu Leu Val Glu Leu Gln Asn Ser Thr Ser
                85                  90                  95

Ser Lys Phe Tyr Glu Ile Gly Asn Glu Leu Val Asn Leu Asp Leu Arg
            100                 105                 110

Val Gln Ser Leu Glu
        115

<210> SEQ ID NO 27
<211> LENGTH: 107
<212> TYPE: PRT
<213> ORGANISM: mosquito baculovirus

<400> SEQUENCE: 27

Met Pro Gln Thr Leu Leu Phe Leu Ile Leu Leu Leu Val Thr Met
1               5                   10                  15
```

-continued

```
Val Ala Val Leu Ile Met Arg Tyr Pro Ala Gln Pro Pro Glu Cys Lys
            20                  25                  30

Cys Glu Glu Gly Ser Gly Val Asp Leu Thr Lys Leu Thr Ala Arg Val
        35                  40                  45

Asp Glu Leu Glu Gln Lys Leu Gly Pro Met Asn Thr Thr Leu Gly Lys
    50                  55                  60

Leu Asn Asp Asp Leu Ser Glu Leu Ser Ser Ser Ser Asp Asp Lys Phe
65                  70                  75                  80

Ser Tyr Ile Asn Val Ala Ile Asn Glu Leu Ala Asp Ser Ile Lys Thr
                85                  90                  95

Met Asp Gln Arg Leu Lys Val Leu Glu Gly Glu
            100                 105

<210> SEQ ID NO 28
<211> LENGTH: 6624
<212> TYPE: DNA
<213> ORGANISM: mosquito baculovirus
<220> FEATURE:
<221> NAME/KEY: CDS
<222> LOCATION: (1444)...(1788)
<221> NAME/KEY: CDS
<222> LOCATION: (3977)...(4285)
<221> NAME/KEY: CDS
<222> LOCATION: (965)...(1153)
<221> NAME/KEY: CDS
<222> LOCATION: (534)...(857)

<400> SEQUENCE: 28
gaattctctc atgataacgg ggtatataaa ggttggtttc ggggctcggc tggaacctag      60
cagcatgaat cgaaagcggc taactaaatt cgtgcgcgac ttgtatcgcg agtttaatga     120
ggttcactgc gaacagagac tggaagcgtt agaccgcgct gtggacgccg aaacggaggg     180
tatttatctt gggcttagtg tgcgcaatcg ttacagtcat cgggtggttt accgggcatg     240
gatcgagcgt ggggtcgcgc agcggaactg gttttgtgaa attgaattac cacaagcggt     300
gctcgacgct aaccattaca ttttaattta tttcggcaca cgagtctatt gccaacagcc     360
gtggctaacg tacctggaca aaacgtacaa gtgttggggt aatagtgcac gacaaccaac     420
tcggtcggaa ctgaagcgcg tacctagcac ctactggcgc cacaacacca cctatataac     480
gatggacgcg cgatcatttc gaccacttgt ccgcttcatg atcgacgtcc acg atg        536
                                                           Met
                                                            1 aac gct gac tgt ttc tgc cca ccc gga ccc tgc tac cat gca ctc ttc       584
Asn Ala Asp Cys Phe Cys Pro Pro Gly Pro Cys Tyr His Ala Leu Phe
            5                   10                  15 agc cac tgc gga ggt atc tgc cag tcc tgt gga acc cac tac gaa gac       632
Ser His Cys Gly Gly Ile Cys Gln Ser Cys Gly Thr His Tyr Glu Asp
        20                  25                  30 cta gac gag ttc gtg cgc tgt atg agg ggc cag acc acc cac aaa ccg       680
Leu Asp Glu Phe Val Arg Cys Met Arg Gly Gln Thr Thr His Lys Pro
    35                  40                  45 aac ccc atc gcc ata aca atg ggg ctc tgc gaa tac tgt ccg aga agg       728
Asn Pro Ile Ala Ile Thr Met Gly Leu Cys Glu Tyr Cys Pro Arg Arg
 50                  55                  60                  65 cac ccg gtc ggc gtg tcc tgc caa ggc tat cca gcg tgc gaa aaa tgt       776
His Pro Val Gly Val Ser Cys Gln Gly Tyr Pro Ala Cys Glu Lys Cys
                70                  75                  80 tcc ctg tcg cac gcc cca ctc ccc caa tgt ccc cac cga tta agc cta       824
Ser Leu Ser His Ala Pro Leu Pro Gln Cys Pro His Arg Leu Ser Leu
            85                  90                  95
```

-continued

```
tat ttc ttt ctt ttc aag aaa aat aat aaa aaa tgataaaatt tatacacctc    877
Tyr Phe Phe Leu Phe Lys Lys Asn Asn Lys Lys
            100                 105 gttttattgc agcagtaaat atatcactct ccctccagca ccttcaagcg ttggtccatc    937
gttttgatac tgtcggccag ctcattg atg gcg acg ttt atg tat gaa aat tta   991
                              Met Ala Thr Phe Met Tyr Glu Asn Leu
                                      110                 115 tca tca ctg gag ctg gac agc tcc gac agg tcg tcg ttc agt ttg ccc    1039
Ser Ser Leu Glu Leu Asp Ser Ser Asp Arg Ser Ser Phe Ser Leu Pro
            120                 125                 130 aag gtg gtg ttc atg ggg cca agc ttt tgc tcg agc tcg tcc act cta    1087
Lys Val Val Phe Met Gly Pro Ser Phe Cys Ser Ser Ser Ser Thr Leu
    135                 140                 145 gcc gtg agt ttg gtg agg tcc acc ccc gag ccc tcc tcg cac ttg cac    1135
Ala Val Ser Leu Val Arg Ser Thr Pro Glu Pro Ser Ser His Leu His
150                 155                 160                 165 tcg gga ggt tgg gct ggg tagcgcatga tgagcacggc caccattgtg            1183
Ser Gly Gly Trp Ala Gly
                170 accagtagta gtagaattag aaatagtaaa gtttgggca tcgttggctc ttacttgcag    1243 ctaccgtcaa accactggta ctgaatttcg gcactcactc tagcgactgg acgcgcagat   1303 ccaggttcac cagctcgttg ccaatttcgt aaaactttga cgaggtcgag ttttgcagct   1363 ccaccagctc gcccgatata ttctccaatg tttcgccgat tgcgctaaaa ttttccacac   1423 ccgaccgttc gacctcgtca atg cgc tgc tcc gtg tcg ctc aac tgt tgc tcc   1476
                      Met Arg Cys Ser Val Ser Leu Asn Cys Cys Ser
                                      175                 180 gtg gcg gta acg cgc tcc ttc aat ggg gac agg tcc ggc aaa tgg tcg    1524
Val Ala Val Thr Arg Ser Phe Asn Gly Asp Arg Ser Gly Lys Trp Ser
            185                 190                 195 tcc cca cat tca cgc ttg gca ccc ttg acg gtg aag att gtg atc gcg    1572
Ser Pro His Ser Arg Leu Ala Pro Leu Thr Val Lys Ile Val Ile Ala
    200                 205                 210 gtc att atc gtt aac att gtc agt ata aaa att aaa aat att aca agg    1620
Val Ile Ile Val Asn Ile Val Ser Ile Lys Ile Lys Asn Ile Thr Arg
215                 220                 225                 230 ggt gac gac atc gtg agg ctt atg gcg ggg aac agg tgc acc gtg aga    1668
Gly Asp Asp Ile Val Arg Leu Met Ala Gly Asn Arg Cys Thr Val Arg
            235                 240                 245 cca acc gca gcg gac cga aac cct cca ggg tgt cct cga gta acc ggc    1716
Pro Thr Ala Ala Asp Arg Asn Pro Pro Gly Cys Pro Arg Val Thr Gly
    250                 255                 260 cgt caa cgg tca cca ccg ccc ggc ccg ttc gtg aca cca aat aca ctc    1764
Arg Gln Arg Ser Pro Pro Pro Gly Pro Phe Val Thr Pro Asn Thr Leu
    265                 270                 275 cgt act cac agg cac cca tat aac tgatctcgct gtgcccctct ggtagcacaa   1818
Arg Thr His Arg His Pro Tyr Asn
    280                 285 aattccgccg gtagaagcgc cgtttgcgca ggttccgcac acaatatca accgagactc    1878 gacacatttt acgcccgctc gtaaactcgt cctagcagcg cagcttgctg cttggtcaag   1938
cacaccggaa tggggcgatt atacggcccc gggcggtaaa tgtatttcgt tgtaccagtc   1998
ccgcacacac aagcgtccgg agtgaacgct tgctcgagca agtttatctc caattgaccg   2058
ccggtacaca catacggttg cagtttgtta tcgtcggtga aaatgtcgcg ataggttgaa   2118
aggcaggatt gatttataac gaattcgtct gcagtgaata cccgtaaaat tccatgctct   2178
```

-continued

```
tcgacacaat ttcgcttctc gggaatagat ttatgatccg tgctgcagaa cccgcctatg   2238
cacgatgaaa ctcctccgtc tctggtcaaa gcgcagttac gttgacagtc cgcattatca   2298
atacacggta atttggtgtt gtggcaatct acgtgctgag agccggcgaa atgaatctct   2358
ggcagcaccg attcaccccg agctcgtgcg gcccgttccc gcgactcttg ggcgtgtttg   2418
gctagaaatt ttgcacccga agttaaaatc aactgaatca ttacgagcac cagtatgagc   2478
accactaaac cgtacaacat ttcttcccct tctatttcca caggaatccc aacttaaaga   2538
catttggaac actttcgaga agcccgagga gcgcaaatgg gcccttcagc taagcgacaa   2598
ggtgtggttg ccaccggaag aattcgacac aatgagtgaa ttcatcgaga ccgtacacta   2658
caacaccgac ccgatccggt cgagctatgg catttgtggg ctgcacaccc gcgggaaccg   2718
gggctgccga gagtgggtga ttgatatcga tttgaaaact gacgaccccg agttggccaa   2778
ctttgtgctc aacgtgtccg tggtcacctc aatgttcttc ttcggtaccg aaaacattaa   2838
agtttaccac acgggcaacg acggcatcca catttggctc aacccggcca acttcccggt   2898
ggactcgagc gccgaattgc gcggattcta cctcgccgcc atgcagctac caaaggtga   2958 ggaggaacta cacgagctgg tgcggaccac cgagtgcagg ttgttttgcg acgccgactg   3018
ctgcggaatc gattgcaagc ccaagatgcg catcatcgac cccacccca atcccacgga   3078 accgatttcg tttgccgagt gctttgtgcg cgctctctgc tgcaacgaaa cctatatgaa   3138
cgaaatgaca tcgattatac gcaacaaccg ggacgtggtg agcaccgtca ccgacgtgtg   3198
gagactcttt tggccgccca tagatgcggg cctgtttcaa tcgccagcta gactctgccg   3258
tgcacccctc agttaccact tgaagggcgg tcggctttcg cgtcgtattg acttggatga   3318
atattttaaa aatgattgaa ataaaaagtt ttattaacaa tgactcattg aagttttat   3378 tccccccaac atcacaagtt caaccccgac tgcggctcca ttaaatgaaa atgttcatt   3438 tgttagcacg actttaacgg gtccactttt gtggggccgc caaatgttgg gctccatatg   3498
gaaaagttag cccaaccaag acgggtccac ttttgtgggg cccacatttg cggtgctaaa   3558
ggggttgggt tttggttgaa ataaaataaa aattttctaa ctctaacagg tattattata   3618
tttgatcaca tttttcatca caacattagc gcggtgtggt gcgtttatca cagatagacc   3678
accgccgaat cgtacacact ggccgctctt taggtcgacg ttcacacagt gacccaagtt   3738
gcaagcctgt ccagttcggt gcagtaccac catacgagcc tcccaataat gttccagcag   3798
aatctttgca agatcgcgtt gatttttaat atcgagcaat agcaccaccg gaccgttgac   3858
cgtaacatgg ttgagctgac gaattgcagt gccaaagtct ccagtatagt ggtaccaaca   3918
ttggctaacg ttattcacca ataccatcca agtttcgtgc aggcgtcggg cgtcaact    3976 atg gtg cta aaa agt ttc aaa tct acc agc aaa ttt gtg cac tcg tta    4024
Met Val Leu Lys Ser Phe Lys Ser Thr Ser Lys Phe Val His Ser Leu
        290                 295                 300 acc agg tcc ggg tcg cat gaa agt aac acc aag ttg tgg gca cta gcg    4072
Thr Arg Ser Gly Ser His Glu Ser Asn Thr Lys Leu Trp Ala Leu Ala
    305                 310                 315 gcg cgt ata att tgc tcc cgc agt acc tct cgc gga tac gac gcg aca    4120
Ala Arg Ile Ile Cys Ser Arg Ser Thr Ser Arg Gly Tyr Asp Ala Thr
320                 325                 330 agc att gaa cag cga ttc caa caa ctt ggc tgc gaa gca cct cga ctc    4168
Ser Ile Glu Gln Arg Phe Gln Gln Leu Gly Cys Glu Ala Pro Arg Leu
335                 340                 345                 350 gat aac cca gtg gtc cgt agt tgg tgg ata gaa tcc gtc aaa gcg acc    4216
Asp Asn Pro Val Val Arg Ser Trp Trp Ile Glu Ser Val Lys Ala Thr
            355                 360                 365
```

-continued

| | |
|---|---|
| ttt ttc tct cag ttc cag cgc cgt gag cgg tcg aaa ggt ata aaa att<br>Phe Phe Ser Gln Phe Gln Arg Arg Glu Arg Ser Lys Gly Ile Lys Ile<br>370                        375                       380 | 4264 |
| ctc ctg aac tgt ggc gta cca taagagagga tcgtttttac gagcgacatt<br>Leu Leu Asn Cys Gly Val Pro<br>385 | 4315 |
| cataacctcc ccgtttatag gcaaagtgtc gaggtgaaac cagttagatt gagcgttatt | 4375 |
| acggccaaac acgaccgcgc agtccgcatc acgaacatac aaatccatcc ttatcaccgc | 4435 |
| agaccggtgg agtcattgaa ccatgccctt ggtgcacatt gaacagcgcg gattgtcgtg | 4495 |
| ctatgtcgct ggtttcgagg ccaacgtgga acccgacctg taccagtgta ttgtcgattg | 4555 |
| caaaccccac cttatgcgct atatagcact taaccatccg gaattttcg cacagctgag | 4615 |
| gccaatcgat gggcacaacc tttacagttc caccagtggg gattacatcg atctatggct | 4675 |
| tgagctactg aacgaggctg ctatgaagtc gggcttggat gaagagggtg gattagggag | 4735 |
| ctgttgagca acatttttcg cttggaagaa agggaagaga aataaacaaa caactttagt | 4795 |
| ttacatcatc aagtgtttta ttttttctaaa actgccctcg atttctccac caaaccctcc | 4855 |
| ataaattgca gctcatcggg gaagcatttg ccgaccaggt ccagcagttg cttcgcgctt | 4915 |
| agatagcgca catcgatgtt taaacagtag ccaaagtagt actccaaatc tcgactctcg | 4975 |
| tacatcactt ctgtaccgtc gcacaccact cgcatggaga tggaccgcag gtccatgtcg | 5035 |
| taatgtaaaa ctagaagaaa cttttccggt gccaatgagg taacttctcc gtactcgagc | 5095 |
| agctcttggg gcagctcgaa ggggatcatt ttcggtaaac cgtgcggcgt gatgaggacc | 5155 |
| gtattttcgt gccactccca ctcggcgggc gacattaggg ccaaatcgtg gcccgctgcc | 5215 |
| gttacgttgc caaagctgct atttatgttg taggcttcgt actgtacgaa gccccgcacc | 5275 |
| gccaactggt ggtccacgta taaaaatctc gtcaacgggt ggcgcaggta ccgaaagatg | 5335 |
| gttcgacgat tttcagctcc aacgtgcaca aatgtacccg aaaagctgta catgtttgcg | 5395 |
| gtgaagttca gctactcttt aaaatatcgt actataaatc gattcacgct caccaatcgt | 5455 |
| agcagtattc acacaatgtt gtactctgta gaagttcgcg tatttagtac ggagattccg | 5515 |
| tcgcagtcgc tgcaccactc ccaccatatc gccataccgt tcgataaaga tagatggacc | 5575 |
| gtcgatggca ttttaccgaa cgatataccg ctcgaccaca cgatacggtt gtgtgttacc | 5635 |
| gtcagggggta gtaaaaaatt ttcctgcgta tggcgagaga ccacctacaa gtgcggaaat | 5695 |
| gtgtacgatc caccactaga gtaccagttg gagaagctgc cgggcgtgca gtatagcgat | 5755 |
| ctagcgttaa ggataatcga gaagtttgag cgcgctatga agtacacgat agaagtcgat | 5815 |
| ttcactgcaa ataaatctca aagtttggaa ttataaacca cccgtctttc attgttaacc | 5875 |
| cgcccgcaac ccaacgatgt tacaagtttc cctagtagga ccccacttca cactcgtgct | 5935 |
| cgccagtggc gatttgcggt gccagtttct attaccaccg tgggccgcac tggacaacag | 5995 |
| tttgatgctc gtcgtgcagt gggatcagcg caactatacc ctcaactggg cgggcgaaat | 6055 |
| attttacggt ggaattgcag cacgaccggt gacaccgcac atgctcaagt ggtgctacca | 6115 |
| cctcgcggtc caccctgagc ccaactttac cgtggaagaa aaacaacctg gctgtgattt | 6175 |
| acgacaccct ttataataaa aaaaaaatcg cttcaaacag ggacaataaa acccacaagt | 6235 |
| gtatagagtt ttttttttat tttatttttcc caagtatatt ggaactggaa agaaataata | 6295 |
| acaacaataa taacaataat aatatcaata aaaaaggtat tcgatttatg actgtgcgcg | 6355 |
| cgcgcacaac agggccggct tcttgtttac aaactcaact tcctgattct cgaccgtagc | 6415 |

-continued

```
gcccgggagc tcatgcttgt gcactggtaa cctgcacggg atagaggaac gtttccaccc   6475
tatcgagcaa caccccactt tcaccgacca actcactcaa ccatggccga tttggacaca   6535
cagctggggg actttgtcga cccgggccaa catttcgtcg ggctccaggt cgtgcggtat   6595
cgtagaatct cgaacacggc gccaagctt                                      6624

<210> SEQ ID NO 29
<211> LENGTH: 108
<212> TYPE: PRT
<213> ORGANISM: mosquito baculovirus

<400> SEQUENCE: 29

Met Asn Ala Asp Cys Phe Cys Pro Pro Gly Pro Cys Tyr His Ala Leu
 1               5                  10                  15

Phe Ser His Cys Gly Gly Ile Cys Gln Ser Cys Gly Thr His Tyr Glu
            20                  25                  30

Asp Leu Asp Glu Phe Val Arg Cys Met Arg Gly Gln Thr Thr His Lys
        35                  40                  45

Pro Asn Pro Ile Ala Ile Thr Met Gly Leu Cys Glu Tyr Cys Pro Arg
    50                  55                  60

Arg His Pro Val Gly Val Ser Cys Gln Gly Tyr Pro Ala Cys Glu Lys
65                  70                  75                  80

Cys Ser Leu Ser His Ala Pro Leu Pro Gln Cys Pro His Arg Leu Ser
                85                  90                  95

Leu Tyr Phe Phe Leu Phe Lys Lys Asn Asn Lys Lys
            100                 105

<210> SEQ ID NO 30
<211> LENGTH: 63
<212> TYPE: PRT
<213> ORGANISM: mosquito baculovirus

<400> SEQUENCE: 30

Met Ala Thr Phe Met Tyr Glu Asn Leu Ser Ser Leu Glu Leu Asp Ser
 1               5                  10                  15

Ser Asp Arg Ser Ser Phe Ser Leu Pro Lys Val Val Phe Met Gly Pro
            20                  25                  30

Ser Phe Cys Ser Ser Ser Ser Thr Leu Ala Val Ser Leu Val Arg Ser
        35                  40                  45

Thr Pro Glu Pro Ser Ser His Leu His Ser Gly Gly Trp Ala Gly
    50                  55                  60

<210> SEQ ID NO 31
<211> LENGTH: 115
<212> TYPE: PRT
<213> ORGANISM: mosquito baculovirus

<400> SEQUENCE: 31

Met Arg Cys Ser Val Ser Leu Asn Cys Cys Ser Val Ala Val Thr Arg
 1               5                  10                  15

Ser Phe Asn Gly Asp Arg Ser Gly Lys Trp Ser Ser Pro His Ser Arg
            20                  25                  30

Leu Ala Pro Leu Thr Val Lys Ile Val Ile Ala Val Ile Ile Val Asn
        35                  40                  45

Ile Val Ser Ile Lys Ile Lys Asn Ile Thr Arg Gly Asp Asp Ile Val
    50                  55                  60

Arg Leu Met Ala Gly Asn Arg Cys Thr Val Arg Pro Thr Ala Ala Asp
65                  70                  75                  80
```

```
Arg Asn Pro Pro Gly Cys Pro Arg Val Thr Gly Arg Gln Arg Ser Pro
                85                  90                  95

Pro Pro Gly Pro Phe Val Thr Pro Asn Thr Leu Arg Thr His Arg His
            100                 105                 110

Pro Tyr Asn
        115

<210> SEQ ID NO 32
<211> LENGTH: 103
<212> TYPE: PRT
<213> ORGANISM: mosquito baculovirus

<400> SEQUENCE: 32

Met Val Leu Lys Ser Phe Lys Ser Thr Ser Lys Phe Val His Ser Leu
 1               5                  10                  15

Thr Arg Ser Gly Ser His Glu Ser Asn Thr Lys Leu Trp Ala Leu Ala
            20                  25                  30

Ala Arg Ile Ile Cys Ser Arg Ser Thr Ser Arg Gly Tyr Asp Ala Thr
            35                  40                  45

Ser Ile Glu Gln Arg Phe Gln Gln Leu Gly Cys Glu Ala Pro Arg Leu
 50                  55                  60

Asp Asn Pro Val Val Arg Ser Trp Trp Ile Glu Ser Val Lys Ala Thr
65                  70                  75                  80

Phe Phe Ser Gln Phe Gln Arg Arg Glu Arg Ser Lys Gly Ile Lys Ile
            85                  90                  95

Leu Leu Asn Cys Gly Val Pro
            100

<210> SEQ ID NO 33
<211> LENGTH: 6624
<212> TYPE: DNA
<213> ORGANISM: mosquito baculovirus
<220> FEATURE:
<221> NAME/KEY: CDS
<222> LOCATION: (2202)...(2555)
<221> NAME/KEY: CDS
<222> LOCATION: (4084)...(4251)

<400> SEQUENCE: 33
aagcttggcg ccgtgttcga gattctacga taccgcacga cctggagccc gacgaaatgt      60
tggcccgggt cgacaaagtc ccccagctgt gtgtccaaat cggccatggt tgagtgagtt    120
ggtcggtgaa agtggggtgt tgctcgatag ggtggaaacg ttcctctatc ccgtgcaggt    180
taccagtgca caagcatgag ctcccgggcg ctacggtcga gaatcaggaa gttgagtttg    240
taaacaagaa gccggccctg ttgtgcgcgc gcgcacagtc ataaatcgaa tacctttttt    300
attgatatta ttattgttat tattgttgtt attatttctt tccagttcca atatacttgg    360
gaaaataaaa taaaaaaaaa actctataca cttgtgggtt ttattgtccc tgtttgaagc    420
gatttttttt ttattataaa gggtgtcgta atcacagcc aggttgtttt tcttccacgg     480 taaagtttggg ctcagggtgg accgcgaggt ggtagcacca cttgagcatg tgcggtgtca    540
ccggtcgtgc tgcaattcca ccgtaaaata tttcgcccgc ccagttgagg gtatagttgc    600
gctgatccca ctgcacgacg agcatcaaac tgttgtccag tgcggcccac ggtggtaata    660
gaaactggca ccgcaaatcg ccactggcga gcacgagtgt gaagtggggt cctactaggg    720
aaacttgtaa catcgttggg ttgcggcgg gttaacaatg aaagacgggt ggtttataat     780
tccaaacttt gagatttatt tgcagtgaaa tcgacttcta tcgtgtactt catagcgcgc    840
```

```
tcaaacttct cgattatcct taacgctaga tcgctatact gcacgcccgg cagcttctcc    900
aactggtact ctagtggtgg atcgtacaca tttccgcact tgtaggtggt ctctcgccat    960
acgcaggaaa attttttact accoctgacg gtaacacaca accgtatcgt gtggtcgagc   1020
ggtatatcgt tcggtaaaat gccatcgacg gtccatctat ctttatcgaa cggtatggcg   1080
atatggtggg agtggtgcag cgactgcgac ggaatctccg tactaaatac gcgaacttct   1140
acagagtaca acattgtgtg aatactgcta cgattggtga gcgtgaatcg atttatagta   1200
cgatatttta aagagtagct gaacttcacc gcaaacatgt acagcttttc gggtacattt   1260
gtgcacgttg gagctgaaaa tcgtcgaacc atctttcggt acctgcgcca cccgttgacg   1320 agattttat acgtggacca ccagttggcg gtgcggggct tcgtacagta cgaagcctac   1380
aacataaata gcagctttgg caacgtaacg gcagcgggcc acgatttggc cctaatgtcg   1440
cccgccgagt gggagtggca cgaaaatacg gtcctcatca cgccgcacgg tttaccgaaa   1500
atgatcccct tcgagctgcc ccaagagctg ctcgagtacg gagaagttac ctcattggca   1560
ccggaaaagt ttcttctagt tttacattac gacatggacc tgcggtccat ctccatgcga   1620
gtggtgtgcg acggtacaga agtgatgtac gagagtcgag atttggagta ctactttggc   1680
tactgtttaa acatcgatgt gcgctatcta agcgcgaagc aactgctgga cctggtcggc   1740
aaatgcttcc ccgatgagct gcaatttatg gagggtttgg tggagaaatc gagggcagtt   1800
ttagaaaaat aaaacacttg atgatgtaaa ctaaagttgt ttgtttattt ctcttcccct   1860
tcttccaagc gaaaatgttt gctcaacagc tccctaatcc acccctcttca tccaagcccg   1920 acttcatagc agcctcgttc agtagctcaa gccatagatc gatgtaatcc ccactggtgg   1980
aactgtaaag gttgtgccca tcgattggcc tcagctgtgc gaaaaattcc ggatggttaa   2040
gtgctatata gcgcataagg tggggttgc aatcgacaat acactggtac aggtcgggtt    2100
ccacgttggc ctcgaaacca gcgacatagc acgacaatcc gcgctgttca atgtgcacca   2160
agggcatggt tcaatgactc caccggtctg cggtgataag g atg gat ttg tat gtt   2216
                                              Met Asp Leu Tyr Val
                                                1               5 cgt gat gcg gac tgc gcg gtc gtg ttt ggc cgt aat aac gct caa tct      2264
Arg Asp Ala Asp Cys Ala Val Val Phe Gly Arg Asn Asn Ala Gln Ser
             10                  15                  20 aac tgg ttt cac ctc gac act ttg cct ata aac ggg gag gtt atg aat      2312
Asn Trp Phe His Leu Asp Thr Leu Pro Ile Asn Gly Glu Val Met Asn
         25                  30                  35 gtc gct cgt aaa aac gat cct ctc tta tgg tac gcc aca gtt cag gag      2360
Val Ala Arg Lys Asn Asp Pro Leu Leu Trp Tyr Ala Thr Val Gln Glu
     40                  45                  50 aat ttt tat acc ttt cga ccg ctc acg gcg ctg gaa ctg aga gaa aaa      2408
Asn Phe Tyr Thr Phe Arg Pro Leu Thr Ala Leu Glu Leu Arg Glu Lys
 55                  60                  65 ggt cgc ttt gac gga ttc tat cca cca act acg gac cac tgg gtt atc      2456
Gly Arg Phe Asp Gly Phe Tyr Pro Pro Thr Thr Asp His Trp Val Ile
             70                  75                  80              85 gag tcg agg tgc ttc gca gcc aag ttg ttg gaa tcg ctg ttc aat gct      2504
Glu Ser Arg Cys Phe Ala Ala Lys Leu Leu Glu Ser Leu Phe Asn Ala
                 90                  95                 100 tgt cgc gtc gta tcc gcg aga ggt act gcg gga gca aat tat acg cgc     2552
Cys Arg Val Val Ser Ala Arg Gly Thr Ala Gly Ala Asn Tyr Thr Arg
            105                 110                 115 cgc tagtgcccac aacttggtgt tactttcatg cgacccggac ctggttaacg           2605
Arg
```

```
agtgcacaaa tttgctggta gatttgaaac tttttagcac catagttgac gcccgacgcc    2665
tgcacgaaac ttggatggta ttggtgaata acgttagcca atgttggtac cactatactg    2725
gagactttgg cactgcaatt cgtcagctca accatgttac ggtcaacggt ccggtggtgc    2785
tattgctcga tattaaaaat caacgcgatc ttgcaaagat tctgctggaa cattattggg    2845
aggctcgtat ggtggtactg caccgaactg gacaggcttg caacttgggt cactgtgtga    2905
acgtcgacct aaagagcggc cagtgtgtac gattcggcgg tggtctatct gtgataaacg    2965
caccacaccg cgctaatgtt gtgatgaaaa atgtgatcaa atataataat acctgttaga    3025
gttagaaaat ttttatttta tttcaaccaa aacccaaccc ctttagcacc gcaaatgtgg    3085
gccccacaaa agtggacccg tcttggttgg gctaactttt ccatatggag cccaacattt    3145
ggcggcccca caaagtgga cccgttaaag tcgtgctaac aaatgaacat ttttcattta    3205
atggagccgc agtcggggtt gaacttgtga tgttgggggg aataaaaact tcaatgagtc    3265
attgttaata aaacttttta tttcaatcat ttttaaaata ttcatccaag tcaatacgac    3325
gcgaaagccg accgcccttc aagtggtaac tgaggggtgc acggcagagt ctagctggcg    3385
attgaaacag gcccgcatct atgggcggcc aaaagagtct ccacacgtcg gtgacggtgc    3445
tcaccacgtc ccggttgttg cgtataatcg atgtcatttc gttcatatag gtttcgttgc    3505
agcagagagc gcgcacaaag cactcggcaa acgaaatcgg ttccgtggga ttgggtgggg    3565
tgtcgatgat gcgcatcttg ggcttgcaat cgattccgca gcagtcggcg tcgcaaaaca    3625
acctgcactc ggtggtccgc accagctcgt gtagttcctc ctcacctttg ggtagctgca    3685
tggcggcgag gtagaatccg cgcaattcgg cgctcgagtc caccgggaag ttggccgggt    3745
tgagccaaat gtggatgccg tcgttgcccg tgtggtaaac tttaatgttt tcggtaccga    3805
agaagaacat tgaggtgacc acggacacgt tgagcacaaa gttggccaac tcggggtcgt    3865
cagttttcaa atcgatatca atcacccact ctcggcagcc ccggttcccg cgggtgtgca    3925
gcccacaaat gccatagctc gaccggatcg ggtcggtgtt gtagtgtacg gtctcgatga    3985
attcactcat tgtgtcgaat tcttccggtg gcaaccacac cttgtcgctt agctgaaggg    4045
cccatttgcg ctcctcgggc ttctcgaaag tgttccaa atg tct tta agt tgg gat    4101
                                            Met Ser Leu Ser Trp Asp
                                                          120 tcc tgt gga aat aga aag gga aga aat gtt gta cgg ttt agt ggt gct    4149
Ser Cys Gly Asn Arg Lys Gly Arg Asn Val Val Arg Phe Ser Gly Ala
125                 130                 135                 140 cat act ggt gct cgt aat gat tca gtt gat ttt aac ttc ggg tgc aaa    4197
His Thr Gly Ala Arg Asn Asp Ser Val Asp Phe Asn Phe Gly Cys Lys
                145                 150                 155 att tct agc caa aca cgc cca aga gtc gcg gga acg ggc cgc acg agc    4245
Ile Ser Ser Gln Thr Arg Pro Arg Val Ala Gly Thr Gly Arg Thr Ser
            160                 165                 170 tcg ggg tgaatcggtg ctgccagaga ttcatttcgc cggctctcag cacgtagatt    4301
Ser Gly gccacaacac caaattaccg tgtattgata atgcggactg tcaacgtaac tgcgctttga    4361
ccagagacgg aggagtttca tcgtgcatag gcgggttctg cagcacggat cataaatcta    4421
ttcccgagaa gcgaaattgt gtcgaagagc atggaatttt acgggtattc actgcagacg    4481
aattcgttat aaatcaatcc tgcctttcaa cctatcgcga cattttcacc gacgataaca    4541
aactgcaacc gtatgtgtgt accggcgtc aattggagat aaacttgctc gagcaagcgt    4601
tcactccgga cgcttgtgtg tgcgggactg gtacaacgaa atacatttac cgcccgggc    4661
```

```
cgtataatcg ccccattccg gtgtgcttga ccaagcagca agctgcgctg ctaggacgag      4721
tttacgagcg ggcgtaaaat gtgtcgagtc tcggttgata ttgtggtgcg gaacctgcgc      4781
aaacggcgct tctaccggcg gaattttgtg ctaccagagg ggcacagcga gatcagttat      4841
atgggtgcct gtgagtacgg agtgtatttg gtgtcacgaa cgggccgggc ggtggtgacc      4901
gttgacggcc ggttactcga ggacaccctg gagggtttcg gtccgctgcg gttggtctca      4961
cggtgcacct gttccccgcc ataagcctca cgatgtcgtc accccttgta atatttttaa      5021
tttttatact gacaatgtta acgataatga ccgcgatcac aatcttcacc gtcaagggtg      5081
ccaagcgtga atgtggggac gaccatttgc cggacctgtc cccattgaag gagcgcgtta      5141
ccgccacgga gcaacagttg agcgacacgg agcagcgcat tgacgaggtc gaacggtcgg      5201
gtgtggaaaa ttttagcgca atcggcgaaa cattggagaa tatatcgggc gagctggtgg      5261
agctgcaaaa ctcgacctcg tcaaagtttt acgaaattgg caacgagctg gtgaacctgg      5321
atctgcgcgt ccagtcgcta gagtgagtgc cgaaattcag taccagtggt ttgacggtag      5381
ctgcaagtaa gagccaacga tgccccaaac tttactattt ctaattctac tactactggt      5441
cacaatggtg gccgtgctca tcatgcgcta cccagcccaa cctcccgagt gcaagtgcga      5501
ggagggctcg ggggtggacc tcaccaaact cacggctaga gtggacgagc tcgagcaaaa      5561
gcttggcccc atgaacacca ccttgggcaa actgaacgac gacctgtcgg agctgtccag      5621
ctccagtgat gataaatttt catacataaa cgtcgccatc aatgagctgg ccgacagtat      5681
caaaacgatg gaccaacgct tgaaggtgct ggagggagag tgatatattt actgctgcaa      5741
taaaacgagg tgtataaatt ttatcatttt ttattatttt tcttgaaaag aaagaaatat      5801
aggcttaatc ggtggggaca ttgggggagt ggggcgtgcg acagggaaca tttttcgcac      5861
gctggatagc cttggcagga cacgccgacc gggtgccttc tcggacagta ttcgcagagc      5921
cccattgtta tggcgatggg gttcggtttg tgggtggtct ggcccctcat acagcgcacg      5981
aactcgtcta ggtcttcgta gtgggttcca caggactggc agataccctcc gcagtggctg     6041 aagagtgcat ggtagcaggg tccgggtggg cagaaacagt cagcgttcat cgtggacgtc      6101
gatcatgaag cggacaagtg gtcgaaatga tcgcgcgtcc atcgttatat aggtggtgtt      6161
gtggcgccag taggtgctag gtacgcgctt cagttccgac cgagttggtt gtcgtgcact      6221 attacccccaa cacttgtacg ttttgtccag gtacgttagc cacggctgtt ggcaatagac      6281
tcgtgtgccg aaataaatta aaatgtaatg gttagcgtcg agcaccgctt gtggtaattc      6341
aatttcacaa aaccagttcc gctgcgcgac cccacgctcg atccatgccc ggtaaaccac      6401
ccgatgactg taacgattgc gcacactaag cccaagataa ataccctccg tttcggcgtc      6461
cacagcgcgg tctaacgctt ccagtctctg ttcgcagtga acctcattaa actcgcgata      6521
caagtcgcgc acgaatttag ttagccgctt tcgattcatg ctgctaggtt ccagccgagc      6581
cccgaaacca accttta tat accccgttat catgagagaa ttc                      6624
```

<210> SEQ ID NO 34
<211> LENGTH: 118
<212> TYPE: PRT
<213> ORGANISM: mosquito baculovirus

<400> SEQUENCE: 34

```
Met Asp Leu Tyr Val Arg Asp Ala Asp Cys Ala Val Val Phe Gly Arg
 1               5                  10                  15

Asn Asn Ala Gln Ser Asn Trp Phe His Leu Asp Thr Leu Pro Ile Asn
```

-continued

```
            20                  25                  30

Gly Glu Val Met Asn Val Ala Arg Lys Asn Asp Pro Leu Leu Trp Tyr
        35                  40                  45

Ala Thr Val Gln Glu Asn Phe Tyr Thr Phe Arg Pro Leu Thr Ala Leu
    50                  55                  60

Glu Leu Arg Glu Lys Gly Arg Phe Asp Gly Phe Tyr Pro Pro Thr Thr
65                  70                  75                  80

Asp His Trp Val Ile Glu Ser Arg Cys Phe Ala Ala Lys Leu Leu Glu
            85                  90                  95

Ser Leu Phe Asn Ala Cys Arg Val Val Ser Ala Arg Gly Thr Ala Gly
            100                 105                 110

Ala Asn Tyr Thr Arg Arg
        115

<210> SEQ ID NO 35
<211> LENGTH: 56
<212> TYPE: PRT
<213> ORGANISM: mosquito baculovirus

<400> SEQUENCE: 35

Met Ser Leu Ser Trp Asp Ser Cys Gly Asn Arg Lys Gly Arg Asn Val
 1               5                  10                  15

Val Arg Phe Ser Gly Ala His Thr Gly Ala Arg Asn Asp Ser Val Asp
            20                  25                  30

Phe Asn Phe Gly Cys Lys Ile Ser Ser Gln Thr Arg Pro Arg Val Ala
        35                  40                  45

Gly Thr Gly Arg Thr Ser Ser Gly
    50                  55

<210> SEQ ID NO 36
<211> LENGTH: 6624
<212> TYPE: DNA
<213> ORGANISM: mosquito baculovirus
<220> FEATURE:
<221> NAME/KEY: CDS
<222> LOCATION: (2033)...(2218)

<400> SEQUENCE: 36
gaattctctc atgataacgg ggtatataaa ggttggtttc ggggctcggc tggaacctag     60
cagcatgaat cgaaagcggc taactaaatt cgtgcgcgac ttgtatcgcg agtttaatga    120
ggttcactgc gaacagagac tggaagcgtt agaccgcgct gtggacgccg aaacggaggg    180
tatttatctt gggcttagtg tgcgcaatcg ttacagtcat cgggtggttt accgggcatg    240
gatcgagcgt ggggtcgcgc agcggaactg gttttgtgaa attgaattac cacaagcggt    300
gctcgacgct aaccattaca ttttaattta tttcggcaca cgagtctatt gccaacagcc    360
gtggctaacg tacctggaca aaacgtacaa gtgttggggt aatagtgcac gacaaccaac    420
tcggtcggaa ctgaagcgcg tacctagcac ctactggcgc cacaacacca cctatataac    480
gatggacgcg cgatcatttc gaccacttgt ccgcttcatg atcgacgtcc acgatgaacg    540
ctgactgttt ctgcccaccc ggaccctgct accatgcact cttcagccac tgcggaggta    600
tctgccagtc ctgtggaacc cactacgaag acctagacga gttcgtgcgc tgtatgaggg    660
gccagaccac ccacaaaccg aaccccatcg ccataacaat ggggctctgc gaatactgtc    720
cgagaaggca cccggtcggc gtgtcctgcc aaggctatcc agcgtgcgaa aaatgttccc    780
tgtcgcacgc cccactcccc caatgtcccc accgattaag cctatatttc tttcttttca    840
```

-continued

| | |
|---|---|
| agaaaaataa taaaaaatga taaaatttat acacctcgtt ttattgcagc agtaaatata | 900 |
| tcactctccc tccagcacct tcaagcgttg gtccatcgtt ttgatactgt cggccagctc | 960 |
| attgatggcg acgtttatgt atgaaaattt atcatcactg gagctggaca gctccgacag | 1020 |
| gtcgtcgttc agtttgccca aggtggtgtt catggggcca agcttttgct cgagctcgtc | 1080 |
| cactctagcc gtgagtttgg tgaggtccac ccccgagccc tcctcgcact tgcactcggg | 1140 |
| aggttgggct gggtagcgca tgatgagcac ggccaccatt gtgaccagta gtagtagaat | 1200 |
| tagaaatagt aaagtttggg gcatcgttgg ctcttacttg cagctaccgt caaaccactg | 1260 |
| gtactgaatt tcggcactca ctctagcgac tggacgcgca gatccaggtt caccagctcg | 1320 |
| ttgccaattt cgtaaaactt tgacgaggtc gagttttgca gctccaccag ctcgcccgat | 1380 |
| atattctcca atgtttcgcc gattgcgcta aaattttcca cacccgaccg ttcgacctcg | 1440 |
| tcaatgcgct gctccgtgtc gctcaactgt tgctccgtgg cggtaacgcg ctccttcaat | 1500 |
| ggggacaggt ccggcaaatg gtcgtcccca cattcacgct tggcaccctt gacggtgaag | 1560 |
| attgtgatcg cggtcattat cgttaacatt gtcagtataa aaattaaaaa tattacaagg | 1620 |
| ggtgacgaca tcgtgaggct tatggcgggg aacaggtgca ccgtgagacc aaccgcagcg | 1680 |
| gaccgaaacc ctccagggtg tcctcgagta accggccgtc aacggtcacc accgcccggc | 1740 |
| ccgttcgtga caccaaatac actccgtact cacaggcacc catataactg atctcgctgt | 1800 |
| gcccctctgg tagcacaaaa ttccgccggt agaagcgccg tttgcgcagg ttccgcacca | 1860 |
| caatatcaac cgagactcga cacattttac gcccgctcgt aaactcgtcc tagcagcgca | 1920 |
| gcttgctgct tggtcaagca caccggaatg gggcgattat acggccccgg gcggtaaatg | 1980 |
| tatttcgttg taccagtccc gcacacacaa gcgtccggag tgaacgcttg ct cga gca | 2038 |
|                                                                                                                                                                                                                                                                                                                                                                                              Arg Ala | |
|                                                                                                                                                                                                                                                                                                                                                                                                  1 | |
| agt tta tct cca att gac cgc cgg tac aca cat acg gtt gca gtt tgt | 2086 |
| Ser Leu Ser Pro Ile Asp Arg Arg Tyr Thr His Thr Val Ala Val Cys | |
|             5                      10                       15 | |
| tat cgt cgg tga aaa tgt cgc gat agg ttg aaa ggc agg att gat tta | 2134 |
| Tyr Arg Arg * Lys Cys Arg Asp Arg Leu Lys Gly Arg Ile Asp Leu | |
|  20                         25                       30 | |
| taa cga att cgt ctg cag tga ata ccc gta aaa ttc cat gct ctt cga | 2182 |
| * Arg Ile Arg Leu Gln * Ile Pro Val Lys Phe His Ala Leu Arg | |
|      35                          40                     45 | |
| cac aat ttc gct tct cgg gaa tag att tat gat ccg tgctgcagaa | 2228 |
| His Asn Phe Ala Ser Arg Glu * Ile Tyr Asp Pro | |
|      50                          55 | |
| cccgcctatg cacgatgaaa ctcctccgtc tctggtcaaa gcgcagttac gttgacagtc | 2288 |
| cgcattatca atacacggta atttggtgtt gtggcaatct acgtgctgag agccggcgaa | 2348 |
| atgaatctct ggcagcaccg attcaccccg agctcgtgcg gcccgttccc gcgactcttg | 2408 |
| ggcgtgtttg gctagaaatt ttgcacccga gttaaaatc aactgaatca ttacgagcac | 2468 |
| cagtatgagc accactaaac cgtacaacat ttcttcccctt tctatttcca caggaatccc | 2528 |
| aacttaaaga catttggaac actttcgaga agcccgagga gcgcaaatgg gcccttcagc | 2588 |
| taagcgacaa ggtgtggttg ccaccggaag aattcgacac aatgagtgaa ttcatcgaga | 2648 |
| ccgtacacta caacaccgac ccgatccggt cgagctatgg catttgtggg ctgcacaccc | 2708 |
| gcgggaaccg gggctgccga gagtgggtga ttgatatcga tttgaaaact gacgaccccg | 2768 |
| agttggccaa ctttgtgctc aacgtgtccg tggtcacctc aatgttcttc ttcggtaccg | 2828 |
| aaaacattaa agtttaccac acgggcaacg acggcatcca catttggctc aacccggcca | 2888 |

-continued

```
acttcccggt ggactcgagc gccgaattgc gcggattcta cctcgccgcc atgcagctac    2948
ccaaaggtga ggaggaacta cacgagctgg tgcggaccac cgagtgcagg ttgttttgcg    3008
acgccgactg ctgcggaatc gattgcaagc ccaagatgcg catcatcgac accccaccca    3068
atcccacgga accgatttcg tttgccgagt gctttgtgcg cgctctctgc tgcaacgaaa    3128
cctatatgaa cgaaatgaca tcgattatac gcaacaaccg ggacgtggtg agcaccgtca    3188
ccgacgtgtg gagactcttt tggccgccca tagatgcggg cctgtttcaa tcgccagcta    3248
gactctgccg tgcacccctc agttaccact tgaagggcg tcggctttcg cgtcgtattg     3308
acttggatga atattttaaa aatgattgaa ataaaagtt ttattaacaa tgactcattg     3368
aagtttttat tcccccaac atcacaagtt caaccccgac tgcggctcca ttaaatgaaa     3428
aatgttcatt tgttagcacg actttaacgg gtccactttt gtggggccgc caaatgttgg    3488
gctccatatg gaaaagttag cccaaccaag acgggtccac ttttgtgggg cccacatttg    3548
cggtgctaaa ggggttgggt tttggttgaa ataaaataaa aattttctaa ctctaacagg    3608
tattattata tttgatcaca ttttttcatca caacattagc gcggtgtggt gcgtttatca    3668
cagatagacc accgccgaat cgtacacact ggccgctctt taggtcgacg ttcacacagt    3728
gacccaagtt gcaagcctgt ccagttcggt gcagtaccac catacgagcc tcccaataat    3788
gttccagcag aatctttgca agatcgcgtt gattttttaat atcgagcaat agcaccaccg    3848
gaccgttgac cgtaacatgg ttgagctgac gaattgcagt gccaaagtct ccagtatagt    3908
ggtaccaaca ttggctaacg ttattcacca ataccatcca agtttcgtgc aggcgtcggg    3968
cgtcaactat ggtgctaaaa agtttcaaat ctaccagcaa atttgtgcac tcgttaacca    4028
ggtccgggtc gcatgaaagt aacaccaagt tgtgggcact agcggcgcgt ataatttgct    4088
cccgcagtac ctctcgcgga tacgacgcga caagcattga acagcgattc caacaacttg    4148
gctgcgaagc acctcgactc gataacccag tggtccgtag ttggtggata gaatccgtca    4208
aagcgacctt tttctctcag ttccagcgcc gtgagcggtc gaaaggtata aaaattctcc    4268
tgaactgtgg cgtaccataa gagaggatcg tttttacgag cgacattcat aacctccccg    4328
tttataggca aagtgtcgag gtgaaaccag ttagattgag cgttattacg gccaaacacg    4388
accgcgcagt ccgcatcacg aacatacaaa tccatcctta tcaccgcaga ccggtggagt    4448
cattgaacca tgcccttggt gcacattgaa cagcgcggat tgtcgtgcta tgtcgctggt    4508
ttcgaggcca acgtggaacc cgacctgtac cagtgtattg tcgattgcaa accccacctt    4568
atgcgctata tagcacttaa ccatccggaa ttttcgcac agctgaggcc aatcgatggg     4628
cacaaccttt acagttccac cagtggggat tacatcgatc tatggcttga gctactgaac    4688
gaggctgcta tgaagtcggg cttggatgaa gagggtggat tagggagctg ttgagcaaac    4748
attttcgctt ggaagaaagg gaagagaaat aaacaaacaa ctttagttta catcatcaag    4808
tgttttattt ttctaaaact gccctcgatt tctccaccaa accctccata aattgcagct    4868
catcggggaa gcatttgccg accaggtcca gcagttgctt cgcgcttaga tagcgcacat    4928
cgatgtttaa acagtagcca aagtagtact ccaaatctcg actctcgtac atcacttctg    4988
taccgtcgca caccactcgc atggagatgg accgcaggtc catgtcgtaa tgtaaaacta    5048
gaagaaactt ttccggtgcc aatgaggtaa cttctccgta ctcgagcagc tcttggggca    5108
gctcgaaggg gatcatttc ggtaaaccgt gcggcgtgat gaggaccgta ttttcgtgcc     5168
actcccactc ggcgggcgac attagggcca aatcgtggcc cgctgccgtt acgttgccaa    5228
```

-continued

```
agctgctatt tatgttgtag gcttcgtact gtacgaagcc ccgcaccgcc aactggtggt    5288
ccacgtataa aaatctcgtc aacgggtggc gcaggtaccg aaagatggtt cgacgatttt    5348
cagctccaac gtgcacaaat gtacccgaaa agctgtacat gtttgcggtg aagttcagct    5408
actctttaaa atatcgtact ataaatcgat tcacgctcac caatcgtagc agtattcaca    5468
caatgttgta ctctgtagaa gttcgcgtat ttagtacgga gattccgtcg cagtcgctgc    5528
accactccca ccatatcgcc ataccgttcg ataaagatag atggaccgtc gatggcattt    5588
taccgaacga tataccgctc gaccacacga tacggttgtg tgttaccgtc aggggtagta    5648
aaaaattttc ctgcgtatgg cgagagacca cctacaagtg cggaaatgtg tacgatccac    5708
cactagagta ccagttggag aagctgccgg gcgtgcagta tagcgatcta gcgttaagga    5768
taatcgagaa gtttgagcgc gctatgaagt acacgataga agtcgatttc actgcaaata    5828
aatctcaaag tttggaatta taaaccaccc gtctttcatt gttaacccgc cgcaaccca    5888 acgatgttac aagtttccct agtaggaccc cacttcacac tcgtgctcgc cagtggcgat    5948
ttgcggtgcc agtttctatt accaccgtgg gccgcactgg acaacagttt gatgctcgtc    6008
gtgcagtggg atcagcgcaa ctataccctc aactgggcgg gcgaaatatt ttacggtgga    6068
attgcagcac gaccggtgac accgcacatg ctcaagtggt gctaccacct cgcggtccac    6128
cctgagccca actttaccgt ggaagaaaaa caacctgggct gtgatttacg cacccttta    6188 taataaaaaa aaaatcgctt caaacaggga caataaaacc cacaagtgta tagagttttt    6248
tttttatttt attttcccaa gtatattgga actggaaaga aataataaca acaataataa    6308
caataataat atcaataaaa aaggtattcg atttatgact gtgcgcgcgc gcacaacagg    6368
gccggcttct tgtttacaaa ctcaacttcc tgattctcga ccgtagcgcc cgggagctca    6428
tgcttgtgca ctggtaacct gcacgggata gaggaacgtt tccaccctat cgagcaacac    6488
cccactttca ccgaccaact cactcaacca tggccgattt ggacacacag ctgggggact    6548
ttgtcgaccc gggccaacat ttcgtcgggc tccaggtcgt gcggtatcgt agaatctcga    6608
acacggcgcc aagctt                                                    6624
```

<210> SEQ ID NO 37
<211> LENGTH: 58
<212> TYPE: PRT
<213> ORGANISM: mosquito baculovirus

<400> SEQUENCE: 37

Arg Ala Ser Leu Ser Pro Ile Asp Arg Arg Tyr Thr His Thr Val Ala
1               5                   10                  15

Val Cys Tyr Arg Arg Lys Cys Arg Asp Arg Leu Lys Gly Arg Ile Asp
            20                  25                  30

Leu Arg Ile Arg Leu Gln Ile Pro Val Lys Phe His Ala Leu Arg His
        35                  40                  45

Asn Phe Ala Ser Arg Glu Ile Tyr Asp Pro
    50                  55

<210> SEQ ID NO 38
<211> LENGTH: 1300
<212> TYPE: DNA
<213> ORGANISM: mosquito baculovirus
<220> FEATURE:
<221> NAME/KEY: CDS
<222> LOCATION: (539)...(916)

<400> SEQUENCE: 38

```
actgcagctc cacgctgacg aagttaacct gctcggaaat cgaaccaccg cggttggggt      60
taattttgag cgtggtgacg gcaaaatcga agaatttctt cagctcactg tagtagaacg     120
cggccagctt catcttttcg ttcaaattga tctccgtact accaccgaca attttgttca     180
gctccaccac gtactcctcc aagtccaggt tgttgtacag gtcgagcttt actcgcgccc     240
ggcccaactg catcatcaca ctgcgaagcg cctcacgggc cagcgtcacc tcgccctgtt     300
tagactcctt tgtggcctcg accgctttct ggattttgta ctcgacgtca aaacatctag     360
acttgaactc gctgtccgag atggggctgc cgagcacatc gatcatggtg ctcaagtcgt     420
tcatatagcc cacaatttca cccaccagcg gaccgggcag ttcggccgac tttgtctcgc     480
gaatatttct caaattatcc aagcaaattt tcagctgacg gcgggccata ttgtagta      538
```

| | | | | | | | | | | | | | | | | |
|---|---|---|---|---|---|---|---|---|---|---|---|---|---|---|---|---|
| atg | cac | cac | ctc | gcg | ggc | cct | ctc | ggt | gca | gat | ttt | aat | gtg | cat | att | 586 |
| Met | His | His | Leu | Ala | Gly | Pro | Leu | Gly | Ala | Asp | Phe | Asn | Val | His | Ile | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| ttg | caa | ttt | gaa | aat | ttt | ctc | agc | caa | ctc | cat | cga | agg | ggt | ttc | gcg | 634 |
| Leu | Gln | Phe | Glu | Asn | Phe | Leu | Ser | Gln | Leu | His | Arg | Arg | Gly | Phe | Ala | |
| | | | 20 | | | | | 25 | | | | | 30 | | | |

| | | | | | | | | | | | | | | | | |
|---|---|---|---|---|---|---|---|---|---|---|---|---|---|---|---|---|
| gta | cga | cat | cag | cat | gct | gtc | cag | cat | gaa | ctt | gtt | ttg | ctg | ctc | cag | 682 |
| Val | Arg | His | Gln | His | Ala | Val | Gln | His | Glu | Leu | Val | Leu | Leu | Leu | Gln | |
| | | 35 | | | | | 40 | | | | | 45 | | | | |

| | | | | | | | | | | | | | | | | |
|---|---|---|---|---|---|---|---|---|---|---|---|---|---|---|---|---|
| ctg | aca | atc | gtc | gcc | cgt | ggc | aac | att | ttt | atc | gaa | gct | caa | gtc | ctt | 730 |
| Leu | Thr | Ile | Val | Ala | Arg | Gly | Asn | Ile | Phe | Ile | Glu | Ala | Gln | Val | Leu | |
| 50 | | | | | 55 | | | | | 60 | | | | | | |

| | | | | | | | | | | | | | | | | |
|---|---|---|---|---|---|---|---|---|---|---|---|---|---|---|---|---|
| ggt | gca | ctc | gtt | caa | ctt | gga | ccg | caa | agc | ctc | aat | ttc | acg | cgt | ggc | 778 |
| Gly | Ala | Leu | Val | Gln | Leu | Gly | Pro | Gln | Ser | Leu | Asn | Phe | Thr | Arg | Gly | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| cac | cgc | caa | atc | ctc | gcc | aac | gtt | ttg | cgc | atc | cga | ata | tac | acc | ctc | 826 |
| His | Arg | Gln | Ile | Leu | Ala | Asn | Val | Leu | Arg | Ile | Arg | Ile | Tyr | Thr | Leu | |
| | | | | 85 | | | | | 90 | | | | | 95 | | |

| | | | | | | | | | | | | | | | | |
|---|---|---|---|---|---|---|---|---|---|---|---|---|---|---|---|---|
| gag | att | ggc | aat | ttt | act | ctt | gag | ctg | cac | aat | gtt | cgc | ctc | gag | gtc | 874 |
| Glu | Ile | Gly | Asn | Phe | Thr | Leu | Glu | Leu | His | Asn | Val | Arg | Leu | Glu | Val | |
| | | | 100 | | | | | 105 | | | | | 110 | | | |

| | | | | | | | | | | | | | | |
|---|---|---|---|---|---|---|---|---|---|---|---|---|---|---|
| gga | aat | ttt | ctc | cat | ata | ccg | ctt | caa | gtt | gcc | gct | gtc | ggt | 916 |
| Gly | Asn | Phe | Leu | His | Ile | Pro | Leu | Gln | Val | Ala | Ala | Val | Gly | |
| | | 115 | | | | | 120 | | | | | 125 | | |

```
taacagcttc gaaatgccct ccctcacatc accccgaaaa ccgttctcct ccagctcaac     976
ttttatttcc ctctccaggt ttacggcgct atcgtacagc ttctccgacc gcttcaaacg    1036
gctgtactcg cgcgctcaact gtagcaaact ttgttccaaa ccgtcgacgg ttagcaaacc   1096 ctttttcctttt agaatatttt caacacgttc gatcaggtcg aggttggtca tcgcgatgtc  1156
gtactccaca gcctgcttgt tcttggcctc tcgacccaga attattttct cctgaaggtc    1216
tgttataaaa tcgtccacct cctggtccga catcgtgtcc ataaacaacg cagcatcgtt    1276
cgcgatttta cgcagcccct gcag                                            1300
```

<210> SEQ ID NO 39
<211> LENGTH: 126
<212> TYPE: PRT
<213> ORGANISM: mosquito baculovirus

<400> SEQUENCE: 39

| Met | His | His | Leu | Ala | Gly | Pro | Leu | Gly | Ala | Asp | Phe | Asn | Val | His | Ile |
|---|---|---|---|---|---|---|---|---|---|---|---|---|---|---|---|
| 1 | | | | 5 | | | | | 10 | | | | | 15 | |

| Leu | Gln | Phe | Glu | Asn | Phe | Leu | Ser | Gln | Leu | His | Arg | Arg | Gly | Phe | Ala |
|---|---|---|---|---|---|---|---|---|---|---|---|---|---|---|---|
| | | | 20 | | | | | 25 | | | | | 30 | | |

| Val | Arg | His | Gln | His | Ala | Val | Gln | His | Glu | Leu | Val | Leu | Leu | Leu | Gln |
|---|---|---|---|---|---|---|---|---|---|---|---|---|---|---|---|

```
                35                  40                  45
Leu Thr Ile Val Ala Arg Gly Asn Ile Phe Ile Glu Ala Gln Val Leu
    50                  55                  60
Gly Ala Leu Val Gln Leu Gly Pro Gln Ser Leu Asn Phe Thr Arg Gly
65                  70                  75                  80
His Arg Gln Ile Leu Ala Asn Val Leu Arg Ile Arg Ile Tyr Thr Leu
                85                  90                  95
Glu Ile Gly Asn Phe Thr Leu Glu Leu His Asn Val Arg Leu Glu Val
                100                 105                 110
Gly Asn Phe Leu His Ile Pro Leu Gln Val Ala Ala Val Gly
                115                 120                 125

<210> SEQ ID NO 40
<211> LENGTH: 1300
<212> TYPE: DNA
<213> ORGANISM: mosquito baculovirus
<220> FEATURE:
<221> NAME/KEY: CDS
<222> LOCATION: (858)...(1208)

<400> SEQUENCE: 40
actgcagctc cacgctgacg aagttaacct gctcggaaat cgaaccaccg cggttggggt    60
taattttgag cgtggtgacg gcaaaatcga agaatttctt cagctcactg tagtagaacg   120
cggccagctt catcttttcg ttcaaattga tctccgtact accaccgaca attttgttca   180
gctccaccac gtactcctcc aagtccaggt tgttgtacag gtcgagcttt actcgcgccc   240
ggcccaactg catcatcaca ctgcgaagcg cctcacgggc cagcgtcacc tcgccctgtt   300
tagactcctt tgtggcctcg accgctttct ggattttgta ctcgacgtca aacatctag    360 acttgaactc gctgtccgag atggggctgc cgagcacatc gatcatggtg ctcaagtcgt   420
tcatatagcc cacaatttca cccaccagcg gaccgggcag ttcggccgac tttgtctcgc   480
gaatatttct caaattatcc aagcaaattt tcagctgacg gcgggccata ttgtagtaat   540
gcaccacctc gcgggccctc tcggtgcaga ttttaatgtg catattttgc aatttgaaaa   600
ttttctcagc caactccatc gaaggggttt cgcggtacga catcagcatg ctgtccagca   660
tgaacttgtt tgctgctcc agctgacaat cgtcgcccgt ggcaacattt ttatcgaagc   720
tcaagtcctt ggtgcactcg ttcaacttgg accgcaaagc ctcaatttca cgcgtggcca   780
ccgccaaatc ctcgccaacg ttttgcgcat ccgaatatac ccctcgaga ttggcaattt    840 tactcttgag ctgcaca atg ttc gcc tcg agg tcg gaa att ttc tcc ata      890
                    Met Phe Ala Ser Arg Ser Glu Ile Phe Ser Ile
                      1               5                  10 tac cgc ttc aag ttg ccg ctg tcg gtt aac agc ttc gaa atg ccc tcc     938
Tyr Arg Phe Lys Leu Pro Leu Ser Val Asn Ser Phe Glu Met Pro Ser
             15                  20                  25 ctc aca tca ccc cga aaa ccg ttc tcc tcc agc tca act ttt att tcc    986
Leu Thr Ser Pro Arg Lys Pro Phe Ser Ser Ser Ser Thr Phe Ile Ser
         30                  35                  40 ctc tcc agg ttt acg gcg cta tcg tac agc ttc tcc gac cgc ttc aaa   1034
Leu Ser Arg Phe Thr Ala Leu Ser Tyr Ser Phe Ser Asp Arg Phe Lys
     45                  50                  55 cgg ctg tac tcg gcg ctc aac tgt agc aaa ctt tgt tcc aaa ccg tcg   1082
Arg Leu Tyr Ser Ala Leu Asn Cys Ser Lys Leu Cys Ser Lys Pro Ser
 60                  65                  70                  75 acg gtt agc aaa ccc ttt tcc ttt aga ata ttt tca aca cgt tcg atc   1130
Thr Val Ser Lys Pro Phe Ser Phe Arg Ile Phe Ser Thr Arg Ser Ile
                 80                  85                  90
```

| | |
|---|---|
| agg tcg agg ttg gtc atc gcg atg tcg tac tcc aca gcc tgc ttg ttc<br>Arg Ser Arg Leu Val Ile Ala Met Ser Tyr Ser Thr Ala Cys Leu Phe<br>               95                        100                    105 | 1178 |
| ttg gcc tct cga ccc aga att att ttc tcc tgaaggtctg ttataaaatc<br>Leu Ala Ser Arg Pro Arg Ile Ile Phe Ser<br>           110                    115 | 1228 |
| gtccacctcc tggtccgaca tcgtgtccat aaacaacgca gcatcgttcg cgattttacg | 1288 |
| cagcccctgc ag | 1300 |

<210> SEQ ID NO 41
<211> LENGTH: 117
<212> TYPE: PRT
<213> ORGANISM: mosquito baculovirus

<400> SEQUENCE: 41

Met Phe Ala Ser Arg Ser Glu Ile Phe Ser Ile Tyr Arg Phe Lys Leu
  1               5                  10                  15

Pro Leu Ser Val Asn Ser Phe Glu Met Pro Ser Leu Thr Ser Pro Arg
             20                  25                  30

Lys Pro Phe Ser Ser Ser Ser Thr Phe Ile Ser Leu Ser Arg Phe Thr
         35                  40                  45

Ala Leu Ser Tyr Ser Phe Ser Asp Arg Phe Lys Arg Leu Tyr Ser Ala
     50                  55                  60

Leu Asn Cys Ser Lys Leu Cys Ser Lys Pro Ser Thr Val Ser Lys Pro
 65                  70                  75                  80

Phe Ser Phe Arg Ile Phe Ser Thr Arg Ser Ile Arg Ser Arg Leu Val
                 85                  90                  95

Ile Ala Met Ser Tyr Ser Thr Ala Cys Leu Phe Leu Ala Ser Arg Pro
            100                 105                 110

Arg Ile Ile Phe Ser
        115

<210> SEQ ID NO 42
<211> LENGTH: 1300
<212> TYPE: DNA
<213> ORGANISM: mosquito baculovirus
<220> FEATURE:
<221> NAME/KEY: CDS
<222> LOCATION: (1)...(1299)

<400> SEQUENCE: 42

| | |
|---|---|
| ctg cag ggg ctg cgt aaa atc gcg aac gat gct gcg ttg ttt atg gac<br>Leu Gln Gly Leu Arg Lys Ile Ala Asn Asp Ala Ala Leu Phe Met Asp<br>  1               5                    10                    15 | 48 |
| acg atg tcg gac cag gag gtg gac gat ttt ata aca gac ctt cag gag<br>Thr Met Ser Asp Gln Glu Val Asp Asp Phe Ile Thr Asp Leu Gln Glu<br>           20                    25                    30 | 96 |
| aaa ata att ctg ggt cga gag gcc aag aac aag cag gct gtg gag tac<br>Lys Ile Ile Leu Gly Arg Glu Ala Lys Asn Lys Gln Ala Val Glu Tyr<br>        35                    40                    45 | 144 |
| gac atc gcg atg acc aac ctc gac ctg atc gaa cgt gtt gaa aat att<br>Asp Ile Ala Met Thr Asn Leu Asp Leu Ile Glu Arg Val Glu Asn Ile<br>    50                    55                    60 | 192 |
| cta aag gaa aag ggt ttg cta acc gtc gac ggt ttg gaa caa agt ttg<br>Leu Lys Glu Lys Gly Leu Leu Thr Val Asp Gly Leu Glu Gln Ser Leu<br> 65                 70                    75                    80 | 240 |
| cta cag ttg agc gcc gag tac agc cgt ttg aag cgg tcg gag aag ctg<br>Leu Gln Leu Ser Ala Glu Tyr Ser Arg Leu Lys Arg Ser Glu Lys Leu<br>                 85                    90                    95 | 288 |

```
tac gat agc gcc gta aac ctg gag agg gaa ata aaa gtt gag ctg gag      336
Tyr Asp Ser Ala Val Asn Leu Glu Arg Glu Ile Lys Val Glu Leu Glu
            100                 105                 110 gag aac ggt ttt cgg ggt gat gtg agg gag ggc att tcg aag ctg tta      384
Glu Asn Gly Phe Arg Gly Asp Val Arg Glu Gly Ile Ser Lys Leu Leu
        115                 120                 125 acc gac agc ggc aac ttg aag cgg tat atg gag aaa att tcc gac ctc      432
Thr Asp Ser Gly Asn Leu Lys Arg Tyr Met Glu Lys Ile Ser Asp Leu
    130                 135                 140 gag gcg aac att gtg cag ctc aag agt aaa att gcc aat ctc gag ggt      480
Glu Ala Asn Ile Val Gln Leu Lys Ser Lys Ile Ala Asn Leu Glu Gly
145                 150                 155                 160 gta tat tcg gat gcg caa aac gtt ggc gag gat ttg gcg gtg gcc acg      528
Val Tyr Ser Asp Ala Gln Asn Val Gly Glu Asp Leu Ala Val Ala Thr
                165                 170                 175 cgt gaa att gag gct ttg cgg tcc aag ttg aac gag tgc acc aag gac      576
Arg Glu Ile Glu Ala Leu Arg Ser Lys Leu Asn Glu Cys Thr Lys Asp
            180                 185                 190 ttg agc ttc gat aaa aat gtt gcc acg ggc gac gat tgt cag ctg gag      624
Leu Ser Phe Asp Lys Asn Val Ala Thr Gly Asp Asp Cys Gln Leu Glu
        195                 200                 205 cag caa aac aag ttc atg ctg gac agc atg ctg atg tcg tac cgc gaa      672
Gln Gln Asn Lys Phe Met Leu Asp Ser Met Leu Met Ser Tyr Arg Glu
    210                 215                 220 acc cct tcg atg gag ttg gct gag aaa att ttc aaa ttg caa aat atg      720
Thr Pro Ser Met Glu Leu Ala Glu Lys Ile Phe Lys Leu Gln Asn Met
225                 230                 235                 240 cac att aaa atc tgc acc gag agg gcc cgc gag gtg gtg cat tac tac      768
His Ile Lys Ile Cys Thr Glu Arg Ala Arg Glu Val Val His Tyr Tyr
                245                 250                 255 aat atg gcc cgc cgt cag ctg aaa att tgc ttg gat aat ttg aga aat      816
Asn Met Ala Arg Arg Gln Leu Lys Ile Cys Leu Asp Asn Leu Arg Asn
            260                 265                 270 att cgc gag aca aag tcg gcc gaa ctg ccc ggt ccg ctg gtg ggt gaa      864
Ile Arg Glu Thr Lys Ser Ala Glu Leu Pro Gly Pro Leu Val Gly Glu
        275                 280                 285 att gtg ggc tat atg aac gac ttg agc acc atg atc gat gtg ctc ggc      912
Ile Val Gly Tyr Met Asn Asp Leu Ser Thr Met Ile Asp Val Leu Gly
    290                 295                 300 agc ccc atc tcg gac agc gag ttc aag tct aga tgt ttt gac gtc gag      960
Ser Pro Ile Ser Asp Ser Glu Phe Lys Ser Arg Cys Phe Asp Val Glu
305                 310                 315                 320 tac aaa atc cag aaa gcg gtc gag gcc aca aag gag tct aaa cag ggc     1008
Tyr Lys Ile Gln Lys Ala Val Glu Ala Thr Lys Glu Ser Lys Gln Gly
                325                 330                 335 gag gtg acg ctg gcc cgt gag gcg ctt cgc agt gtg atg atg cag ttg     1056
Glu Val Thr Leu Ala Arg Glu Ala Leu Arg Ser Val Met Met Gln Leu
            340                 345                 350 ggc cgg gcg cga gta aag ctc gac ctg tac aac aac ctg gac ttg gag     1104
Gly Arg Ala Arg Val Lys Leu Asp Leu Tyr Asn Asn Leu Asp Leu Glu
        355                 360                 365 gag tac gtg gtg gag ctg aac aaa att gtc ggt ggt agt acg gag atc     1152
Glu Tyr Val Val Glu Leu Asn Lys Ile Val Gly Gly Ser Thr Glu Ile
    370                 375                 380 aat ttg aac gaa aag atg aag ctg gcc gcg ttc tac tac agt gag ctg     1200
Asn Leu Asn Glu Lys Met Lys Leu Ala Ala Phe Tyr Tyr Ser Glu Leu
385                 390                 395                 400 aag aaa ttc ttc gat ttt gcc gtc acc acg ctc aaa att aac ccc aac     1248
Lys Lys Phe Phe Asp Phe Ala Val Thr Thr Leu Lys Ile Asn Pro Asn
```

-continued

```
                      405                 410                 415
cgc ggt ggt tcg att tcc gag cag gtt aac ttc gtc agc gtg gag ctg    1296
Arg Gly Gly Ser Ile Ser Glu Gln Val Asn Phe Val Ser Val Glu Leu
            420                 425                 430 cag t                                                              1300
Gln
```

<210> SEQ ID NO 43
<211> LENGTH: 433
<212> TYPE: PRT
<213> ORGANISM: mosquito baculovirus

<400> SEQUENCE: 43

```
Leu Gln Gly Leu Arg Lys Ile Ala Asn Asp Ala Ala Leu Phe Met Asp
 1               5                  10                  15

Thr Met Ser Asp Gln Glu Val Asp Asp Phe Ile Thr Asp Leu Gln Glu
            20                  25                  30

Lys Ile Ile Leu Gly Arg Glu Ala Lys Asn Lys Gln Ala Val Glu Tyr
        35                  40                  45

Asp Ile Ala Met Thr Asn Leu Asp Leu Ile Glu Arg Val Glu Asn Ile
    50                  55                  60

Leu Lys Glu Lys Gly Leu Leu Thr Val Asp Gly Leu Glu Gln Ser Leu
65                  70                  75                  80

Leu Gln Leu Ser Ala Glu Tyr Ser Arg Leu Lys Arg Ser Glu Lys Leu
                85                  90                  95

Tyr Asp Ser Ala Val Asn Leu Glu Arg Glu Ile Lys Val Glu Leu Glu
            100                 105                 110

Glu Asn Gly Phe Arg Gly Asp Val Arg Glu Gly Ile Ser Lys Leu Leu
        115                 120                 125

Thr Asp Ser Gly Asn Leu Lys Arg Tyr Met Glu Lys Ile Ser Asp Leu
    130                 135                 140

Glu Ala Asn Ile Val Gln Leu Lys Ser Lys Ile Ala Asn Leu Glu Gly
145                 150                 155                 160

Val Tyr Ser Asp Ala Gln Asn Val Gly Glu Asp Leu Ala Val Ala Thr
                165                 170                 175

Arg Glu Ile Glu Ala Leu Arg Ser Lys Leu Asn Glu Cys Thr Lys Asp
            180                 185                 190

Leu Ser Phe Asp Lys Asn Val Ala Thr Gly Asp Asp Cys Gln Leu Glu
        195                 200                 205

Gln Gln Asn Lys Phe Met Leu Asp Ser Met Leu Met Ser Tyr Arg Glu
    210                 215                 220

Thr Pro Ser Met Glu Leu Ala Glu Lys Ile Phe Lys Leu Gln Asn Met
225                 230                 235                 240

His Ile Lys Ile Cys Thr Glu Arg Ala Arg Glu Val Val His Tyr Tyr
                245                 250                 255

Asn Met Ala Arg Arg Gln Leu Lys Ile Cys Leu Asp Asn Leu Arg Asn
            260                 265                 270

Ile Arg Glu Thr Lys Ser Ala Glu Leu Pro Gly Pro Leu Val Gly Glu
        275                 280                 285

Ile Val Gly Tyr Met Asn Asp Leu Ser Thr Met Ile Asp Val Leu Gly
    290                 295                 300

Ser Pro Ile Ser Asp Ser Glu Phe Lys Ser Arg Cys Phe Asp Val Glu
305                 310                 315                 320

Tyr Lys Ile Gln Lys Ala Val Glu Ala Thr Lys Glu Ser Lys Gln Gly
                325                 330                 335
```

-continued

```
Glu Val Thr Leu Ala Arg Glu Ala Leu Arg Ser Val Met Met Gln Leu
            340                 345                 350

Gly Arg Ala Arg Val Lys Leu Asp Leu Tyr Asn Asn Leu Asp Leu Glu
            355                 360                 365

Glu Tyr Val Val Glu Leu Asn Lys Ile Val Gly Gly Ser Thr Glu Ile
            370                 375                 380

Asn Leu Asn Glu Lys Met Lys Leu Ala Ala Phe Tyr Tyr Ser Glu Leu
385                 390                 395                 400

Lys Lys Phe Phe Asp Phe Ala Val Thr Thr Leu Lys Ile Asn Pro Asn
                405                 410                 415

Arg Gly Gly Ser Ile Ser Glu Gln Val Asn Phe Val Ser Val Glu Leu
            420                 425                 430

Gln
```

<210> SEQ ID NO 44
<211> LENGTH: 1017
<212> TYPE: DNA
<213> ORGANISM: mosquito baculovirus
<220> FEATURE:
<221> NAME/KEY: CDS
<222> LOCATION: (85)...(966)

<400> SEQUENCE: 44

```
ctgcagcgca tattcgacct cccaatacgg gaggtgccca cggtgtcccg aaatggggac      60
caactttacg agccccactt ggtg atg cgg ccc gac gaa ccg act atg cct        111
                          Met Arg Pro Asp Glu Pro Thr Met Pro
                            1               5 atg cgt gaa ttt gac acc ggt tta cga cgt gga gac caa cag gtg ctc       159
Met Arg Glu Phe Asp Thr Gly Leu Arg Arg Gly Asp Gln Gln Val Leu
 10                  15                  20                  25 aac agg ttg cgc atg acc tcg tcc gag cgg gct ggg ctc aac aat ata       207
Asn Arg Leu Arg Met Thr Ser Ser Glu Arg Ala Gly Leu Asn Asn Ile
                 30                  35                  40 cgg ggc aat tcg ctg ccc gat aat ctg tac cag gcg gtg cgc gca gac       255
Arg Gly Asn Ser Leu Pro Asp Asn Leu Tyr Gln Ala Val Arg Ala Asp
             45                  50                  55 gag gcc gca att cgc gtt agg gat ccg aac ttg gcc aac gcg aga acc       303
Glu Ala Ala Ile Arg Val Arg Asp Pro Asn Leu Ala Asn Ala Arg Thr
         60                  65                  70 gag cag gaa att acg gat gca ctt gcg cgt cat ccg agg cta cgt gac       351
Glu Gln Glu Ile Thr Asp Ala Leu Ala Arg His Pro Arg Leu Arg Asp
     75                  80                  85 cgg ctt acg gcc ggt ggc gtg atc aag ggt gca ggt gtt tca ctt gta       399
Arg Leu Thr Ala Gly Gly Val Ile Lys Gly Ala Gly Val Ser Leu Val
 90                  95                 100                 105 att gta ggt ggg gct ctg ctc gcg gcc gag ctc tac caa tat ttg aat       447
Ile Val Gly Gly Ala Leu Leu Ala Ala Glu Leu Tyr Gln Tyr Leu Asn
                110                 115                 120 cgt atg ggt ggt gcg ttt att gaa caa cgt gag gcg gac ggt tcg gtg       495
Arg Met Gly Gly Ala Phe Ile Glu Gln Arg Glu Ala Asp Gly Ser Val
            125                 130                 135 gtg cgc cat tat tta ctt tgg aga tcc tgc ggt atg gat ccg tct gtg       543
Val Arg His Tyr Leu Leu Trp Arg Ser Cys Gly Met Asp Pro Ser Val
        140                 145                 150 gtt tcg ttg gag gag gtt ttc ccg ggc gaa tcg ggt gac ccc att tac       591
Val Ser Leu Glu Glu Val Phe Pro Gly Glu Ser Gly Asp Pro Ile Tyr
    155                 160                 165 gat agc gtt ggg gag gcc caa gcc att tgc agc ggt tat aat aaa agt       639
```

-continued

```
Asp Ser Val Gly Glu Ala Gln Ala Ile Cys Ser Gly Tyr Asn Lys Ser
170                 175                 180                 185 gta gaa cga agt gtt tgc cgc caa gcg gac gtg ttg gcc gag ccg tcc      687
Val Glu Arg Ser Val Cys Arg Gln Ala Asp Val Leu Ala Glu Pro Ser
                190                 195                 200 agc caa caa ttt tta gac gca cgt aca ctg cca gaa aac gct cac att      735
Ser Gln Gln Phe Leu Asp Ala Arg Thr Leu Pro Glu Asn Ala His Ile
            205                 210                 215 tac tgc gtt gag ccg ggt acg ttg gga cga ctg gtg gcc gac ctc ggg      783
Tyr Cys Val Glu Pro Gly Thr Leu Gly Arg Leu Val Ala Asp Leu Gly
        220                 225                 230 cta gca gat tta gtt gac gct gta ggc ggt tcg gtc agt ggg agc agc      831
Leu Ala Asp Leu Val Asp Ala Val Gly Gly Ser Val Ser Gly Ser Ser
    235                 240                 245 ggt aac agc agc ggc aag agc tcc ggc aac ccg ctg att ctg att agt      879
Gly Asn Ser Ser Gly Lys Ser Ser Gly Asn Pro Leu Ile Leu Ile Ser
250                 255                 260                 265 gcg ttc gtc gtg tta att ata ata atc ttc gtt gta gtc ttc ggt tat      927
Ala Phe Val Val Leu Ile Ile Ile Ile Phe Val Val Val Phe Gly Tyr
                270                 275                 280 tcc cgc acc cgt cgg aac tca gac gcg gat cgc acg ata taagtagaat      976
Ser Arg Thr Arg Arg Asn Ser Asp Ala Asp Arg Thr Ile
            285                 290 tgtgcttcta taagcaactg aaagtgaagc taaacctgca g                      1017

<210> SEQ ID NO 45
<211> LENGTH: 294
<212> TYPE: PRT
<213> ORGANISM: mosquito baculovirus

<400> SEQUENCE: 45

Met Arg Pro Asp Glu Pro Thr Met Pro Met Arg Glu Phe Asp Thr Gly
 1               5                  10                  15

Leu Arg Arg Gly Asp Gln Gln Val Leu Asn Arg Leu Arg Met Thr Ser
            20                  25                  30

Ser Glu Arg Ala Gly Leu Asn Asn Ile Arg Gly Asn Ser Leu Pro Asp
        35                  40                  45

Asn Leu Tyr Gln Ala Val Arg Ala Asp Glu Ala Ala Ile Arg Val Arg
    50                  55                  60

Asp Pro Asn Leu Ala Asn Ala Arg Thr Glu Gln Glu Ile Thr Asp Ala
65                  70                  75                  80

Leu Ala Arg His Pro Arg Leu Arg Asp Arg Leu Thr Ala Gly Gly Val
                85                  90                  95

Ile Lys Gly Ala Gly Val Ser Leu Val Ile Val Gly Gly Ala Leu Leu
            100                 105                 110

Ala Ala Glu Leu Tyr Gln Tyr Leu Asn Arg Met Gly Gly Ala Phe Ile
        115                 120                 125

Glu Gln Arg Glu Ala Asp Gly Ser Val Val Arg His Tyr Leu Leu Trp
    130                 135                 140

Arg Ser Cys Gly Met Asp Pro Ser Val Val Ser Leu Glu Glu Val Phe
145                 150                 155                 160

Pro Gly Glu Ser Gly Asp Pro Ile Tyr Asp Ser Val Gly Glu Ala Gln
                165                 170                 175

Ala Ile Cys Ser Gly Tyr Asn Lys Ser Val Glu Arg Ser Val Cys Arg
            180                 185                 190

Gln Ala Asp Val Leu Ala Glu Pro Ser Ser Gln Gln Phe Leu Asp Ala
        195                 200                 205
```

```
Arg Thr Leu Pro Glu Asn Ala His Ile Tyr Cys Val Glu Pro Gly Thr
    210                 215                 220

Leu Gly Arg Leu Val Ala Asp Leu Gly Leu Ala Asp Leu Val Asp Ala
225                 230                 235                 240

Val Gly Gly Ser Val Ser Gly Ser Ser Gly Asn Ser Ser Gly Lys Ser
                245                 250                 255

Ser Gly Asn Pro Leu Ile Leu Ile Ser Ala Phe Val Val Leu Ile Ile
            260                 265                 270

Ile Ile Phe Val Val Phe Gly Tyr Ser Arg Thr Arg Asn Ser
        275                 280                 285

Asp Ala Asp Arg Thr Ile
    290

<210> SEQ ID NO 46
<211> LENGTH: 1017
<212> TYPE: DNA
<213> ORGANISM: mosquito baculovirus
<220> FEATURE:
<221> NAME/KEY: CDS
<222> LOCATION: (682)...(882)

<400> SEQUENCE: 46
ctgcaggttt agcttcactt tcagttgctt atagaagcac aattctactt atatcgtgcg      60
atccgcgtct gagttccgac gggtgcggga ataaccgaag actacaacga agattattat     120
aattaacacg acgaacgcac taatcagaat cagcgggttg ccggagctct tgccgctgct     180
gttaccgctg ctcccactga ccgaaccgcc tacagcgtca actaaatctg ctagcccgag     240
gtcggccacc agtcgtccca acgtacccgg ctcaacgcag taaatgtgag cgttttctgg     300
cagtgtacgt gcgtctaaaa attgttggct ggacggctcg ccaacacgt ccgcttggcg      360 gcaaacactt cgttctacac ttttattata accgctgcaa atggcttggg cctccccaac     420
gctatcgtaa atggggtcac ccgattcgcc cgggaaaacc tcctccaacg aaaccacaga     480
cggatccata ccgcaggatc tccaaagtaa ataatggcgc accaccgaac cgtccgcctc     540
acgttgttca ataaacgcac cacccatacg attcaaatat tggtagagct cggccgcgag     600
cagagcccca cctacaatta caagtgaaac acctgcaccc ttgatcacgc caccggccgt     660
aagccggtca cgtagcctcg g atg acg cgc aag tgc atc cgt aat ttc ctg      711
                        Met Thr Arg Lys Cys Ile Arg Asn Phe Leu
                          1               5                   10 ctc ggt tct cgc gtt ggc caa gtt cgg atc cct aac gcg aat tgc ggc      759
Leu Gly Ser Arg Val Gly Gln Val Arg Ile Pro Asn Ala Asn Cys Gly
            15                  20                  25 ctc gtc tgc gcg cac cgc ctg gta cag att atc ggg cag cga att gcc      807
Leu Val Cys Ala His Arg Leu Val Gln Ile Ile Gly Gln Arg Ile Ala
        30                  35                  40 ccg tat att gtt gag ccc agc ccg ctc gga cga ggt cat gcg caa cct      855
Pro Tyr Ile Val Glu Pro Ser Pro Leu Gly Arg Gly His Ala Gln Pro
    45                  50                  55 gtt gag cac ctg ttg gtc tcc acg tcg taaaccggtg tcaaattcac             902
Val Glu His Leu Leu Val Ser Thr Ser
60                  65 gcataggcat agtcggttcg tcgggccgca tcaccaagtg gggctcgtaa agttggtccc    962
catttcggga caccgtgggc acctcccgta ttgggaggtc gaatatgcgc tgcag        1017

<210> SEQ ID NO 47
<211> LENGTH: 67
```

-continued

```
<212> TYPE: PRT
<213> ORGANISM: mosquito baculovirus

<400> SEQUENCE: 47

Met Thr Arg Lys Cys Ile Arg Asn Phe Leu Leu Gly Ser Arg Val Gly
 1               5                  10                  15

Gln Val Arg Ile Pro Asn Ala Asn Cys Gly Leu Val Cys Ala His Arg
            20                  25                  30

Leu Val Gln Ile Ile Gly Gln Arg Ile Ala Pro Tyr Ile Val Glu Pro
        35                  40                  45

Ser Pro Leu Gly Arg Gly His Ala Gln Pro Val Glu His Leu Leu Val
    50                  55                  60

Ser Thr Ser
65

<210> SEQ ID NO 48
<211> LENGTH: 1076
<212> TYPE: DNA
<213> ORGANISM: mosquito baculovirus
<220> FEATURE:
<221> NAME/KEY: CDS
<222> LOCATION: (1)...(1071)

<400> SEQUENCE: 48 ctg cag ccc cgg gtc cag ccc aag ccg cag aag gag cgt att gtc gtg       48
Leu Gln Pro Arg Val Gln Pro Lys Pro Gln Lys Glu Arg Ile Val Val
 1               5                  10                  15 gtg act tcg gtc acc aaa atc acc gcc gac gag gat gat gtc gat ggt       96
Val Thr Ser Val Thr Lys Ile Thr Ala Asp Glu Asp Asp Val Asp Gly
            20                  25                  30 gag cag aag gtt acc ttt cgc gag ggt gaa aaa act tcg tgg gcc ttt      144
Glu Gln Lys Val Thr Phe Arg Glu Gly Glu Lys Thr Ser Trp Ala Phe
        35                  40                  45 tac gac caa ccg gag gaa ctg gag gtt aat ggc gct tac tcg gtg gtg      192
Tyr Asp Gln Pro Glu Glu Leu Glu Val Asn Gly Ala Tyr Ser Val Val
    50                  55                  60 atc aaa acc gag cgc aac aac ttt atg atg gtg aac cgt atc gtg gag      240
Ile Lys Thr Glu Arg Asn Asn Phe Met Met Val Asn Arg Ile Val Glu
 65                  70                  75                  80 gcg aaa aag tcc act att gtc gaa aac agg tac gtt tca ccg ttt gta      288
Ala Lys Lys Ser Thr Ile Val Glu Asn Arg Tyr Val Ser Pro Phe Val
                85                  90                  95 gag aaa att gcg atg ggt aat ttg ctc ggt cgc gtt gtg cac ttt acg      336
Glu Lys Ile Ala Met Gly Asn Leu Leu Gly Arg Val Val His Phe Thr
            100                 105                 110 tac tcg ggc agg gac aaa acg ttc atg atg tta ctg gaa gtt ttg act      384
Tyr Ser Gly Arg Asp Lys Thr Phe Met Met Leu Leu Glu Val Leu Thr
        115                 120                 125 ctc gat gtg aac gta tgt acg gtg gag gtt cga gtg cag cgg gaa ttt      432
Leu Asp Val Asn Val Cys Thr Val Glu Val Arg Val Gln Arg Glu Phe
    130                 135                 140 gaa tcg gag cac aat ttg atg caa gtt gtg cac gac cgg gcc aag tcc      480
Glu Ser Glu His Asn Leu Met Gln Val Val His Asp Arg Ala Lys Ser
145                 150                 155                 160 agg ctc aac tgg acc gtg ttg tat gat gtg cgc gta aat tca cgc agt      528
Arg Leu Asn Trp Thr Val Leu Tyr Asp Val Arg Val Asn Ser Arg Ser
                165                 170                 175 tac cgc ttt gag cgc atc gat gag acg aga aat tta acc acc gta tac      576
Tyr Arg Phe Glu Arg Ile Asp Glu Thr Arg Asn Leu Thr Thr Val Tyr
            180                 185                 190
```

```
atg ttg tct acg agc aac atc aag ttc tac gac acc ctg aac gac ctg      624
Met Leu Ser Thr Ser Asn Ile Lys Phe Tyr Asp Thr Leu Asn Asp Leu
        195                 200                 205 ctc gag gcc aac acg tgc acg ctt agc tcg aag gag cag acg ctt ttg      672
Leu Glu Ala Asn Thr Cys Thr Leu Ser Ser Lys Glu Gln Thr Leu Leu
    210                 215                 220 acg aag gct aca ttt acc cct ctt aaa ttt cat tcc ctc acc cgc gga      720
Thr Lys Ala Thr Phe Thr Pro Leu Lys Phe His Ser Leu Thr Arg Gly
225                 230                 235                 240 tac gac ctg cac atc ttc aac gtc aag caa gta aag gtg ttc ctc acc      768
Tyr Asp Leu His Ile Phe Asn Val Lys Gln Val Lys Val Phe Leu Thr
            245                 250                 255 gag gag ggc ggc atc atg agg ggc atc tgt tcc ttc ccg tac gcc aaa      816
Glu Glu Gly Gly Ile Met Arg Gly Ile Cys Ser Phe Pro Tyr Ala Lys
        260                 265                 270 cgc cag tgg tca ctg tcc atc tat aac aac gaa aag aat cca aac gtt      864
Arg Gln Trp Ser Leu Ser Ile Tyr Asn Asn Glu Lys Asn Pro Asn Val
    275                 280                 285 ttc aaa aac tac atc gag cgg cta agc gac tac acc tcc acc gaa aac      912
Phe Lys Asn Tyr Ile Glu Arg Leu Ser Asp Tyr Thr Ser Thr Glu Asn
290                 295                 300 agc tac ttc aac gtt tac ttc aac gac acc ggc tcc tcg tac acc ttc      960
Ser Tyr Phe Asn Val Tyr Phe Asn Asp Thr Gly Ser Ser Tyr Thr Phe
305                 310                 315                 320 att gcc att tcg ggc cgc tac gaa agt tca gag gaa tcg ttt tgc acc     1008
Ile Ala Ile Ser Gly Arg Tyr Glu Ser Ser Glu Glu Ser Phe Cys Thr
            325                 330                 335 gtt atg aat cca cca ccg gag gag cgt aag gtc gct gtc aag cgc ccc     1056
Val Met Asn Pro Pro Pro Glu Glu Arg Lys Val Ala Val Lys Arg Pro
        340                 345                 350 atc gtt gat gac aac tgcag                                           1076
Ile Val Asp Asp Asn
    355

<210> SEQ ID NO 49
<211> LENGTH: 357
<212> TYPE: PRT
<213> ORGANISM: mosquito baculovirus

<400> SEQUENCE: 49

Leu Gln Pro Arg Val Gln Pro Lys Pro Gln Lys Glu Arg Ile Val Val
 1               5                  10                  15

Val Thr Ser Val Thr Lys Ile Thr Ala Asp Glu Asp Val Asp Gly
            20                  25                  30

Glu Gln Lys Val Thr Phe Arg Glu Gly Glu Lys Thr Ser Trp Ala Phe
        35                  40                  45

Tyr Asp Gln Pro Glu Glu Leu Glu Val Asn Gly Ala Tyr Ser Val Val
    50                  55                  60

Ile Lys Thr Glu Arg Asn Asn Phe Met Met Val Asn Arg Ile Val Glu
65                  70                  75                  80

Ala Lys Lys Ser Thr Ile Val Gly Asn Arg Tyr Val Ser Pro Phe Val
                85                  90                  95

Glu Lys Ile Ala Met Gly Asn Leu Leu Gly Arg Val Val His Phe Thr
            100                 105                 110

Tyr Ser Gly Arg Asp Lys Thr Phe Met Met Leu Leu Glu Val Leu Thr
        115                 120                 125

Leu Asp Val Asn Val Cys Thr Val Glu Val Arg Val Gln Arg Glu Phe
    130                 135                 140
```

| Glu | Ser | Glu | His | Asn | Leu | Met | Gln | Val | Val | His | Asp | Arg | Ala | Lys | Ser |
145 | | | | 150 | | | | | 155 | | | | | 160 | |

Arg Leu Asn Trp Thr Val Leu Tyr Asp Val Arg Val Asn Ser Arg Ser
                  165                  170              175

Tyr Arg Phe Glu Arg Ile Asp Glu Thr Arg Asn Leu Thr Thr Val Tyr
            180                  185                  190

Met Leu Ser Thr Ser Asn Ile Lys Phe Tyr Asp Thr Leu Asn Asp Leu
        195                  200              205

Leu Glu Ala Asn Thr Cys Thr Leu Ser Ser Lys Glu Gln Thr Leu Leu
    210                  215              220

Thr Lys Ala Thr Phe Thr Pro Leu Lys Phe His Ser Leu Thr Arg Gly
225              230                  235            240

Tyr Asp Leu His Ile Phe Asn Val Lys Gln Val Lys Val Phe Leu Thr
            245                  250              255

Glu Glu Gly Gly Ile Met Arg Gly Ile Cys Ser Phe Pro Tyr Ala Lys
        260                  265              270

Arg Gln Trp Ser Leu Ser Ile Tyr Asn Asn Glu Lys Asn Pro Asn Val
    275                  280              285

Phe Lys Asn Tyr Ile Glu Arg Leu Ser Asp Tyr Thr Ser Thr Glu Asn
290              295                  300

Ser Tyr Phe Asn Val Tyr Phe Asn Asp Thr Gly Ser Ser Tyr Thr Phe
305              310                  315            320

Ile Ala Ile Ser Gly Arg Tyr Glu Ser Ser Glu Glu Ser Phe Cys Thr
            325                  330              335

Val Met Asn Pro Pro Glu Glu Arg Lys Val Ala Val Lys Arg Pro
        340                  345              350

Ile Val Asp Asp Asn
    355

```
<210> SEQ ID NO 50
<211> LENGTH: 1076
<212> TYPE: DNA
<213> ORGANISM: mosquito baculovirus
<220> FEATURE:
<221> NAME/KEY: CDS
<222> LOCATION: (715)...(894)
<221> NAME/KEY: CDS
<222> LOCATION: (927)...(1076)

<400> SEQUENCE: 50
ctgcagttgt catcaacgat ggggcgcttg acagcgacct tacgctcctc cggtggtgga      60
ttcataacgg tgcaaaacga ttcctctgaa ctttcgtagc ggcccgaaat ggcaatgaag     120
gtgtacgagg agccggtgtc gttgaagtaa acgttgaagt agctgttttc ggtggaggtg     180
tagtcgctta gccgctcgat gtagtttttg aaaacgtttg gattcttttc gttgttatag     240
atggacagtg accactggcg tttggcgtac gggaaggaac agatgcccct catgatgccg     300
ccctcctcgg tgaggaacac ctttacttgc ttgacgttga agatgtgcag gtcgtatccg     360
cgggtgaggg aatgaaattt aagagggta aatgtagcct cgtcaaaag cgtctgctcc       420 ttcgagctaa gcgtgcacgt gttggcctcg agcaggtcgt tcagggtgtc gtagaacttg     480
atgttgctcg tagacaacat gtatacggtg gttaaatttc tcgtctcatc gatgcgctca     540
aagcggtaac tgcgtgaatt tacgcgcaca tcatacaaca cggtccagtt gagcctggac     600
ttggcccggt cgtgcacaac ttgcatcaaa ttgtgctccg attcaaattc ccgctgcact     660
cgaacctcca ccgtacatac gttcacatcg agagtcaaaa cttccagtaa catc atg     717
                                                                Met
```

-continued

```
                                                              1 aac gtt ttg tcc ctg ccc gag tac gta aag tgc aca acg cga ccg agc      765
Asn Val Leu Ser Leu Pro Glu Tyr Val Lys Cys Thr Thr Arg Pro Ser
            5                  10                  15 aaa tta ccc atc gca att ttc tct aca aac ggt gaa acg tac ctg ttt      813
Lys Leu Pro Ile Ala Ile Phe Ser Thr Asn Gly Glu Thr Tyr Leu Phe
        20                  25                  30 tcg aca ata gtg gac ttt ttc gcc tcc acg ata cgg ttc acc atc ata      861
Ser Thr Ile Val Asp Phe Phe Ala Ser Thr Ile Arg Phe Thr Ile Ile
    35                  40                  45 aag ttg ttg cgc tcg gtt ttg atc acc acc gag taagcgccat taacctccag    914
Lys Leu Leu Arg Ser Val Leu Ile Thr Thr Glu
 50                  55                  60 ttcctccggt tg gtc gta aaa ggc cca cga agt ttt ttc acc ctc gcg aaa    965
              Val Val Lys Gly Pro Arg Ser Phe Phe Thr Leu Ala Lys
                                  65                  70 ggt aac ctt ctg ctc acc atc gac atc atc ctc gtc ggc ggt gat ttt     1013
Gly Asn Leu Leu Leu Thr Ile Asp Ile Ile Leu Val Gly Gly Asp Phe
    75                  80                  85 ggt gac cga agt cac cac gac aat acg ctc ctt ctg cgg ctt ggg ctg     1061
Gly Asp Arg Ser His His Asp Asn Thr Leu Leu Leu Arg Leu Gly Leu
 90                  95                 100                 105 gac ccg ggg ctg cag                                                 1076
Asp Pro Gly Leu Gln
              110

<210> SEQ ID NO 51
<211> LENGTH: 60
<212> TYPE: PRT
<213> ORGANISM: mosquito baculovirus

<400> SEQUENCE: 51

Met Asn Val Leu Ser Leu Pro Glu Tyr Val Lys Cys Thr Thr Arg Pro
 1               5                  10                  15

Ser Lys Leu Pro Ile Ala Ile Phe Ser Thr Asn Gly Glu Thr Tyr Leu
            20                  25                  30

Phe Ser Thr Ile Val Asp Phe Phe Ala Ser Thr Ile Arg Phe Thr Ile
        35                  40                  45

Ile Lys Leu Leu Arg Ser Val Leu Ile Thr Thr Glu
    50                  55                  60

<210> SEQ ID NO 52
<211> LENGTH: 50
<212> TYPE: PRT
<213> ORGANISM: mosquito baculovirus

<400> SEQUENCE: 52

Val Val Lys Gly Pro Arg Ser Phe Phe Thr Leu Ala Lys Gly Asn Leu
 1               5                  10                  15

Leu Leu Thr Ile Asp Ile Ile Leu Val Gly Gly Asp Phe Gly Asp Arg
            20                  25                  30

Ser His His Asp Asn Thr Leu Leu Leu Arg Leu Gly Leu Asp Pro Gly
        35                  40                  45

Leu Gln
    50

<210> SEQ ID NO 53
<211> LENGTH: 1656
<212> TYPE: DNA
<213> ORGANISM: mosquito baculovirus
```

<220> FEATURE:
<221> NAME/KEY: CDS
<222> LOCATION: (434)...(1656)
<221> NAME/KEY: CDS
<222> LOCATION: (94)...(252)

<400> SEQUENCE: 53

| | | |
|---|---|---:|
| ctgcaggtga agcggatagg tgagctgggc agaagttatc tgtacattgc ccaggaggag | | 60 |
| gtttcaatta cggcccgttg cactaatcgc acc atg att cgt cag ctt acg ggc | | 114 |
|                                             Met Ile Arg Gln Leu Thr Gly | | |
|                                              1               5 | | |
| gtc ggt atc gtc aca gcg gac agt ggc tgc agc cga acc cgg cgc cgt | | 162 |
| Val Gly Ile Val Thr Ala Asp Ser Gly Cys Ser Arg Thr Arg Arg Arg | | |
|         10                     15                   20 | | |
| aaa tgg cgc acg gcc cgc acg gca gcg acg ccg cgg cgg gcc gca ccg | | 210 |
| Lys Trp Arg Thr Ala Arg Thr Ala Ala Thr Pro Arg Arg Ala Ala Pro | | |
|  25                    30                   35 | | |
| gcg gcg cat cgc tgc gcc gtc gtt tct tgc gtt acc gca tct | | 252 |
| Ala Ala His Arg Cys Ala Val Val Ser Cys Val Thr Ala Ser | | |
| 40                   45                   50 | | |
| tgagccgcgt gcgcgcgacg aacaacgcgg caaggctcag caccgcgcag cccatcagat | | 312 |
| aaagcgcggg cgacagccgg ttgccggtcg cgctgatcag ccaggtgatg acgaacggcg | | 372 |
| cgaagccgcc gaacagcgtg acaccgtgt tgtagctgac cgcgagcccc gtagcgcgcg | | 432 |
| t ctg cga cgg gaa cag ctc ggc cat cag cgc cgg cag cgc gcc gca gta | | 481 |
|   Leu Arg Arg Glu Gln Leu Gly His Gln Arg Arg Gln Arg Ala Ala Val | | |
|     55                       60                     65 | | |
| cat cgc ctt caa tgc gcc gat cca gac cag cgc cgc gag cat cgt cgc | | 529 |
| His Arg Leu Gln Cys Ala Asp Pro Asp Gln Arg Arg Glu His Arg Arg | | |
| 70                   75                     80                     85 | | |
| gaa cga tgc gtg acg cgt gag cca ctc gaa cgt cgg gta cac ggt gac | | 577 |
| Glu Arg Cys Val Thr Arg Glu Pro Leu Glu Arg Arg Val His Gly Asp | | |
|          90                        95                  100 | | |
| gag cat cag gac cgc cgc gac cgc cat cat gcg gat ccg ccc ggt gcg | | 625 |
| Glu His Gln Asp Arg Arg Asp Arg His His Ala Asp Pro Pro Gly Ala | | |
|              105                        110                  115 | | |
| atc gga cag gtg gcc gac gat cgg cgt gac gag cgt gag cac gaa gcc | | 673 |
| Ile Gly Gln Val Ala Asp Asp Arg Arg Asp Glu Arg Glu His Glu Ala | | |
|           120                      125                  130 | | |
| ggt cgc gag cgt cgc cgc gaa acc cgt cga cgc ggg cag ccc gag ctg | | 721 |
| Gly Arg Glu Arg Arg Arg Glu Thr Arg Arg Arg Gly Gln Pro Glu Leu | | |
| 135                    140                     145 | | |
| ctt gat cgc gta agt cgg cat gta cag gat cat gta gtt gat cgc ggt | | 769 |
| Leu Asp Arg Val Ser Arg His Val Gln Asp His Val Val Asp Arg Gly | | |
| 150                  155                     160                  165 | | |
| cga gat cac gag cgc gcc gat cga cag cag cac ccg cac ctt ttg ttc | | 817 |
| Arg Asp His Glu Arg Ala Asp Arg Gln Gln His Pro His Leu Leu Phe | | |
|              170                        175                  180 | | |
| cgc gaa cag ctc gcg cac cgg cgc ttc gga gcg tgc ctg cgt ctt gaa | | 865 |
| Arg Glu Gln Leu Ala His Arg Arg Phe Gly Ala Cys Leu Arg Leu Glu | | |
|           185                      190                  195 | | |
| ttc aac gcc ttc gtc gac gta acg gcg gat gta cag ccc gac cgg gcc | | 913 |
| Phe Asn Ala Phe Val Asp Val Thr Ala Asp Val Gln Pro Asp Arg Ala | | |
|              200                        205                  210 | | |
| gat cgc gag ccc gaa cag gaa cgg cac gcg cca gcc cca gct ttc gag | | 961 |
| Asp Arg Glu Pro Glu Gln Glu Arg His Ala Pro Ala Pro Ala Phe Glu | | |
| 215                    220                     225 | | |
| ttg cgc agg cgt cag cgt gga tgt cag cag cgc acc gaa gcc cga tgc | | 1009 |
| Leu Arg Arg Arg Gln Arg Gly Cys Gln Gln Arg Thr Glu Ala Arg Cys | | |
| 230                    235                     240                  245 | | |

```
gag cag cgt cgc gag gcc ctg gct cgc gaa ctg cca gct cga cat gaa   1057
Glu Gln Arg Arg Glu Ala Leu Ala Arg Glu Leu Pro Ala Arg His Glu
            250                 255                 260 acc gcg ccg ctg cgg cgc gtg ctc gac gag gaa cgc ggt cga gct cgc   1105
Thr Ala Pro Leu Arg Arg Val Leu Asp Glu Glu Arg Gly Arg Ala Arg
                265                 270                 275 gaa ttc gcc gcc cgc gga aaa gcc ctg cat caa ccg cga cag cat gat   1153
Glu Phe Ala Ala Arg Gly Lys Ala Leu His Gln Pro Arg Gln His Asp
            280                 285                 290 ccc gag cgg tgc gag tat gcc gat cga tgc gta ggt cgg cat cag cgc   1201
Pro Glu Arg Cys Glu Tyr Ala Asp Arg Cys Val Gly Arg His Gln Arg
        295                 300                 305 gat cag cag cgt gcc ggc cat cat cat cgc gat cga cag cag cag cga   1249
Asp Gln Gln Arg Ala Gly His His His Arg Asp Arg Gln Gln Gln Arg
310                 315                 320                 325 cgc ctt gcg gcc cgc tcg atc ggc gta tgc gcc gag cac gaa gcc gcc   1297
Arg Leu Ala Ala Arg Ser Ile Gly Val Cys Ala Glu His Glu Ala Ala
                330                 335                 340 gat cgg ccg gat cag gta gga cag ccc gaa cgt gcc gag cgt gag cat   1345
Asp Arg Pro Asp Gln Val Gly Gln Pro Glu Arg Ala Glu Arg Glu His
            345                 350                 355 cag cga tgt cgc ttc gct cgt ggc ggg gaa gaa cag ctt ggc gat cgt   1393
Gln Arg Cys Arg Phe Ala Arg Gly Gly Glu Glu Gln Leu Gly Asp Arg
        360                 365                 370 cac cgc gaa gaa gcc gta gac gat cag gtc gaa cca ttc gag cgc gtt   1441
His Arg Glu Glu Ala Val Asp Asp Gln Val Glu Pro Phe Glu Arg Val
    375                 380                 385 gcc gat cga cgc cgc gaa gat gat gcg ccg gat ctt cgc ggc gct ggg   1489
Ala Asp Arg Arg Arg Glu Asp Asp Ala Pro Asp Leu Arg Gly Ala Gly
390                 395                 400                 405 gcg ggc ggc ttc gtg cga ggt cag ggt ggt cgt att cat cgc gta tgc   1537
Ala Gly Gly Phe Val Arg Gly Gln Gly Gly Arg Ile His Arg Val Cys
                410                 415                 420 agg tcc cgt gaa agg ggc gaa gcg cgt tac agg gcg gcg ccg gcc gcg   1585
Arg Ser Arg Glu Arg Gly Glu Ala Arg Tyr Arg Ala Ala Pro Ala Ala
            425                 430                 435 gcg ggc gcc gcg tgg cga acg gtc ggc gcg tcg tcg ccg aga tcc cag   1633
Ala Gly Ala Ala Trp Arg Thr Val Gly Ala Ser Ser Pro Arg Ser Gln
        440                 445                 450 aag agg ccg gcc atc atc tgc ag                                    1656
Lys Arg Pro Ala Ile Ile Cys
    455                 460

<210> SEQ ID NO 54
<211> LENGTH: 53
<212> TYPE: PRT
<213> ORGANISM: mosquito baculovirus

<400> SEQUENCE: 54

Met Ile Arg Gln Leu Thr Gly Val Gly Ile Val Thr Ala Asp Ser Gly
  1               5                  10                  15

Cys Ser Arg Thr Arg Arg Arg Lys Trp Arg Thr Ala Arg Thr Ala Ala
                20                  25                  30

Thr Pro Arg Arg Ala Ala Pro Ala His Arg Cys Ala Val Val Ser
            35                  40                  45

Cys Val Thr Ala Ser
 50

<210> SEQ ID NO 55
```

-continued

```
<211> LENGTH: 407
<212> TYPE: PRT
<213> ORGANISM: mosquito baculovirus

<400> SEQUENCE: 55

Leu Arg Arg Glu Gln Leu Gly His Gln Arg Arg Gln Arg Ala Ala Val
 1               5                  10                  15

His Arg Leu Gln Cys Ala Asp Pro Asp Gln Arg Arg Glu His Arg Arg
            20                  25                  30

Glu Arg Cys Val Thr Arg Glu Pro Leu Glu Arg Arg Val His Gly Asp
        35                  40                  45

Glu His Gln Asp Arg Arg Asp Arg His His Ala Asp Pro Pro Gly Ala
    50                  55                  60

Ile Gly Gln Val Ala Asp Asp Arg Arg Asp Glu Arg Glu His Glu Ala
65                  70                  75                  80

Gly Arg Glu Arg Arg Arg Glu Thr Arg Arg Arg Gly Gln Pro Glu Leu
                85                  90                  95

Leu Asp Arg Val Ser Arg His Val Gln Asp His Val Val Asp Arg Gly
            100                 105                 110

Arg Asp His Glu Arg Ala Asp Arg Gln Gln His Pro His Leu Leu Phe
        115                 120                 125

Arg Glu Gln Leu Ala His Arg Arg Phe Gly Ala Cys Leu Arg Leu Glu
    130                 135                 140

Phe Asn Ala Phe Val Asp Val Thr Ala Asp Val Gln Pro Asp Arg Ala
145                 150                 155                 160

Asp Arg Glu Pro Glu Gln Glu Arg His Ala Pro Ala Pro Ala Phe Glu
                165                 170                 175

Leu Arg Arg Arg Gln Arg Gly Cys Gln Gln Arg Thr Glu Ala Arg Cys
            180                 185                 190

Glu Gln Arg Arg Glu Ala Leu Ala Arg Glu Leu Pro Ala Arg His Glu
        195                 200                 205

Thr Ala Pro Leu Arg Arg Val Leu Asp Glu Glu Arg Gly Arg Ala Arg
    210                 215                 220

Glu Phe Ala Ala Arg Gly Lys Ala Leu His Gln Pro Arg Gln His Asp
225                 230                 235                 240

Pro Glu Arg Cys Glu Tyr Ala Asp Arg Cys Val Gly Arg His Gln Arg
                245                 250                 255

Asp Gln Gln Arg Ala Gly His His His Arg Asp Arg Gln Gln Gln Arg
            260                 265                 270

Arg Leu Ala Ala Arg Ser Ile Gly Val Cys Ala Glu His Glu Ala Ala
        275                 280                 285

Asp Arg Pro Asp Gln Val Gly Gln Pro Glu Arg Ala Glu Arg Glu His
    290                 295                 300

Gln Arg Cys Arg Phe Ala Arg Gly Gly Glu Glu Gln Leu Gly Asp Arg
305                 310                 315                 320

His Arg Glu Glu Ala Val Asp Asp Gln Val Glu Pro Phe Glu Arg Val
                325                 330                 335

Ala Asp Arg Arg Glu Asp Asp Ala Pro Asp Leu Arg Gly Ala Gly
            340                 345                 350

Ala Gly Gly Phe Val Arg Gly Gln Gly Gly Arg Ile His Arg Val Cys
        355                 360                 365

Arg Ser Arg Glu Arg Gly Glu Ala Arg Tyr Arg Ala Ala Pro Ala Ala
    370                 375                 380

Ala Gly Ala Ala Trp Arg Thr Val Gly Ala Ser Ser Pro Arg Ser Gln
```

-continued

```
                385                 390                 395                 400
Lys Arg Pro Ala Ile Ile Cys
                405

<210> SEQ ID NO 56
<211> LENGTH: 1656
<212> TYPE: DNA
<213> ORGANISM: mosquito baculovirus
<220> FEATURE:
<221> NAME/KEY: CDS
<222> LOCATION: (894)...(1184)
<221> NAME/KEY: CDS
<222> LOCATION: (1440)...(1656)

<400> SEQUENCE: 56
ctgcaggtga agcggatagg tgagctgggc agaagttatc tgtacattgc ccaggaggag     60
gtttcaatta cggcccgttg cactaatcgc accatgattc gtcagcttac gggcgtcggt   120
atcgtcacag cggacagtgg ctgcagccga acccggcgcc gtaaatggcg cacggcccgc   180
acggcagcga cgccgcggcg ggccgcaccg gcggcgcatc gctgcgccgt cgtttcttgc   240
gttaccgcat cttgagccgc gtgcgcgcga cgaacaacgc ggcaaggctc agcaccgcgc   300
agcccatcag ataaagcgcg ggcgacagcc ggttgccggt cgcgctgatc agccaggtga   360
tgacgaacgc gcgaagccg ccgaacagcg tgacacccgt gttgtagctg accgcgagcc   420
ccgtagcgcg cgtctgcgac gggaacagct cggccatcag cgccggcagc gcgccgcagt   480
acatcgcctt caatgcgccg atccagacca cgccgcgag catcgtcgcg aacgatgcgt   540
gacgcgtgag ccactcgaac gtcgggtaca cggtgacgag catcaggacc gccgcgaccg   600
ccatcatgcg gatccgcccg gtgcgatcgg acaggtggcc gacgatcggc gtgacgagcg   660
tgagcacgaa gccggtcgcg agcgtcgccg cgaaacccgt cgacgcgggc agcccgagct   720
gcttgatcgc gtaagtcggc atgtacagga tcatgtagtt gatcgcggtc gagatcacga   780
gcgcgccgat cgacagcagc acccgcacct tttgttccgc gaacagctcg cgcaccggcg   840
cttcggagcg tgcctgcgtc ttgaattcaa cgccttcgtc gacgtaacgg cgg atg       896
                                                               Met
                                                                 1 tac agc ccg acc ggg ccg atc gcg agc ccg aac agg aac ggc acg cgc   944
Tyr Ser Pro Thr Gly Pro Ile Ala Ser Pro Asn Arg Asn Gly Thr Arg
         5                  10                  15 cag ccc cag ctt tcg agt tgc gca ggc gtc agc gtg gat gtc agc agc   992
Gln Pro Gln Leu Ser Ser Cys Ala Gly Val Ser Val Asp Val Ser Ser
     20                  25                  30 gca ccg aag ccc gat gcg agc agc gtc gcg agg ccc tgg ctc gcg aac  1040
Ala Pro Lys Pro Asp Ala Ser Ser Val Ala Arg Pro Trp Leu Ala Asn
 35                  40                  45 tgc cag ctc gac atg aaa ccg cgc cgc tgc ggc gcg tgc tcg acg agg  1088
Cys Gln Leu Asp Met Lys Pro Arg Arg Cys Gly Ala Cys Ser Thr Arg
 50                  55                  60                  65 aac gcg gtc gag ctc gcg aat tcg ccg ccc gcg gaa aag ccc tgc atc  1136
Asn Ala Val Glu Leu Ala Asn Ser Pro Pro Ala Glu Lys Pro Cys Ile
                 70                  75                  80 aac cgc gac agc atg atc ccg agc ggt gcg agt atg ccg atc gat gcg  1184
Asn Arg Asp Ser Met Ile Pro Ser Gly Ala Ser Met Pro Ile Asp Ala
             85                  90                  95 taggtcggca tcagcgcgat cagcagcgtg ccggccatca tcatcgcgat cgacagcagc  1244
agcgacgcct tgcggcccgc tcgatcggcg tatgcgccga gcacgaagcc gccgatcggc  1304
cggatcaggt aggacagccc gaacgtgccg agcgtgagca tcagcgatgt cgcttcgctc  1364
```

```
gtggcgggga agaacagctt ggcgatcgtc accgcgaaga agccgtagac gatcaggtcg      1424
aaccattcga gcgcg ttg ccg atc gac gcc gcg aag atg atg cgc cgg atc      1475
           Leu Pro Ile Asp Ala Ala Lys Met Met Arg Arg Ile
               100                 105 ttc gcg gcg ctg ggg cgg gcg gct tcg tgc gag gtc agg gtg gtc gta      1523
Phe Ala Ala Leu Gly Arg Ala Ala Ser Cys Glu Val Arg Val Val Val
110             115                 120                 125 ttc atc gcg tat gca ggt ccc gtg aaa ggg gcg aag cgc gtt aca ggg      1571
Phe Ile Ala Tyr Ala Gly Pro Val Lys Gly Ala Lys Arg Val Thr Gly
            130                 135                 140 cgg cgc cgg ccg cgg cgg gcg ccg cgt ggc gaa cgg tcg gcg cgt cgt      1619
Arg Arg Arg Pro Arg Arg Ala Pro Arg Gly Glu Arg Ser Ala Arg Arg
                145                 150                 155 cgc cga gat ccc aga aga ggc cgg cca tca tct gca g                     1656
Arg Arg Asp Pro Arg Arg Gly Arg Pro Ser Ser Ala
        160                 165
```

<210> SEQ ID NO 57
<211> LENGTH: 97
<212> TYPE: PRT
<213> ORGANISM: mosquito baculovirus

<400> SEQUENCE: 57

```
Met Tyr Ser Pro Thr Gly Pro Ile Ala Ser Pro Asn Arg Asn Gly Thr
1               5                   10                  15

Arg Gln Pro Gln Leu Ser Ser Cys Ala Gly Val Ser Val Asp Val Ser
            20                  25                  30

Ser Ala Pro Lys Pro Asp Ala Ser Ser Val Ala Arg Pro Trp Leu Ala
        35                  40                  45

Asn Cys Gln Leu Asp Met Lys Pro Arg Arg Cys Gly Ala Cys Ser Thr
    50                  55                  60

Arg Asn Ala Val Glu Leu Ala Asn Ser Pro Pro Ala Glu Lys Pro Cys
65                  70                  75                  80

Ile Asn Arg Asp Ser Met Ile Pro Ser Gly Ala Ser Met Pro Ile Asp
                85                  90                  95

Ala
```

<210> SEQ ID NO 58
<211> LENGTH: 72
<212> TYPE: PRT
<213> ORGANISM: mosquito baculovirus

<400> SEQUENCE: 58

```
Leu Pro Ile Asp Ala Ala Lys Met Met Arg Arg Ile Phe Ala Ala Leu
1               5                   10                  15

Gly Arg Ala Ala Ser Cys Glu Val Arg Val Val Val Phe Ile Ala Tyr
            20                  25                  30

Ala Gly Pro Val Lys Gly Ala Lys Arg Val Thr Gly Arg Arg Arg Pro
        35                  40                  45

Arg Arg Ala Pro Arg Gly Glu Ser Ala Arg Arg Arg Asp Pro
    50                  55                  60

Arg Arg Gly Arg Pro Ser Ser Ala
65                  70
```

<210> SEQ ID NO 59
<211> LENGTH: 1656
<212> TYPE: DNA
<213> ORGANISM: mosquito baculovirus

```
<220> FEATURE:
<221> NAME/KEY: CDS
<222> LOCATION: (1180)...(1338)

<400> SEQUENCE: 59
```

| | | | | | |
|---|---|---|---|---|---|
| ctgcaggtga | agcggatagg | tgagctgggc | agaagttatc | tgtacattgc | ccaggaggag | 60 |
| gtttcaatta | cggcccgttg | cactaatcgc | accatgattc | gtcagcttac | gggcgtcggt | 120 |
| atcgtcacag | cggacagtgg | ctgcagccga | acccggcgcc | gtaaatggcg | cacggcccgc | 180 |
| acggcagcga | cgccgcggcg | ggccgcaccg | gcggcgcatc | gctgcgccgt | cgtttcttgc | 240 |
| gttaccgcat | cttgagccgc | gtgcgcgcga | cgaacaacgc | ggcaaggctc | agcaccgcgc | 300 |
| agcccatcag | ataaagcgcg | ggcgacagcc | ggttgccggt | cgcgctgatc | agccaggtga | 360 |
| tgacgaacgg | cgcgaagccg | ccgaacagcg | tgacacccgt | gttgtagctg | accgcgagcc | 420 |
| ccgtagcgcg | cgtctgcgac | gggaacagct | cggccatcag | cgccggcagc | gcgccgcagt | 480 |
| acatcgcctt | caatgcgccg | atccagacca | gcgccgcgag | catcgtcgcg | aacgatgcgt | 540 |
| gacgcgtgag | ccactcgaac | gtcgggtaca | cggtgacgag | catcaggacc | gccgcgaccg | 600 |
| ccatcatgcg | gatccgcccg | gtgcgatcgg | acaggtggcc | gacgatcggc | gtgacgagcg | 660 |
| tgagcacgaa | gccggtcgcg | agcgtcgccg | cgaaacccgt | cgacgcgggc | agcccgagct | 720 |
| gcttgatcgc | gtaagtcggc | atgtacagga | tcatgtagtt | gatcgcggtc | gagatcacga | 780 |
| gcgcgccgat | cgacagcagc | acccgcacct | tttgttccgc | gaacagctcg | cgcaccggcg | 840 |
| cttcggagcg | tgcctgcgtc | ttgaattcaa | cgccttcgtc | gacgtaacgg | cggatgtaca | 900 |
| gcccgaccgg | gccgatcgcg | agcccgaaca | ggaacggcac | gcgccagccc | agctttcga | 960 |
| gttgcgcagg | cgtcagcgtg | gatgtcagca | gcgcaccgaa | gcccgatgcg | agcagcgtcg | 1020 |
| cgaggccctg | gctcgcgaac | tgccagctcg | acatgaaacc | gcgccgctgc | ggcgcgtgct | 1080 |
| cgacgaggaa | cgcggtcgag | ctcgcgaatt | cgccgcccgc | ggaaaagccc | tgcatcaacc | 1140 |
| gcgacagcat | gatcccgagc | ggtgcgagta | tgccgatcg | | | 1170 |

```
                                             atg cgt agg tcg gca       1194
                                             Met Arg Arg Ser Ala
                                               1               5 tca gcg cga tca gca gcg tgc cgg cca tca tca tcg cga tcg aca gca       1242
Ser Ala Arg Ser Ala Ala Cys Arg Pro Ser Ser Ser Arg Ser Thr Ala
         10                  15                  20 gca gcg acg cct tgc ggc ccg ctc gat cgg cgt atg cgc cga gca cga       1290
Ala Ala Thr Pro Cys Gly Pro Leu Asp Arg Arg Met Arg Arg Ala Arg
     25                  30                  35 agc cgc cga tcg gcc gga tca ggt agg aca gcc cga acg tgc cga gcg       1338
Ser Arg Arg Ser Ala Gly Ser Gly Arg Thr Ala Arg Thr Cys Arg Ala
 40                  45                  50
```

| | | | | | |
|---|---|---|---|---|---|
| tgagcatcag | cgatgtcgct | tcgctcgtgg | cggggaagaa | cagcttggcg | atcgtcaccg | 1398 |
| cgaagaagcc | gtagacgatc | aggtcgaacc | attcgagcgc | gttgccgatc | gacgccgcga | 1458 |
| agatgatgcg | ccggatcttc | gcggcgctgg | ggcgggcggc | ttcgtgcgag | gtcagggtgg | 1518 |
| tcgtattcat | cgcgtatgca | ggtcccgtga | aggggcgaa | gcgcgttaca | gggcggcgcc | 1578 |
| ggccgcggcg | ggcgccgcgt | ggcgaacggt | cggcgcgtcg | tcgccgagat | cccagaagag | 1638 |
| gccggccatc | atctgcag | | | | | 1656 |

```
<210> SEQ ID NO 60
<211> LENGTH: 53
<212> TYPE: PRT
<213> ORGANISM: mosquito baculovirus

<400> SEQUENCE: 60
```

```
Met Arg Arg Ser Ala Ser Ala Arg Ser Ala Ala Cys Arg Pro Ser Ser
 1               5                  10                  15

Ser Arg Ser Thr Ala Ala Ala Thr Pro Cys Gly Pro Leu Asp Arg Arg
            20                  25                  30

Met Arg Arg Ala Arg Ser Arg Arg Ser Ala Gly Ser Gly Arg Thr Ala
            35                  40                  45

Arg Thr Cys Arg Ala
        50
```

<210> SEQ ID NO 61
<211> LENGTH: 1656
<212> TYPE: DNA
<213> ORGANISM: mosquito baculovirus
<220> FEATURE:
<221> NAME/KEY: CDS
<222> LOCATION: (129)...(1412)

<400> SEQUENCE: 61

```
ctgcagatga tggccggcct cttctgggat ctcggcgacg acgcgccgac cgttcgccac        60
gcggcgcccg ccgcggccgg cgccgccctg taacgcgctt cgcccctttc acgggacctg       120 catacgcg atg aat acg acc acc ctg acc tcg cac gaa gcc gcc cgc ccc        170
         Met Asn Thr Thr Thr Leu Thr Ser His Glu Ala Ala Arg Pro
          1               5                  10 agc gcc gcg aag atc cgg cgc atc atc ttc gcg gcg tcg atc ggc aac        218
Ser Ala Ala Lys Ile Arg Arg Ile Ile Phe Ala Ala Ser Ile Gly Asn
 15                  20                  25                  30 gcg ctc gaa tgg ttc gac ctg atc gtc tac ggc ttc ttc gcg gtg acg        266
Ala Leu Glu Trp Phe Asp Leu Ile Val Tyr Gly Phe Phe Ala Val Thr
                 35                  40                  45 atc gcc aag ctg ttc ttc ccc gcc acg agc gaa gcg aca tcg ctg atg        314
Ile Ala Lys Leu Phe Phe Pro Ala Thr Ser Glu Ala Thr Ser Leu Met
         50                  55                  60 ctc acg ctc ggc acg ttc ggg ctg tcc tac ctg atc cgg ccg atc ggc        362
Leu Thr Leu Gly Thr Phe Gly Leu Ser Tyr Leu Ile Arg Pro Ile Gly
     65                  70                  75 ggc ttc gtg ctc ggc gca tac gcc gat cga gcg ggc cgc aag gcg tcg        410
Gly Phe Val Leu Gly Ala Tyr Ala Asp Arg Ala Gly Arg Lys Ala Ser
 80                  85                  90 ctg ctg ctg tcg atc gcg atg atg atg gcc ggc acg ctg ctg atc gcg        458
Leu Leu Leu Ser Ile Ala Met Met Met Ala Gly Thr Leu Leu Ile Ala
 95                 100                 105                 110 ctg atg ccg acc tac gca tcg atc ggc ata ctc gca ccg ctc ggg atc        506
Leu Met Pro Thr Tyr Ala Ser Ile Gly Ile Leu Ala Pro Leu Gly Ile
                115                 120                 125 atg ctg tcg cgg ttg atg cag ggc ttt tcc gcg ggc ggc gaa ttc gcg        554
Met Leu Ser Arg Leu Met Gln Gly Phe Ser Ala Gly Gly Glu Phe Ala
         130                 135                 140 agc tcg acc gcg ttc ctc gtc gag cac gcg ccg cag cgg cgc ggt ttc        602
Ser Ser Thr Ala Phe Leu Val Glu His Ala Pro Gln Arg Arg Gly Phe
     145                 150                 155 atg tcg agc tgg cag ttc gcg agc cag ggc ctc gcg acg ctg ctc gca        650
Met Ser Ser Trp Gln Phe Ala Ser Gln Gly Leu Ala Thr Leu Leu Ala
 160                 165                 170 tcg ggc ttc ggt gcg ctg ctg aca tcc acg ctg acg cct gcg caa ctc        698
Ser Gly Phe Gly Ala Leu Leu Thr Ser Thr Leu Thr Pro Ala Gln Leu
175                 180                 185                 190 gaa agc tgg ggc tgg cgc gtg ccg ttc ctg ttc ggg ctc gcg atc ggc        746
Glu Ser Trp Gly Trp Arg Val Pro Phe Leu Phe Gly Leu Ala Ile Gly
                195                 200                 205
```

-continued

```
ccg gtc ggg ctg tac atc cgc cgt tac gtc gac gaa ggc gtt gaa ttc      794
Pro Val Gly Leu Tyr Ile Arg Arg Tyr Val Asp Glu Gly Val Glu Phe
            210                 215                 220 aag acg cag gca cgc tcc gaa gcg ccg gtg cgc gag ctg ttc gcg gaa      842
Lys Thr Gln Ala Arg Ser Glu Ala Pro Val Arg Glu Leu Phe Ala Glu
            225                 230                 235 caa aag gtg cgg gtg ctg ctg tcg atc ggc gcg ctc gtg atc tcg acc      890
Gln Lys Val Arg Val Leu Leu Ser Ile Gly Ala Leu Val Ile Ser Thr
        240                 245                 250 gcg atc aac tac atg atc ctg tac atg ccg act tac gcg atc aag cag      938
Ala Ile Asn Tyr Met Ile Leu Tyr Met Pro Thr Tyr Ala Ile Lys Gln
255                 260                 265                 270 ctc ggg ctg ccc gcg tcg acg ggt ttc gcg gcg acg ctc gcg acc ggc      986
Leu Gly Leu Pro Ala Ser Thr Gly Phe Ala Ala Thr Leu Ala Thr Gly
                275                 280                 285 ttc gtg ctc acg ctc gtc acg ccg atc gtc ggc cac ctg tcc gat cgc     1034
Phe Val Leu Thr Leu Val Thr Pro Ile Val Gly His Leu Ser Asp Arg
            290                 295                 300 acc ggg cgg atc cgc atg atg gcg gtc gcg gcg gtc ctg atg ctc gtc     1082
Thr Gly Arg Ile Arg Met Met Ala Val Ala Ala Val Leu Met Leu Val
            305                 310                 315 acc gtg tac ccg acg ttc gag tgg ctc acg cgt cac gca tcg ttc gcg     1130
Thr Val Tyr Pro Thr Phe Glu Trp Leu Thr Arg His Ala Ser Phe Ala
        320                 325                 330 acg atg ctc gcg gcg ctg gtc tgg atc ggc gca ttg aag gcg atg tac     1178
Thr Met Leu Ala Ala Leu Val Trp Ile Gly Ala Leu Lys Ala Met Tyr
335                 340                 345                 350 tgc ggc gcg ctg ccg gcg ctg atg gcc gag ctg ttc ccg tcg cag acg     1226
Cys Gly Ala Leu Pro Ala Leu Met Ala Glu Leu Phe Pro Ser Gln Thr
                355                 360                 365 cgc gct acg ggg ctc gcg gtc agc tac aac acg ggt gtc acg ctg ttc     1274
Arg Ala Thr Gly Leu Ala Val Ser Tyr Asn Thr Gly Val Thr Leu Phe
            370                 375                 380 ggc ggc ttc gcg ccg ttc gtc atc acc tgg ctg atc agc gcg acc ggc     1322
Gly Gly Phe Ala Pro Phe Val Ile Thr Trp Leu Ile Ser Ala Thr Gly
            385                 390                 395 aac cgg ctg tcg ccc gcg ctt tat ctg atg ggc tgc gcg gtg ctg agc     1370
Asn Arg Leu Ser Pro Ala Leu Tyr Leu Met Gly Cys Ala Val Leu Ser
400                 405                 410 ctt gcc gcg ttg ttc gtc gcg cgc acg cgg ctc aag atg cgg              1412
Leu Ala Ala Leu Phe Val Ala Arg Thr Arg Leu Lys Met Arg
415                 420                 425 taacgcaaga aacgacggcg cagcgatgcg ccgccggtgc ggcccgccgc ggcgtcgctg    1472
ccgtgcgggc cgtgcgccat ttacggcgcc gggttcggct gcagccactg tccgctgtga    1532
cgataccgac gcccgtaagc tgacgaatca tggtgcgatt agtgcaacgg gccgtaattg    1592
aaacctcctc ctgggcaatg tacagataac ttctgcccag ctcacctatc cgcttcacct    1652
gcag                                                                 1656
```

<210> SEQ ID NO 62
<211> LENGTH: 428
<212> TYPE: PRT
<213> ORGANISM: mosquito baculovirus

<400> SEQUENCE: 62

```
Met Asn Thr Thr Thr Leu Thr Ser His Glu Ala Ala Arg Pro Ser Ala
1               5                   10                  15

Ala Lys Ile Arg Arg Ile Ile Phe Ala Ala Ser Ile Gly Asn Ala Leu
```

```
                 20                  25                  30
Glu Trp Phe Asp Leu Ile Val Tyr Gly Phe Phe Ala Val Thr Ile Ala
                35                  40                  45
Lys Leu Phe Phe Pro Ala Thr Ser Glu Ala Thr Ser Leu Met Leu Thr
 50                  55                  60
Leu Gly Thr Phe Gly Leu Ser Tyr Leu Ile Arg Pro Ile Gly Gly Phe
 65                  70                  75                  80
Val Leu Gly Ala Tyr Ala Asp Arg Ala Gly Arg Lys Ala Ser Leu Leu
                 85                  90                  95
Leu Ser Ile Ala Met Met Met Ala Gly Thr Leu Leu Ile Ala Leu Met
                100                 105                 110
Pro Thr Tyr Ala Ser Ile Gly Ile Leu Ala Pro Leu Gly Ile Met Leu
                115                 120                 125
Ser Arg Leu Met Gln Gly Phe Ser Ala Gly Gly Glu Phe Ala Ser Ser
130                 135                 140
Thr Ala Phe Leu Val Glu His Ala Pro Gln Arg Arg Gly Phe Met Ser
145                 150                 155                 160
Ser Trp Gln Phe Ala Ser Gln Gly Leu Ala Thr Leu Leu Ala Ser Gly
                165                 170                 175
Phe Gly Ala Leu Leu Thr Ser Thr Leu Thr Pro Ala Gln Leu Glu Ser
                180                 185                 190
Trp Gly Trp Arg Val Pro Phe Leu Phe Gly Leu Ala Ile Gly Pro Val
                195                 200                 205
Gly Leu Tyr Ile Arg Arg Tyr Val Asp Glu Gly Val Glu Phe Lys Thr
                210                 215                 220
Gln Ala Arg Ser Glu Ala Pro Val Arg Glu Leu Phe Ala Glu Gln Lys
225                 230                 235                 240
Val Arg Val Leu Leu Ser Ile Gly Ala Leu Val Ile Ser Thr Ala Ile
                245                 250                 255
Asn Tyr Met Ile Leu Tyr Met Pro Thr Tyr Ala Ile Lys Gln Leu Gly
                260                 265                 270
Leu Pro Ala Ser Thr Gly Phe Ala Ala Thr Leu Ala Thr Gly Phe Val
                275                 280                 285
Leu Thr Leu Val Thr Pro Ile Val Gly His Leu Ser Asp Arg Thr Gly
                290                 295                 300
Arg Ile Arg Met Met Ala Val Ala Ala Val Leu Met Leu Val Thr Val
305                 310                 315                 320
Tyr Pro Thr Phe Glu Trp Leu Thr Arg His Ala Ser Phe Ala Thr Met
                325                 330                 335
Leu Ala Ala Leu Val Trp Ile Gly Ala Leu Lys Ala Met Tyr Cys Gly
                340                 345                 350
Ala Leu Pro Ala Leu Met Ala Glu Leu Phe Pro Ser Gln Thr Arg Ala
                355                 360                 365
Thr Gly Leu Ala Val Ser Tyr Asn Thr Gly Val Thr Leu Phe Gly Gly
370                 375                 380
Phe Ala Pro Phe Val Ile Thr Trp Leu Ile Ser Ala Thr Gly Asn Arg
385                 390                 395                 400
Leu Ser Pro Ala Leu Tyr Leu Met Gly Cys Ala Val Leu Ser Leu Ala
                405                 410                 415
Ala Leu Phe Val Ala Arg Thr Arg Leu Lys Met Arg
                420                 425
```

<210> SEQ ID NO 63

```
-continued

<211> LENGTH: 1656
<212> TYPE: DNA
<213> ORGANISM: mosquito baculovirus
<220> FEATURE:
<221> NAME/KEY: CDS
<222> LOCATION: (227)...(787)
<221> NAME/KEY: CDS
<222> LOCATION: (1438)...(1590)

<400> SEQUENCE: 63
ctgcagatga tggccggcct cttctgggat ctcggcgacg acgcgccgac cgttcgccac     60
gcggcgcccg ccgcggccgg cgccgccctg taacgcgctt cgcccctttc acgggacctg    120
catacgcgat gaatacgacc accctgacct cgcacgaagc cgcccgcccc agcgccgcga    180
agatccggcg catcatcttc gcggcgtcga tcggcaacgc gctcga atg gtt cga       235
                                                    Met Val Arg
                                                    1 cct gat cgt cta cgg ctt ctt cgc ggt gac gat cgc caa gct gtt ctt      283
Pro Asp Arg Leu Arg Leu Leu Arg Gly Asp Asp Arg Gln Ala Val Leu
      5                  10                  15 ccc cgc cac gag cga agc gac atc gct gat gct cac gct cgg cac gtt      331
Pro Arg His Glu Arg Ser Asp Ile Ala Asp Ala His Ala Arg His Val
 20                  25                  30                  35 cgg gct gtc cta cct gat ccg gcc gat cgg cgg ctt cgt gct cgg cgc      379
Arg Ala Val Leu Pro Asp Pro Ala Asp Arg Arg Leu Arg Ala Arg Arg
                 40                  45                  50 ata cgc cga tcg agc ggg ccg caa ggc gtc gct gct gct gtc gat cgc      427
Ile Arg Arg Ser Ser Gly Pro Gln Gly Val Ala Ala Ala Val Asp Arg
             55                  60                  65 gat gat gat ggc cgg cac gct gct gat cgc gct gat gcc gac cta cgc      475
Asp Asp Asp Gly Arg His Ala Ala Asp Arg Ala Asp Ala Asp Leu Arg
         70                  75                  80 atc gat cgg cat act cgc acc gct cgg gat cat gct gtc gcg gtt gat      523
Ile Asp Arg His Thr Arg Thr Ala Arg Asp His Ala Val Ala Val Asp
     85                  90                  95 gca ggg ctt ttc cgc ggg cgg cga att cgc gag ctc gac cgc gtt cct      571
Ala Gly Leu Phe Arg Gly Arg Arg Ile Arg Glu Leu Asp Arg Val Pro
100                 105                 110                 115 cgt cga gca cgc gcc gca gcg gcg cgg ttt cat gtc gag ctg gca gtt      619
Arg Arg Ala Arg Ala Ala Ala Arg Phe His Val Glu Leu Ala Val
                 120                 125                 130 cgc gag cca ggg cct cgc gac gct gct cgc atc ggg ctt cgg tgc gct      667
Arg Glu Pro Gly Pro Arg Asp Ala Ala Arg Ile Gly Leu Arg Cys Ala
             135                 140                 145 gct gac atc cac gct gac gcc tgc gca act cga aag ctg ggg ctg gcg      715
Ala Asp Ile His Ala Asp Ala Cys Ala Thr Arg Lys Leu Gly Leu Ala
         150                 155                 160 cgt gcc gtt cct gtt cgg gct cgc gat cgg ccc ggt cgg gct gta cat      763
Arg Ala Val Pro Val Arg Ala Arg Asp Arg Pro Gly Arg Ala Val His
     165                 170                 175 ccg ccg tta cgt cga cga agg cgt tgaattcaag acgcaggcac gctccgaagc     817
Pro Pro Leu Arg Arg Arg Arg Arg
180                 185 gccggtgcgc gagctgttcg cggaacaaaa ggtgcgggtg ctgctgtcga tcggcgcgct    877
cgtgatctcg accgcgatca actacatgat cctgtacatg ccgacttacg cgatcaagca    937
gctcgggctg cccgcgtcga cgggtttcgc ggcgacgctc gcgaccggct cgtgctcac     997 gctcgtcacg ccgatcgtcg gccacctgtc cgatcgcacc gggcggatcc gcatgatggc   1057
ggtcgcggcg gtcctgatgc tcgtcaccgt gtacccgacg ttcgagtggc tcacgcgtca   1117
```

-continued

```
cgcatcgttc gcgacgatgc tcgcggcgct ggtctggatc ggcgcattga aggcgatgta      1177
ctgcggcgcg ctgccggcgc tgatggccga gctgttcccg tcgcagacgc gcgctacggg      1237
gctcgcggtc agctacaaca cgggtgtcac gctgttcggc ggcttcgcgc cgttcgtcat      1297
cacctggctg atcagcgcga ccggcaaccg gctgtcgccc gcgctttatc tgatgggctg      1357
cgcggtgctg agccttgccg cgttgttcgt cgcgcgcacg cggctcaaga tgcggtaacg      1417
caagaaacga cggcgcagcg atg cgc cgc cgg tgc ggc ccg ccg cgg cgt cgc      1470
                     Met Arg Arg Arg Cys Gly Pro Pro Arg Arg Arg
                         190                 195 tgc cgt gcg ggc cgt gcg cca ttt acg gcg ccg ggt tcg gct gca gcc       1518
Cys Arg Ala Gly Arg Ala Pro Phe Thr Ala Pro Gly Ser Ala Ala Ala
200                 205                 210 act gtc cgc tgt gac gat acc gac gcc cgt aag ctg acg aat cat ggt       1566
Thr Val Arg Cys Asp Asp Thr Asp Ala Arg Lys Leu Thr Asn His Gly
215                 220                 225                 230 gcg att agt gca acg ggc cgt aat tgaaacctcc tcctgggcaa tgtacagata      1620
Ala Ile Ser Ala Thr Gly Arg Asn
                235 acttctgccc agctcaccta tccgcttcac ctgcag                               1656
```

<210> SEQ ID NO 64
<211> LENGTH: 187
<212> TYPE: PRT
<213> ORGANISM: mosquito baculovirus

<400> SEQUENCE: 64

```
Met Val Arg Pro Asp Arg Leu Arg Leu Leu Arg Gly Asp Asp Arg Gln
1               5                   10                  15

Ala Val Leu Pro Arg His Glu Arg Ser Asp Ile Ala Asp Ala His Ala
            20                  25                  30

Arg His Val Arg Ala Val Leu Pro Asp Pro Ala Asp Arg Arg Leu Arg
        35                  40                  45

Ala Arg Arg Ile Arg Arg Ser Ser Gly Pro Gln Gly Val Ala Ala Ala
    50                  55                  60

Val Asp Arg Asp Asp Gly Arg His Ala Ala Asp Arg Ala Asp Ala
65                  70                  75                  80

Asp Leu Arg Ile Asp Arg His Thr Arg Thr Ala Arg Asp His Ala Val
                85                  90                  95

Ala Val Asp Ala Gly Leu Phe Arg Gly Arg Ile Arg Glu Leu Asp
            100                 105                 110

Arg Val Pro Arg Arg Ala Arg Ala Ala Ala Arg Phe His Val Glu
        115                 120                 125

Leu Ala Val Arg Glu Pro Gly Pro Arg Asp Ala Ala Arg Ile Gly Leu
    130                 135                 140

Arg Cys Ala Ala Asp Ile His Asp Ala Cys Ala Thr Arg Lys Leu
145                 150                 155                 160

Gly Leu Ala Arg Ala Val Pro Val Arg Ala Arg Asp Arg Pro Gly Arg
                165                 170                 175

Ala Val His Pro Pro Leu Arg Arg Arg Arg Arg
            180                 185
```

<210> SEQ ID NO 65
<211> LENGTH: 51
<212> TYPE: PRT
<213> ORGANISM: mosquito baculovirus

<400> SEQUENCE: 65

-continued

```
Met Arg Arg Arg Cys Gly Pro Pro Arg Arg Arg Cys Arg Ala Gly Arg
 1               5                  10                  15

Ala Pro Phe Thr Ala Pro Gly Ser Ala Ala Ala Thr Val Arg Cys Asp
            20                  25                  30

Asp Thr Asp Ala Arg Lys Leu Thr Asn His Gly Ala Ile Ser Ala Thr
        35                  40                  45

Gly Arg Asn
    50

<210> SEQ ID NO 66
<211> LENGTH: 2227
<212> TYPE: DNA
<213> ORGANISM: mosquito baculovirus
<220> FEATURE:
<221> NAME/KEY: CDS
<222> LOCATION: (222)...(1253)

<400> SEQUENCE: 66
aagcttggcg ccgtgttcga gattctacga taccgcacga cctggaggtg aactttagcg      60
atcccaccag gttggatctg gacaagttgg ggctggggtt gagcttgcgc gcaatttacg     120
ttgcaaatcg gggtttaact ttcgagccgc gaaccgactc acccgagcgt gagtttcgtg     180
aaactagaag gcccactcgg cacaccaacg gtggtcccat a atg cgc ctc gaa gat     236
                                              Met Arg Leu Glu Asp
                                               1               5 gaa ccg agc ctc gag gac cag atg att gat ttt ata aac aat aac cca       284
Glu Pro Ser Leu Glu Asp Gln Met Ile Asp Phe Ile Asn Asn Asn Pro
                10                  15                  20 cta ata tcg agc ctg ctg gtt tca gcg ggt ttc gat ttc ata aac gac       332
Leu Ile Ser Ser Leu Leu Val Ser Ala Gly Phe Asp Phe Ile Asn Asp
            25                  30                  35 ggt ttc cgc gcc ctc atg aag aag gcc atg gtg cgg tac atc ccg atg       380
Gly Phe Arg Ala Leu Met Lys Lys Ala Met Val Arg Tyr Ile Pro Met
        40                  45                  50 ctg caa gcc gcc gca ata cgg ttc ggt gaa ggc ttg aca cgt aaa atg       428
Leu Gln Ala Ala Ala Ile Arg Phe Gly Glu Gly Leu Thr Arg Lys Met
    55                  60                  65 gtc tcg gag gcg ttt cgt gtg ctc atg ttt agc cgc ata aac cag atg       476
Val Ser Glu Ala Phe Arg Val Leu Met Phe Ser Arg Ile Asn Gln Met
 70                  75                  80                  85 gcc gtg cag ctg acc ggc gct cta gcg aag gca att gca cgc ttt ggt       524
Ala Val Gln Leu Thr Gly Ala Leu Ala Lys Ala Ile Ala Arg Phe Gly
                90                  95                 100 gcg atg gcc agt tcg gtg att gga atc gtg ttg ata ttt ttc gtc gca       572
Ala Met Ala Ser Ser Val Ile Gly Ile Val Leu Ile Phe Phe Val Ala
            105                 110                 115 gcc gat ata att ctc atg ttc tgg gac ccg tac ggt tac agc aac atg       620
Ala Asp Ile Ile Leu Met Phe Trp Asp Pro Tyr Gly Tyr Ser Asn Met
        120                 125                 130 ttt ccg ccc gag ttt ctg ggc gat ttg acg ctc aac ttt ctg tcg gcg       668
Phe Pro Pro Glu Phe Leu Gly Asp Leu Thr Leu Asn Phe Leu Ser Ala
    135                 140                 145 ttt ttc gag caa acg ggt acg cga aac gta atc gaa atg ata ccc caa       716
Phe Phe Glu Gln Thr Gly Thr Arg Asn Val Ile Glu Met Ile Pro Gln
150                 155                 160                 165 gcg tac gac tct atg gtg aaa ggt ggt gag gag gat gga ctc tac cta       764
Ala Tyr Asp Ser Met Val Lys Gly Gly Glu Glu Asp Gly Leu Tyr Leu
                170                 175                 180 aca ttt gcc gcc cta caa tac gtg agc cat atg gag gtg aac tcg gac       812
```

```
         Thr Phe Ala Ala Leu Gln Tyr Val Ser His Met Glu Val Asn Ser Asp
                     185                 190                 195 gggcagttgttgctgctacgaacagtaacccaatcaagcaggaggaa                              860
Gly Gln Leu Leu Leu Leu Arg Asn Ser Asn Pro Ile Lys Gln Glu Glu
        200                 205                 210 cttgagccgcacaacctcacggtggccctcttcggcgctataaacctg                             908
Leu Glu Pro His Asn Leu Thr Val Ala Leu Phe Gly Ala Ile Asn Leu
    215                 220                 225 cagagttatgaggatcttaagcggcatatggccagcgccaaccgggcc                             956
Gln Ser Tyr Glu Asp Leu Lys Arg His Met Ala Ser Ala Asn Arg Ala
230                 235                 240                 245 ttcggtatagaccccgaaacgttgcagcaagtggccccgtggagagat                            1004
Phe Gly Ile Asp Pro Glu Thr Leu Gln Gln Val Ala Pro Trp Arg Asp
                250                 255                 260 agacccgggacagtaattcagctggcgtcctagttgcgcttgtggtc                             1052
Arg Pro Gly Thr Val Ile Ser Ala Gly Val Leu Val Ala Leu Val Val
            265                 270                 275 gttttgaccgggagtcaacttttcagcacaaaagcgcccgatctagct                            1100
Val Leu Thr Gly Ser Gln Leu Phe Ser Thr Lys Ala Pro Asp Leu Ala
        280                 285                 290 acggtggtgctcattgtaattctggtggccatagtgataatcgtgcta                            1148
Thr Val Val Leu Ile Val Ile Leu Val Ala Ile Val Ile Ile Val Leu
    295                 300                 305 caactcgaccgtataacacccctggccgacttgccatcgtaaagcat                             1196
Gln Leu Asp Arg Ile Thr Pro Leu Ala Arg Leu Ala Ile Val Lys His
310                 315                 320                 325 gaagagaacgagaaaaatcgcgtcggccaacgcttcgccggactgctt                            1244
Glu Glu Asn Glu Lys Asn Arg Val Gly Gln Arg Phe Ala Gly Leu Leu
                330                 335                 340 agacgtgct tgagcaccgc tacctaacgg tggacctgcc cagctcgatg               1293
Arg Arg Ala gaattttgcg cgaaaccgtt tgcgtatcac gtggtggccg tacacggctt cgtggacgtg   1353
agcaactgcg cgctggatgt gaccgtacgc gcacccagaa gctgtatccc ggaccgcata   1413
gacctggagg ttaatttgcg cgtgtacaca aaggtggaca atttttttgc cgcactgatc   1473
cgacggccgg aaagtgggca aagtcggac gagctgtgca acccgtatt gggctacttt    1533 atggaagtgg tgtacggaaa ccggctaccg ttgacgaaat accagcgcga gaaaatgaaa   1593 cttttttgtaa tgaacgcgat tcaccagcgc agggagcact gggctacct gtatcgggta  1653 cacctgaagg gtacggatgc gctgagaacc tttaccgagc acatgatgga ataaccgtc   1713 gagcgcaagt tggaggacgg gtttccactg ggcccaatt tggtaaccct ttggacgcag   1773
gactttcaga aggcgctcaa cgctaagcga cacatctacg gtgccgcggg cgaggaagac   1833
acctgcggct gggatccgga aattttcatc gaactaaagc ccgccgcact gccagattta   1893
cgcttcatga ccgtgtacaa gaaccacaag aagcggcatc cgctgctggt gctggaaacg   1953
agcagtgcaa cgaattcgca aattttttgca aactattgcg aggagcgcgg tttgaggtgt   2013
tgggtcaaca gcaggaacaa ctgcctggtg gccgtgggca cagatggagt caacttggat   2073
tcattggccg catttttaga tagttgtggt cgaccaatta ggccggcatt tcacacgaac   2133
gtgtaccaat ttctcgaacg tggacggcca gatttgttct tggcaacgc actgttttac    2193 aactttacc gatactctgg ccggttaacg gtga                                2227
```

<210> SEQ ID NO 67
<211> LENGTH: 344
<212> TYPE: PRT
<213> ORGANISM: mosquito baculovirus

```
<400> SEQUENCE: 67

Met Arg Leu Glu Asp Glu Pro Ser Leu Glu Asp Gln Met Ile Asp Phe
 1               5                  10                  15

Ile Asn Asn Asn Pro Leu Ile Ser Ser Leu Leu Val Ser Ala Gly Phe
            20                  25                  30

Asp Phe Ile Asn Asp Gly Phe Arg Ala Leu Met Lys Lys Ala Met Val
        35                  40                  45

Arg Tyr Ile Pro Met Leu Gln Ala Ala Ile Arg Phe Gly Glu Gly
    50                  55                  60

Leu Thr Arg Lys Met Val Ser Glu Ala Phe Arg Val Leu Met Phe Ser
65                  70                  75                  80

Arg Ile Asn Gln Met Ala Val Gln Leu Thr Gly Ala Leu Ala Lys Ala
                85                  90                  95

Ile Ala Arg Phe Gly Ala Met Ala Ser Ser Val Ile Gly Ile Val Leu
            100                 105                 110

Ile Phe Phe Val Ala Ala Asp Ile Ile Leu Met Phe Trp Asp Pro Tyr
        115                 120                 125

Gly Tyr Ser Asn Met Phe Pro Pro Glu Phe Leu Gly Asp Leu Thr Leu
    130                 135                 140

Asn Phe Leu Ser Ala Phe Phe Gln Thr Gly Thr Arg Asn Val Ile
145                 150                 155                 160

Glu Met Ile Pro Gln Ala Tyr Asp Ser Met Val Lys Gly Gly Glu Glu
                165                 170                 175

Asp Gly Leu Tyr Leu Thr Phe Ala Ala Leu Gln Tyr Val Ser His Met
            180                 185                 190

Glu Val Asn Ser Asp Gly Gln Leu Leu Leu Arg Asn Ser Asn Pro
        195                 200                 205

Ile Lys Gln Glu Glu Leu Glu Pro His Asn Leu Thr Val Ala Leu Phe
    210                 215                 220

Gly Ala Ile Asn Leu Gln Ser Tyr Glu Asp Leu Lys Arg His Met Ala
225                 230                 235                 240

Ser Ala Asn Arg Ala Phe Gly Ile Asp Pro Glu Thr Leu Gln Gln Val
                245                 250                 255

Ala Pro Trp Arg Asp Arg Pro Gly Thr Val Ile Ser Ala Gly Val Leu
            260                 265                 270

Val Ala Leu Val Val Val Leu Thr Gly Ser Gln Leu Phe Ser Thr Lys
        275                 280                 285

Ala Pro Asp Leu Ala Thr Val Val Leu Ile Val Ile Leu Val Ala Ile
    290                 295                 300

Val Ile Ile Val Leu Gln Leu Asp Arg Ile Thr Pro Leu Ala Arg Leu
305                 310                 315                 320

Ala Ile Val Lys His Glu Glu Asn Glu Lys Asn Arg Val Gly Gln Arg
                325                 330                 335

Phe Ala Gly Leu Leu Arg Arg Ala
            340

<210> SEQ ID NO 68
<211> LENGTH: 2227
<212> TYPE: DNA
<213> ORGANISM: mosquito baculovirus
<220> FEATURE:
<221> NAME/KEY: CDS
<222> LOCATION: (1195)...(2223)

<400> SEQUENCE: 68
```

```
aagcttggcg ccgtgttcga gattctacga taccgcacga cctggaggtg aactttagcg      60
atcccaccag gttggatctg acaagttgg ggctggggtt gagcttgcgc gcaatttacg     120
ttgcaaatcg gggtttaact ttcgagccgc gaaccgactc acccgagcgt gagtttcgtg     180
aaactagaag gcccactcgg cacaccaacg gtggtcccat aatgcgcctc gaagatgaac     240
cgagcctcga ggaccagatg attgatttta taaacaataa cccactaata tcgagcctgc     300
tggtttcagc gggtttcgat ttcataaacg acggtttccg cgccctcatg aagaaggcca     360
tggtgcggta catcccgatg ctgcaagccg ccgcaatacg gttcggtgaa ggcttgacac     420
gtaaaatggt ctcggaggcg tttcgtgtgc tcatgtttag ccgcataaac cagatggccg     480
tgcagctgac cggcgctcta gcgaaggcaa ttgcacgctt tggtgcgatg gccagttcgg     540
tgattggaat cgtgttgata ttttcgtcg cagccgatat aattctcatg ttctgggacc     600
cgtacggtta cagcaacatg tttccgcccg agtttctggg cgatttgacg ctcaactttc     660
tgtcggcgtt tttcgagcaa acgggtacgc gaaacgtaat cgaaatgata ccccaagcgt     720
acgactctat ggtgaaaggt ggtgaggagg atggactcta cctaacattt gccgccctac     780
aatacgtgag ccatatggag gtgaactcgg acgggcagtt gttgctgcta cgaaacagta     840
acccaatcaa gcaggaggaa cttgagccgc acaacctcac ggtggccctc ttcggcgcta     900
taaacctgca gagttatgag gatcttaagc ggcatatggc cagcgccaac cgggccttcg     960
gtatagaccc cgaaacgttg cagcaagtgg ccccgtggag agatagaccc gggacagtaa    1020
tttcagctgg cgtcctagtt gcgcttgtgg tcgttttgac cgggagtcaa cttttcagca    1080
caaaagcgcc cgatctagct acggtggtgc tcattgtaat tctggtggcc atagtgataa    1140
tcgtgctaca actcgaccgt ataacacccc tggcccgact tgccatcgta aagc atg     1197
                                                               Met
                                                                1 aag aga acg aga aaa atc gcg tcg gcc aac gct tcg ccg gac tgc tta    1245
Lys Arg Thr Arg Lys Ile Ala Ser Ala Asn Ala Ser Pro Asp Cys Leu
         5                  10                  15 gac gtg ctt gag cac cgc tac cta acg gtg gac ctg ccc agc tcg atg    1293
Asp Val Leu Glu His Arg Tyr Leu Thr Val Asp Leu Pro Ser Ser Met
             20                  25                  30 gaa ttt tgc gcg aaa ccg ttt gcg tat cac gtg gtg gcc gta cac ggc    1341
Glu Phe Cys Ala Lys Pro Phe Ala Tyr His Val Val Ala Val His Gly
 35                  40                  45 ttc gtg gac gtg agc aac tgc gcg ctg gat gtg acc gta cgc gca ccc    1389
Phe Val Asp Val Ser Asn Cys Ala Leu Asp Val Thr Val Arg Ala Pro
 50                  55                  60                  65 aga agc tgt atc ccg gac cgc ata gac ctg gag gtt aat ttg cgc gtg    1437
Arg Ser Cys Ile Pro Asp Arg Ile Asp Leu Glu Val Asn Leu Arg Val
                 70                  75                  80 tac aca aag gtg gac gaa ttt ttt gcc gca ctg atc cga cgg ccg gaa    1485
Tyr Thr Lys Val Asp Glu Phe Phe Ala Ala Leu Ile Arg Arg Pro Glu
             85                  90                  95 agt ggg cac aag tcg gac gag ctg tgc aaa ccc gta ttg ggc tac ttt    1533
Ser Gly His Lys Ser Asp Glu Leu Cys Lys Pro Val Leu Gly Tyr Phe
            100                 105                 110 atg gaa gtg gtg tac gga aac cgg cta ccg ttg acg aaa tac cag cgc    1581
Met Glu Val Val Tyr Gly Asn Arg Leu Pro Leu Thr Lys Tyr Gln Arg
        115                 120                 125 gag aaa atg aaa ctt ttt gta atg aac gcg att cac cag cgc agg gag    1629
Glu Lys Met Lys Leu Phe Val Met Asn Ala Ile His Gln Arg Arg Glu
130                 135                 140                 145
```

| | | | | | | | | | | | | | | | |
|---|---|---|---|---|---|---|---|---|---|---|---|---|---|---|---|
| cac | ttg | ggc | tac | ctg | tat | cgg | gta | cac | ctg | aag | ggt | acg | gat | gcg | ctg | 1677 |
| His | Leu | Gly | Tyr | Leu | Tyr | Arg | Val | His | Leu | Lys | Gly | Thr | Asp | Ala | Leu |
| | | | | 150 | | | | | 155 | | | | | 160 | |

```
cac ttg ggc tac ctg tat cgg gta cac ctg aag ggt acg gat gcg ctg       1677
His Leu Gly Tyr Leu Tyr Arg Val His Leu Lys Gly Thr Asp Ala Leu
                150                 155                 160 aga acc ttt acc gag cac atg atg gaa ata acc gtc gag cgc aag ttg       1725
Arg Thr Phe Thr Glu His Met Met Glu Ile Thr Val Glu Arg Lys Leu
            165                 170                 175 gag gac ggg ttt cca ctg ggg ccc aat ttg gta acc ctt tgg acg cag       1773
Glu Asp Gly Phe Pro Leu Gly Pro Asn Leu Val Thr Leu Trp Thr Gln
        180                 185                 190 gac ttt cag aag gcg ctc aac gct aag cga cac atc tac ggt gcc gcg       1821
Asp Phe Gln Lys Ala Leu Asn Ala Lys Arg His Ile Tyr Gly Ala Ala
    195                 200                 205 ggc gag gaa gac acc tgc ggc tgg gat ccg gaa att ttc atc gaa cta       1869
Gly Glu Glu Asp Thr Cys Gly Trp Asp Pro Glu Ile Phe Ile Glu Leu
210                 215                 220                 225 aag ccc gcc gca ctg cca gat tta cgc ttc atg acc gtg tac aag aac       1917
Lys Pro Ala Ala Leu Pro Asp Leu Arg Phe Met Thr Val Tyr Lys Asn
                230                 235                 240 cac aag aag cgg cat ccg ctg ctg gtg ctg gaa acg agc agt gca acg       1965
His Lys Lys Arg His Pro Leu Leu Val Leu Glu Thr Ser Ser Ala Thr
            245                 250                 255 aat tcg caa att ttt gca aac tat tgc gag gag cgc ggt ttg agg tgt       2013
Asn Ser Gln Ile Phe Ala Asn Tyr Cys Glu Glu Arg Gly Leu Arg Cys
        260                 265                 270 tgg gtc aac agc agg aac aac tgc ctg gtg gcc gtg ggc aca gat gga       2061
Trp Val Asn Ser Arg Asn Asn Cys Leu Val Ala Val Gly Thr Asp Gly
    275                 280                 285 gtc aac ttg gat tca ttg gcc gca ttt tta gat agt tgt ggt cga cca       2109
Val Asn Leu Asp Ser Leu Ala Ala Phe Leu Asp Ser Cys Gly Arg Pro
290                 295                 300                 305 att agg ccg gca ttt cac acg aac gtg tac caa ttt ctc gaa cgt gga       2157
Ile Arg Pro Ala Phe His Thr Asn Val Tyr Gln Phe Leu Glu Arg Gly
                310                 315                 320 cgg cca gat ttg ttc ttt ggc aac gca ctg ttt tac aac ttt tac cga       2205
Arg Pro Asp Leu Phe Phe Gly Asn Ala Leu Phe Tyr Asn Phe Tyr Arg
            325                 330                 335 tac tct ggc cgg tta acg gtga                                          2227
Tyr Ser Gly Arg Leu Thr
        340
```

<210> SEQ ID NO 69
<211> LENGTH: 343
<212> TYPE: PRT
<213> ORGANISM: mosquito baculovirus

<400> SEQUENCE: 69

```
Met Lys Arg Thr Arg Lys Ile Ala Ser Ala Asn Ala Ser Pro Asp Cys
 1               5                  10                  15

Leu Asp Val Leu Glu His Arg Tyr Leu Thr Val Asp Leu Pro Ser Ser
            20                  25                  30

Met Glu Phe Cys Ala Lys Pro Phe Ala Tyr His Val Val Ala Val His
        35                  40                  45

Gly Phe Val Asp Val Ser Asn Cys Ala Leu Asp Val Thr Val Arg Ala
    50                  55                  60

Pro Arg Ser Cys Ile Pro Asp Arg Ile Asp Leu Glu Val Asn Leu Arg
65                  70                  75                  80

Val Tyr Thr Lys Val Asp Glu Phe Phe Ala Ala Leu Ile Arg Arg Pro
                85                  90                  95

Glu Ser Gly His Lys Ser Asp Glu Leu Cys Lys Pro Val Leu Gly Tyr
```

-continued

```
                   100                 105                 110
Phe Met Glu Val Val Tyr Gly Asn Arg Leu Pro Leu Thr Lys Tyr Gln
        115                 120                 125
Arg Glu Lys Met Lys Leu Phe Val Met Asn Ala Ile His Gln Arg Arg
    130                 135                 140
Glu His Leu Gly Tyr Leu Tyr Arg Val His Leu Lys Gly Thr Asp Ala
145                 150                 155                 160
Leu Arg Thr Phe Thr Glu His Met Met Glu Ile Thr Val Glu Arg Lys
                165                 170                 175
Leu Glu Asp Gly Phe Pro Leu Gly Pro Asn Leu Val Thr Leu Trp Thr
            180                 185                 190
Gln Asp Phe Gln Lys Ala Leu Asn Ala Lys Arg His Ile Tyr Gly Ala
        195                 200                 205
Ala Gly Glu Glu Asp Thr Cys Gly Trp Asp Pro Glu Ile Phe Ile Glu
    210                 215                 220
Leu Lys Pro Ala Ala Leu Pro Asp Leu Arg Phe Met Thr Val Tyr Lys
225                 230                 235                 240
Asn His Lys Lys Arg His Pro Leu Leu Val Leu Glu Thr Ser Ser Ala
                245                 250                 255
Thr Asn Ser Gln Ile Phe Ala Asn Tyr Cys Glu Glu Arg Gly Leu Arg
            260                 265                 270
Cys Trp Val Asn Ser Arg Asn Asn Cys Leu Val Ala Val Gly Thr Asp
        275                 280                 285
Gly Val Asn Leu Asp Ser Leu Ala Ala Phe Leu Asp Ser Cys Gly Arg
    290                 295                 300
Pro Ile Arg Pro Ala Phe His Thr Asn Val Tyr Gln Phe Leu Glu Arg
305                 310                 315                 320
Gly Arg Pro Asp Leu Phe Phe Gly Asn Ala Leu Phe Tyr Asn Phe Tyr
                325                 330                 335
Arg Tyr Ser Gly Arg Leu Thr
            340

<210> SEQ ID NO 70
<211> LENGTH: 2227
<212> TYPE: DNA
<213> ORGANISM: mosquito baculovirus
<220> FEATURE:
<221> NAME/KEY: CDS
<222> LOCATION: (1639)...(2109)

<400> SEQUENCE: 70
tcaccgttaa ccggccagag tatcggtaaa agttgtaaaa cagtgcgttg ccaaagaaca      60
aatctggccg tccacgttcg agaaattggt acacgttcgt gtgaaatgcc ggcctaattg     120
gtcgaccaca actatctaaa aatgcggcca atgaatccaa gttgactcca tctgtgccca     180
cggccaccag gcagttgttc ctgctgttga cccaacacct caaaccgcgc tcctcgcaat     240
agtttgcaaa aatttgcgaa ttcgttgcac tgctcgtttc cagcaccagc agcggatgcc     300
gcttcttgtg gttcttgtac acggtcatga agcgtaaatc tggcagtgcg gcgggcttta     360
gttcgatgaa aatttccgga tcccagccgc aggtgtcttc ctcgcccgcg caccgtaga      420 tgtgtcgctt agcgttgagc gccttctgaa agtcctgcgt ccaagggggtt accaaattgg     480 gccccagtgg aaaccgtcc tccaacttgc gctcgacggt tatttccatc atgtgctcgg      540
taaaggttct cagcgcatcc gtaccttca ggtgtacccg atacaggtag cccaagtgct      600
ccctgcgctg gtgaatcgcg ttcattacaa aagtttcat tttctcgcgc tggtatttcg      660
```

```
tcaacggtag ccggtttccg tacaccactt ccataaagta gcccaatacg ggtttgcaca      720
gctcgtccga cttgtgccca ctttccggcc gtcggatcag tgcggcaaaa aattcgtcca      780
cctttgtgta cacgcgcaaa ttaacctcca ggtctatgcg gtccgggata cagcttctgg      840
gtgcgcgtac ggtcacatcc agcgcgcagt tgctcacgtc cacgaagccg tgtacggcca      900
ccacgtgata cgcaaacggt ttcgcgcaaa attccatcga gctgggcagg tccaccgtta      960
ggtagcggtg ctcaagcacg tctaagcagt ccggcgaagc gttggccgac gcgatttttc     1020
tcgttctctt catgctttac gatggcaagt cgggccaggt gtgttatacg gtcgagttgt     1080
agcacgatta tcactatggc caccagaatt acaatgagca ccaccgtagc tagatcgggc     1140
gcttttgtgc tgaaaagttg actcccggtc aaaacgacca caagcgcaac taggacgcca     1200
gctgaaatta ctgtcccggg tctatctctc cacggggcca cttgctgcaa cgtttcgggg     1260
tctataccga aggcccggtt ggcgctggcc atatgccgct taagatcctc ataactctgc     1320
aggtttatag cgccgaagag ggccaccgtg aggttgtgcg gctcaagttc ctcctgcttg     1380
attgggttac tgtttcgtag cagcaacaac tgcccgtccg agttcacctc catatggctc     1440
acgtattgta gggcggcaaa tgttaggtag agtccatcct cctcaccacc tttcaccata     1500
gagtcgtacg cttggggtat catttcgatt acgtttcgcg tacccgtttg ctcgaaaaac     1560
gccgacagaa agttgagcgt caaatcgccc agaaactcgg gcggaaacat gttgctgtaa     1620
ccgtacgggt cccagaac atg aga att ata tcg gct gcg acg aaa aat atc        1671
                    Met Arg Ile Ile Ser Ala Ala Thr Lys Asn Ile
                      1               5                  10 aac acg att cca atc acc gaa ctg gcc atc gca cca aag cgt gca att        1719
Asn Thr Ile Pro Ile Thr Glu Leu Ala Ile Ala Pro Lys Arg Ala Ile
            15                  20                  25 gcc ttc gct aga gcg ccg gtc agc tgc acg gcc atc tgg ttt atg cgg        1767
Ala Phe Ala Arg Ala Pro Val Ser Cys Thr Ala Ile Trp Phe Met Arg
     30                  35                  40 cta aac atg agc aca cga aac gcc tcc gag acc att tta cgt gtc aag        1815
Leu Asn Met Ser Thr Arg Asn Ala Ser Glu Thr Ile Leu Arg Val Lys
 45                  50                  55 cct tca ccg aac cgt att gcg gcg gct tgc agc atc ggg atg tac cgc        1863
Pro Ser Pro Asn Arg Ile Ala Ala Ala Cys Ser Ile Gly Met Tyr Arg
 60                  65                  70                  75 acc atg gcc ttc ttc atg agg gcg cgg aaa ccg tcg ttt atg aaa tcg        1911
Thr Met Ala Phe Phe Met Arg Ala Arg Lys Pro Ser Phe Met Lys Ser
             80                  85                  90 aaa ccc gct gaa acc agc agg ctc gat att agt ggg tta ttg ttt ata        1959
Lys Pro Ala Glu Thr Ser Arg Leu Asp Ile Ser Gly Leu Leu Phe Ile
     95                 100                 105 aaa tca atc atc tgg tcc tcg agg ctc ggt tca tct tcg agg cgc att        2007
Lys Ser Ile Ile Trp Ser Ser Arg Leu Gly Ser Ser Arg Arg Ile
 110                 115                 120 atg gga cca ccg ttg gtg tgc cga gtg ggc ctt cta gtt tca cga aac        2055
Met Gly Pro Pro Leu Val Cys Arg Val Gly Leu Leu Val Ser Arg Asn
             125                 130                 135 tca cgc tcg ggt gag tcg gtt cgc ggc tcg aaa gtt aaa ccc cga ttt        2103
Ser Arg Ser Gly Glu Ser Val Arg Gly Ser Lys Val Lys Pro Arg Phe
 140                 145                 150                 155 gca acg taaattgcgc gcaagctcaa ccccagcccc aacttgtcca gatccaacct        2159
Ala Thr ggtgggatcg ctaaagttca cctccaggtc gtgcggtatc gtagaatctc gaacacggcg     2219
ccaagctt                                                              2227
```

-continued

```
<210> SEQ ID NO 71
<211> LENGTH: 157
<212> TYPE: PRT
<213> ORGANISM: mosquito baculovirus

<400> SEQUENCE: 71

Met Arg Ile Ile Ser Ala Ala Thr Lys Asn Ile Asn Thr Ile Pro Ile
 1               5                  10                  15

Thr Glu Leu Ala Ile Ala Pro Lys Arg Ala Ile Ala Phe Ala Arg Ala
            20                  25                  30

Pro Val Ser Cys Thr Ala Ile Trp Phe Met Arg Leu Asn Met Ser Thr
        35                  40                  45

Arg Asn Ala Ser Glu Thr Ile Leu Arg Val Lys Pro Ser Pro Asn Arg
    50                  55                  60

Ile Ala Ala Ala Cys Ser Ile Gly Met Tyr Arg Thr Met Ala Phe Phe
65                  70                  75                  80

Met Arg Ala Arg Lys Pro Ser Phe Met Lys Ser Lys Pro Ala Glu Thr
                85                  90                  95

Ser Arg Leu Asp Ile Ser Gly Leu Leu Phe Ile Lys Ser Ile Ile Trp
            100                 105                 110

Ser Ser Arg Leu Gly Ser Ser Ser Arg Arg Ile Met Gly Pro Pro Leu
        115                 120                 125

Val Cys Arg Val Gly Leu Leu Val Ser Arg Asn Ser Arg Ser Gly Glu
    130                 135                 140

Ser Val Arg Gly Ser Lys Val Lys Pro Arg Phe Ala Thr
145                 150                 155

<210> SEQ ID NO 72
<211> LENGTH: 827
<212> TYPE: DNA
<213> ORGANISM: mosquito baculovirus
<220> FEATURE:
<221> NAME/KEY: CDS
<222> LOCATION: (256)...(693)

<400> SEQUENCE: 72
aagcttgacg gtgttcgggg caaggcgatc gttgagcccc acgagggcca ccaccggatc      60
caccttgcgc tggacgatga gcgtggattt ttgttctcgt tacccggcgg cttgcacgac     120
cgggcgtggg tttcacgggc ggggctaacg ctgctgcagg tcgagtacgt ggaacagatt     180
gaaacctttt tcgtcgtgga cgtgcttggt gtgcacggct ttggctacct gtacggcggc     240
tgttacgttg acgag atg caa aat tac cgc agc tta acg ttg gac tcg atc      291
                 Met Gln Asn Tyr Arg Ser Leu Thr Leu Asp Ser Ile
                  1               5                  10 acc atg ctt cgt tcg ggc aac ctg gcc gac aag ttg acc ctg tac gac       339
Thr Met Leu Arg Ser Gly Asn Leu Ala Asp Lys Leu Thr Leu Tyr Asp
         15                  20                  25 cac att gac cac tcg cca aca atg tac agc ttg gcg aca caa ttt ttc       387
His Ile Asp His Ser Pro Thr Met Tyr Ser Leu Ala Thr Gln Phe Phe
     30                  35                  40 gtc cgc ggt aaa cgg gcc aac agt acg ctc gcg gac ccc atg ggt gaa       435
Val Arg Gly Lys Arg Ala Asn Ser Thr Leu Ala Asp Pro Met Gly Glu
 45                  50                  55                  60 cag ttt tgg cac gcg cac gga gca cca ctg gac ggc cgt atc gtg gta       483
Gln Phe Trp His Ala His Gly Ala Pro Leu Asp Gly Arg Ile Val Val
                 65                  70                  75 act aga agt ggg gac cta tac aag tta aag tgt gaa aaa tcg tac gaa       531
```

```
Thr Arg Ser Gly Asp Leu Tyr Lys Leu Lys Cys Glu Lys Ser Tyr Glu
                80                  85                  90 ctt cga ttc aac gga gcc caa ctc gag gat gcg gtc ggg aaa acg ttc      579
Leu Arg Phe Asn Gly Ala Gln Leu Glu Asp Ala Val Gly Lys Thr Phe
         95                 100                 105 att ccg agt cgg gtt gac ctc gag ccc gac acc atc tac gag tgt act      627
Ile Pro Ser Arg Val Asp Leu Glu Pro Asp Thr Ile Tyr Glu Cys Thr
    110                 115                 120 atc gtg gac aat ttt gcc acg gtt aag cgg gcc agg ttg gac agg gct      675
Ile Val Asp Asn Phe Ala Thr Val Lys Arg Ala Arg Leu Asp Arg Ala
125                 130                 135                 140 acg gcg aat acg gtt gaa taaagagtaa attgttatta ttaatacact             723
Thr Ala Asn Thr Val Glu
                145 tgttgttggt tttcattcaa atagaaggga agaaataaa gtttatcctc agtgaggctc     783 gaggttgtcc gactgggtgg tggtcgtcag ggcgaataa gctt                      827

<210> SEQ ID NO 73
<211> LENGTH: 146
<212> TYPE: PRT
<213> ORGANISM: mosquito baculovirus

<400> SEQUENCE: 73

Met Gln Asn Tyr Arg Ser Leu Thr Leu Asp Ser Ile Thr Met Leu Arg
 1               5                  10                  15

Ser Gly Asn Leu Ala Asp Lys Leu Thr Leu Tyr Asp His Ile Asp His
                20                  25                  30

Ser Pro Thr Met Tyr Ser Leu Ala Thr Gln Phe Phe Val Arg Gly Lys
             35                  40                  45

Arg Ala Asn Ser Thr Leu Ala Asp Pro Met Gly Glu Gln Phe Trp His
         50                  55                  60

Ala His Gly Ala Pro Leu Asp Gly Arg Ile Val Val Thr Arg Ser Gly
 65                  70                  75                  80

Asp Leu Tyr Lys Leu Lys Cys Glu Lys Ser Tyr Glu Leu Arg Phe Asn
                 85                  90                  95

Gly Ala Gln Leu Glu Asp Ala Val Gly Lys Thr Phe Ile Pro Ser Arg
            100                 105                 110

Val Asp Leu Glu Pro Asp Thr Ile Tyr Glu Cys Thr Ile Val Asp Asn
        115                 120                 125

Phe Ala Thr Val Lys Arg Ala Arg Leu Asp Arg Ala Thr Ala Asn Thr
    130                 135                 140

Val Glu
145

<210> SEQ ID NO 74
<211> LENGTH: 827
<212> TYPE: DNA
<213> ORGANISM: mosquito baculovirus
<220> FEATURE:
<221> NAME/KEY: CDS
<222> LOCATION: (214)...(561)

<400> SEQUENCE: 74
aagcttattc gcccctgacg accaccaccc agtcggacaa cctcgagcct cactgaggat     60
aaactttatt tctttccctt ctatttgaat gaaaaccaac aacaagtgta ttaataataa    120
caatttactc tttattcaac cgtattcgcc gtagccctgt ccaacctggc ccgcttaacc    180
gtggcaaaat tgtccacgat agtcacactc gag atg gtg tcg ggc tcg agg tca    234
```

```
                        Met Val Ser Gly Ser Arg Ser
                          1               5
acc cga ctc gga atg aac gtt ttc ccg acc gca tcc tcg agt tgg gct      282
Thr Arg Leu Gly Met Asn Val Phe Pro Thr Ala Ser Ser Ser Trp Ala
         10                  15                  20 ccg ttg aat cga agt tcg tac gat ttt tca cac ttt aac ttg tat agg      330
Pro Leu Asn Arg Ser Ser Tyr Asp Phe Ser His Phe Asn Leu Tyr Arg
         25                  30                  35 tcc cca ctt cta gtt acc acg ata cgg ccg tcc agt ggt gct ccg tgc      378
Ser Pro Leu Leu Val Thr Thr Ile Arg Pro Ser Ser Gly Ala Pro Cys
 40                  45                  50                  55 gcg tgc caa aac tgt tca ccc atg ggg tcc gcg agc gta ctg ttg gcc      426
Ala Cys Gln Asn Cys Ser Pro Met Gly Ser Ala Ser Val Leu Leu Ala
                 60                  65                  70 cgt tta ccg cgg acg aaa aat tgt gtc gcc aag ctg tac att gtt ggc      474
Arg Leu Pro Arg Thr Lys Asn Cys Val Ala Lys Leu Tyr Ile Val Gly
             75                  80                  85 gag tgg tca atg tgg tcg tac agg gtc aac ttg tcg gcc agg ttg ccc      522
Glu Trp Ser Met Trp Ser Tyr Arg Val Asn Leu Ser Ala Arg Leu Pro
         90                  95                 100 gaa cga agc atg gtg atc gag tcc aac gtt aag ctg cgg taattttgca       571
Glu Arg Ser Met Val Ile Glu Ser Asn Val Lys Leu Arg
        105                 110                 115 tctcgtcaac gtaacagccg ccgtacaggt agccaaagcc gtgcacacca agcacgtcca    631
cgacgaaaaa ggtttcaatc tgttccacgt actcgacctg cagcagcgtt agccccgccc    691
gtgaaaccca cgcccggtcg tgcaagccgc cgggtaacga aacaaaaat ccacgctcat     751 cgtccagcgc aaggtggatc cggtggtggc cctcgtgggg ctcaacgatc gccttgcccc    811
gaacaccgtc aagctt                                                    827

<210> SEQ ID NO 75
<211> LENGTH: 116
<212> TYPE: PRT
<213> ORGANISM: mosquito baculovirus

<400> SEQUENCE: 75

Met Val Ser Gly Ser Arg Ser Thr Arg Leu Gly Met Asn Val Phe Pro
 1               5                  10                  15

Thr Ala Ser Ser Ser Trp Ala Pro Leu Asn Arg Ser Ser Tyr Asp Phe
             20                  25                  30

Ser His Phe Asn Leu Tyr Arg Ser Pro Leu Leu Val Thr Thr Ile Arg
         35                  40                  45

Pro Ser Ser Gly Ala Pro Cys Ala Cys Gln Asn Cys Ser Pro Met Gly
 50                  55                  60

Ser Ala Ser Val Leu Leu Ala Arg Leu Pro Arg Thr Lys Asn Cys Val
65                  70                  75                  80

Ala Lys Leu Tyr Ile Val Gly Glu Trp Ser Met Trp Ser Tyr Arg Val
                 85                  90                  95

Asn Leu Ser Ala Arg Leu Pro Arg Ser Met Val Ile Glu Ser Asn
             100                 105                 110

Val Lys Leu Arg
        115

<210> SEQ ID NO 76
<211> LENGTH: 692
<212> TYPE: DNA
<213> ORGANISM: mosquito baculovirus
<220> FEATURE:
```

```
<221> NAME/KEY: CDS
<222> LOCATION: (27)...(689)

<400> SEQUENCE: 76
gaattcaatg tgatgaagcc cgaccg atg tcc cag ctc ctg ctc aac ccc aag         53
                              Met Ser Gln Leu Leu Leu Asn Pro Lys
                                1               5 ccc ctg gta tcg gaa ctg gaa gcc ccg atg gtt ggt caa ctt gtg ggt         101
Pro Leu Val Ser Glu Leu Glu Ala Pro Met Val Gly Gln Leu Val Gly
 10              15                  20                  25 aat acg gaa atc gag caa aaa atc gta cga act gtt gcc agc gaa tat         149
Asn Thr Glu Ile Glu Gln Lys Ile Val Arg Thr Val Ala Ser Glu Tyr
                 30                  35                  40 gca gct cat cga cat cta att cgg cgc tgc ctg atg ccg ttt cgg cag         197
Ala Ala His Arg His Leu Ile Arg Arg Cys Leu Met Pro Phe Arg Gln
             45                  50                  55 aac gtt ctg cag ggt tgc tac aac gaa gtc gta cgg tac gtc gtc gag         245
Asn Val Leu Gln Gly Cys Tyr Asn Glu Val Val Arg Tyr Val Val Glu
         60                  65                  70 att caa acc agc cgc ata cta ttt tac cag cac gac ttg gaa cat tat         293
Ile Gln Thr Ser Arg Ile Leu Phe Tyr Gln His Asp Leu Glu His Tyr
     75                  80                  85 tgt gtg gtc agc aag ccg ccc cac ttg gcc tca cac tac ggc gac tgc         341
Cys Val Val Ser Lys Pro Pro His Leu Ala Ser His Tyr Gly Asp Cys
 90                  95                 100                 105 tat tgc gag gtc aac ctg agc tcc aca ccg atg gtg aca ctg gat gtg         389
Tyr Cys Glu Val Asn Leu Ser Ser Thr Pro Met Val Thr Leu Asp Val
                110                 115                 120 gcg cga gag ttt gtg agc ccg ctg ctg ttg gat gaa att tgc aaa cag         437
Ala Arg Glu Phe Val Ser Pro Leu Leu Leu Asp Glu Ile Cys Lys Gln
            125                 130                 135 gtt aac ttt ccg gtg cac agc gag ccc cag ttg tcc gca tat ctg tac         485
Val Asn Phe Pro Val His Ser Glu Pro Gln Leu Ser Ala Tyr Leu Tyr
        140                 145                 150 aca ata cga att gca ggt aag ttt gta cgt gtg act cac gtt cgc aac         533
Thr Ile Arg Ile Ala Gly Lys Phe Val Arg Val Thr His Val Arg Asn
    155                 160                 165 gag tat tgg tac tgc gtg gcg gac ctg aag ctg gcg gtc gac gga aca         581
Glu Tyr Trp Tyr Cys Val Ala Asp Leu Lys Leu Ala Val Asp Gly Thr
170                 175                 180                 185 aaa acg cgc aaa ctg ttc gaa ctc caa ccc ggg cac gat ttg cgc cct         629
Lys Thr Arg Lys Leu Phe Glu Leu Gln Pro Gly His Asp Leu Arg Pro
                190                 195                 200 gac gaa tac ccc ttg ctg ttt gtg aat cag cga cac ctg cgg ccc gcc         677
Asp Glu Tyr Pro Leu Leu Phe Val Asn Gln Arg His Leu Arg Pro Ala
            205                 210                 215 aac gac cac gaa ttc                                                     692
Asn Asp His Glu
        220

<210> SEQ ID NO 77
<211> LENGTH: 221
<212> TYPE: PRT
<213> ORGANISM: mosquito baculovirus

<400> SEQUENCE: 77

Met Ser Gln Leu Leu Leu Asn Pro Lys Pro Leu Val Ser Glu Leu Glu
  1               5                  10                  15

Ala Pro Met Val Gly Gln Leu Val Gly Asn Thr Glu Ile Glu Gln Lys
             20                  25                  30
```

-continued

```
Ile Val Arg Thr Val Ala Ser Glu Tyr Ala Ala His Arg His Leu Ile
        35                  40                  45

Arg Arg Cys Leu Met Pro Phe Arg Gln Asn Val Leu Gln Gly Cys Tyr
    50                  55                  60

Asn Glu Val Val Arg Tyr Val Val Glu Ile Gln Thr Ser Arg Ile Leu
65                  70                  75                  80

Phe Tyr Gln His Asp Leu Glu His Tyr Cys Val Val Ser Lys Pro Pro
                85                  90                  95

His Leu Ala Ser His Tyr Gly Asp Cys Tyr Cys Glu Val Asn Leu Ser
            100                 105                 110

Ser Thr Pro Met Val Thr Leu Asp Val Ala Arg Glu Phe Val Ser Pro
        115                 120                 125

Leu Leu Leu Asp Glu Ile Cys Lys Gln Val Asn Phe Pro Val His Ser
    130                 135                 140

Glu Pro Gln Leu Ser Ala Tyr Leu Tyr Thr Ile Arg Ile Ala Gly Lys
145                 150                 155                 160

Phe Val Arg Val Thr His Val Arg Asn Glu Tyr Trp Tyr Cys Val Ala
                165                 170                 175

Asp Leu Lys Leu Ala Val Asp Gly Thr Lys Thr Arg Lys Leu Phe Glu
            180                 185                 190

Leu Gln Pro Gly His Asp Leu Arg Pro Asp Glu Tyr Pro Leu Leu Phe
        195                 200                 205

Val Asn Gln Arg His Leu Arg Pro Ala Asn Asp His Glu
    210                 215                 220

<210> SEQ ID NO 78
<211> LENGTH: 692
<212> TYPE: DNA
<213> ORGANISM: mosquito baculovirus
<220> FEATURE:
<221> NAME/KEY: CDS
<222> LOCATION: (13)...(165)

<400> SEQUENCE: 78
gaattcaatg tg atg aag ccc gac cga tgt ccc agc tcc tgc tca acc cca      51
              Met Lys Pro Asp Arg Cys Pro Ser Ser Cys Ser Thr Pro
                1               5                   10 agc ccc tgg tat cgg aac tgg aag ccc cga tgg ttg gtc aac ttg tgg        99
Ser Pro Trp Tyr Arg Asn Trp Lys Pro Arg Trp Leu Val Asn Leu Trp
     15                  20                  25 gta ata cgg aaa tcg agc aaa aaa tcg tac gaa ctg ttg cca gcg aat       147
Val Ile Arg Lys Ser Ser Lys Lys Ser Tyr Glu Leu Leu Pro Ala Asn
 30                  35                  40                  45 atg cag ctc atc gac atc taattcggcg ctgcctgatg ccgtttcggc             195
Met Gln Leu Ile Asp Ile
                 50 agaacgttct gcagggttgc tacaacgaag tcgtacggta cgtcgtcgag attcaaacca    255 gccgcatact attttaccag cacgacttgg aacattattg tgtggtcagc aagccgcccc    315 acttggcctc acactacggc gactgctatt gcgaggtcaa cctgagctcc acaccgatgg    375 tgacactgga tgtggcgcga gagtttgtga gcccgctgct gttggatgaa atttgcaaac    435 aggttaactt tccggtgcac agcgagcccc agttgtccgc atatctgtac acaatacgaa    495 ttgcaggtaa gtttgtacgt gtgactcacg ttcgcaacga gtattggtac tgcgtggcgg    555 acctgaagct ggcggtcgac ggaacaaaaa cgcgcaaact gttcgaactc caacccgggc    615 acgatttgcg ccctgacgaa taccccttgc tgtttgtgaa tcagcgacac ctgcggcccg    675
```

-continued

```
ccaacgacca cgaattc                                                   692

<210> SEQ ID NO 79
<211> LENGTH: 51
<212> TYPE: PRT
<213> ORGANISM: mosquito baculovirus

<400> SEQUENCE: 79

Met Lys Pro Asp Arg Cys Pro Ser Ser Cys Ser Thr Pro Ser Pro Trp
 1               5                  10                  15

Tyr Arg Asn Trp Lys Pro Arg Trp Leu Val Asn Leu Trp Val Ile Arg
            20                  25                  30

Lys Ser Ser Lys Lys Ser Tyr Glu Leu Leu Pro Ala Asn Met Gln Leu
        35                  40                  45

Ile Asp Ile
    50

<210> SEQ ID NO 80
<211> LENGTH: 692
<212> TYPE: DNA
<213> ORGANISM: mosquito baculovirus
<220> FEATURE:
<221> NAME/KEY: CDS
<222> LOCATION: (1)...(366)
<221> NAME/KEY: CDS
<222> LOCATION: (529)...(690)

<400> SEQUENCE: 80 gaa ttc gtg gtc gtt ggc ggg ccg cag gtg tcg ctg att cac aaa cag       48
Glu Phe Val Val Val Gly Gly Pro Gln Val Ser Leu Ile His Lys Gln
 1               5                  10                  15 caa ggg gta ttc gtc agg gcg caa atc gtg ccc ggg ttg gag ttc gaa       96
Gln Gly Val Phe Val Arg Ala Gln Ile Val Pro Gly Leu Glu Phe Glu
            20                  25                  30 cag ttt gcg cgt ttt tgt tcc gtc gac cgc cag ctt cag gtc cgc cac      144
Gln Phe Ala Arg Phe Cys Ser Val Asp Arg Gln Leu Gln Val Arg His
        35                  40                  45 gca gta cca ata ctc gtt gcg aac gtg agt cac acg tac aaa ctt acc      192
Ala Val Pro Ile Leu Val Ala Asn Val Ser His Thr Tyr Lys Leu Thr
    50                  55                  60 tgc aat tcg tat tgt gta cag ata tgc gga caa ctg ggg ctc gct gtg      240
Cys Asn Ser Tyr Cys Val Gln Ile Cys Gly Gln Leu Gly Leu Ala Val
65                  70                  75                  80 cac cgg aaa gtt aac ctg ttt gca aat ttc atc caa cag cag cgg gct      288
His Arg Lys Val Asn Leu Phe Ala Asn Phe Ile Gln Gln Gln Arg Ala
                85                  90                  95 cac aaa ctc tcg cgc cac atc cag tgt cac cat cgg tgt gga gct cag      336
His Lys Leu Ser Arg His Ile Gln Cys His His Arg Cys Gly Ala Gln
            100                 105                 110 gtt gac ctc gca ata gca gtc gcc gta gtg tgaggccaag tggggcggct        386
Val Asp Leu Ala Ile Ala Val Ala Val Val
        115                 120 tgctgaccac acaataatgt tccaagtcgt gctggtaaaa tagtatgcgg ctggtttgaa    446
tctcgacgac gtaccgtacg acttcgttgt agcaaccctg cagaacgttc tgccgaaacg    506
gcatcaggca gcgccgaatt ag atg tcg atg agc tgc ata ttc gct ggc aac     558
                         Met Ser Met Ser Cys Ile Phe Ala Gly Asn
                                 125                 130 agt tcg tac gat ttt ttg ctc gat ttc cgt att acc cac aag ttg acc      606
Ser Ser Tyr Asp Phe Leu Leu Asp Phe Arg Ile Thr His Lys Leu Thr
        135                 140                 145
```

```
aac cat cgg ggc ttc cag ttc cga tac cag ggg ctt ggg gtt gag cag      654
Asn His Arg Gly Phe Gln Phe Arg Tyr Gln Gly Leu Gly Val Glu Gln
    150                 155                 160 gag ctg gga cat cgg tcg ggc ttc atc aca ttg aat tc                   692
Glu Leu Gly His Arg Ser Gly Phe Ile Thr Leu Asn
165                 170                 175

<210> SEQ ID NO 81
<211> LENGTH: 122
<212> TYPE: PRT
<213> ORGANISM: mosquito baculovirus

<400> SEQUENCE: 81

Glu Phe Val Val Gly Gly Pro Gln Val Ser Leu Ile His Lys Gln
1               5                   10                  15

Gln Gly Val Phe Val Arg Ala Gln Ile Val Pro Gly Leu Glu Phe Glu
            20                  25                  30

Gln Phe Ala Arg Phe Cys Ser Val Asp Arg Gln Leu Gln Val Arg His
        35                  40                  45

Ala Val Pro Ile Leu Val Ala Asn Val Ser His Thr Tyr Lys Leu Thr
    50                  55                  60

Cys Asn Ser Tyr Cys Val Gln Ile Cys Gly Gln Leu Gly Leu Ala Val
65                  70                  75                  80

His Arg Lys Val Asn Leu Phe Ala Asn Phe Ile Gln Gln Arg Ala
                85                  90                  95

His Lys Leu Ser Arg His Ile Gln Cys His His Arg Cys Gly Ala Gln
            100                 105                 110

Val Asp Leu Ala Ile Ala Val Ala Val Val
            115                 120

<210> SEQ ID NO 82
<211> LENGTH: 54
<212> TYPE: PRT
<213> ORGANISM: mosquito baculovirus

<400> SEQUENCE: 82

Met Ser Met Ser Cys Ile Phe Ala Gly Asn Ser Ser Tyr Asp Phe Leu
1               5                   10                  15

Leu Asp Phe Arg Ile Thr His Lys Leu Thr Asn His Arg Gly Phe Gln
            20                  25                  30

Phe Arg Tyr Gln Gly Leu Gly Val Glu Gln Glu Leu Gly His Arg Ser
        35                  40                  45

Gly Phe Ile Thr Leu Asn
    50

<210> SEQ ID NO 83
<211> LENGTH: 3198
<212> TYPE: DNA
<213> ORGANISM: mosquito baculovirus
<220> FEATURE:
<221> NAME/KEY: CDS
<222> LOCATION: (2545)...(3198)
<221> NAME/KEY: CDS
<222> LOCATION: (742)...(1056)
<221> NAME/KEY: CDS
<222> LOCATION: (1837)...(1998)

<400> SEQUENCE: 83
gaattcgcaa tcaagctgcc acttttgccg ctgtagctaa ttgtgcggga taacgagtcc     60
acgctaaagt cctcctcttg aattttacgc aaatcttcaa gcaaaatatc cgtagctaaa    120
```

-continued

```
ctgtacgaaa gggcgccctc ttcgcacaac ttcatcgtat actcgatcca tcgcttgtag    180
caccggacga tggctctggt caaatttctg cccaccaaaa gtccccgata cttgtagata    240
ttgtcggcaa tgtgaaacac gtacgacttt tgcggtgtg taaacacgga cgaccgcaca    300
atcaactcga gcgccatatt ataaccgacg cccacagttt tcgccaatcc agcggaaaaa    360
tgttcaatta aaccgggaaa cgcattcggg tccaccgtta caccgctggt gggctgcata    420
aatttaaaca tgatcgaatc ggtgtctccg taaacgaaaa atgcgcacag gccgtactgc    480
tcattccagt actcggtagt gtaattgacc gctgatcgaa ctttaccgcg gccagttttt    540
gtgataaagt ttcccaacgg tggaaaccgt agcgcaaaga aaccgtacac cgaatttgcg    600
gtgatcttgt acgcaccctg cgcagcgtcg tgcatcatat actcgtacga atccttgtca    660
tactttgccg cctcgctgcg gtgaaattta cgattcttca acgcctcctt tataatcgaa    720
gacgtgaggt tttctttggg c atg ggt acc agc aac aag tcc cca tta ctt    771
                        Met Gly Thr Ser Asn Lys Ser Pro Leu Leu
                         1               5                  10 tcc acc gca atg ttg ttg ggg caa acg cgc tca gcg agc ata atc gaa    819
Ser Thr Ala Met Leu Leu Gly Gln Thr Arg Ser Ala Ser Ile Ile Glu
             15                  20                  25 ggg tac agc gaa tta aag tcc ata atc acc aaa tgt tcg tgc agt ccc    867
Gly Tyr Ser Glu Leu Lys Ser Ile Ile Thr Lys Cys Ser Cys Ser Pro
         30                  35                  40 ggc acc gtt gga agc acc agt cca cct cca att tta gtg tta ccc tgg    915
Gly Thr Val Gly Ser Thr Ser Pro Pro Pro Ile Leu Val Leu Pro Trp
     45                  50                  55 tca ccc caa gtt tgc tgt gcg gtc gag ata cga aac aac gat tta cgc    963
Ser Pro Gln Val Cys Cys Ala Val Glu Ile Arg Asn Asn Asp Leu Arg
 60                  65                  70 tcc agg tca tcg agc tcg tct tgg cgc tcc ggt gaa cgt tta cgc tcc    1011
Ser Arg Ser Ser Ser Ser Trp Arg Ser Gly Glu Arg Leu Arg Ser
 75                  80                  85                  90 tcc tcg atg gca cgc ttg aac gat atg ttt aaa att tcc gca tca         1056
Ser Ser Met Ala Arg Leu Asn Asp Met Phe Lys Ile Ser Ala Ser
             95                 100                 105 taacgttgcc tccggccacc caaaacctcg ggcgaaagtt tgttgcgcag cgaatccgta    1116 aagtgtaaa tttggttcat ctcgagccca cggtaaaaga acaaagtgtt gtacgccttt     1176
acggcaccct cgtccagcgc ataattcatc gtgtaaccgg tcatacgtgc cttggtgaag    1236
agccgttcgg gcgcttggag gtgcagcgag agcattgtca ccaaaattgc atccaccatg    1296
ttatactcga tgatgaggtg tggtcgtccc tgctcgtagt ccactttcat cactttaaaa    1356
tcataactaa ttttcttcgc accgaggtac ttggaggcca ggtcgtccag cttgaagctg    1416
gtttcgccgg ggtgccactt gcgggcaaac ttgaacatgt ccagcatttg gtaggacgag    1476
ctggtgatgc ggttcacgtc aacgtacgag tcattcttta caaattaat cgtcggatca     1536 gtgacaccgt atcgcataaa cttgaacgtg ttcagcttcg ggtcaccact ttggcgtgta    1596
atcatgtacg gtatatcgta gccgtgtccg ttaaagtcca ccaccaggtc cgggttgagg    1656
gcgtcaatca gcgttataaa gttgtccatc agttcagctt catccttgca caaaatgacc    1716
ctaatggtgg taccctcctt gaacgtgtcc accgtgggcc ggtactcgct atcgatgacc    1776
gcattcgggt ccaggtagag ttgaaaatat tcctgcacct cggcgctctc gtagtagtga    1836 atg gaa atg gag aaa act gta tca ccc tcg atg gtg ggg tcg gcc atg    1884
Met Glu Met Glu Lys Thr Val Ser Pro Ser Met Val Gly Ser Ala Met
            110                 115                 120 cgg tgg tgc ttg gaa cta tta tac gtt tct ata tcg tac gag gcc ata    1932
Arg Trp Cys Leu Glu Leu Leu Tyr Val Ser Ile Ser Tyr Glu Ala Ile
```

```
                                -continued

Arg Trp Cys Leu Glu Leu Leu Tyr Val Ser Ile Ser Tyr Glu Ala Ile
        125                 130                 135 gtc atc ttg atg ggc ttc agc ggc acc agt tgg tca tcg gtc atc ttt      1980
Val Ile Leu Met Gly Phe Ser Gly Thr Ser Trp Ser Ser Val Ile Phe
140                 145                 150 ttg ggg cca cgc gga ttg taggcaattt gaaacccgtt cacctcctcg             2028
Leu Gly Pro Arg Gly Leu
    155 ggtagagcaa gcgttggcac gtaaacctgg gcgatgttta gcccacgtac ggtcccattt    2088 tgcggcgtga ggtgggtggt gaaggccaca taactggatt caaaaatttt ataataattc    2148 atgaacctct cgacgtccga catgttggaa tcgcacagat agttcctcac accgtttgta    2208 gtctggcgaa cccgctttat caccggggttg atgtggtccg gtgcgaggac cggtgtgcat   2268 ggtacgcaca gtttacagtc aacctcgccc tttctttcac agttgcagaa ggcgtacccc    2328 acgattggta cactgtacag gatcaccttg attccgatga agggattgcg cagatagagg    2388 tgcacctcgc tcggttgtag atagctgttc ggacgctcgt ctgagatgca ccgaatcttg    2448 gtaataagga atacggcgtt ggccggtaca gtgtattcgc accgtgtaga gtccacatag    2508 ttgcgcacct cctcccagga acatttcttc ataaac atg gct gaa gtg cac aat      2562
                                        Met Ala Glu Val His Asn
                                        160                 165 gtg gtg gtg aga cca acc gtg tcg gct cta act gcg tac cgt tta cag      2610
Val Val Val Arg Pro Thr Val Ser Ala Leu Thr Ala Tyr Arg Leu Gln
                170                 175                 180 cgc gtg aat cgt gat ttg gaa aca aaa gta tcg cga atg gcg cag cac      2658
Arg Val Asn Arg Asp Leu Glu Thr Lys Val Ser Arg Met Ala Gln His
            185                 190                 195 tct agc gcg gaa ccg ttt atc agg cag act ttg ata cgt gaa ctg gga      2706
Ser Ser Ala Glu Pro Phe Ile Arg Gln Thr Leu Ile Arg Glu Leu Gly
        200                 205                 210 gac ttg cga gat gct gaa caa ata ccc acc acg tcc ctg ttg gat ctt      2754
Asp Leu Arg Asp Ala Glu Gln Ile Pro Thr Thr Ser Leu Leu Asp Leu
    215                 220                 225 ttt atc acc cga acc aac gct gag aag gag agt tta cgg ctc ggt gta      2802
Phe Ile Thr Arg Thr Asn Ala Glu Lys Glu Ser Leu Arg Leu Gly Val
230                 235                 240                 245 act atg tcg ggc gaa gag gta tcg cga atg aat gaa aac ttt att caa      2850
Thr Met Ser Gly Glu Glu Val Ser Arg Met Asn Glu Asn Phe Ile Gln
                250                 255                 260 cga ttt cgc tcc aac aag gac aat gaa gct gag gcc gaa ggt gca gtg      2898
Arg Phe Arg Ser Asn Lys Asp Asn Glu Ala Glu Ala Glu Gly Ala Val
            265                 270                 275 gtg acc ccc aac gaa cgc tta tgt agt act gag ggt gac gtt gaa aag      2946
Val Thr Pro Asn Glu Arg Leu Cys Ser Thr Glu Gly Asp Val Glu Lys
        280                 285                 290 att gcg atg aac tac cgc tcg gac ctg gtg gcc ata aac cgt gag ctc      2994
Ile Ala Met Asn Tyr Arg Ser Asp Leu Val Ala Ile Asn Arg Glu Leu
    295                 300                 305 acc cag gcc atc gaa aat ctg agc ccg gga aat gtg gaa acg ttg tac      3042
Thr Gln Ala Ile Glu Asn Leu Ser Pro Gly Asn Val Glu Thr Leu Tyr
310                 315                 320                 325 gag cgg ttt gag ttg gtt cgc acc act cta gct cca att cta ccc cgc      3090
Glu Arg Phe Glu Leu Val Arg Thr Thr Leu Ala Pro Ile Leu Pro Arg
                330                 335                 340 ctt tcg ggg ttg ggt aaa ctg gcg ctt aac gcg ctc ccc ctg ctg tac      3138
Leu Ser Gly Leu Gly Lys Leu Ala Leu Asn Ala Leu Pro Leu Leu Tyr
            345                 350                 355
```

```
gaa aag acc aac agt gac aac aaa gac gtg ctg aag ttg gac att cgt    3186
Glu Lys Thr Asn Ser Asp Asn Lys Asp Val Leu Lys Leu Asp Ile Arg
        360                 365                 370 atc aaa gaa ttc                                                    3198
Ile Lys Glu Phe
    375
```

<210> SEQ ID NO 84
<211> LENGTH: 105
<212> TYPE: PRT
<213> ORGANISM: mosquito baculovirus

<400> SEQUENCE: 84

```
Met Gly Thr Ser Asn Lys Ser Pro Leu Leu Ser Thr Ala Met Leu Leu
 1               5                  10                  15

Gly Gln Thr Arg Ser Ala Ser Ile Ile Glu Gly Tyr Ser Glu Leu Lys
            20                  25                  30

Ser Ile Ile Thr Lys Cys Ser Cys Ser Pro Gly Thr Val Gly Ser Thr
        35                  40                  45

Ser Pro Pro Ile Leu Val Leu Pro Trp Ser Pro Gln Val Cys Cys
    50                  55                  60

Ala Val Glu Ile Arg Asn Asn Asp Leu Arg Ser Arg Ser Ser Ser
65                  70                  75                  80

Ser Trp Arg Ser Gly Glu Arg Leu Arg Ser Ser Met Ala Arg Leu
            85                  90                  95

Asn Asp Met Phe Lys Ile Ser Ala Ser
            100                 105
```

<210> SEQ ID NO 85
<211> LENGTH: 54
<212> TYPE: PRT
<213> ORGANISM: mosquito baculovirus

<400> SEQUENCE: 85

```
Met Glu Met Glu Lys Thr Val Ser Pro Ser Met Val Gly Ser Ala Met
 1               5                  10                  15

Arg Trp Cys Leu Glu Leu Leu Tyr Val Ser Ile Ser Tyr Glu Ala Ile
            20                  25                  30

Val Ile Leu Met Gly Phe Ser Gly Thr Ser Trp Ser Ser Val Ile Phe
        35                  40                  45

Leu Gly Pro Arg Gly Leu
    50
```

<210> SEQ ID NO 86
<211> LENGTH: 218
<212> TYPE: PRT
<213> ORGANISM: mosquito baculovirus

<400> SEQUENCE: 86

```
Met Ala Glu Val His Asn Val Val Arg Pro Thr Val Ser Ala Leu
 1               5                  10                  15

Thr Ala Tyr Arg Leu Gln Arg Val Asn Arg Asp Leu Glu Thr Lys Val
            20                  25                  30

Ser Arg Met Ala Gln His Ser Ser Ala Glu Pro Phe Ile Arg Gln Thr
        35                  40                  45

Leu Ile Arg Glu Leu Gly Asp Leu Arg Asp Ala Glu Gln Ile Pro Thr
    50                  55                  60

Thr Ser Leu Leu Asp Leu Phe Ile Thr Arg Thr Asn Ala Glu Lys Glu
65                  70                  75                  80
```

```
                    Ser Leu Arg Leu Gly Val Thr Met Ser Gly Glu Glu Val Ser Arg Met
                                85                  90                  95

Asn Glu Asn Phe Ile Gln Arg Phe Arg Ser Asn Lys Asp Asn Glu Ala
                                100                 105                 110

Glu Ala Glu Gly Ala Val Val Thr Pro Asn Glu Arg Leu Cys Ser Thr
                            115                 120                 125

Glu Gly Asp Val Glu Lys Ile Ala Met Asn Tyr Arg Ser Asp Leu Val
                        130                 135                 140

Ala Ile Asn Arg Glu Leu Thr Gln Ala Ile Glu Asn Leu Ser Pro Gly
                    145                 150                 155                 160

Asn Val Glu Thr Leu Tyr Glu Arg Phe Glu Leu Val Arg Thr Thr Leu
                                    165                 170                 175

Ala Pro Ile Leu Pro Arg Leu Ser Gly Leu Gly Lys Leu Ala Leu Asn
                                180                 185                 190

Ala Leu Pro Leu Leu Tyr Glu Lys Thr Asn Ser Asp Asn Lys Asp Val
                                195                 200                 205

Leu Lys Leu Asp Ile Arg Ile Lys Glu Phe
                                210                 215

<210> SEQ ID NO 87
<211> LENGTH: 3198
<212> TYPE: DNA
<213> ORGANISM: mosquito baculovirus
<220> FEATURE:
<221> NAME/KEY: CDS
<222> LOCATION: (428)...(3195)
<221> NAME/KEY: CDS
<222> LOCATION: (20)...(241)

<400> SEQUENCE: 87
gaattctttg atacgaatg tcc aac ttc agc acg tct ttg ttg tca ctg ttg      52
                    Ser Asn Phe Ser Thr Ser Leu Leu Ser Leu Leu
                     1               5                   10 gtc ttt tcg tac agc agg ggg agc gcg tta agc gcc agt tta ccc aac      100
Val Phe Ser Tyr Ser Arg Gly Ser Ala Leu Ser Ala Ser Leu Pro Asn
            15                  20                  25 ccc gaa agg cgg ggt aga att gga gct aga gtg gtg cga acc aac tca      148
Pro Glu Arg Arg Gly Arg Ile Gly Ala Arg Val Val Arg Thr Asn Ser
        30                  35                  40 aac cgc tcg tac aac gtt tcc aca ttt ccc ggg ctc aga ttt tcg atg      196
Asn Arg Ser Tyr Asn Val Ser Thr Phe Pro Gly Leu Arg Phe Ser Met
    45                  50                  55 gcc tgg gtg agc tca cgg ttt atg gcc acc agg tcc gag cgg tag          241
Ala Trp Val Ser Ser Arg Phe Met Ala Thr Arg Ser Glu Arg *
60                  65                  70 ttcatcgcaa tcttttcaac gtcaccctca gtactacata agcgttcgtt ggggtcacc     301 actgcacctt cggcctcagc ttcattgtcc ttgttggagc gaaatcgttg aataaagttt    361
tcattcattc gcgatacctc ttcgcccgac atagttacac cgagccgtaa actctccttc    421 tcagcg ttg gtt cgg gtg ata aaa aga tcc aac agg gac gtg gtg ggt       469
       Leu Val Arg Val Ile Lys Arg Ser Asn Arg Asp Val Val Gly
            75                  80                  85 att tgt tca gca tct cgc aag tct ccc agt tca cgt atc aaa gtc tgc      517
Ile Cys Ser Ala Ser Arg Lys Ser Pro Ser Ser Arg Ile Lys Val Cys
            90                  95                  100 ctg ata aac ggt tcc gcg cta gag tgc tgc gcc att cgc gat act ttt      565
Leu Ile Asn Gly Ser Ala Leu Glu Cys Cys Ala Ile Arg Asp Thr Phe
        105                 110                 115
```

```
gtt tcc aaa tca cga ttc acg cgc tgt aaa cgg tac gca gtt aga gcc      613
Val Ser Lys Ser Arg Phe Thr Arg Cys Lys Arg Tyr Ala Val Arg Ala
120             125             130             135 gac acg gtt ggt ctc acc acc aca ttg tgc act tca gcc atg ttt atg      661
Asp Thr Val Gly Leu Thr Thr Thr Leu Cys Thr Ser Ala Met Phe Met
        140             145             150 aag aaa tgt tcc tgg gag gag gtg cgc aac tat gtg gac tct aca cgg      709
Lys Lys Cys Ser Trp Glu Glu Val Arg Asn Tyr Val Asp Ser Thr Arg
            155             160             165 tgc gaa tac act gta ccg gcc aac gcc gta ttc ctt att acc aag att      757
Cys Glu Tyr Thr Val Pro Ala Asn Ala Val Phe Leu Ile Thr Lys Ile
                170             175             180 cgg tgc atc tca gac gag cgt ccg aac agc tat cta caa ccg agc gag      805
Arg Cys Ile Ser Asp Glu Arg Pro Asn Ser Tyr Leu Gln Pro Ser Glu
        185             190             195 gtg cac ctc tat ctg cgc aat ccc ttc atc gga atc aag gtg atc ctg      853
Val His Leu Tyr Leu Arg Asn Pro Phe Ile Gly Ile Lys Val Ile Leu
200             205             210             215 tac agt gta cca atc gtg ggg tac gcc ttc tgc aac tgt gaa aga aag      901
Tyr Ser Val Pro Ile Val Gly Tyr Ala Phe Cys Asn Cys Glu Arg Lys
            220             225             230 ggc gag gtt gac tgt aaa ctg tgc gta cca tgc aca ccg gtc ctc gca      949
Gly Glu Val Asp Cys Lys Leu Cys Val Pro Cys Thr Pro Val Leu Ala
        235             240             245 ccg gac cac atc aac ccg gtg ata aag cgg gtt cgc cag act aca aac      997
Pro Asp His Ile Asn Pro Val Ile Lys Arg Val Arg Gln Thr Thr Asn
                250             255             260 ggt gtg agg aac tat ctg tgc gat tcc aac atg tcg gac gtc gag agg     1045
Gly Val Arg Asn Tyr Leu Cys Asp Ser Asn Met Ser Asp Val Glu Arg
265             270             275 ttc atg aat tat tat aaa att ttt gaa tcc agt tat gtg gcc ttc acc     1093
Phe Met Asn Tyr Tyr Lys Ile Phe Glu Ser Ser Tyr Val Ala Phe Thr
280             285             290             295 acc cac ctc acg ccg caa aat ggg acc gta cgt ggg cta aac atc gcc     1141
Thr His Leu Thr Pro Gln Asn Gly Thr Val Arg Gly Leu Asn Ile Ala
        300             305             310 cag gtt tac gtg cca acg ctt gct cta ccc gag gag gtg aac ggg ttt     1189
Gln Val Tyr Val Pro Thr Leu Ala Leu Pro Glu Glu Val Asn Gly Phe
            315             320             325 caa att gcc tac aat ccg cgt ggc ccc aaa aag atg acc gat gac caa     1237
Gln Ile Ala Tyr Asn Pro Arg Gly Pro Lys Lys Met Thr Asp Asp Gln
        330             335             340 ctg gtg ccg ctg aag ccc atc aag atg act atg gcc tcg tac gat ata     1285
Leu Val Pro Leu Lys Pro Ile Lys Met Thr Met Ala Ser Tyr Asp Ile
345             350             355 gaa acg tat aat agt tcc aag cac cac cgc atg gcc gac ccc acc atc     1333
Glu Thr Tyr Asn Ser Ser Lys His His Arg Met Ala Asp Pro Thr Ile
360             365             370             375 gag ggt gat aca gtt ttc tcc att tcc att cac tac tac gag agc gcc     1381
Glu Gly Asp Thr Val Phe Ser Ile Ser Ile His Tyr Tyr Glu Ser Ala
        380             385             390 gag gtg cag gaa tat ttt caa ctc tac ctg gac ccg aat gcg gtc atc     1429
Glu Val Gln Glu Tyr Phe Gln Leu Tyr Leu Asp Pro Asn Ala Val Ile
            395             400             405 gat agc gag tac cgg ccc acg gtg gac acg ttc aag gag ggt acc acc     1477
Asp Ser Glu Tyr Arg Pro Thr Val Asp Thr Phe Lys Glu Gly Thr Thr
        410             415             420 att agg gtc att ttg tgc aag gat gaa gct gaa ctg atg gac aac ttt     1525
Ile Arg Val Ile Leu Cys Lys Asp Glu Ala Glu Leu Met Asp Asn Phe
            425             430             435
```

-continued

| | | | | | | | | | | | | | | | | |
|---|---|---|---|---|---|---|---|---|---|---|---|---|---|---|---|---|
| ata | acg | ctg | att | gac | gcc | ctc | aac | ccg | gac | ctg | gtg | gtg | gac | ttt | aac | 1573 |
| Ile | Thr | Leu | Ile | Asp | Ala | Leu | Asn | Pro | Asp | Leu | Val | Val | Asp | Phe | Asn | |
| 440 | | | | 445 | | | | | 450 | | | | | 455 | | |

```
ata acg ctg att gac gcc ctc aac ccg gac ctg gtg gtg gac ttt aac      1573
Ile Thr Leu Ile Asp Ala Leu Asn Pro Asp Leu Val Val Asp Phe Asn
440             445                 450                 455 gga cac ggc tac gat ata ccg tac atg att aca cgc caa agt ggt gac      1621
Gly His Gly Tyr Asp Ile Pro Tyr Met Ile Thr Arg Gln Ser Gly Asp
                460                 465                 470 ccg aag ctg aac acg ttc aag ttt atg cga tac ggt gtc act gat ccg      1669
Pro Lys Leu Asn Thr Phe Lys Phe Met Arg Tyr Gly Val Thr Asp Pro
            475                 480                 485 acg att aat ttt gta aag aat gac tcg tac gtt gac gtg aac cgc atc      1717
Thr Ile Asn Phe Val Lys Asn Asp Ser Tyr Val Asp Val Asn Arg Ile
        490                 495                 500 acc agc tcg tcc tac caa atg ctg gac atg ttc aag ttt gcc cgc aag      1765
Thr Ser Ser Ser Tyr Gln Met Leu Asp Met Phe Lys Phe Ala Arg Lys
505                 510                 515 tgg cac ccc ggc gaa acc agc ttc aag ctg gac gac ctg gcc tcc aag      1813
Trp His Pro Gly Glu Thr Ser Phe Lys Leu Asp Asp Leu Ala Ser Lys
520                 525                 530                 535 tac ctc ggt gcg aag aaa att agt tat gat ttt aaa gtg atg aaa gtg      1861
Tyr Leu Gly Ala Lys Lys Ile Ser Tyr Asp Phe Lys Val Met Lys Val
                540                 545                 550 gac tac gag cag gga cga cca cac ctc atc atc gag tat aac atg gtg      1909
Asp Tyr Glu Gln Gly Arg Pro His Leu Ile Ile Glu Tyr Asn Met Val
            555                 560                 565 gat gca att ttg gtg aca atg ctc tcg ctg cac ctc caa gcg ccc gaa      1957
Asp Ala Ile Leu Val Thr Met Leu Ser Leu His Leu Gln Ala Pro Glu
        570                 575                 580 cgg ctc ttc acc aag gca cgt atg acc ggt tac acg atg aat tat gcg      2005
Arg Leu Phe Thr Lys Ala Arg Met Thr Gly Tyr Thr Met Asn Tyr Ala
585                 590                 595 ctg gac gag ggt gcc gta aag gcg tac aac act ttg ttc ttt tac cgt      2053
Leu Asp Glu Gly Ala Val Lys Ala Tyr Asn Thr Leu Phe Phe Tyr Arg
600                 605                 610                 615 ggg ctc gag atg aac caa att tac acc ttt acg gat tcg ctg cgc aac      2101
Gly Leu Glu Met Asn Gln Ile Tyr Thr Phe Thr Asp Ser Leu Arg Asn
                620                 625                 630 aaa ctt tcg ccc gag gtt ttg ggt ggc cgg agg caa cgt tat gat gcg      2149
Lys Leu Ser Pro Glu Val Leu Gly Gly Arg Arg Gln Arg Tyr Asp Ala
            635                 640                 645 gaa att tta aac ata tcg ttc aag cgt gcc atc gag gag gag cgt aaa      2197
Glu Ile Leu Asn Ile Ser Phe Lys Arg Ala Ile Glu Glu Glu Arg Lys
        650                 655                 660 cgt tca ccg gag cgc caa gac gag ctc gat gac ctg gag cgt aaa tcg      2245
Arg Ser Pro Glu Arg Gln Asp Glu Leu Asp Asp Leu Glu Arg Lys Ser
665                 670                 675 ttg ttt cgt atc tcg acc gca cag caa act tgg ggt gac cag ggt aac      2293
Leu Phe Arg Ile Ser Thr Ala Gln Gln Thr Trp Gly Asp Gln Gly Asn
680                 685                 690                 695 act aaa att gga ggt gga ctg gtg ctt cca acg gtg ccg gga ctg cac      2341
Thr Lys Ile Gly Gly Gly Leu Val Leu Pro Thr Val Pro Gly Leu His
                700                 705                 710 gaa cat ttg gtg att atg gac ttt aat tcg ctg tac cct tcg att atg      2389
Glu His Leu Val Ile Met Asp Phe Asn Ser Leu Tyr Pro Ser Ile Met
            715                 720                 725 ctc gct gag cgc gtt tgc ccc aac aac att gcg gtg gaa agt aat ggg      2437
Leu Ala Glu Arg Val Cys Pro Asn Asn Ile Ala Val Glu Ser Asn Gly
        730                 735                 740 gac ttg ttg ctg gta ccc atg ccc aaa gaa aac ctc acg tct tcg att      2485
Asp Leu Leu Leu Val Pro Met Pro Lys Glu Asn Leu Thr Ser Ser Ile
```

```
                745                  750                   755
ata aag gag gcg ttg aag aat cgt aaa ttt cac cgc agc gag gcg gca    2533
Ile Lys Glu Ala Leu Lys Asn Arg Lys Phe His Arg Ser Glu Ala Ala
760                 765                   770                 775 aag tat gac aag gat tcg tac gag tat atg atg cac gac gct gcg cag    2581
Lys Tyr Asp Lys Asp Ser Tyr Glu Tyr Met Met His Asp Ala Ala Gln
                780                  785                  790 ggt gcg tac aag atc acc gca aat tcg gtg tac ggt ttc ttt gcg cta    2629
Gly Ala Tyr Lys Ile Thr Ala Asn Ser Val Tyr Gly Phe Phe Ala Leu
            795                 800                  805 cgg ttt cca ccg ttg gga aac ttt atc aca aaa act ggc cgc ggt aaa    2677
Arg Phe Pro Pro Leu Gly Asn Phe Ile Thr Lys Thr Gly Arg Gly Lys
        810                  815                 820 gtt cga tca gcg gtc aat tac act acc gag tac tgg aat gag cag tac    2725
Val Arg Ser Ala Val Asn Tyr Thr Thr Glu Tyr Trp Asn Glu Gln Tyr
825                 830                  835 ggc ctg tgc gca ttt ttc gtt tac gga gac acc gat tcg atc atg ttt    2773
Gly Leu Cys Ala Phe Phe Val Tyr Gly Asp Thr Asp Ser Ile Met Phe
840                 845                  850                 855 aaa ttt atg cag ccc acc agc ggt gta acg gtg gac ccg aat gcg ttt    2821
Lys Phe Met Gln Pro Thr Ser Gly Val Thr Val Asp Pro Asn Ala Phe
                860                  865                 870 ccc ggt tta att gaa cat ttt tcc gct gga ttg gcg aaa act gtg ggc    2869
Pro Gly Leu Ile Glu His Phe Ser Ala Gly Leu Ala Lys Thr Val Gly
            875                 880                  885 gtc ggt tat aat atg gcg ctc gag ttg att gtg cgg tcg tcc gtg ttt    2917
Val Gly Tyr Asn Met Ala Leu Glu Leu Ile Val Arg Ser Ser Val Phe
        890                  895                 900 aca cac cgc aaa aag tcg tac gtg ttt cac att gcc gac aat atc tac    2965
Thr His Arg Lys Lys Ser Tyr Val Phe His Ile Ala Asp Asn Ile Tyr
905                 910                  915 aag tat cgg gga ctt ttg gtg ggc aga aat ttg acc aga gcc atc gtc    3013
Lys Tyr Arg Gly Leu Leu Val Gly Arg Asn Leu Thr Arg Ala Ile Val
920                 925                  930                 935 cgg tgc tac aag cga tgg atc gag tat acg atg aag ttg tgc gaa gag    3061
Arg Cys Tyr Lys Arg Trp Ile Glu Tyr Thr Met Lys Leu Cys Glu Glu
                940                  945                 950 ggc gcc ctt tcg tac agt tta gct acg gat att ttg ctt gaa gat ttg    3109
Gly Ala Leu Ser Tyr Ser Leu Ala Thr Asp Ile Leu Leu Glu Asp Leu
            955                 960                  965 cgt aaa att caa gag gag gac ttt agc gtg gac tcg tta tcc cgc aca    3157
Arg Lys Ile Gln Glu Glu Asp Phe Ser Val Asp Ser Leu Ser Arg Thr
        970                  975                 980 att agc tac agc ggc aaa agt ggc agc ttg att gcg aa ttc              3198
Ile Ser Tyr Ser Gly Lys Ser Gly Ser Leu Ile Ala
985                 990                  995

<210> SEQ ID NO 88
<211> LENGTH: 73
<212> TYPE: PRT
<213> ORGANISM: mosquito baculovirus

<400> SEQUENCE: 88

Ser Asn Phe Ser Thr Ser Leu Leu Ser Leu Leu Val Phe Ser Tyr Ser
1               5                   10                  15

Arg Gly Ser Ala Leu Ser Ala Ser Leu Pro Asn Pro Glu Arg Arg Gly
            20                  25                  30

Arg Ile Gly Ala Arg Val Val Arg Thr Asn Ser Asn Arg Ser Tyr Asn
        35                  40                  45
```

```
Val Ser Thr Phe Pro Gly Leu Arg Phe Ser Met Ala Trp Val Ser Ser
 50                  55                  60

Arg Phe Met Ala Thr Arg Ser Glu Arg
 65                  70
```

<210> SEQ ID NO 89
<211> LENGTH: 922
<212> TYPE: PRT
<213> ORGANISM: mosquito baculovirus

<400> SEQUENCE: 89

```
Leu Val Arg Val Ile Lys Arg Ser Asn Arg Asp Val Val Gly Ile Cys
 1               5                  10                  15

Ser Ala Ser Arg Lys Ser Pro Ser Ser Arg Ile Lys Val Cys Leu Ile
                20                  25                  30

Asn Gly Ser Ala Leu Glu Cys Cys Ala Ile Arg Asp Thr Phe Val Ser
            35                  40                  45

Lys Ser Arg Phe Thr Arg Cys Lys Arg Tyr Ala Val Arg Ala Asp Thr
 50                  55                  60

Val Gly Leu Thr Thr Thr Leu Cys Thr Ser Ala Met Phe Met Lys Lys
 65                  70                  75                  80

Cys Ser Trp Glu Glu Val Arg Asn Tyr Val Asp Ser Thr Arg Cys Glu
                85                  90                  95

Tyr Thr Val Pro Ala Asn Ala Val Phe Leu Ile Thr Lys Ile Arg Cys
                100                 105                 110

Ile Ser Asp Glu Arg Pro Asn Ser Tyr Leu Gln Pro Ser Glu Val His
            115                 120                 125

Leu Tyr Leu Arg Asn Pro Phe Ile Gly Ile Lys Val Ile Leu Tyr Ser
130                 135                 140

Val Pro Ile Val Gly Tyr Ala Phe Cys Asn Cys Glu Arg Lys Gly Glu
145                 150                 155                 160

Val Asp Cys Lys Leu Cys Val Pro Cys Thr Pro Val Leu Ala Pro Asp
                165                 170                 175

His Ile Asn Pro Val Ile Lys Arg Val Arg Gln Thr Thr Asn Gly Val
            180                 185                 190

Arg Asn Tyr Leu Cys Asp Ser Asn Met Ser Asp Val Glu Arg Phe Met
        195                 200                 205

Asn Tyr Tyr Lys Ile Phe Glu Ser Ser Tyr Val Ala Phe Thr Thr His
210                 215                 220

Leu Thr Pro Gln Asn Gly Thr Val Arg Gly Leu Asn Ile Ala Gln Val
225                 230                 235                 240

Tyr Val Pro Thr Leu Ala Leu Pro Glu Glu Val Asn Gly Phe Gln Ile
                245                 250                 255

Ala Tyr Asn Pro Arg Gly Pro Lys Lys Met Thr Asp Asp Gln Leu Val
            260                 265                 270

Pro Leu Lys Pro Ile Lys Met Thr Met Ala Ser Tyr Asp Ile Glu Thr
        275                 280                 285

Tyr Asn Ser Ser Lys His His Arg Met Ala Asp Pro Thr Ile Glu Gly
    290                 295                 300

Asp Thr Val Phe Ser Ile Ser Ile His Tyr Tyr Glu Ser Ala Glu Val
305                 310                 315                 320

Gln Glu Tyr Phe Gln Leu Tyr Leu Asp Pro Asn Ala Val Ile Asp Ser
                325                 330                 335

Glu Tyr Arg Pro Thr Val Asp Thr Phe Lys Glu Gly Thr Thr Ile Arg
                340                 345                 350
```

```
Val Ile Leu Cys Lys Asp Glu Ala Glu Leu Met Asp Asn Phe Ile Thr
            355                 360                 365
Leu Ile Asp Ala Leu Asn Pro Asp Leu Val Val Asp Phe Asn Gly His
        370                 375                 380
Gly Tyr Asp Ile Pro Tyr Met Ile Thr Arg Gln Ser Gly Asp Pro Lys
385                 390                 395                 400
Leu Asn Thr Phe Lys Phe Met Arg Tyr Gly Val Thr Asp Pro Thr Ile
                405                 410                 415
Asn Phe Val Lys Asn Asp Ser Tyr Val Asp Val Asn Arg Ile Thr Ser
            420                 425                 430
Ser Ser Tyr Gln Met Leu Asp Met Phe Lys Phe Ala Arg Lys Trp His
        435                 440                 445
Pro Gly Glu Thr Ser Phe Lys Leu Asp Asp Leu Ala Ser Lys Tyr Leu
450                 455                 460
Gly Ala Lys Lys Ile Ser Tyr Asp Phe Lys Val Met Lys Val Asp Tyr
465                 470                 475                 480
Glu Gln Gly Arg Pro His Leu Ile Ile Glu Tyr Asn Met Val Asp Ala
                485                 490                 495
Ile Leu Val Thr Met Leu Ser Leu His Leu Gln Ala Pro Glu Arg Leu
            500                 505                 510
Phe Thr Lys Ala Arg Met Thr Gly Tyr Thr Met Asn Tyr Ala Leu Asp
        515                 520                 525
Glu Gly Ala Val Lys Ala Tyr Asn Thr Leu Phe Phe Tyr Arg Gly Leu
530                 535                 540
Glu Met Asn Gln Ile Tyr Thr Phe Thr Asp Ser Leu Arg Asn Lys Leu
545                 550                 555                 560
Ser Pro Glu Val Leu Gly Gly Arg Arg Gln Arg Tyr Asp Ala Glu Ile
                565                 570                 575
Leu Asn Ile Ser Phe Lys Arg Ala Glu Glu Arg Lys Arg Ser
            580                 585                 590
Pro Glu Arg Gln Asp Glu Leu Asp Asp Leu Glu Arg Lys Ser Leu Phe
        595                 600                 605
Arg Ile Ser Thr Ala Gln Gln Thr Trp Gly Asp Gln Gly Asn Thr Lys
610                 615                 620
Ile Gly Gly Gly Leu Val Leu Pro Thr Val Pro Gly Leu His Glu His
625                 630                 635                 640
Leu Val Ile Met Asp Phe Asn Ser Leu Tyr Pro Ser Ile Met Leu Ala
                645                 650                 655
Glu Arg Val Cys Pro Asn Asn Ile Ala Val Glu Ser Asn Gly Asp Leu
            660                 665                 670
Leu Leu Val Pro Met Pro Lys Glu Asn Leu Thr Ser Ser Ile Ile Lys
        675                 680                 685
Glu Ala Leu Lys Asn Arg Lys Phe His Arg Ser Glu Ala Ala Lys Tyr
690                 695                 700
Asp Lys Asp Ser Tyr Glu Tyr Met Met His Asp Ala Ala Gln Gly Ala
705                 710                 715                 720
Tyr Lys Ile Thr Ala Asn Ser Val Tyr Gly Phe Phe Ala Leu Arg Phe
                725                 730                 735
Pro Pro Leu Gly Asn Phe Ile Thr Lys Thr Gly Arg Gly Lys Val Arg
            740                 745                 750
Ser Ala Val Asn Tyr Thr Thr Glu Tyr Trp Asn Glu Gln Tyr Gly Leu
        755                 760                 765
```

```
Cys Ala Phe Phe Val Tyr Gly Asp Thr Asp Ser Ile Met Phe Lys Phe
        770                 775                 780

Met Gln Pro Thr Ser Gly Val Thr Val Asp Pro Asn Ala Phe Pro Gly
785                 790                 795                 800

Leu Ile Glu His Phe Ser Ala Gly Leu Ala Lys Thr Val Gly Val Gly
                805                 810                 815

Tyr Asn Met Ala Leu Glu Leu Ile Val Arg Ser Val Phe Thr His
            820                 825                 830

Arg Lys Lys Ser Tyr Val Phe His Ile Ala Asp Asn Ile Tyr Lys Tyr
                835                 840                 845

Arg Gly Leu Leu Val Gly Arg Asn Leu Thr Arg Ala Ile Val Arg Cys
850                 855                 860

Tyr Lys Arg Trp Ile Glu Tyr Thr Met Lys Leu Cys Glu Glu Gly Ala
865                 870                 875                 880

Leu Ser Tyr Ser Leu Ala Thr Asp Ile Leu Leu Glu Asp Leu Arg Lys
                885                 890                 895

Ile Gln Glu Glu Asp Phe Ser Val Asp Ser Leu Ser Arg Thr Ile Ser
            900                 905                 910

Tyr Ser Gly Lys Ser Gly Ser Leu Ile Ala
            915                 920

<210> SEQ ID NO 90
<211> LENGTH: 3198
<212> TYPE: DNA
<213> ORGANISM: mosquito baculovirus
<220> FEATURE:
<221> NAME/KEY: CDS
<222> LOCATION: (667)...(897)

<400> SEQUENCE: 90
gaattctttg atacgaatgt ccaacttcag cacgtctttg ttgtcactgt tggtcttttc    60
gtacagcagg gggagcgcgt taagcgccag tttacccaac cccgaaaggc ggggtagaat   120
tggagctaga gtggtgcgaa ccaactcaaa ccgctcgtac aacgtttcca catttcccgg   180
gctcagattt tcgatggcct gggtgagctc acggtttatg ccaccaggt ccgagcggta    240 gttcatcgca atcttttcaa cgtcaccctc agtactacat aagcgttcgt tgggggtcac   300
cactgcacct tcggcctcag cttcattgtc cttgttggag cgaaatcgtt gaataaagtt   360
ttcattcatt cgcgatacct cttcgcccga catagttaca ccgagccgta aactctcctt   420
ctcagcgttg gttcgggtga taaaaagatc aacagggac gtggtgggta tttgttcagc    480
atctcgcaag tctcccagtt cacgtatcaa agtctgcctg ataaacggtt ccgcgctaga   540
gtgctgcgcc attcgcgata cttttgtttc caaatcacga ttcacgcgct gtaaacggta   600
cgcagttaga gccgacacgg ttggtctcac caccacattg tgcacttcag ccatgtttat   660 gaagaa atg ttc ctg gga gga ggt gcg caa cta tgt gga ctc tac acg       708
       Met Phe Leu Gly Gly Gly Ala Gln Leu Cys Gly Leu Tyr Thr
         1               5                  10 gtg cga ata cac tgt acc ggc caa cgc cgt att cct tat tac caa gat      756
Val Arg Ile His Cys Thr Gly Gln Arg Arg Ile Pro Tyr Tyr Gln Asp
 15                  20                  25                  30 tcg gtg cat ctc aga cga gcg tcc gaa cag cta tct aca acc gag cga      804
Ser Val His Leu Arg Arg Ala Ser Glu Gln Leu Ser Thr Thr Glu Arg
                 35                  40                  45 ggt gca cct cta tct gcg caa tcc ctt cat cgg aat caa ggt gat cct      852
Gly Ala Pro Leu Ser Ala Gln Ser Leu His Arg Asn Gln Gly Asp Pro
             50                  55                  60
```

| | |
|---|---|
| gta cag tgt acc aat cgt ggg gta cgc ctt ctg caa ctg tga aag<br>Val Gln Cys Thr Asn Arg Gly Val Arg Leu Leu Gln Leu * Lys<br>65                    70                    75 | 897 |
| aaagggcgag gttgactgta aactgtgcgt accatgcaca ccggtcctcg caccggacca | 957 |
| catcaacccg gtgataaagc gggttcgcca gactacaaac ggtgtgagga actatctgtg | 1017 |
| cgattccaac atgtcggacg tcgagaggtt catgaattat tataaaattt ttgaatccag | 1077 |
| ttatgtggcc ttcaccaccc acctcacgcc gcaaaatggg accgtacgtg gctaaacat | 1137 |
| cgcccaggtt tacgtgccaa cgcttgctct acccgaggag gtgaacgggt ttcaaattgc | 1197 |
| ctacaatccg cgtggcccca aaagatgac cgatgaccaa ctggtgccgc tgaagcccat | 1257 |
| caagatgact atggcctcgt acgatataga aacgtataat agttccaagc accaccgcat | 1317 |
| ggccgacccc accatcgagg gtgatacagt tttctccatt tccattcact actacgagag | 1377 |
| cgccgaggtg caggaatatt ttcaactcta cctggacccg aatgcggtca tcgatagcga | 1437 |
| gtaccggccc acgtggaca cgttcaagga gggtaccacc attagggtca ttttgtgcaa | 1497 |
| ggatgaagct gaactgatgg acaactttat aacgctgatt gacgccctca acccggacct | 1557 |
| ggtggtggac tttaacggac acggctacga tataccgtac atgattacac gccaaagtgg | 1617 |
| tgacccgaag ctgaacacgt tcaagtttat gcgatacggt gtcactgatc cgacgattaa | 1677 |
| ttttgtaaag aatgactcgt acgttgacgt gaaccgcatc accagctcgt cctaccaaat | 1737 |
| gctggacatg ttcaagtttg cccgcaagtg gcaccccggc gaaaccagct tcaagctgga | 1797 |
| cgacctggcc tccaagtacc tcggtgcgaa gaaaattagt tatgatttta agtgatgaa | 1857 |
| agtggactac gagcagggac gaccacacct catcatcgag tataacatgg tggatgcaat | 1917 |
| tttggtgaca atgctctcgc tgcacctcca agcgcccgaa cggctcttca ccaaggcacg | 1977 |
| tatgaccggt tacacgatga attatgcgct ggacgagggt gccgtaaagg cgtacaacac | 2037 |
| tttgttcttt taccgtgggc tcgagatgaa ccaaatttac acctttacgg attcgctgcg | 2097 |
| caacaaactt tcgcccgagg ttttgggtgg ccggaggcaa cgttatgatg cggaaattt | 2157 |
| aaacatatcg ttcaagcgtg ccatcgagga ggagcgtaaa cgttcaccgg agcgccaaga | 2217 |
| cgagctcgat gacctggagc gtaaatcgtt gtttcgtatc tcgaccgcac agcaaacttg | 2277 |
| gggtgaccag ggtaacacta aaattggagg tggactggtg cttccaacgg tgccgggact | 2337 |
| gcacgaacat ttggtgatta tggacttaa ttcgctgtac ccttcgatta tgctcgctga | 2397 |
| gcgcgtttgc cccaacaaca ttgcggtgga agtaatggg gacttgttgc tggtacccat | 2457 |
| gcccaaagaa aacctcacgt cttcgattat aaaggaggcg ttgaagaatc gtaaatttca | 2517 |
| ccgcagcgag gcggcaaagt atgacaagga ttcgtacgag tatatgatgc acgacgctgc | 2577 |
| gcagggtgcg tacaagatca ccgcaaattc ggtgtacggt ttctttgcgc tacggtttcc | 2637 |
| accgttggga aactttatca caaaaactgg ccgcggtaaa gttcgatcag cggtcaatta | 2697 |
| cactaccgag tactggaatg agcagtacgg cctgtgcgca ttttcgtttt acggagacac | 2757 |
| cgattcgatc atgtttaaat ttatgcagcc caccagcggt gtaacggtgg acccgaatgc | 2817 |
| gtttcccggt ttaattgaac attttccgc tggattggcg aaaactgtgg cgtcggtta | 2877 |
| taatatggcg ctcgagttga ttgtgcggtc gtccgtgttt acacaccgca aaagtcgta | 2937 |
| cgtgtttcac attgccgaca atatctacaa gtatcgggga cttttggtgg cagaaattt | 2997 |
| gaccagagcc atcgtccggt gctacaagcg atggatcgag tatacgatga agttgtgcga | 3057 |
| agagggcgcc ctttcgtaca gtttagctac ggatattttg cttgaagatt tgcgtaaaat | 3117 |
| tcaagaggag gactttagcg tggactcgtt atcccgcaca attagctaca gcggcaaaag | 3177 |

-continued

```
tggcagcttg attgcgaatt c                                              3198

<210> SEQ ID NO 91
<211> LENGTH: 76
<212> TYPE: PRT
<213> ORGANISM: mosquito baculovirus

<400> SEQUENCE: 91

Met Phe Leu Gly Gly Gly Ala Gln Leu Cys Gly Leu Tyr Thr Val Arg
 1               5                  10                  15

Ile His Cys Thr Gly Gln Arg Arg Ile Pro Tyr Tyr Gln Asp Ser Val
            20                  25                  30

His Leu Arg Arg Ala Ser Glu Gln Leu Ser Thr Thr Glu Arg Gly Ala
        35                  40                  45

Pro Leu Ser Ala Gln Ser Leu His Arg Asn Gln Gly Asp Pro Val Gln
    50                  55                  60

Cys Thr Asn Arg Gly Val Arg Leu Leu Gln Leu Lys
65                  70                  75

<210> SEQ ID NO 92
<211> LENGTH: 3198
<212> TYPE: DNA
<213> ORGANISM: mosquito baculovirus
<220> FEATURE:
<221> NAME/KEY: CDS
<222> LOCATION: (696)...(848)

<400> SEQUENCE: 92
gaattctttg atacgaatgt ccaacttcag cacgtctttg ttgtcactgt tggtcttttc     60
gtacagcagg gggagcgcgt taagcgccag tttacccaac cccgaaaggc ggggtagaat    120
tggagctaga gtggtgcgaa ccaactcaaa ccgctcgtac aacgtttcca catttcccgg    180
gctcagattt tcgatggcct gggtgagctc acggtttatg gccaccaggt ccgagcggta    240
gttcatcgca atcttttcaa cgtcaccctc agtactacat aagcgttcgt tgggggtcac    300
cactgcacct tcggcctcag cttcattgtc cttgttggag cgaaatcgtt gaataaagtt    360
ttcattcatt cgcgatacct cttcgcccga catagttaca ccgagccgta aactctcctt    420
ctcagcgttg gttcgggtga taaaaagatc caacagggac gtggtgggta tttgttcagc    480
atctcgcaag tctcccagtt cacgtatcaa agtctgcctg ataaacggtt ccgcgctaga    540
gtgctgcgcc attcgcgata cttttgtttc caaatcacga ttcacgcgct gtaaacggta    600
cgcagttaga gccgacacgg ttggtctcac caccacattg tgcacttcag ccatgtttat    660
gaagaaatgt tcctgggagg aggtgcgcaa ctatg tgg act cta cac ggt gcg       713
                                       Trp Thr Leu His Gly Ala
                                        1               5 aat aca ctg tac cgg cca acg ccg tat tcc tta tta cca aga ttc ggt      761
Asn Thr Leu Tyr Arg Pro Thr Pro Tyr Ser Leu Leu Pro Arg Phe Gly
            10                  15                  20 gca tct cag acg agc gtc cga aca gct atc tac aac cga gcg agg tgc      809
Ala Ser Gln Thr Ser Val Arg Thr Ala Ile Tyr Asn Arg Ala Arg Cys
        25                  30                  35 acc tct atc tgc gca atc cct tca tcg gaa tca agg tga tcctgtacag       858
Thr Ser Ile Cys Ala Ile Pro Ser Ser Glu Ser Arg  *
     40                  45                  50 tgtaccaatc gtggggtacg ccttctgcaa ctgtgaaaga aagggcgagg ttgactgtaa    918
actgtgcgta ccatgcacac cggtcctcgc accggaccac atcaacccgg tgataaagcg    978
```

```
ggttcgccag actacaaacg gtgtgaggaa ctatctgtgc gattccaaca tgtcggacgt    1038
cgagaggttc atgaattatt ataaaatttt tgaatccagt tatgtggcct tcaccaccca    1098
cctcacgccg caaaatggga ccgtacgtgg gctaaacatc gcccaggttt acgtgccaac    1158
gcttgctcta cccgaggagg tgaacggggtt tcaaattgcc tacaatccgc gtggcccaa     1218 aaagatgacc gatgaccaac tggtgccgct gaagcccatc aagatgacta tggcctcgta    1278
cgatatagaa acgtataata gttccaagca ccaccgcatg gccgaccccca ccatcgaggg    1338 tgatacagtt ttctccattt ccattcacta ctacgagagc gccgaggtgc aggaatattt    1398
tcaactctac ctggacccga atgcggtcat cgatagcgag taccggccca cggtggacac    1458
gttcaaggag gtaccacca ttagggtcat tttgtgcaag gatgaagctg aactgatgga     1518
caactttata cgctgattg acgccctcaa cccggacctg gtggtggact taacggaca      1578 cggctacgat ataccgtaca tgattacacg ccaaagtggt gacccgaagc tgaacacgtt    1638
caagtttatg cgatacggtg tcactgatcc gacgattaat tttgtaaaga atgactcgta    1698
cgttgacgtg aaccgcatca ccagctcgtc ctaccaaatg ctggacatgt tcaagtttgc    1758
ccgcaagtgg caccccggcg aaaccagctt caagctggac gacctggcct ccaagtacct    1818
cggtgcgaag aaaattagtt atgattttaa agtgatgaaa gtggactacg agcagggacg    1878
accacacctc atcatcgagt ataacatggt ggatgcaatt ttggtgacaa tgctctcgct    1938
gcacctccaa gcgcccgaac ggctcttcac caaggcacgt atgaccggtt acacgatgaa    1998
ttatgcgctg gacgagggtg ccgtaaaggc gtacaacact ttgttctttt accgtgggct    2058
cgagatgaac caaatttaca cctttacgga ttcgctgcgc aacaaacttt cgcccgaggt    2118
tttgggtggc cggaggcaac gttatgatgc ggaaatttta aacatatcgt tcaagcgtgc    2178
catcgaggag gagcgtaaac gttcaccgga gcgccaagac gagctcgatg acctggagcg    2238
taaatcgttg tttcgtatct cgaccgcaca gcaaacttgg ggtgaccagg gtaacactaa    2298
aattggaggt ggactggtgc ttccaacggt gccgggactg cacgaacatt tggtgattat    2358
ggactttaat tcgctgtacc cttcgattat gctcgctgag gcgtttgcc ccaacaacat     2418 tgcggtggaa agtaatgggg acttgttgct ggtacccatg cccaaagaaa acctcacgtc    2478
ttcgattata aaggaggcgt tgaagaatcg taaatttcac cgcagcgagg cggcaaagta    2538
tgacaaggat tcgtacgagt atatgatgca cgacgctgcg cagggtgcgt acaagatcac    2598
cgcaaattcg gtgtacggtt tctttgcgct acggtttcca ccgttgggaa actttatcac    2658
aaaaactggc cgcggtaaag ttcgatcagc ggtcaattac actaccgagt actggaatga    2718
gcagtacggg ctgtgcgcat ttttcgttta cggagacacc gattcgatca tgtttaaatt    2778
tatgcagccc accagcggtg taacggtgga cccgaatgcg tttcccggtt taattgaaca    2838
tttttccgct ggattggcga aaactgtggg cgtcggttat aatatggcgc tcgagttgat    2898
tgtgcggtcg tccgtgttta cacaccgcaa aaagtcgtac gtgtttcaca ttgccgacaa    2958
tatctacaag tatcggggac ttttggtggg cagaaatttg accagagcca tcgtccggtg    3018
ctacaagcga tggatcgagt atacgatgaa gttgtgcgaa gagggcgccc tttcgtacag    3078
tttagctacg gatattttgc ttgaagattt gcgtaaaatt caagaggagg actttagcgt    3138
ggactcgtta tcccgcacaa ttagctacag cggcaaaagt ggcagcttga ttgcgaattc    3198
```

<210> SEQ ID NO 93
<211> LENGTH: 50
<212> TYPE: PRT
<213> ORGANISM: mosquito baculovirus

<400> SEQUENCE: 93

| Trp | Thr | Leu | His | Gly | Ala | Asn | Thr | Leu | Tyr | Arg | Pro | Thr | Pro | Tyr | Ser |
|---|---|---|---|---|---|---|---|---|---|---|---|---|---|---|---|
| 1 | | | | 5 | | | | | 10 | | | | | 15 | |

| Leu | Leu | Pro | Arg | Phe | Gly | Ala | Ser | Gln | Thr | Ser | Val | Arg | Thr | Ala | Ile |
|---|---|---|---|---|---|---|---|---|---|---|---|---|---|---|---|
| | | | 20 | | | | | 25 | | | | | 30 | | |

| Tyr | Asn | Arg | Ala | Arg | Cys | Thr | Ser | Ile | Cys | Ala | Ile | Pro | Ser | Ser | Glu |
|---|---|---|---|---|---|---|---|---|---|---|---|---|---|---|---|
| | | 35 | | | | | 40 | | | | | 45 | | | |

Ser Arg
  50

<210> SEQ ID NO 94
<211> LENGTH: 6627
<212> TYPE: DNA
<213> ORGANISM: mosquito baculovirus
<220> FEATURE:
<221> NAME/KEY: CDS
<222> LOCATION: (3407)...(5044)
<221> NAME/KEY: CDS
<222> LOCATION: (5065)...(5775)
<221> NAME/KEY: CDS
<222> LOCATION: (1530)...(2066)
<221> NAME/KEY: CDS
<222> LOCATION: (2389)...(2625)
<221> NAME/KEY: CDS
<222> LOCATION: (1)...(237)

<400> SEQUENCE: 94

```
gaa ttc tgc aca ctc gca cca ccc gtt tgc cct ctc caa ctg cac gtt        48
Glu Phe Cys Thr Leu Ala Pro Pro Val Cys Pro Leu Gln Leu His Val
  1               5                  10                  15 cgt aca gtg cga tat agt tca gct tgc agc tgg gca cct cgg gga caa        96
Arg Thr Val Arg Tyr Ser Ser Ala Cys Ser Trp Ala Pro Arg Gly Gln
             20                  25                  30 tgt gcg gtg aga ggc ctt cac aaa ttt cct gaa tat cgc ggt acg tgt       144
Cys Ala Val Arg Gly Leu His Lys Phe Pro Glu Tyr Arg Gly Thr Cys
         35                  40                  45 cgg cga tca act ggt ccc gtt tac cga tac cca ttg cca gct cga tca       192
Arg Arg Ser Thr Gly Pro Val Tyr Arg Tyr Pro Leu Pro Ala Arg Ser
     50                  55                  60 gct tca gct tgc act cga gct tca tgc gcc ggt gct cca tat cgg           237
Ala Ser Ala Cys Thr Arg Ala Ser Cys Ala Gly Ala Pro Tyr Arg
 65                  70                  75 taatttcaa tttagactcg tacgattcct gtacgcgcaa ctgttccaac ttgaccactt      297
tcaattcact attggaccgc gacagggcca actccagctc caaaatcttt tcgtttgact    357
gtagttgatt tgtgggctcc actgcacctc catcaccctg tccaatggtg ccaatttgca    417
gctcacctcg ggcacgggcc gctggtaaaa ttttaccaaa cacaagctcc ttgtactttt    477
gcacattggg cagccgtgaa ccgatcagca tctggtggat tccaccctcg ttgaccacca    537
caatgtcccg ttcgcgagac gatagctcca ccggtgcacc ctccagtcgt gctacctctg    597
attcaacggt acccgaaaaa ggttcggtgt gaactaggtc cgacagcttt cgcttgaagg    657
cggcgaggat tcgcgtgtgc gtttggcgat acttttcgta acccaagcag cgcgctagat    717
ccgccgccac gacccacggc tcgttggtga tcgggtggat gtacaaccgc agcacgacac    777
tcttgtcgtc cacgtcccaa ttttgcagct gaaacacgct cgaccccaca tcgcactcca    837
cctcgataat attatcgtct tcgaaaaagt tacagtcaaa cgtttcgttc cacagtttgc    897
ttagctgggg ccaaatatccc tccttggtgg ccgccagttg gcgcagtcca tctcgattta    957
tcatcgtcgt ttccatcttc caattgatgg gcaattttac gcacaacccg gccgccaaca   1017
```

-continued

```
ccttccactg gatgcgattt cggctggaca ccttgcggca catgctggcc gtgggatcct    1077
tgaagccgag gcccgcgctg acggtgcgcc cagaaacgta aacctttcca ctggttggtt    1137
cggtaaagtg gtaaaattgt aacacaagct cagcaccacc gtatcccacc acggtccaca    1197
cttggaactt gagctctaga tcgttgcacg ccatgacttc actatccgca ccacacggga    1257
cagctccacc cttttatagc gcataaaccg caacttttag gttaataaaa aaatgatat    1317 taattttatt ataaaatgga ccgttgagct agagtccacc tcaccacctc acaacctatg    1377
tttccaagtg gcccaattcg gggccggtct gatcatcggt aatttgctgt gatatgcatt    1437
aaaaaaaaaa acgaatctgg gtttgggggg aaaatatttt tattatttct accttcaaac    1497
taaacttcta ccaactgcgg cgactcatca ac atg tcc atc aac cgg agc gac     1550
                                    Met Ser Ile Asn Arg Ser Asp
                                     80              85 gac tgg tgc tgc tgg cac tgg ttc tct aga gtc gga ctc agg ctc agg    1598
Asp Trp Cys Cys Trp His Trp Phe Ser Arg Val Gly Leu Arg Leu Arg
         90                  95                 100 ctc ggg ctt tgg atc ggg ctc ggg ctc gtg ctc gag ttg ggc atc atc    1646
Leu Gly Leu Trp Ile Gly Leu Gly Leu Val Leu Glu Leu Gly Ile Ile
        105                 110                 115 agt tgg cat atc ggg cag ctc tgg tcc cgg ttc agc tgc aga ctc ggg    1694
Ser Trp His Ile Gly Gln Leu Trp Ser Arg Phe Ser Cys Arg Leu Gly
    120                 125                 130 ctc tgg ttt tgg ttc ggg caa atc ttg atc gac tgg ggc tgg act cgg    1742
Leu Trp Phe Trp Phe Gly Gln Ile Leu Ile Asp Trp Gly Trp Thr Arg
135                 140                 145                 150 cgt acg ggc gcg ctt gtt aac cgg ttc gtt tgg ttc aac gac ggt ggt    1790
Arg Thr Gly Ala Leu Val Asn Arg Phe Val Trp Phe Asn Asp Gly Gly
                155                 160                 165 gtc gac cga acg ttt tcc atc tcc aca gcc ttt agg ttt gat aaa gtt    1838
Val Asp Arg Thr Phe Ser Ile Ser Thr Ala Phe Arg Phe Asp Lys Val
            170                 175                 180 cac ctc ggc aat atg ttc acc ggc gcc gaa tgt ggt cgc ttt aag gac    1886
His Leu Gly Asn Met Phe Thr Gly Ala Glu Cys Gly Arg Phe Lys Asp
        185                 190                 195 gta cac ttg cag acg aaa agc gat ctt att gag ctc cgt gcc ctc gcg    1934
Val His Leu Gln Thr Lys Ser Asp Leu Ile Glu Leu Arg Ala Leu Ala
    200                 205                 210 ctg aat cac aaa gac cgc caa att cgg gtt gta att gtg tac ggt cgt    1982
Leu Asn His Lys Asp Arg Gln Ile Arg Val Val Ile Val Tyr Gly Arg
215                 220                 225                 230 gtg cag ctt gat gtc gtg cgg gtg gtc ctc acc aaa ggg tcc act cgt    2030
Val Gln Leu Asp Val Val Arg Val Val Leu Thr Lys Gly Ser Thr Arg
                235                 240                 245 gct tac ata gtg ata gta cac gtc ggt gag ccc ggg taaaattagt         2076
Ala Tyr Ile Val Ile Val His Val Gly Glu Pro Gly
            250                 255 tggttgcgcg atgagtacaa ctggttaccg ttgctgatct caatctcaaa ctgcattgtc    2136
gtatcgaaca aaaagttcct cgatgttctt cgtaaaaacg ttccacaact cgggactggg    2196
gttgcgcttt ccgcgtatat tctgggtcat agattttaac gacttaatgt ccaccgcctt    2256
atcctcaccg tcccgcttga taacggtttt gcggtataga aaggaccgtt tgaactgctc    2316
gattgggatg cagaagatgt gcctatccat gaccgtcccc gtaacgcggt tcgtcagttt    2376
acagaccgcc at atg gtc cgg gta gta cgg gca aat gcc aac gct gtg gat   2427
               Met Val Arg Val Val Arg Ala Asn Ala Asn Ala Val Asp
                260                 265                 270
```

| | |
|---|---|
| gat ttt cga tgc ggc cat ggt tgt gct gag caa atc gct gtt acc aat<br>Asp Phe Arg Cys Gly His Gly Cys Ala Glu Gln Ile Ala Val Thr Asn<br>275                 280                 285 | 2475 |
| cag gca ggt tac gag cgt gat ggc aat caa cac ggc cct gta gta gcg<br>Gln Ala Gly Tyr Glu Arg Asp Gly Asn Gln His Gly Pro Val Val Ala<br>        290                 295                 300 | 2523 |
| gta att tac tat cac ctc gtc gtc cag tgg gta gcc gcg cga gac cag<br>Val Ile Tyr Tyr His Leu Val Val Gln Trp Val Ala Ala Arg Asp Gln<br>305                 310                 315 | 2571 |
| tgg gta ctc gag atc ttc aac gaa ggg gtg tat aat gag gag gtc ctg<br>Trp Val Leu Glu Ile Phe Asn Glu Gly Val Tyr Asn Glu Glu Val Leu<br>320                 325                 330                 335 | 2619 |
| tgg tgc tagcaccgca gattccgcgc taacgtacaa ctctagcgcc gagttgggcg<br>Trp Cys | 2675 |
| aaattaaaat ttgtctatct agcgttctgt atatgcggtc aagttcatcg taaacgtggc | 2735 |
| caatgtttat aactctaccc ccaaagctgg agcggaacag gtccaggtcg aaccgcagca | 2795 |
| cacaattgat cttgttggac gcgtataaac aggcgtcaac tgtacctcgg ttttccctgc | 2855 |
| acatgcccat cagggccaca taatggtgca ccatgttcga gttcaggtac ccatcgaga | 2915 |
| gttcggtgac gtgagttttg ctgtagtttt tgatgaaaat tttacacttg attttttgtat | 2975 |
| ccacatgcac cggacagggg ttccgccgac cctcgcgacc ggcttgggat tttgttcgat | 3035 |
| gaaccgccgc taacgtcacg ttcggtaaca gggtgaggca tttgaccgac cgtgaagtaa | 3095 |
| gtgtatccaa ctccatcact gcaaactgcg cgaacttcaa tctccttcgt ctccggattg | 3155 |
| attataaccc tttgccgcag aaaagtctcg gtaaacgcat ccatatggaa acaattcgcc | 3215 |
| tcgttacggc cggtaaacct tacaagcggt ttgagcagtc gccgtttgtt acaatgtccc | 3275 |
| gctctgaata cgaactgcga accgcaccta acgcaaacaa tgactactct ttcgtgatgc | 3335 |
| gaatgggtaa taagacacgt attgtgaacc tctgggcgcc cgtacacggc caggttgttt | 3395 |
| tatacgacta a atg aat cga agc tcg aga gcc gag ggt cta cgt gaa tcc<br>            Met Asn Arg Ser Ser Arg Ala Glu Gly Leu Arg Glu Ser<br>                    340                 345                 350 | 3445 |
| ggt ggc gtt aaa ggc cgc cca aaa tca cgc gcc act aca acc atc aaa<br>Gly Gly Val Lys Gly Arg Pro Lys Ser Arg Ala Thr Thr Thr Ile Lys<br>                355                 360                 365 | 3493 |
| gct ggt aga ccg gtg cgc cca gct cgg cag cga caa gtt gat gaa att<br>Ala Gly Arg Pro Val Arg Pro Ala Arg Gln Arg Gln Val Asp Glu Ile<br>        370                 375                 380 | 3541 |
| tta aac caa gat gaa aat gac gat gta gca cca cct gta gcc gag ccc<br>Leu Asn Gln Asp Glu Asn Asp Asp Val Ala Pro Pro Val Ala Glu Pro<br>385                 390                 395 | 3589 |
| cag cta aat ttg gat gat aat gtt tgg acc ggt ggt gct acg agt ggt<br>Gln Leu Asn Leu Asp Asp Asn Val Trp Thr Gly Gly Ala Thr Ser Gly<br>400                 405                 410 | 3637 |
| gat caa aat gtg gcc cca ggt tca ccc acg ggt ccc gtg gca atg tcg<br>Asp Gln Asn Val Ala Pro Gly Ser Pro Thr Gly Pro Val Ala Met Ser<br>415                 420                 425                 430 | 3685 |
| gtg ata tcg aag cgt ctc gtg agc gag tgg cac tcg gac gga gaa ggt<br>Val Ile Ser Lys Arg Leu Val Ser Glu Trp His Ser Asp Gly Glu Gly<br>                435                 440                 445 | 3733 |
| gag gat gaa ggt ggg cag gat aac gat ccc gag ccc gag tcg gcg gcc<br>Glu Asp Glu Gly Gly Gln Asp Asn Asp Pro Glu Pro Glu Ser Ala Ala<br>        450                 455                 460 | 3781 |
| aag gtg gac gac ttt tta ttt ccc gag ctc gag gaa gac gga ccg gac<br>Lys Val Asp Asp Phe Leu Phe Pro Glu Leu Glu Glu Asp Gly Pro Asp<br>465                 470                 475 | 3829 |

-continued

| | |
|---|---|
| tcg gtt ggc gga att ggc aac gtt tct ggt tca gtt ttc gaa gtt gtc<br>Ser Val Gly Gly Ile Gly Asn Val Ser Gly Ser Val Phe Glu Val Val<br>480                      485                      490 | 3877 |
| ggt ggt ggc ccc gag ggc gac tat gct gct ggt gag gag gac gaa gta<br>Gly Gly Gly Pro Glu Gly Asp Tyr Ala Ala Gly Glu Glu Asp Glu Val<br>495                      500                      505               510 | 3925 |
| agc aga aat tcg cta aac ttc gac atg gcg tcc gag gtg caa agt act<br>Ser Arg Asn Ser Leu Asn Phe Asp Met Ala Ser Glu Val Gln Ser Thr<br>                 515                      520                      525 | 3973 |
| gat gcc gct aag gtg atg gag ctg ttt agc gcc cta tcc gag gag cag<br>Asp Ala Ala Lys Val Met Glu Leu Phe Ser Ala Leu Ser Glu Glu Gln<br>            530                      535                      540 | 4021 |
| cga aat gtg att cta aac aac ttt ggt gcg gca cca tcc ggt agc gga<br>Arg Asn Val Ile Leu Asn Asn Phe Gly Ala Ala Pro Ser Gly Ser Gly<br>545                      550                      555 | 4069 |
| acc aca ccg cca acc tcg gct caa ccc gat atg gag gtt gag gat gtt<br>Thr Thr Pro Pro Thr Ser Ala Gln Pro Asp Met Glu Val Glu Asp Val<br>            560                      565                      570 | 4117 |
| gag act gtg gaa aag ccg gag aat tta aac gac att att acg gac cag<br>Glu Thr Val Glu Lys Pro Glu Asn Leu Asn Asp Ile Ile Thr Asp Gln<br>575                      580                      585               590 | 4165 |
| ttg cgc gat ttc atg gca cag gag ctg aaa aag gcc gct gaa aat tat<br>Leu Arg Asp Phe Met Ala Gln Glu Leu Lys Lys Ala Ala Glu Asn Tyr<br>                 595                      600                      605 | 4213 |
| gta cca aag tgg ggc tca acg gtt ggt gag tcg aaa agt gcg ctc gca<br>Val Pro Lys Trp Gly Ser Thr Val Gly Glu Ser Lys Ser Ala Leu Ala<br>            610                      615                      620 | 4261 |
| att acg gtt gcc gat cgc gtg agc aga tcg ttc atg tac gag ggt cgt<br>Ile Thr Val Ala Asp Arg Val Ser Arg Ser Phe Met Tyr Glu Gly Arg<br>625                      630                      635 | 4309 |
| att gtc gac tat aac cag gtt gtg cta cac ata ctg gac aat tat gac<br>Ile Val Asp Tyr Asn Gln Val Val Leu His Ile Leu Asp Asn Tyr Asp<br>            640                      645                      650 | 4357 |
| caa agg ttg gag gag ctg ctc tcg ttc cgc acg aaa acc tac ata atc<br>Gln Arg Leu Glu Glu Leu Leu Ser Phe Arg Thr Lys Thr Tyr Ile Ile<br>655                      660                      665               670 | 4405 |
| gcc gaa ggt gta ccg cac gac tcg aag gtg cac gac tat gtg gac ctg<br>Ala Glu Gly Val Pro His Asp Ser Lys Val His Asp Tyr Val Asp Leu<br>                 675                      680                      685 | 4453 |
| acc cag tat cgg gaa acc gtg ccg tat tca att gcc ctc aac aac ctg<br>Thr Gln Tyr Arg Glu Thr Val Pro Tyr Ser Ile Ala Leu Asn Asn Leu<br>            690                      695                      700 | 4501 |
| agc cgc ggt gtg gac cag gcc aac acg ctc cag ttg gcc gag ggg tgc<br>Ser Arg Gly Val Asp Gln Ala Asn Thr Leu Gln Leu Ala Glu Gly Cys<br>                 705                      710                      715 | 4549 |
| ttg gag cag ctg aat atg gca aaa att ttc aaa gat ttc aac gaa aac<br>Leu Glu Gln Leu Asn Met Ala Lys Ile Phe Lys Asp Phe Asn Glu Asn<br>720                      725                      730 | 4597 |
| att gtg ccc aac aac ctg cac aag cac aag ccc acc ttc ttc tat gcg<br>Ile Val Pro Asn Asn Leu His Lys His Lys Pro Thr Phe Phe Tyr Ala<br>735                      740                      745               750 | 4645 |
| aaa att atg aag ctg ttt gca cga ctg gtg gat agg gtg gac aat gag<br>Lys Ile Met Lys Leu Phe Ala Arg Leu Val Asp Arg Val Asp Asn Glu<br>                 755                      760                      765 | 4693 |
| acg atg act gcg gtc gag aag cgt ttg ttt cta atg tca caa cgg ttg<br>Thr Met Thr Ala Val Glu Lys Arg Leu Phe Leu Met Ser Gln Arg Leu<br>            770                      775                      780 | 4741 |
| atc cat tgt atc cca ctg gta ata atc ggt cta acg ttc gcc tcc aag<br>Ile His Cys Ile Pro Leu Val Ile Ile Gly Leu Thr Phe Ala Ser Lys<br>785                      790                      795 | 4789 |

```
tac cgc acc tcg aag ata gac tgc gaa gct ttg gcc ctg tac gcc gtg       4837
Tyr Arg Thr Ser Lys Ile Asp Cys Glu Ala Leu Ala Leu Tyr Ala Val
        800                 805                 810 aac cat gcg ctg tct gaa aag gtg gat aaa ttg ttc aca ttt gcg gaa       4885
Asn His Ala Leu Ser Glu Lys Val Asp Lys Leu Phe Thr Phe Ala Glu
815                 820                 825                 830 gca cag tac ggt gaa ccg ctg ctc agc cgc cgt ata cta att gaa gag       4933
Ala Gln Tyr Gly Glu Pro Leu Leu Ser Arg Arg Ile Leu Ile Glu Glu
                835                 840                 845 cag gcg tat ctg tct ttc ggg aac cac ctc gag cag cgc aac cgc gag       4981
Gln Ala Tyr Leu Ser Phe Gly Asn His Leu Glu Gln Arg Asn Arg Glu
            850                 855                 860 ctg aat gtg att ctg gat acc gta ctc aac gcc gta cga aag acg tac       5029
Leu Asn Val Ile Leu Asp Thr Val Leu Asn Ala Val Arg Lys Thr Tyr
        865                 870                 875 agg gtg tct aga gtt taagttgaca ccgattaaag atg ggc tgc gac gta acg     5082
Arg Val Ser Arg Val                         Met Gly Cys Asp Val Thr
        880                                     885 ttc acc ttg atc cac gag gta tat tct gag gtt ccc gtc gat gga aag       5130
Phe Thr Leu Ile His Glu Val Tyr Ser Glu Val Pro Val Asp Gly Lys
890                 895                 900                 905 cac gtc ccg gtc gaa tat gac cgg tac aaa atc agg tta ttg aag gag       5178
His Val Pro Val Glu Tyr Asp Arg Tyr Lys Ile Arg Leu Leu Lys Glu
                910                 915                 920 ctg acg cgt ttc ctg tgc ggt gaa acg gat aag gtt gac ggt gcc acg       5226
Leu Thr Arg Phe Leu Cys Gly Glu Thr Asp Lys Val Asp Gly Ala Thr
            925                 930                 935 agt gaa gct aaa gcg gat tgt ggg ggc aag tac acg gat gaa gag cgc       5274
Ser Glu Ala Lys Ala Asp Cys Gly Gly Lys Tyr Thr Asp Glu Glu Arg
        940                 945                 950 aag ctg ttt ggg ttt aaa tcg aag cag gtg att gac gat gaa agg ttg       5322
Lys Leu Phe Gly Phe Lys Ser Lys Gln Val Ile Asp Asp Glu Arg Leu
    955                 960                 965 tcc agg ctg ctg gag gat aac aag ttg ctg tac tct gcg gtg agt gag       5370
Ser Arg Leu Leu Glu Asp Asn Lys Leu Leu Tyr Ser Ala Val Ser Glu
970                 975                 980                 985 cgt gat gcg gcg aaa cgt gag cgc atg gag cag ctg aag cgg gag gaa       5418
Arg Asp Ala Ala Lys Arg Glu Arg Met Glu Gln Leu Lys Arg Glu Glu
                990                 995                 1000 atg gag ctc aag agc caa acg cga aga ttg cgc aaa ctg aac cag ggt       5466
Met Glu Leu Lys Ser Gln Thr Arg Arg Leu Arg Lys Leu Asn Gln Gly
            1005                1010                1015 cgt ttg ctg tcc aag tct gaa aac ttt ctt tcg atg gac ccc aag ttg       5514
Arg Leu Leu Ser Lys Ser Glu Asn Phe Leu Ser Met Asp Pro Lys Leu
        1020                1025                1030 cgc gac aag ttg atc gat cgc acc gtc ata ttg gaa cca cag tac gac       5562
Arg Asp Lys Leu Ile Asp Arg Thr Val Ile Leu Glu Pro Gln Tyr Asp
    1035                1040                1045 att ttg gcc ctg tcc gag tat aac gat ttg gta gcg caa aag gat gcc       5610
Ile Leu Ala Leu Ser Glu Tyr Asn Asp Leu Val Ala Gln Lys Asp Ala
1050                1055                1060                1065 ctc gag aag tac gaa cga atg tcc aga cga tcg ata aag aat ccg tac       5658
Leu Glu Lys Tyr Glu Arg Met Ser Arg Arg Ser Ile Lys Asn Pro Tyr
                1070                1075                1080 acc cgc tcc gcc ata aac atc gtt gag cgc cgt gag ggt gcg tca atg       5706
Thr Arg Ser Ala Ile Asn Ile Val Glu Arg Arg Glu Gly Ala Ser Met
            1085                1090                1095 ttc cgt gag aag aag cgc gaa aac att att gac aac atc cgc ggt atc       5754
Phe Arg Glu Lys Lys Arg Glu Asn Ile Ile Asp Asn Ile Arg Gly Ile
```

```
                1100              1105              1110
gac agt agc gaa agt gta gcg tgatatattt ttgaaatata aatatataaa    5805
Asp Ser Ser Glu Ser Val Ala
    1115              1120 attaataaat agataaataa ataaatgttt ctggttgaaa ttaaccaata tttattatcg    5865
ttgtatcaca cgtacccata gtaattatat atataaaaaa aagtccaatg taatttattg    5925
ggccctggaa tactttagcg gtggaccagt gctatcatcc ggtgcgggtc gctttcgtac    5985
gggtgaaatg ggtgcaattt caccgcgcct ctgcttgtcg tacagttccc aggtcatggt    6045
tgggccttct tggaacgctt tgaggtagac cttgatgtcg gcctgttcga tgggtctgtt    6105
gctgcgcaaa tgtccactgg cctgttgtac aattcggtac gagttgatat agttgtgcag    6165
ctggaccatt tcgtacgcta gtaaattttt aacaaaggcg ttgttcagta cgccggggtt    6225
ggcgatgtac tcgtccagct caacggttgg gattcgcagc aactcgatgg tgcggcccga    6285
aatggaacct tcacggcgct ttagctcctc gagcaccagt aggcggaaga gttgttcgaa    6345
ctttaccagt atgacgcccc gcaacaatag gtagtgtgaa acgcaggttt ggcagcccaa    6405
cgaaatgtac atgtttgcca ccacgttgtg cacaacttgc agtggtgcga gcgccaacat    6465
gtcattacgt tgggcaacaa tttggtcgcc cacctcggcc atgaggtgca tcacgtccca    6525
cgagttgtga aaatgttcac cgtgaatgta gggtagtggg accaccgcaa tggggtccag    6585
ctcgcactcc ttggccgcgc tgttgtagtg ggcaacgaat tc    6627

<210> SEQ ID NO 95
<211> LENGTH: 79
<212> TYPE: PRT
<213> ORGANISM: mosquito baculovirus

<400> SEQUENCE: 95

Glu Phe Cys Thr Leu Ala Pro Pro Val Cys Pro Leu Gln Leu His Val
1               5                  10                  15

Arg Thr Val Arg Tyr Ser Ser Ala Cys Ser Trp Ala Pro Arg Gly Gln
            20                  25                  30

Cys Ala Val Arg Gly Leu His Lys Phe Pro Glu Tyr Arg Gly Thr Cys
        35                  40                  45

Arg Arg Ser Thr Gly Pro Val Tyr Arg Tyr Pro Leu Pro Ala Arg Ser
    50                  55                  60

Ala Ser Ala Cys Thr Arg Ala Ser Cys Ala Gly Ala Pro Tyr Arg
65                  70                  75

<210> SEQ ID NO 96
<211> LENGTH: 179
<212> TYPE: PRT
<213> ORGANISM: mosquito baculovirus

<400> SEQUENCE: 96

Met Ser Ile Asn Arg Ser Asp Asp Trp Cys Cys Trp His Trp Phe Ser
1               5                  10                  15

Arg Val Gly Leu Arg Leu Arg Leu Gly Leu Trp Ile Gly Leu Gly Leu
            20                  25                  30

Val Leu Glu Leu Gly Ile Ile Ser Trp His Ile Gly Gln Leu Trp Ser
        35                  40                  45

Arg Phe Ser Cys Arg Leu Gly Leu Trp Phe Trp Phe Gly Gln Ile Leu
    50                  55                  60

Ile Asp Trp Gly Trp Thr Arg Arg Thr Gly Ala Leu Val Asn Arg Phe
65                  70                  75                  80
```

-continued

```
Val Trp Phe Asn Asp Gly Gly Val Asp Arg Thr Phe Ser Ile Ser Thr
                85                  90                  95

Ala Phe Arg Phe Asp Lys Val His Leu Gly Asn Met Phe Thr Gly Ala
            100                 105                 110

Glu Cys Gly Arg Phe Lys Asp Val His Leu Gln Thr Lys Ser Asp Leu
        115                 120                 125

Ile Glu Leu Arg Ala Leu Ala Leu Asn His Lys Asp Arg Gln Ile Arg
    130                 135                 140

Val Val Ile Val Tyr Gly Arg Val Gln Leu Asp Val Val Arg Val Val
145                 150                 155                 160

Leu Thr Lys Gly Ser Thr Arg Ala Tyr Ile Val Ile Val His Val Gly
                165                 170                 175

Glu Pro Gly

<210> SEQ ID NO 97
<211> LENGTH: 79
<212> TYPE: PRT
<213> ORGANISM: mosquito baculovirus

<400> SEQUENCE: 97

Met Val Arg Val Val Arg Ala Asn Ala Asn Ala Val Asp Asp Phe Arg
 1               5                  10                  15

Cys Gly His Gly Cys Ala Glu Gln Ile Ala Val Thr Asn Gln Ala Gly
            20                  25                  30

Tyr Glu Arg Asp Gly Asn Gln His Gly Pro Val Val Ala Val Ile Tyr
        35                  40                  45

Tyr His Leu Val Val Gln Trp Val Ala Ala Arg Asp Gln Trp Val Leu
    50                  55                  60

Glu Ile Phe Asn Glu Gly Val Tyr Asn Glu Glu Val Leu Trp Cys
65                  70                  75

<210> SEQ ID NO 98
<211> LENGTH: 546
<212> TYPE: PRT
<213> ORGANISM: mosquito baculovirus

<400> SEQUENCE: 98

Met Asn Arg Ser Ser Arg Ala Glu Gly Leu Arg Glu Ser Gly Gly Val
 1               5                  10                  15

Lys Gly Arg Pro Lys Ser Arg Ala Thr Thr Thr Ile Lys Ala Gly Arg
            20                  25                  30

Pro Val Arg Pro Ala Arg Gln Arg Gln Val Asp Glu Ile Leu Asn Gln
        35                  40                  45

Asp Glu Asn Asp Asp Val Ala Pro Pro Val Ala Glu Pro Gln Leu Asn
    50                  55                  60

Leu Asp Asp Asn Val Trp Thr Gly Gly Ala Thr Ser Gly Asp Gln Asn
65                  70                  75                  80

Val Ala Pro Gly Ser Pro Thr Gly Pro Val Ala Met Ser Val Ile Ser
                85                  90                  95

Lys Arg Leu Val Ser Glu Trp His Ser Asp Gly Glu Gly Glu Asp Glu
            100                 105                 110

Gly Gly Gln Asp Asn Asp Pro Glu Pro Glu Ser Ala Ala Lys Val Asp
        115                 120                 125

Asp Phe Leu Phe Pro Glu Leu Glu Glu Asp Gly Pro Asp Ser Val Gly
    130                 135                 140
```

```
Gly Ile Gly Asn Val Ser Gly Ser Val Phe Glu Val Gly Gly
145                 150                 155                 160

Pro Glu Gly Asp Tyr Ala Ala Gly Glu Glu Asp Glu Val Ser Arg Asn
                165                 170                 175

Ser Leu Asn Phe Asp Met Ala Ser Glu Val Gln Ser Thr Asp Ala Ala
                180                 185                 190

Lys Val Met Glu Leu Phe Ser Ala Leu Ser Glu Glu Gln Arg Asn Val
    195                 200                 205

Ile Leu Asn Asn Phe Gly Ala Ala Pro Ser Gly Ser Gly Thr Thr Pro
    210                 215                 220

Pro Thr Ser Ala Gln Pro Asp Met Glu Val Glu Asp Val Glu Thr Val
225                 230                 235                 240

Glu Lys Pro Glu Asn Leu Asn Asp Ile Ile Thr Asp Gln Leu Arg Asp
                245                 250                 255

Phe Met Ala Gln Glu Leu Lys Lys Ala Ala Glu Asn Tyr Val Pro Lys
                260                 265                 270

Trp Gly Ser Thr Val Gly Glu Ser Lys Ser Ala Leu Ala Ile Thr Val
    275                 280                 285

Ala Asp Arg Val Ser Arg Ser Phe Met Tyr Glu Gly Arg Ile Val Asp
    290                 295                 300

Tyr Asn Gln Val Val Leu His Ile Leu Asp Asn Tyr Asp Gln Arg Leu
305                 310                 315                 320

Glu Glu Leu Leu Ser Phe Arg Thr Lys Thr Tyr Ile Ile Ala Glu Gly
                325                 330                 335

Val Pro His Asp Ser Lys Val His Asp Tyr Val Asp Leu Thr Gln Tyr
                340                 345                 350

Arg Glu Thr Val Pro Tyr Ser Ile Ala Leu Asn Asn Leu Ser Arg Gly
                355                 360                 365

Val Asp Gln Ala Asn Thr Leu Gln Leu Ala Glu Gly Cys Leu Glu Gln
    370                 375                 380

Leu Asn Met Ala Lys Ile Phe Lys Asp Phe Asn Glu Asn Ile Val Pro
385                 390                 395                 400

Asn Asn Leu His Lys His Lys Pro Thr Phe Phe Tyr Ala Lys Ile Met
                405                 410                 415

Lys Leu Phe Ala Arg Leu Val Asp Arg Val Asp Asn Glu Thr Met Thr
                420                 425                 430

Ala Val Glu Lys Arg Leu Phe Leu Met Ser Gln Arg Leu Ile His Cys
    435                 440                 445

Ile Pro Leu Val Ile Ile Gly Leu Thr Phe Ala Ser Lys Tyr Arg Thr
    450                 455                 460

Ser Lys Ile Asp Cys Glu Ala Leu Ala Leu Tyr Ala Val Asn His Ala
465                 470                 475                 480

Leu Ser Glu Lys Val Asp Lys Leu Phe Thr Phe Ala Glu Ala Gln Tyr
                485                 490                 495

Gly Glu Pro Leu Leu Ser Arg Arg Ile Leu Ile Glu Glu Gln Ala Tyr
                500                 505                 510

Leu Ser Phe Gly Asn His Leu Glu Gln Arg Asn Arg Glu Leu Asn Val
    515                 520                 525

Ile Leu Asp Thr Val Leu Asn Ala Val Arg Lys Thr Tyr Arg Val Ser
    530                 535                 540

Arg Val
545
```

-continued

<210> SEQ ID NO 99
<211> LENGTH: 237
<212> TYPE: PRT
<213> ORGANISM: mosquito baculovirus

<400> SEQUENCE: 99

```
Met Gly Cys Asp Val Thr Phe Thr Leu Ile His Glu Val Tyr Ser Glu
 1               5                  10                  15

Val Pro Val Asp Gly Lys His Val Pro Val Glu Tyr Asp Arg Tyr Lys
            20                  25                  30

Ile Arg Leu Leu Lys Glu Leu Thr Arg Phe Leu Cys Gly Glu Thr Asp
        35                  40                  45

Lys Val Asp Gly Ala Thr Ser Glu Ala Lys Ala Asp Cys Gly Gly Lys
    50                  55                  60

Tyr Thr Asp Glu Glu Arg Lys Leu Phe Gly Phe Lys Ser Lys Gln Val
65                  70                  75                  80

Ile Asp Asp Glu Arg Leu Ser Arg Leu Leu Glu Asp Asn Lys Leu Leu
                85                  90                  95

Tyr Ser Ala Val Ser Glu Arg Asp Ala Ala Lys Arg Glu Arg Met Glu
            100                 105                 110

Gln Leu Lys Arg Glu Glu Met Glu Leu Lys Ser Gln Thr Arg Arg Leu
        115                 120                 125

Arg Lys Leu Asn Gln Gly Arg Leu Leu Ser Lys Ser Glu Asn Phe Leu
    130                 135                 140

Ser Met Asp Pro Lys Leu Arg Asp Lys Leu Ile Asp Arg Thr Val Ile
145                 150                 155                 160

Leu Glu Pro Gln Tyr Asp Ile Leu Ala Leu Ser Glu Tyr Asn Asp Leu
                165                 170                 175

Val Ala Gln Lys Asp Ala Leu Glu Lys Tyr Glu Arg Met Ser Arg Arg
            180                 185                 190

Ser Ile Lys Asn Pro Tyr Thr Arg Ser Ala Ile Asn Ile Val Glu Arg
        195                 200                 205

Arg Glu Gly Ala Ser Met Phe Arg Glu Lys Lys Arg Glu Asn Ile Ile
    210                 215                 220

Asp Asn Ile Arg Gly Ile Asp Ser Ser Glu Ser Val Ala
225                 230                 235
```

<210> SEQ ID NO 100
<211> LENGTH: 6627
<212> TYPE: DNA
<213> ORGANISM: mosquito baculovirus
<220> FEATURE:
<221> NAME/KEY: CDS
<222> LOCATION: (2159)...(2398)
<221> NAME/KEY: CDS
<222> LOCATION: (402)...(626)
<221> NAME/KEY: CDS
<222> LOCATION: (3200)...(3403)
<221> NAME/KEY: CDS
<222> LOCATION: (3738)...(3923)
<221> NAME/KEY: CDS
<222> LOCATION: (2878)...(3045)

<400> SEQUENCE: 100

```
gaattctgca cactcgcacc acccgtttgc cctctccaac tgcacgttcg tacagtgcga     60
tatagttcag cttgcagctg ggcacctcgg ggacaatgtg cggtgagagg ccttcacaaa    120
tttcctgaat atcgcggtac gtgtcggcga tcaactggtc ccgtttaccg atacccattg    180
ccagctcgat cagcttcagc ttgcactcga gcttcatgcg ccggtgctcc atatcggtaa    240
```

-continued

```
ttttcaattt agactcgtac gattcctgta cgcgcaactg ttccaacttg accactttca    300
attcactatt ggaccgcgac agggccaact ccagctccaa aatcttttcg tttgactgta    360
gttgatttgt gggctccact gcacctccat caccctgtcc a atg gtg cca att tgc    416
                                              Met Val Pro Ile Cys
                                                1             5 agc tca cct cgg gca cgg gcc gct ggt aaa att tta cca aac aca agc      464
Ser Ser Pro Arg Ala Arg Ala Ala Gly Lys Ile Leu Pro Asn Thr Ser
         10                  15                  20 tcc ttg tac ttt tgc aca ttg ggc agc cgt gaa ccg atc agc atc tgg      512
Ser Leu Tyr Phe Cys Thr Leu Gly Ser Arg Glu Pro Ile Ser Ile Trp
             25                  30                  35 tgg att cca ccc tcg ttg acc acc aca atg tcc cgt tcg cga gac gat      560
Trp Ile Pro Pro Ser Leu Thr Thr Thr Met Ser Arg Ser Arg Asp Asp
         40                  45                  50 agc tcc acc ggt gca ccc tcc agt cgt gct acc tct gat tca acg gta      608
Ser Ser Thr Gly Ala Pro Ser Ser Arg Ala Thr Ser Asp Ser Thr Val
         55                  60                  65 ccc gaa aaa ggt tcg gtg tgaactaggt ccgacagctt tcgcttgaag             656
Pro Glu Lys Gly Ser Val
 70              75 gcggcgagga ttcgcgtgtg cgtttggcga tacttttcgt aacccaagca gcgcgctaga   716
tccgccgcca cgacccacgg ctcgttggtg atcgggtgga tgtacaaccg cagcacgaca   776
ctcttgtcgt ccacgtccca attttgcagc tgaaacacgc tcgacccac atcgcactcc    836 acctcgataa tattatcgtc ttcgaaaaag ttacagtcaa acgtttcgtt ccacagtttg   896
cttagctggg gccaaatacc ctccttggtg gccgccagtt ggcgcagtcc atctcgattt   956
atcatcgtcg tttccatctt ccaattgatg gcaatttta cgcacaaccc ggccgccaac   1016
accttccact ggatgcgatt tcggctggac accttgcggc acatgctggc cgtgggatcc   1076
ttgaagccga ggcccgcgct gacggtgcgc ccagaaacga aaacctttcc actggttggt   1136
tcggtaaagt ggtaaaattg taacacaagc tcagcaccac cgtatcccac cacggtccac   1196
acttggaact tgagctctag atcgttcac gccatgactt cactatccgc accacacggg    1256
acagctccac cctttatag cgcataaacc gcaacttta ggttaataaa aaaatgata    1316 ttaattttat tataaaatgg accgttgagc tagagtccac ctcaccacct cacaacctat   1376
gtttccaagt ggcccaattc ggggccggtc tgatcatcgg taatttgctg tgatatgcat   1436 taaaaaaaa aacgaatctg ggtttggggg gaaaatattt ttattatttc taccttcaaa   1496
ctaaacttct accaactgcg gcgactcatc aacatgtcca tcaaccggag cgacgactgg   1556
tgctgctggc actggttctc tagagtcgga ctcaggctca ggctcggct ttggatcggg   1616 ctcgggctcg tgctcgagtt gggcatcatc agttggcata tcgggcagct ctggtcccgg   1676
ttcagctgca gactcgggct ctggttttgg ttcgggcaaa tcttgatcga ctggggctgg   1736
actcggcgta cgggcgcgct tgttaaccgg ttcgtttggt tcaacgacgg tggtgtcgac   1796
cgaacgtttt ccatctccac agcctttagg tttgataaag ttcacctcgg caatatgttc   1856
accggcgccg aatgtggtcg ctttaaggac gtacacttgc agacgaaaag cgatcttatt   1916
gagctccgtg ccctcgcgct gaatcacaaa gaccgcaaa ttcgggttgt aattgtgtac   1976
ggtcgtgtgc agcttgatgt cgtgcgggtg gtcctcacca aagggtccac tcgtgcttac   2036
atagtgatag tacacgtcgg tgagcccggg taaaattagt tggttgcgcg atgagtacaa   2096
ctggttaccg ttgctgatct caatctcaaa ctgcattgtc gtatcgaaca aaaagttcct   2156 cg atg ttc ttc gta aaa acg ttc cac aac tcg gga ctg ggg ttg cgc      2203
```

```
                Met Phe Phe Val Lys Thr Phe His Asn Ser Gly Leu Gly Leu Arg
                         80                  85                  90 ttt ccg cgt ata ttc tgg gtc ata gat ttt aac gac tta atg tcc acc           2251
Phe Pro Arg Ile Phe Trp Val Ile Asp Phe Asn Asp Leu Met Ser Thr
             95                 100                 105 gcc tta tcc tca ccg tcc cgc ttg ata acg gtt ttg cgg tat aga aag           2299
Ala Leu Ser Ser Pro Ser Arg Leu Ile Thr Val Leu Arg Tyr Arg Lys
            110                 115                 120 gac cgt ttg aac tgc tcg att ggg atg cag aag atg tgc cta tcc atg           2347
Asp Arg Leu Asn Cys Ser Ile Gly Met Gln Lys Met Cys Leu Ser Met
        125                 130                 135 acc gtc ccc gta acg cgg ttc gtc agt tta cag acc gcc ata tgg tcc           2395
Thr Val Pro Val Thr Arg Phe Val Ser Leu Gln Thr Ala Ile Trp Ser
    140                 145                 150 ggg tagtacgggc aaatgccaac gctgtggatg attttcgatg cggccatggt               2448
Gly
155 tgtgctgagc aaatcgctgt taccaatcag gcaggttacg agcgtgatgg caatcaacac        2508 ggccctgtag tagcggtaat ttactatcac ctcgtcgtcc agtgggtagc cgcgcgagac        2568 cagtgggtac tcgagatctt caacgaaggg gtgtataatg aggaggtcct gtggtgctag        2628 caccgcagat tccgcgctaa cgtacaactc tagcgccgag ttgggcgaaa ttaaaatttg        2688 tctatctagc gttctgtata tgcggtcaag ttcatcgtaa acgtggccaa tgtttataac        2748 tctaccccca aagctggagc ggaacaggtc caggtcgaac cgcagcacac aattgatctt        2808 gttggacgcg tataaacagg cgtcaactgt acctcggttt ccctgcaca tgcccatcag         2868 ggccacata atg gtg cac cat gtt cga gtt cag gta ccc cat cga gag ttc        2919
             Met Val His His Val Arg Val Gln Val Pro His Arg Glu Phe
                         160                 165 ggt gac gtg agt ttt gct gta gtt ttt gat gaa aat ttt aca ctt gat           2967
Gly Asp Val Ser Phe Ala Val Val Phe Asp Glu Asn Phe Thr Leu Asp
170                 175                 180                 185 ttt tgt atc cac atg cac cgg aca ggg gtt ccg ccg acc ctc gcg acc           3015
Phe Cys Ile His Met His Arg Thr Gly Val Pro Pro Thr Leu Ala Thr
            190                 195                 200 ggc ttg gga ttt tgt tcg atg aac cgc cgc taacgtcacg ttcggtaaca            3065
Gly Leu Gly Phe Cys Ser Met Asn Arg Arg
            205                 210 gggtgaggca tttgaccgac cgtgaagtaa gtgtatccaa ctccatcact gcaaactgcg        3125
cgaacttcaa tctccttcgt ctccggattg attataaccc tttgccgcag aaaagtctcg       3185
gtaaacgcat ccat atg gaa aca att cgc ctc gtt acg gcc ggt aaa cct         3235
                Met Glu Thr Ile Arg Leu Val Thr Ala Gly Lys Pro
                                215                 220 tac aag cgg ttt gag cag tcg ccg ttt gtt aca atg tcc cgc tct gaa          3283
Tyr Lys Arg Phe Glu Gln Ser Pro Phe Val Thr Met Ser Arg Ser Glu
    225                 230                 235 tac gaa ctg cga acc gca cct aac gca aac aat gac tac tct ttc gtg          3331
Tyr Glu Leu Arg Thr Ala Pro Asn Ala Asn Asn Asp Tyr Ser Phe Val
240                 245                 250                 255 atg cga atg ggt aat aag aca cgt att gtg aac ctc tgg gcg ccc gta         3379
Met Arg Met Gly Asn Lys Thr Arg Ile Val Asn Leu Trp Ala Pro Val
            260                 265                 270 cac ggc cag gtt gtt tta tac gac taaatgaatc gaagctcgag agccgagggt        3433
His Gly Gln Val Val Leu Tyr Asp
        275 ctacgtgaat ccggtggcgt taaggccggc ccaaaatcac gcgccactac aaccatcaaa       3493
```

```
                                                  -continued gctggtagac cggtgcgccc agctcggcag cgacaagttg atgaaatttt aaaccaagat    3553
gaaaatgacg atgtagcacc acctgtagcc gagccccagc taaatttgga tgataatgtt    3613
tggaccggtg gtgctacgag tggtgatcaa aatgtggccc caggttcacc cacgggtccc    3673
gtggcaatgt cggtgatatc gaagcgtctc gtgagcgagt ggcactcgga cggagaaggt    3733 gagg atg aag gtg ggc agg ata acg atc ccg agc ccg agt cgg cgg cca      3782
     Met Lys Val Gly Arg Ile Thr Ile Pro Ser Pro Ser Arg Arg Pro
         280             285                 290 agg tgg acg act ttt tat ttc ccg agc tcg agg aag acg gac cgg act       3830
Arg Trp Thr Thr Phe Tyr Phe Pro Ser Ser Arg Lys Thr Asp Arg Thr
295                 300                 305                 310 cgg ttg gcg gaa ttg gca acg ttt ctg gtt cag ttt tcg aag ttg tcg       3878
Arg Leu Ala Glu Leu Ala Thr Phe Leu Val Gln Phe Ser Lys Leu Ser
                315                 320                 325 gtg gtg gcc ccg agg gcg act atg ctg ctg gtg agg agg acg aag           3923
Val Val Ala Pro Arg Ala Thr Met Leu Leu Val Arg Arg Thr Lys
            330                 335                 340 taagcagaaa ttcgctaaac ttcgacatgg cgtccgaggt gcaaagtact gatgccgcta    3983
aggtgatgga gctgtttagc gccctatccg aggagcagcg aaatgtgatt ctaaacaact    4043
ttggtgcggc accatccggt agcggaacca caccgccaac ctcggctcaa cccgatatgg    4103
aggttgagga tgttgagact gtggaaaagc cggagaattt aaacgacatt attacggacc    4163
agttgcgcga tttcatggca caggagctga aaaaggccgc tgaaaattat gtaccaaagt    4223
ggggctcaac ggttggtgag tcgaaaagtg cgctcgcaat tacggttgcc gatcgcgtga    4283
gcagatcgtt catgtacgag ggtcgtattg tcgactataa ccaggttgtg ctacacatac    4343
tggacaatta tgaccaaagg ttggaggagc tgctctcgtt ccgcacgaaa acctacataa    4403
tcgccgaagg tgtaccgcac gactcgaagg tgcacgacta tgtggacctg acccagtatc    4463
gggaaaccgt gccgtattca attgccctca caaacctgag ccgcgtgtgt gaccaggcca    4523
acacgctcca gttggccgag gggtgcttgg agcagctgaa tatggcaaaa attttcaaag    4583
atttcaacga aacattgtgt cccaacaacc tgcacaagca aagcccacc ttcttctatg     4643 cgaaaattat gaagctgttt gcacgactgg tggatagggt ggacaatgag acgatgactg    4703
cggtcgagaa gcgtttgttt ctaatgtcac aacggttgat ccattgtatc ccactggtaa    4763
taatcggtct aacgttcgcc tccaagtacc gcacctcgaa gatagactgc gaagctttgg    4823
ccctgtacgc cgtgaaccat gcgctgtctg aaaaggtgga taaattgttc acatttgcgg    4883
aagcacagta cggtgaaccg ctgctcagcc gccgtatact aattgaagag caggcgtatc    4943
tgtctttcgg gaaccactc gagcagcgca accgcgagct gaatgtgatt ctggataccg      5003
tactcaacgc cgtacgaaag acgtacaggg tgtctagagt ttaagttgac accgattaaa    5063
gatgggctgc gacgtaacgt tcaccttgat ccacgaggta tattctgagg ttcccgtcga    5123
tggaaagcac gtcccggtcg aatatgaccg gtacaaaatc aggttattga aggagctgac    5183
gcgtttcctg tgcggtgaaa cggataaggt tgacggtgcc acgagtgaag ctaaagcgga    5243 ttgtggggc aagtacacgg atgaagagcg caagctgttt gggtttaaat cgaagcaggt     5303
gattgacgat gaaaggttgt ccaggctgct ggaggataac aagttgctgt actctgcggt    5363
gagtgagcgt gatgcggcga acgtgagcg catggagcag ctgaagcggg aggaaatgga     5423
gctcaagagc caaacgcgaa gattgcgcaa actgaaccag ggtcgtttgc tgtccaagtc    5483 tgaaaactttc ctttcgatgg accccaagtt gcgcgacaag ttgatcgatc gcaccgtcat   5543
attggaacca cagtacgaca ttttggccct gtccgagtat aacgatttgg tagcgcaaaa    5603
```

-continued

```
ggatgccctc gagaagtacg aacgaatgtc cagacgatcg ataaagaatc cgtacacccg   5663
ctccgccata aacatcgttg agcgccgtga gggtgcgtca atgttccgtg agaagaagcg   5723
cgaaaacatt attgacaaca tccgcggtat cgacagtagc gaaagtgtag cgtgatatat   5783
ttttgaaata taaatatata aaattaataa atagataaat aaataaatgt ttctggttga   5843
aattaaccaa tatttattat cgttgtatca cacgtaccca tagtaattat atatataaaa   5903
aaaagtccaa tgtaatttat tggccctgg aatactttag cggtggacca gtgctatcat   5963
ccggtgcggg tcgctttcgt acgggtgaaa tgggtgcaat ttcaccgcgc ctctgcttgt   6023
cgtacagttc ccaggtcatg gttgggcctt cttggaacgc tttgaggtag accttgatgt   6083
cggcctgttc gatgggtctg ttgctgcgca aatgtccact ggcctgttgt acaattcggt   6143
acgagttgat atagttgtgc agctggacca tttcgtacgc tagtaaattt ttaacaaagg   6203
cgttgttcag tacgccgggg ttggcgatgt actcgtccag ctcaacggtt gggattcgca   6263
gcaactcgat ggtgcggccc gaaatggaac cttcacggcg ctttagctcc tcgagcacca   6323
gtaggcggaa gagttgttcg aactttacca gtatgacgcc ccgcaacaat aggtagtgtg   6383
aaacgcaggt ttggcagccc aacgaaatgt acatgtttgc caccacgttg tgcacaactt   6443
gcagtggtgc gagcgccaac atgtcattac gttgggcaac aatttggtcg cccacctcgg   6503
ccatgaggtg catcacgtcc cacgagttgt gaaaatgttc accgtgaatg tagggtagtg   6563
ggaccaccgc aatggggtcc agctcgcact ccttggccgc gctgttgtag tgggcaacga   6623
attc                                                                6627
```

```

<210> SEQ ID NO 101
<211> LENGTH: 75
<212> TYPE: PRT
<213> ORGANISM: mosquito baculovirus

<400> SEQUENCE: 101

Met Val Pro Ile Cys Ser Ser Pro Arg Ala Arg Ala Ala Gly Lys Ile
 1               5                  10                  15

Leu Pro Asn Thr Ser Ser Leu Tyr Phe Cys Thr Leu Gly Ser Arg Glu
            20                  25                  30

Pro Ile Ser Ile Trp Trp Ile Pro Pro Ser Leu Thr Thr Thr Met Ser
        35                  40                  45

Arg Ser Arg Asp Asp Ser Ser Thr Gly Ala Pro Ser Ser Arg Ala Thr
    50                  55                  60

Ser Asp Ser Thr Val Pro Glu Lys Gly Ser Val
65                  70                  75

<210> SEQ ID NO 102
<211> LENGTH: 80
<212> TYPE: PRT
<213> ORGANISM: mosquito baculovirus

<400> SEQUENCE: 102

Met Phe Phe Val Lys Thr Phe His Asn Ser Gly Leu Gly Leu Arg Phe
 1               5                  10                  15

Pro Arg Ile Phe Trp Val Ile Asp Phe Asn Asp Leu Met Ser Thr Ala
            20                  25                  30

Leu Ser Ser Pro Ser Arg Leu Ile Thr Val Leu Arg Tyr Arg Lys Asp
        35                  40                  45

Arg Leu Asn Cys Ser Ile Gly Met Gln Lys Met Cys Leu Ser Met Thr
    50                  55                  60
```

-continued

```
Val Pro Val Thr Arg Phe Val Ser Leu Gln Thr Ala Ile Trp Ser Gly
65                  70                  75                  80

<210> SEQ ID NO 103
<211> LENGTH: 56
<212> TYPE: PRT
<213> ORGANISM: mosquito baculovirus

<400> SEQUENCE: 103

Met Val His His Val Arg Val Gln Val Pro His Arg Glu Phe Gly Asp
 1               5                  10                  15

Val Ser Phe Ala Val Val Phe Asp Glu Asn Phe Thr Leu Asp Phe Cys
            20                  25                  30

Ile His Met His Arg Thr Gly Val Pro Pro Thr Leu Ala Thr Gly Leu
        35                  40                  45

Gly Phe Cys Ser Met Asn Arg Arg
    50                  55

<210> SEQ ID NO 104
<211> LENGTH: 68
<212> TYPE: PRT
<213> ORGANISM: mosquito baculovirus

<400> SEQUENCE: 104

Met Glu Thr Ile Arg Leu Val Thr Ala Gly Lys Pro Tyr Lys Arg Phe
 1               5                  10                  15

Glu Gln Ser Pro Phe Val Thr Met Ser Arg Ser Glu Tyr Glu Leu Arg
            20                  25                  30

Thr Ala Pro Asn Ala Asn Asn Asp Tyr Ser Phe Val Met Arg Met Gly
        35                  40                  45

Asn Lys Thr Arg Ile Val Asn Leu Trp Ala Pro Val His Gly Gln Val
    50                  55                  60

Val Leu Tyr Asp
65

<210> SEQ ID NO 105
<211> LENGTH: 62
<212> TYPE: PRT
<213> ORGANISM: mosquito baculovirus

<400> SEQUENCE: 105

Met Lys Val Gly Arg Ile Thr Ile Pro Ser Pro Ser Arg Arg Pro Arg
 1               5                  10                  15

Trp Thr Thr Phe Tyr Phe Pro Ser Ser Arg Lys Thr Asp Arg Thr Arg
            20                  25                  30

Leu Ala Glu Leu Ala Thr Phe Leu Val Gln Phe Ser Lys Leu Ser Val
        35                  40                  45

Val Ala Pro Arg Ala Thr Met Leu Leu Val Arg Arg Thr Lys
    50                  55                  60

<210> SEQ ID NO 106
<211> LENGTH: 6627
<212> TYPE: DNA
<213> ORGANISM: mosquito baculovirus
<220> FEATURE:
<221> NAME/KEY: CDS
<222> LOCATION: (5397)...(6627)
<221> NAME/KEY: CDS
<222> LOCATION: (3517)...(4503)
<221> NAME/KEY: CDS
<222> LOCATION: (884)...(1588)
```

```
<221> NAME/KEY: CDS
<222> LOCATION: (43)...(705)
<221> NAME/KEY: CDS
<222> LOCATION: (4818)...(5120)
<221> NAME/KEY: CDS
<222> LOCATION: (2029)...(2184)

<400> SEQUENCE: 106
gaattcgttg cccactacaa cagcgcggcc aaggagtgcg ag ctg gac ccc att        54
                                               Leu Asp Pro Ile
                                                 1 gcg gtg gtc cca cta ccc tac att cac ggt gaa cat ttt cac aac tcg      102
Ala Val Val Pro Leu Pro Tyr Ile His Gly Glu His Phe His Asn Ser
  5              10                  15                  20 tgg gac gtg atg cac ctc atg gcc gag gtg ggc gac caa att gtt gcc      150
Trp Asp Val Met His Leu Met Ala Glu Val Gly Asp Gln Ile Val Ala
              25                  30                  35 caa cgt aat gac atg ttg gcg ctc gca cca ctg caa gtt gtg cac aac      198
Gln Arg Asn Asp Met Leu Ala Leu Ala Pro Leu Gln Val Val His Asn
          40                  45                  50 gtg gtg gca aac atg tac att tcg ttg ggc tgc caa acc tgc gtt tca      246
Val Val Ala Asn Met Tyr Ile Ser Leu Gly Cys Gln Thr Cys Val Ser
      55                  60                  65 cac tac cta ttg ttg cgg ggc gtc ata ctg gta aag ttc gaa caa ctc      294
His Tyr Leu Leu Leu Arg Gly Val Ile Leu Val Lys Phe Glu Gln Leu
 70                  75                  80 ttc cgc cta ctg gtg ctc gag gag cta aag cgc cgt gaa ggt tcc att      342
Phe Arg Leu Leu Val Leu Glu Glu Leu Lys Arg Arg Glu Gly Ser Ile
 85                  90                  95                 100 tcg ggc cgc acc atc gag ttg ctg cga atc cca acc gtt gag ctg gac      390
Ser Gly Arg Thr Ile Glu Leu Leu Arg Ile Pro Thr Val Glu Leu Asp
             105                 110                 115 gag tac atc gcc aac ccc ggc gta ctg aac aac gcc ttt gtt aaa aat      438
Glu Tyr Ile Ala Asn Pro Gly Val Leu Asn Asn Ala Phe Val Lys Asn
         120                 125                 130 tta cta gcg tac gaa atg gtc cag ctg cac aac tat atc aac tcg tac      486
Leu Leu Ala Tyr Glu Met Val Gln Leu His Asn Tyr Ile Asn Ser Tyr
     135                 140                 145 cga att gta caa cag gcc agt gga cat ttg cgc agc aac aga ccc atc      534
Arg Ile Val Gln Gln Ala Ser Gly His Leu Arg Ser Asn Arg Pro Ile
 150                 155                 160 gaa cag gcc gac atc aag gtc tac ctc aaa gcg ttc caa gaa ggc cca      582
Glu Gln Ala Asp Ile Lys Val Tyr Leu Lys Ala Phe Gln Glu Gly Pro
165                 170                 175                 180 acc atg acc tgg gaa ctg tac gac aag cag agg cgc ggt gaa att gca      630
Thr Met Thr Trp Glu Leu Tyr Asp Lys Gln Arg Arg Gly Glu Ile Ala
             185                 190                 195 ccc att tca ccc gta cga aag cga ccc gca ccg gat gat agc act ggt      678
Pro Ile Ser Pro Val Arg Lys Arg Pro Ala Pro Asp Asp Ser Thr Gly
         200                 205                 210 cca ccg cta aag tat tcc agg gcc caa taaattacat tggactttt             725
Pro Pro Leu Lys Tyr Ser Arg Ala Gln
     215                 220 tttatatata taattactat gggtacgtgt gatacaacga taataaatat tggttaattt    785
caaccagaaa catttattta tttatctatt tattaatttt atatatttat atttcaaaaa    845
tatatcacgc tacactttcg ctactgtcga taccgcgg atg ttg tca ata atg ttt    901
                                          Met Leu Ser Ile Met Phe
                                                        225 tcg cgc ttc ttc tca cgg aac att gac gca ccc tca cgg cgc tca acg      949
Ser Arg Phe Phe Ser Arg Asn Ile Asp Ala Pro Ser Arg Arg Ser Thr
```

|     |     |     |     |     |     |     |     |     |     |     |     |     |     |     |     | |
|-----|-----|-----|-----|-----|-----|-----|-----|-----|-----|-----|-----|-----|-----|-----|-----|---|
|     |     | 230 |     |     |     |     | 235 |     |     |     |     | 240 |     |     |     | |
| atg | ttt | atg | gcg | gag | cgg | gtg | tac | gga | ttc | ttt | atc | gat | cgt | ctg | gac | 997 |
| Met | Phe | Met | Ala | Glu | Arg | Val | Tyr | Gly | Phe | Phe | Ile | Asp | Arg | Leu | Asp | |
|     | 245 |     |     |     | 250 |     |     |     |     | 255 |     |     |     |     |     | |
| att | cgt | tcg | tac | ttc | tcg | agg | gca | tcc | ttt | tgc | gct | acc | aaa | tcg | tta | 1045 |
| Ile | Arg | Ser | Tyr | Phe | Ser | Arg | Ala | Ser | Phe | Cys | Ala | Thr | Lys | Ser | Leu | |
| 260 |     |     |     |     | 265 |     |     |     |     | 270 |     |     |     |     | 275 | |
| tac | tcg | gac | agg | gcc | aaa | atg | tcg | tac | tgt | ggt | tcc | aat | atg | acg | gtg | 1093 |
| Tyr | Ser | Asp | Arg | Ala | Lys | Met | Ser | Tyr | Cys | Gly | Ser | Asn | Met | Thr | Val | |
|     |     |     |     | 280 |     |     |     |     | 285 |     |     |     |     | 290 |     | |
| cga | tcg | atc | aac | ttg | tcg | cgc | aac | ttg | ggg | tcc | atc | gaa | aga | aag | ttt | 1141 |
| Arg | Ser | Ile | Asn | Leu | Ser | Arg | Asn | Leu | Gly | Ser | Ile | Glu | Arg | Lys | Phe | |
|     |     |     | 295 |     |     |     |     | 300 |     |     |     |     | 305 |     |     | |
| tca | gac | ttg | gac | agc | aaa | cga | ccc | tgg | ttc | agt | ttg | cgc | aat | ctt | cgc | 1189 |
| Ser | Asp | Leu | Asp | Ser | Lys | Arg | Pro | Trp | Phe | Ser | Leu | Arg | Asn | Leu | Arg | |
|     |     | 310 |     |     |     |     | 315 |     |     |     |     | 320 |     |     |     | |
| gtt | tgg | ctc | ttg | agc | tcc | att | tcc | tcc | cgc | ttc | agc | tgc | tcc | atg | cgc | 1237 |
| Val | Trp | Leu | Leu | Ser | Ser | Ile | Ser | Ser | Arg | Phe | Ser | Cys | Ser | Met | Arg | |
|     | 325 |     |     |     |     | 330 |     |     |     |     | 335 |     |     |     |     | |
| tca | cgt | ttc | gcc | gca | tca | cgc | tca | ctc | acc | gca | gag | tac | agc | aac | ttg | 1285 |
| Ser | Arg | Phe | Ala | Ala | Ser | Arg | Ser | Leu | Thr | Ala | Glu | Tyr | Ser | Asn | Leu | |
| 340 |     |     |     |     | 345 |     |     |     |     | 350 |     |     |     |     | 355 | |
| tta | tcc | tcc | agc | agc | ctg | gac | aac | ctt | tca | tcg | tca | atc | acc | tgc | ttc | 1333 |
| Leu | Ser | Ser | Ser | Ser | Leu | Asp | Asn | Leu | Ser | Ser | Ser | Ile | Thr | Cys | Phe | |
|     |     |     |     | 360 |     |     |     |     | 365 |     |     |     |     | 370 |     | |
| gat | tta | aac | cca | aac | agc | ttg | cgc | tct | tca | tcc | gtg | tac | ttg | ccc | cca | 1381 |
| Asp | Leu | Asn | Pro | Asn | Ser | Leu | Arg | Ser | Ser | Ser | Val | Tyr | Leu | Pro | Pro | |
|     |     |     | 375 |     |     |     |     | 380 |     |     |     |     | 385 |     |     | |
| caa | tcc | gct | tta | gct | tca | ctc | gtg | gca | ccg | tca | acc | tta | tcc | gtt | tca | 1429 |
| Gln | Ser | Ala | Leu | Ala | Ser | Leu | Val | Ala | Pro | Ser | Thr | Leu | Ser | Val | Ser | |
|     |     | 390 |     |     |     |     | 395 |     |     |     |     | 400 |     |     |     | |
| ccg | cac | agg | aaa | cgc | gtc | agc | tcc | ttc | aat | aac | ctg | att | ttg | tac | cgg | 1477 |
| Pro | His | Arg | Lys | Arg | Val | Ser | Ser | Phe | Asn | Asn | Leu | Ile | Leu | Tyr | Arg | |
|     | 405 |     |     |     |     | 410 |     |     |     |     | 415 |     |     |     |     | |
| tca | tat | tcg | acc | ggg | acg | tgc | ttt | cca | tcg | acg | gga | acc | tca | gaa | tat | 1525 |
| Ser | Tyr | Ser | Thr | Gly | Thr | Cys | Phe | Pro | Ser | Thr | Gly | Thr | Ser | Glu | Tyr | |
| 420 |     |     |     |     | 425 |     |     |     |     | 430 |     |     |     |     | 435 | |
| acc | tcg | tgg | atc | aag | gtg | aac | gtt | acg | tcg | cag | ccc | atc | ttt | aat | cgg | 1573 |
| Thr | Ser | Trp | Ile | Lys | Val | Asn | Val | Thr | Ser | Gln | Pro | Ile | Phe | Asn | Arg | |
|     |     |     |     | 440 |     |     |     |     | 445 |     |     |     |     | 450 |     | |
| tgt | caa | ctt | aaa | ctc | tagacaccct gtacgtcttt cgtacggcgt tgagtacggt | | | | | | | | | | | 1628 |
| Cys | Gln | Leu | Lys | Leu | | | | | | | | | | | | |
|     |     |     | 455 |     | | | | | | | | | | | | | atccagaatc acattcagct cgcggttgcg ctgctcgagg tggttcccga aagacagata    1688 cgcctgctct tcaattagta tacggcggct gagcagcggt tcaccgtact gtgcttccgc    1748 aaatgtgaac aatttatcca ccttttcaga cagcgcatgg ttcacggcgt acagggccaa    1808 agcttcgcag tctatcttcg aggtgcggta cttggaggcg aacgttagac cgattattac    1868 cagtgggata caatggatca accgttgtga cattagaaac aaacgcttct cgaccgcagt    1928 catcgtctca ttgtccaccc tatccaccag tcgtgcaaac agcttcataa ttttcgcata    1988

|     |     |     |     |     |     |     |     |     |     |     |     |     |     |     |     | |
|-----|-----|-----|-----|-----|-----|-----|-----|-----|-----|-----|-----|-----|-----|-----|-----|---|
| gaagaaggtg ggcttgtgct tgtgcaggtt gttgggcaca | | | | | atg | ttt | tcg | ttg | aaa | | | | | | | 2043 |
| | | | | | Met | Phe | Ser | Leu | Lys | | | | | | | |
| | | | | | | | | 460 | | | | | | | | |
| tct | ttg | aaa | att | ttt | gcc | ata | ttc | agc | tgc | tcc | aag | cac | ccc | tcg | gcc | 2091 |
| Ser | Leu | Lys | Ile | Phe | Ala | Ile | Phe | Ser | Cys | Ser | Lys | His | Pro | Ser | Ala | |
|     |     |     | 465 |     |     |     |     | 470 |     |     |     |     | 475 |     |     | |
| aac | tgg | agc | gtg | ttg | gcc | tgg | tcc | aca | ccg | cgg | ctc | agg | ttg | ttg | agg | 2139 |

```
Asn Trp Ser Val Leu Ala Trp Ser Thr Pro Arg Leu Arg Leu Leu Arg
        480                 485                 490 gca att gaa tac ggc acg gtt tcc cga tac tgg gtc agg tcc aca        2184
Ala Ile Glu Tyr Gly Thr Val Ser Arg Tyr Trp Val Arg Ser Thr
        495                 500                 505 tagtcgtgca ccttcgagtc gtgcggtaca ccttcggcga ttatgtaggt tttcgtgcgg  2244
aacgagagca gctcctccaa cctttggtca taattgtcca gtatgtgtag cacaacctgg  2304
ttatagtcga caatacgacc ctcgtacatg aacgatctgc tcacgcgatc ggcaaccgta  2364
attgcgagcg cacttttcga ctcaccaacc gttgagcccc actttggtac ataatttca   2424 gcggcctttt tcagctcctg tgccatgaaa tcgcgcaact ggtccgtaat aatgtcgttt  2484
aaattctccg gcttttccac agtctcaaca tcctcaacct ccatatcggg ttgagccgag  2544
gttggcggtg tggttccgct accggatggt gccgcaccaa agttgtttag aatcacattt  2604
cgctgctcct cggatagggc gctaaacagc tccatcacct tagcggcatc agtactttgc  2664
acctcggacg ccatgtcgaa gtttagcgaa tttctgctta cttcgtcctc ctcaccagca  2724
gcatagtcgc cctcggggcc accaccgaca acttcgaaaa ctgaaccaga acgttgcca   2784 attccgccaa ccgagtccgg tccgtcttcc tcgagctcgg aaataaaaa gtcgtccacc   2844 ttggccgccg actcgggctc gggatcgtta tcctgcccac cttcatcctc accttctccg  2904
tccgagtgcc actcgctcac gagacgcttc gatatcaccg acattgccac gggacccgtg  2964
ggtgaacctg gggccacatt ttgatcacca ctcgtagcac caccggtcca aacattatca  3024
tccaaattta gctggggctc ggctacaggt ggtgctacat cgtcattttc atcttggttt  3084
aaaatttcat caacttgtcg ctgccgagct gggcgcaccg gtctaccagc tttgatggtt  3144
gtagtggcgc gtgattttgg gcggccttta acgccaccgg attcacgtag accctcggct  3204
ctcgagcttc gattcattta gtcgtataaa acaacctggc cgtgtacggg cgcccagagg  3264
ttcacaatac gtgtcttatt acccattcgc atcacgaaag agtagtcatt gtttgcgtta  3324
ggtgcggttc gcagttcgta ttcagagcgg acattgtaa caaacggcga ctgctcaaac   3384
cgcttgtaag gtttaccggc cgtaacgagg cgaattgttt ccatatggat gcgtttaccg  3444
agacttttct gcggcaaagg gttataatca atccggagac gaaggagatt gaagttcgcg  3504
cagtttgcag tg atg gag ttg gat aca ctt act tca cgg tcg gtc aaa tgc  3555
           Met Glu Leu Asp Thr Leu Thr Ser Arg Ser Val Lys Cys
                    510                 515                 520 ctc acc ctg tta ccg aac gtg acg tta gcg gcg gtt cat cga aca aaa    3603
Leu Thr Leu Leu Pro Asn Val Thr Leu Ala Ala Val His Arg Thr Lys
        525                 530                 535 tcc caa gcc ggt cgc gag ggt cgg cgg aac ccc tgt ccg gtg cat gtg    3651
Ser Gln Ala Gly Arg Glu Gly Arg Arg Asn Pro Cys Pro Val His Val
        540                 545                 550 gat aca aaa atc aag tgt aaa att ttc atc aaa aac tac agc aaa act    3699
Asp Thr Lys Ile Lys Cys Lys Ile Phe Ile Lys Asn Tyr Ser Lys Thr
        555                 560                 565 cac gtc acc gaa ctc tcg atg ggg tac ctg aac tcg aac atg gtg cac    3747
His Val Thr Glu Leu Ser Met Gly Tyr Leu Asn Ser Asn Met Val His
570         575                 580                 585 cat tat gtg gcc ctg atg ggc atg tgc agg gaa aac cga ggt aca gtt    3795
His Tyr Val Ala Leu Met Gly Met Cys Arg Glu Asn Arg Gly Thr Val
                590                 595                 600 gac gcc tgt tta tac gcg tcc aac aag atc aat tgt gtg ctg cgg ttc    3843
Asp Ala Cys Leu Tyr Ala Ser Asn Lys Ile Asn Cys Val Leu Arg Phe
            605                 610                 615
```

-continued

| | |
|---|---|
| gac ctg gac ctg ttc cgc tcc agc ttt ggg ggt aga gtt ata aac att<br>Asp Leu Asp Leu Phe Arg Ser Ser Phe Gly Gly Arg Val Ile Asn Ile<br>620                        625                    630 | 3891 |
| ggc cac gtt tac gat gaa ctt gac cgc ata tac aga acg cta gat aga<br>Gly His Val Tyr Asp Glu Leu Asp Arg Ile Tyr Arg Thr Leu Asp Arg<br>    635                      640                    645 | 3939 |
| caa att tta att tcg ccc aac tcg gcg cta gag ttg tac gtt agc gcg<br>Gln Ile Leu Ile Ser Pro Asn Ser Ala Leu Glu Leu Tyr Val Ser Ala<br>650                        655                    660                665 | 3987 |
| gaa tct gcg gtg cta gca cca cag gac ctc ctc att ata cac ccc ttc<br>Glu Ser Ala Val Leu Ala Pro Gln Asp Leu Leu Ile Ile His Pro Phe<br>              670                    675                    680 | 4035 |
| gtt gaa gat ctc gag tac cca ctg gtc tcg cgc ggc tac cca ctg gac<br>Val Glu Asp Leu Glu Tyr Pro Leu Val Ser Arg Gly Tyr Pro Leu Asp<br>685                        690                    695 | 4083 |
| gac gag gtg ata gta aat tac cgc tac tac agg gcc gtg ttg att gcc<br>Asp Glu Val Ile Val Asn Tyr Arg Tyr Tyr Arg Ala Val Leu Ile Ala<br>    700                      705                    710 | 4131 |
| atc acg ctc gta acc tgc ctg att ggt aac agc gat ttg ctc agc aca<br>Ile Thr Leu Val Thr Cys Leu Ile Gly Asn Ser Asp Leu Leu Ser Thr<br>715                        720                    725 | 4179 |
| acc atg gcc gca tcg aaa atc atc cac agc gtt ggc att tgc ccg tac<br>Thr Met Ala Ala Ser Lys Ile Ile His Ser Val Gly Ile Cys Pro Tyr<br>730                        735                    740                745 | 4227 |
| tac ccg gac cat atg gcg gtc tgt aaa ctg acg aac cgc gtt acg ggg<br>Tyr Pro Asp His Met Ala Val Cys Lys Leu Thr Asn Arg Val Thr Gly<br>              750                    755                    760 | 4275 |
| acg gtc atg gat agg cac atc ttc tgc atc cca atc gag cag ttc aaa<br>Thr Val Met Asp Arg His Ile Phe Cys Ile Pro Ile Glu Gln Phe Lys<br>765                        770                    775 | 4323 |
| cgg tcc ttt cta tac cgc aaa acc gtt atc aag cgg gac ggt gag gat<br>Arg Ser Phe Leu Tyr Arg Lys Thr Val Ile Lys Arg Asp Gly Glu Asp<br>    780                      785                    790 | 4371 |
| aag gcg gtg gac att aag tcg tta aaa tct atg acc cag aat ata cgc<br>Lys Ala Val Asp Ile Lys Ser Leu Lys Ser Met Thr Gln Asn Ile Arg<br>795                        800                    805 | 4419 |
| gga aag cgc aac ccc agt ccc gag ttg tgg aac gtt ttt acg aag aac<br>Gly Lys Arg Asn Pro Ser Pro Glu Leu Trp Asn Val Phe Thr Lys Asn<br>810                        815                    820                825 | 4467 |
| atc gag gaa ctt ttt gtt cga tac gac aat gca gtt tgagattgag<br>Ile Glu Glu Leu Phe Val Arg Tyr Asp Asn Ala Val<br>              830                    835 | 4513 |
| atcagcaacg gtaaccagtt gtactcatcg cgcaaccaac taattttacc cgggctcacc | 4573 |
| gacgtgtact atcactatgt aagcacgagt ggacccttttg gtgaggacca cccgcacgac | 4633 |
| atcaagctgc acacgaccgt acacaattac aacccgaatt tggcggtctt tgtgattcag | 4693 |
| cgcgagggca cggagctcaa taagatcgct tttcgtctgc aagtgtacgt ccttaaagcg | 4753 |
| accacattcg gcgccggtga acatattgcc gaggtgaact ttatcaaacc taaaggctgt | 4813 |
| ggag atg gaa aac gtt cgg tcg aca cca ccg tcg ttg aac caa acg aac<br>     Met Glu Asn Val Arg Ser Thr Pro Pro Ser Leu Asn Gln Thr Asn<br>                       840                      845                    850 | 4862 |
| cgg tta aca agc gcg ccc gta cgc cga gtc cag ccc cag tcg atc aag<br>Arg Leu Thr Ser Ala Pro Val Arg Arg Val Gln Pro Gln Ser Ile Lys<br>855                        860                    865 | 4910 |
| att tgc ccg aac caa aac cag agc ccg agt ctg cag ctg aac cgg gac<br>Ile Cys Pro Asn Gln Asn Gln Ser Pro Ser Leu Gln Leu Asn Arg Asp<br>870                        875                    880 | 4958 |
| cag agc tgc ccg ata tgc caa ctg atg atg ccc aac tcg agc acg agc | 5006 |

```
Gln Ser Cys Pro Ile Cys Gln Leu Met Met Pro Asn Ser Ser Thr Ser
885                 890                 895                 900 ccg agc ccg atc caa agc ccg agc ctg agc ctg agt ccg act cta gag      5054
Pro Ser Pro Ile Gln Ser Pro Ser Leu Ser Leu Ser Pro Thr Leu Glu
                905                 910                 915 aac cag tgc cag cag cac cag tcg tcg ctc cgg ttg atg gac atg ttg      5102
Asn Gln Cys Gln Gln His Gln Ser Ser Leu Arg Leu Met Asp Met Leu
        920                 925                 930 atg agt cgc cgc agt tgg tagaagttta gtttgaaggt agaaataata             5150
Met Ser Arg Arg Ser Trp
            935 aaaatatttt cccccaaac ccagattcgt ttttttttt aatgcatatc acagcaaatt      5210 accgatgatc agaccggccc cgaattgggc cacttggaaa cataggttgt gaggtggtga    5270 ggtggactct agctcaacgg tccatttat aataaaatta atatcatttt ttttattaac     5330 ctaaaagttg cggtttatgc gctataaaag ggtggagctg tcccgtgtgg tgcggatagt    5390 gaagtc atg gcg tgc aac gat cta gag ctc aag ttc caa gtg tgg acc      5438
       Met Ala Cys Asn Asp Leu Glu Leu Lys Phe Gln Val Trp Thr
           940                 945                 950 gtg gtg gga tac ggt ggt gct gag ctt gtg tta caa ttt tac cac ttt      5486
Val Val Gly Tyr Gly Gly Ala Glu Leu Val Leu Gln Phe Tyr His Phe
        955                 960                 965 acc gaa cca acc agt gga aag gtt tac gtt tct ggg cgc acc gtc agc      5534
Thr Glu Pro Thr Ser Gly Lys Val Tyr Val Ser Gly Arg Thr Val Ser
    970                 975                 980 gcg ggc ctc ggc ttc aag gat ccc acg gcc agc atg tgc cgc aag gtg      5582
Ala Gly Leu Gly Phe Lys Asp Pro Thr Ala Ser Met Cys Arg Lys Val
985                 990                 995                 1000 tcc agc cga aat cgc atc cag tgg aag gtg ttg gcg gcc ggg ttg tgc      5630
Ser Ser Arg Asn Arg Ile Gln Trp Lys Val Leu Ala Ala Gly Leu Cys
        1005                1010                1015 gta aaa ttg ccc atc aat tgg aag atg gaa acg acg atg ata aat cga      5678
Val Lys Leu Pro Ile Asn Trp Lys Met Glu Thr Thr Met Ile Asn Arg
    1020                1025                1030 gat gga ctg cgc caa ctg gcg gcc acc aag gag ggt att tgg ccc cag      5726
Asp Gly Leu Arg Gln Leu Ala Ala Thr Lys Glu Gly Ile Trp Pro Gln
1035                1040                1045 cta agc aaa ctg tgg aac gaa acg ttt gac tgt aac ttt ttc gaa gac      5774
Leu Ser Lys Leu Trp Asn Glu Thr Phe Asp Cys Asn Phe Phe Glu Asp
        1050                1055                1060 gat aat att atc gag gtg gag tgc gat gtg ggg tcg agc gtg ttt cag      5822
Asp Asn Ile Ile Glu Val Glu Cys Asp Val Gly Ser Ser Val Phe Gln
1065                1070                1075                1080 ctg caa aat tgg gac gtg gac gac aag agt gtc gtg ctg cgg ttg tac      5870
Leu Gln Asn Trp Asp Val Asp Asp Lys Ser Val Val Leu Arg Leu Tyr
        1085                1090                1095 atc cac ccg atc acc aac gag ccg tgg gtc gtg gcg gcg gat cta gcg      5918
Ile His Pro Ile Thr Asn Glu Pro Trp Val Val Ala Ala Asp Leu Ala
    1100                1105                1110 cgc tgc ttg ggt tac gaa aag tat cgc caa acg cac acg cga atc ctc      5966
Arg Cys Leu Gly Tyr Glu Lys Tyr Arg Gln Thr His Thr Arg Ile Leu
        1115                1120                1125 gcc gcc ttc aag cga aag ctg tcg gac cta gtt cac acc gaa cct ttt      6014
Ala Ala Phe Lys Arg Lys Leu Ser Asp Leu Val His Thr Glu Pro Phe
    1130                1135                1140 tcg ggt acc gtt gaa tca gag gta gca cga ctg gag ggt gca ccg gtg      6062
Ser Gly Thr Val Glu Ser Glu Val Ala Arg Leu Glu Gly Ala Pro Val
1145                1150                1155                1160
```

```
gag cta tcg tct cgc gaa cgg gac att gtg gtg gtc aac gag ggt gga    6110
Glu Leu Ser Ser Arg Glu Arg Asp Ile Val Val Val Asn Glu Gly Gly
            1165                1170                1175 atc cac cag atg ctg atc ggt tca cgg ctg ccc aat gtg caa aag tac    6158
Ile His Gln Met Leu Ile Gly Ser Arg Leu Pro Asn Val Gln Lys Tyr
        1180                1185                1190 aag gag ctt gtg ttt ggt aaa att tta cca gcg gcc cgt gcc cga ggt    6206
Lys Glu Leu Val Phe Gly Lys Ile Leu Pro Ala Ala Arg Ala Arg Gly
        1195                1200                1205 gag ctg caa att ggc acc att gga cag ggt gat gga ggt gca gtg gag    6254
Glu Leu Gln Ile Gly Thr Ile Gly Gln Gly Asp Gly Gly Ala Val Glu
    1210                1215                1220 ccc aca aat caa cta cag tca aac gaa aag att ttg gag ctg gag ttg    6302
Pro Thr Asn Gln Leu Gln Ser Asn Glu Lys Ile Leu Glu Leu Glu Leu
1225                1230                1235                1240 gcc ctg tcg cgg tcc aat agt gaa ttg aaa gtg gtc aag ttg gaa cag    6350
Ala Leu Ser Arg Ser Asn Ser Glu Leu Lys Val Val Lys Leu Glu Gln
            1245                1250                1255 ttg cgc gta cag gaa tcg tac gag tct aaa ttg aaa att acc gat atg    6398
Leu Arg Val Gln Glu Ser Tyr Glu Ser Lys Leu Lys Ile Thr Asp Met
        1260                1265                1270 gag cac cgg cgc atg aag ctc gag tgc aag ctg aag ctg atc gag ctg    6446
Glu His Arg Arg Met Lys Leu Glu Cys Lys Leu Lys Leu Ile Glu Leu
        1275                1280                1285 gca atg ggt atc ggt aaa cgg gac cag ttg atc gcc gac acg tac cgc    6494
Ala Met Gly Ile Gly Lys Arg Asp Gln Leu Ile Ala Asp Thr Tyr Arg
    1290                1295                1300 gat att cag gaa att tgt gaa ggc ctc tca ccg cac att gtc ccc gag    6542
Asp Ile Gln Glu Ile Cys Glu Gly Leu Ser Pro His Ile Val Pro Glu
1305                1310                1315                1320 gtg ccc agc tgc aag ctg aac tat atc gca ctg tac gaa cgt gca gtt    6590
Val Pro Ser Cys Lys Leu Asn Tyr Ile Ala Leu Tyr Glu Arg Ala Val
            1325                1330                1335 gga gag ggc aaa cgg gtg gtg cga gtg tgc aga att c                  6627
Gly Glu Gly Lys Arg Val Val Arg Val Cys Arg Ile
            1340                1345

<210> SEQ ID NO 107
<211> LENGTH: 221
<212> TYPE: PRT
<213> ORGANISM: mosquito baculovirus

<400> SEQUENCE: 107

Leu Asp Pro Ile Ala Val Val Pro Leu Pro Tyr Ile His Gly Glu His
1               5                   10                  15

Phe His Asn Ser Trp Asp Val Met His Leu Met Ala Glu Val Gly Asp
            20                  25                  30

Gln Ile Val Ala Gln Arg Asn Asp Met Leu Ala Leu Ala Pro Leu Gln
        35                  40                  45

Val Val His Asn Val Val Ala Asn Met Tyr Ile Ser Leu Gly Cys Gln
    50                  55                  60

Thr Cys Val Ser His Tyr Leu Leu Arg Gly Val Ile Leu Val Lys
65                  70                  75                  80

Phe Glu Gln Leu Phe Arg Leu Leu Val Leu Glu Glu Leu Lys Arg Arg
                85                  90                  95

Glu Gly Ser Ile Ser Gly Arg Thr Ile Glu Leu Leu Arg Ile Pro Thr
            100                 105                 110

Val Glu Leu Asp Glu Tyr Ile Ala Asn Pro Gly Val Leu Asn Asn Ala
        115                 120                 125
```

```
Phe Val Lys Asn Leu Leu Ala Tyr Glu Met Val Gln Leu His Asn Tyr
    130                 135                 140

Ile Asn Ser Tyr Arg Ile Val Gln Gln Ala Ser Gly His Leu Arg Ser
145                 150                 155                 160

Asn Arg Pro Ile Glu Gln Ala Asp Ile Lys Val Tyr Leu Lys Ala Phe
                165                 170                 175

Gln Glu Gly Pro Thr Met Thr Trp Glu Leu Tyr Asp Lys Gln Arg Arg
                180                 185                 190

Gly Glu Ile Ala Pro Ile Ser Pro Val Arg Lys Arg Pro Ala Pro Asp
                195                 200                 205

Asp Ser Thr Gly Pro Pro Leu Lys Tyr Ser Arg Ala Gln
    210                 215                 220
```

<210> SEQ ID NO 108
<211> LENGTH: 235
<212> TYPE: PRT
<213> ORGANISM: mosquito baculovirus

<400> SEQUENCE: 108

```
Met Leu Ser Ile Met Phe Ser Arg Phe Phe Ser Arg Asn Ile Asp Ala
1               5                   10                  15

Pro Ser Arg Arg Ser Thr Met Phe Met Ala Glu Arg Val Tyr Gly Phe
                20                  25                  30

Phe Ile Asp Arg Leu Asp Ile Arg Ser Tyr Phe Ser Arg Ala Ser Phe
            35                  40                  45

Cys Ala Thr Lys Ser Leu Tyr Ser Asp Arg Ala Lys Met Ser Tyr Cys
    50                  55                  60

Gly Ser Asn Met Thr Val Arg Ser Ile Asn Leu Ser Arg Asn Leu Gly
65                  70                  75                  80

Ser Ile Glu Arg Lys Phe Ser Asp Leu Asp Ser Lys Arg Pro Trp Phe
                85                  90                  95

Ser Leu Arg Asn Leu Arg Val Trp Leu Leu Ser Ser Ile Ser Ser Arg
            100                 105                 110

Phe Ser Cys Ser Met Arg Ser Arg Phe Ala Ala Ser Arg Ser Leu Thr
    115                 120                 125

Ala Glu Tyr Ser Asn Leu Leu Ser Ser Ser Leu Asp Asn Leu Ser
    130                 135                 140

Ser Ser Ile Thr Cys Phe Asp Leu Asn Pro Asn Ser Leu Arg Ser Ser
145                 150                 155                 160

Ser Val Tyr Leu Pro Pro Gln Ser Ala Leu Ala Ser Leu Val Ala Pro
                165                 170                 175

Ser Thr Leu Ser Val Ser Pro His Arg Lys Arg Val Ser Ser Phe Asn
            180                 185                 190

Asn Leu Ile Leu Tyr Arg Ser Tyr Ser Thr Gly Thr Cys Phe Pro Ser
        195                 200                 205

Thr Gly Thr Ser Glu Tyr Thr Ser Trp Ile Lys Val Asn Val Thr Ser
    210                 215                 220

Gln Pro Ile Phe Asn Arg Cys Gln Leu Lys Leu
225                 230                 235
```

<210> SEQ ID NO 109
<211> LENGTH: 52
<212> TYPE: PRT
<213> ORGANISM: mosquito baculovirus

<400> SEQUENCE: 109

-continued

```
Met Phe Ser Leu Lys Ser Leu Lys Ile Phe Ala Ile Phe Ser Cys Ser
 1               5                  10                  15

Lys His Pro Ser Ala Asn Trp Ser Val Leu Ala Trp Ser Thr Pro Arg
                20                  25                  30

Leu Arg Leu Arg Ala Ile Glu Tyr Gly Thr Val Ser Arg Tyr Trp
            35                  40                  45

Val Arg Ser Thr
        50

<210> SEQ ID NO 110
<211> LENGTH: 329
<212> TYPE: PRT
<213> ORGANISM: mosquito baculovirus

<400> SEQUENCE: 110

Met Glu Leu Asp Thr Leu Thr Ser Arg Ser Val Lys Cys Leu Thr Leu
 1               5                  10                  15

Leu Pro Asn Val Thr Leu Ala Ala Val His Arg Thr Lys Ser Gln Ala
                20                  25                  30

Gly Arg Glu Gly Arg Arg Asn Pro Cys Pro Val His Val Asp Thr Lys
            35                  40                  45

Ile Lys Cys Lys Ile Phe Ile Lys Asn Tyr Ser Lys Thr His Val Thr
 50                  55                  60

Glu Leu Ser Met Gly Tyr Leu Asn Ser Asn Met Val His His Tyr Val
 65                  70                  75                  80

Ala Leu Met Gly Met Cys Arg Glu Asn Arg Gly Thr Val Asp Ala Cys
                85                  90                  95

Leu Tyr Ala Ser Asn Lys Ile Asn Cys Val Leu Arg Phe Asp Leu Asp
                100                 105                 110

Leu Phe Arg Ser Ser Phe Gly Arg Val Ile Asn Ile Gly His Val
            115                 120                 125

Tyr Asp Glu Leu Asp Arg Ile Tyr Arg Thr Leu Asp Arg Gln Ile Leu
 130                 135                 140

Ile Ser Pro Asn Ser Ala Leu Glu Leu Tyr Val Ser Ala Glu Ser Ala
145                 150                 155                 160

Val Leu Ala Pro Gln Asp Leu Leu Ile Ile His Pro Phe Val Glu Asp
                165                 170                 175

Leu Glu Tyr Pro Leu Val Ser Arg Gly Tyr Pro Leu Asp Asp Glu Val
            180                 185                 190

Ile Val Asn Tyr Arg Tyr Tyr Arg Ala Val Leu Ile Ala Ile Thr Leu
        195                 200                 205

Val Thr Cys Leu Ile Gly Asn Ser Asp Leu Leu Ser Thr Thr Met Ala
210                 215                 220

Ala Ser Lys Ile Ile His Ser Val Gly Ile Cys Pro Tyr Tyr Pro Asp
225                 230                 235                 240

His Met Ala Val Cys Lys Leu Thr Asn Arg Val Thr Gly Thr Val Met
                245                 250                 255

Asp Arg His Ile Phe Cys Ile Pro Ile Glu Gln Phe Lys Arg Ser Phe
            260                 265                 270

Leu Tyr Arg Lys Thr Val Ile Lys Arg Asp Gly Glu Asp Lys Ala Val
        275                 280                 285

Asp Ile Lys Ser Leu Lys Ser Met Thr Gln Asn Ile Arg Gly Lys Arg
    290                 295                 300

Asn Pro Ser Pro Glu Leu Trp Asn Val Phe Thr Lys Asn Ile Glu Glu
```

-continued

```
305                 310                 315                 320

Leu Phe Val Arg Tyr Asp Asn Ala Val
                325

<210> SEQ ID NO 111
<211> LENGTH: 101
<212> TYPE: PRT
<213> ORGANISM: mosquito baculovirus

<400> SEQUENCE: 111

Met Glu Asn Val Arg Ser Thr Pro Pro Ser Leu Asn Gln Thr Asn Arg
 1               5                  10                  15

Leu Thr Ser Ala Pro Val Arg Arg Val Gln Pro Gln Ser Ile Lys Ile
            20                  25                  30

Cys Pro Asn Gln Asn Gln Ser Pro Ser Leu Gln Leu Asn Arg Asp Gln
        35                  40                  45

Ser Cys Pro Ile Cys Gln Leu Met Met Pro Asn Ser Ser Thr Ser Pro
    50                  55                  60

Ser Pro Ile Gln Ser Pro Ser Leu Ser Leu Ser Pro Thr Leu Glu Asn
65                  70                  75                  80

Gln Cys Gln Gln His Gln Ser Ser Leu Arg Leu Met Asp Met Leu Met
                85                  90                  95

Ser Arg Arg Ser Trp
            100

<210> SEQ ID NO 112
<211> LENGTH: 410
<212> TYPE: PRT
<213> ORGANISM: mosquito baculovirus

<400> SEQUENCE: 112

Met Ala Cys Asn Asp Leu Glu Leu Lys Phe Gln Val Trp Thr Val Val
 1               5                  10                  15

Gly Tyr Gly Gly Ala Glu Leu Val Leu Gln Phe Tyr His Phe Thr Glu
            20                  25                  30

Pro Thr Ser Gly Lys Val Tyr Val Ser Gly Arg Thr Val Ser Ala Gly
        35                  40                  45

Leu Gly Phe Lys Asp Pro Thr Ala Ser Met Cys Arg Lys Val Ser Ser
    50                  55                  60

Arg Asn Arg Ile Gln Trp Lys Val Leu Ala Ala Gly Leu Cys Val Lys
65                  70                  75                  80

Leu Pro Ile Asn Trp Lys Met Glu Thr Thr Met Ile Asn Arg Asp Gly
                85                  90                  95

Leu Arg Gln Leu Ala Ala Thr Lys Glu Gly Ile Trp Pro Gln Leu Ser
            100                 105                 110

Lys Leu Trp Asn Glu Thr Phe Asp Cys Asn Phe Phe Glu Asp Asp Asn
        115                 120                 125

Ile Ile Glu Val Glu Cys Asp Val Gly Ser Ser Val Phe Gln Leu Gln
    130                 135                 140

Asn Trp Asp Val Asp Asp Lys Ser Val Val Leu Arg Leu Tyr Ile His
145                 150                 155                 160

Pro Ile Thr Asn Glu Pro Trp Val Val Ala Ala Asp Leu Ala Arg Cys
                165                 170                 175

Leu Gly Tyr Glu Lys Tyr Arg Gln Thr His Thr Arg Ile Leu Ala Ala
            180                 185                 190

Phe Lys Arg Lys Leu Ser Asp Leu Val His Thr Glu Pro Phe Ser Gly
```

```
                195                 200                 205
        Thr Val Glu Ser Glu Val Ala Arg Leu Glu Gly Ala Pro Val Glu Leu
                210                 215                 220

Ser Ser Arg Glu Arg Asp Ile Val Val Asn Glu Gly Gly Ile His
        225                 230                 235                 240

Gln Met Leu Ile Gly Ser Arg Leu Pro Asn Val Gln Lys Tyr Lys Glu
                        245                 250                 255

Leu Val Phe Gly Lys Ile Leu Pro Ala Ala Arg Ala Arg Gly Glu Leu
                        260                 265                 270

Gln Ile Gly Thr Ile Gly Gln Gly Asp Gly Gly Ala Val Glu Pro Thr
                    275                 280                 285

Asn Gln Leu Gln Ser Asn Glu Lys Ile Leu Glu Leu Glu Leu Ala Leu
        290                 295                 300

Ser Arg Ser Asn Ser Glu Leu Lys Val Val Lys Leu Glu Gln Leu Arg
        305                 310                 315                 320

Val Gln Glu Ser Tyr Glu Ser Lys Leu Lys Ile Thr Asp Met Glu His
                        325                 330                 335

Arg Arg Met Lys Leu Glu Cys Lys Leu Lys Leu Ile Glu Leu Ala Met
                    340                 345                 350

Gly Ile Gly Lys Arg Asp Gln Leu Ile Ala Asp Thr Tyr Arg Asp Ile
                    355                 360                 365

Gln Glu Ile Cys Glu Gly Leu Ser Pro His Ile Val Pro Glu Val Pro
                370                 375                 380

Ser Cys Lys Leu Asn Tyr Ile Ala Leu Tyr Glu Arg Ala Val Gly Glu
        385                 390                 395                 400

Gly Lys Arg Val Val Arg Val Cys Arg Ile
                        405                 410

<210> SEQ ID NO 113
<211> LENGTH: 6627
<212> TYPE: DNA
<213> ORGANISM: mosquito baculovirus
<220> FEATURE:
<221> NAME/KEY: CDS
<222> LOCATION: (4481)...(5128)
<221> NAME/KEY: CDS
<222> LOCATION: (3240)...(3668)
<221> NAME/KEY: CDS
<222> LOCATION: (6145)...(6327)

<400> SEQUENCE: 113
gaattcgttg cccactacaa cagcgcggcc aaggagtgcg agctggaccc cattgcggtg      60
gtcccactac cctacattca cggtgaacat tttcacaact cgtgggacgt gatgcacctc     120
atggccgagg tgggcgacca aattgttgcc caacgtaatg acatgttggc gctcgcacca     180
ctgcaagttg tgcacaacgt ggtggcaaac atgtacattt cgttgggctg ccaaacctgc     240
gtttcacact acctattgtt gcggggcgtc atactggtaa agttcgaaca actcttccgc     300
ctactggtgc tcgaggagct aaagcgccgt gaaggttcca tttcgggccg caccatcgag     360
ttgctgcgaa tcccaaccgt tgagctggac gagtacatcg ccaaccccgg cgtactgaac     420
aacgcctttg ttaaaaattt actagcgtac gaaatggtcc agctgcacaa ctatatcaac     480
tcgtaccgaa ttgtacaaca ggccagtgga catttgcgca gcaacagacc catcgaacag     540
gccgacatca aggtctacct caaagcgttc aagaaggcc caaccatgac ctgggaactg     600
tacgacaagc agaggcgcgg tgaaattgca cccatttcac ccgtacgaaa gcgacccgca     660
ccggatgata gcactggtcc accgctaaag tattccaggg cccaataaat tacattggac     720
```

-continued

```
tttttttttat atatataatt actatgggta cgtgtgatac aacgataata aatattggtt    780
aatttcaacc agaaacattt atttatttat ctatttatta attttatata tttatatttc    840
aaaaatatat cacgctacac tttcgctact gtcgataccg cggatgttgt caataatgtt    900
ttcgcgcttc ttctcacgga acattgacgc accctcacgg cgctcaacga tgtttatggc    960
ggagcgggtg tacggattct ttatcgatcg tctggacatt cgttcgtact tctcgagggc   1020
atccttttgc gctaccaaat cgttatactc ggacagggcc aaaatgtcgt actgtggttc   1080
caatatgacg gtgcgatcga tcaacttgtc gcgcaacttg gggtccatcg aaagaaagtt   1140
ttcagacttg gacagcaaac gaccctggtt cagtttgcgc aatcttcgcg tttggctctt   1200
gagctccatt tcctcccgct tcagctgctc catgcgctca cgtttcgccg catcacgctc   1260
actcaccgca gagtacagca acttgttatc ctccagcagc ctggacaacc tttcatcgtc   1320
aatcacctgc ttcgatttaa acccaaacag cttgcgctct tcatccgtgt acttgccccc   1380
acaatccgct ttagcttcac tcgtggcacc gtcaacctta tccgtttcac cgcacaggaa   1440
acgcgtcagc tccttcaata acctgatttt gtaccggtca tattcgaccg ggacgtgctt   1500
tccatcgacg ggaacctcag aatataccte gtggatcaag gtgaacgtta cgtcgcagcc   1560
catctttaat cggtgtcaac ttaaactcta gacaccctgt acgtctttcg tacggcgttg   1620
agtacggtat ccagaatcac attcagctcg cggttgcgct gctcgaggtg gttcccgaaa   1680
gacagatacg cctgctcttc aattagtata cggcggctga gcagcggttc accgtactgt   1740
gcttccgcaa atgtgaacaa tttatccacc ttttcagaca gcgcatggtt cacggcgtac   1800
agggccaaag cttcgcagtc tatcttcgag gtgcggtact tggaggcgaa cgttagaccg   1860
attattacca gtgggataca atggatcaac cgttgtgaca ttagaaacaa acgcttctcg   1920
accgcagtca tcgtctcatt gtccacccta tccaccagtc gtgcaaacag cttcataatt   1980
ttcgcataga agaaggtggg cttgtgcttg tgcaggttgt tgggcacaat gttttcgttg   2040
aaatctttga aaattttttgc catattcagc tgctccaagc accctcggc caactggagc   2100
gtgttggcct ggtccacacc gcggctcagg ttgttgaggg caattgaata cggcacggtt   2160
tcccgatact gggtcaggtc cacatagtcg tgcaccttcg agtcgtgcgg tacaccttcg   2220
gcgattatgt aggttttcgt gcggaacgag agcagctcct ccaacctttg gtcataattg   2280
tccagtatgt gtagcacaac ctggttatag tcgacaatac gaccctcgta catgaacgat   2340
ctgctcacgc gatcggcaac cgtaattgcg agcgcacttt tcgactcacc aaccgttgag   2400
ccccactttg gtacataatt ttcagcggcc ttttcagct cctgtgccat gaaatcgcgc   2460
aactggtccg taataatgtc gtttaaattc tccggctttt ccacagtctc aacatcctca   2520
acctccatat cgggttgagc cgaggttggc ggtgtggttc cgctaccgga tggtgccgca   2580
ccaaagttgt ttagaatcac atttcgctgc tcctcggata gggcgctaaa cagctccatc   2640
accttagcgg catcagtact ttgcacctcg gacgccatgt cgaagtttag cgaatttctg   2700
cttacttcgt cctcctcacc agcagcatag tcgccctcgg ggccaccacc gacaacttcg   2760
aaaactgaac cagaaacgtt gccaattccg ccaaccgagt ccggtccgtc ttcctcgagc   2820
tcgggaaata aaaagtcgtc caccttggcc gccgactcgg gctcgggatc gttatcctgc   2880
ccaccttcat cctcaccttc tccgtccgag tgccactcgc tcacgagacg cttcgatatc   2940
accgacattg ccacgggacc cgtgggtgaa cctggggcca cattttgatc accactcgta   3000
gcaccaccgg tccaaacatt atcatccaaa tttagctggg gctcggctac aggtggtgct   3060
```

```
                                                              -continued acatcgtcat tttcatcttg gtttaaaatt tcatcaactt gtcgctgccg agctgggcgc    3120
accggtctac cagctttgat ggttgtagtg gcgcgtgatt ttgggcggcc tttaacgcca    3180
ccggattcac gtagaccctc ggctctcgag cttcgattca tttagtcgta taaaacaac    3239 ctg gcc gtg tac ggg cgc cca gag gtt cac aat acg tgt ctt att acc     3287
Leu Ala Val Tyr Gly Arg Pro Glu Val His Asn Thr Cys Leu Ile Thr
 1               5                  10                  15 cat tcg cat cac gaa aga gta gtc att gtt tgc gtt agg tgc ggt tcg     3335
His Ser His His Glu Arg Val Val Ile Val Cys Val Arg Cys Gly Ser
             20                  25                  30 cag ttc gta ttc aga gcg gga cat tgt aac aaa cgg cga ctg ctc aaa     3383
Gln Phe Val Phe Arg Ala Gly His Cys Asn Lys Arg Arg Leu Leu Lys
         35                  40                  45 ccg ctt gta agg ttt acc ggc cgt aac gag gcg aat tgt ttc cat atg     3431
Pro Leu Val Arg Phe Thr Gly Arg Asn Glu Ala Asn Cys Phe His Met
     50                  55                  60 gat gcg ttt acc gag act ttt ctg cgg caa agg gtt ata atc aat ccg     3479
Asp Ala Phe Thr Glu Thr Phe Leu Arg Gln Arg Val Ile Ile Asn Pro
 65                  70                  75                  80 gag acg aag gag att gaa gtt cgc gca gtt tgc agt gat gga gtt gga     3527
Glu Thr Lys Glu Ile Glu Val Arg Ala Val Cys Ser Asp Gly Val Gly
                 85                  90                  95 tac act tac ttc acg gtc ggt caa atg cct cac cct gtt acc gaa cgt     3575
Tyr Thr Tyr Phe Thr Val Gly Gln Met Pro His Pro Val Thr Glu Arg
             100                 105                 110 gac gtt agc ggc ggt tca tcg aac aaa atc cca agc cgg tcg cga ggg     3623
Asp Val Ser Gly Gly Ser Ser Asn Lys Ile Pro Ser Arg Ser Arg Gly
         115                 120                 125 tcg gcg gaa ccc ctg tcc ggt gca tgt gga tac aaa aat caa gtg         3668
Ser Ala Glu Pro Leu Ser Gly Ala Cys Gly Tyr Lys Asn Gln Val
     130                 135                 140 taaaattttc atcaaaaact acagcaaaac tcacgtcacc gaactctcga tggggtacct    3728
gaactcgaac atggtgcacc attatgtggc cctgatgggc atgtgcaggg aaaaccgagg    3788
tacagttgac gcctgtttat acgcgtccaa caagatcaat tgtgtgctgc ggttcgacct    3848
ggacctgttc cgctccagct ttgggggtag agttataaac attggccacg tttacgatga    3908
acttgaccgc atatacagaa cgctagatag acaaatttta atttcgccca actcggcgct    3968
agagttgtac gttagcgcgg aatctgcggt gctagcacca caggacctcc tcattataca    4028
ccccttcgtt gaagatctcg agtacccact ggtctcgcgc ggctaccac tggacgacga     4088 ggtgatagta aattaccgct actacagggc cgtgttgatt gccatcacgc tcgtaacctg    4148
cctgattggt aacagcgatt tgctcagcac aaccatggcc gcatcgaaaa tcatccacag    4208
cgttggcatt tgcccgtact acccggacca tatggcggtc tgtaaactga cgaaccgcgt    4268 tacgggacg gtcatggata ggcacatctt ctgcatccca atcgagcagt tcaaacggtc     4328 cttttctatac cgcaaaaccg ttatcaagcg ggacggtgag gataaggcgg tggacattaa    4388
gtcgttaaaa tctatgaccc agaatatacg cggaaagcgc aaccccagtc ccgagttgtg    4448
gaacgttttt acgaagaaca tcgaggaact tt ttg ttc gat acg aca atg cag     4501
                                  Leu Phe Asp Thr Thr Met Gln
                                       145                 150 ttt gag att gag atc agc aac ggt aac cag ttg tac tca tcg cgc aac     4549
Phe Glu Ile Glu Ile Ser Asn Gly Asn Gln Leu Tyr Ser Ser Arg Asn
             155                 160                 165 caa cta att tta ccc ggg ctc acc gac gtg tac tat cac tat gta agc     4597
Gln Leu Ile Leu Pro Gly Leu Thr Asp Val Tyr Tyr His Tyr Val Ser
         170                 175                 180
```

```
acg agt gga ccc ttt ggt gag gac cac ccg cac gac atc aag ctg cac     4645
Thr Ser Gly Pro Phe Gly Glu Asp His Pro His Asp Ile Lys Leu His
        185                 190                 195 acg acc gta cac aat tac aac ccg aat ttg gcg gtc ttt gtg att cag     4693
Thr Thr Val His Asn Tyr Asn Pro Asn Leu Ala Val Phe Val Ile Gln
        200                 205                 210 cgc gag ggc acg gag ctc aat aag atc gct ttt cgt ctg caa gtg tac     4741
Arg Glu Gly Thr Glu Leu Asn Lys Ile Ala Phe Arg Leu Gln Val Tyr
215                 220                 225                 230 gtc ctt aaa gcg acc aca ttc ggc gcc ggt gaa cat att gcc gag gtg     4789
Val Leu Lys Ala Thr Thr Phe Gly Ala Gly Glu His Ile Ala Glu Val
                235                 240                 245 aac ttt atc aaa cct aaa ggc tgt gga gat gga aaa cgt tcg gtc gac     4837
Asn Phe Ile Lys Pro Lys Gly Cys Gly Asp Gly Lys Arg Ser Val Asp
            250                 255                 260 acc acc gtc gtt gaa cca aac gaa ccg gtt aac aag cgc gcc cgt acg     4885
Thr Thr Val Val Glu Pro Asn Glu Pro Val Asn Lys Arg Ala Arg Thr
                265                 270                 275 ccg agt cca gcc cca gtc gat caa gat ttg ccc gaa cca aaa cca gag     4933
Pro Ser Pro Ala Pro Val Asp Gln Asp Leu Pro Glu Pro Lys Pro Glu
        280                 285                 290 ccc gag tct gca gct gaa ccg gga cca gag ctg ccc gat atg cca act     4981
Pro Glu Ser Ala Ala Glu Pro Gly Pro Glu Leu Pro Asp Met Pro Thr
295                 300                 305                 310 gat gat gcc caa ctc gag cac gag ccc gag ccc gat cca aag ccc gag     5029
Asp Asp Ala Gln Leu Glu His Glu Pro Glu Pro Asp Pro Lys Pro Glu
                315                 320                 325 cct gag cct gag tcc gac tct aga gaa cca gtg cca gca gca cca gtc     5077
Pro Glu Pro Glu Ser Asp Ser Arg Glu Pro Val Pro Ala Ala Pro Val
                330                 335                 340 gtc gct ccg gtt gat gga cat gtt gat gag tcg ccg cag ttg gta gaa     5125
Val Ala Pro Val Asp Gly His Val Asp Glu Ser Pro Gln Leu Val Glu
            345                 350                 355 gtt tagtttgaag gtagaaataa taaaaatatt ttccccccaa acccagattc         5178
Val gtttttttttt ttaatgcata tcacagcaaa ttaccgatga tcagaccggc cccgaattgg  5238
gccacttgga aacataggtt gtgaggtggt gaggtggact ctagctcaac ggtccatttt   5298
ataataaaat taatatcatt ttttttatta acctaaaagt tgcggtttat gcgctataaa   5358
agggtggagc tgtcccgtgt ggtgcggata gtgaagtcat ggcgtgcaac gatctagagc   5418
tcaagttcca agtgtggacc gtggtgggat acggtggtgc tgagcttgtg ttacaatttt   5478
accactttac cgaaccaacc agtggaaagg tttacgtttc tgggcgcacc gtcagcgcgg   5538
gcctcggctt caaggatccc acggccagca tgtgccgcaa ggtgtccagc cgaaatcgca   5598
tccagtggaa ggtgttggcg gccgggttgt gcgtaaaatt gcccatcaat tggaagatgg   5658
aaacgacgat gataaatcga gatggactgc gccaactggc ggccaccaag gagggtattt   5718
ggccccagct aagcaaactg tggaacgaaa cgtttgactg taacttttttc gaagacgata  5778 atattatcga ggtggagtgc gatgtgggt cgagcgtgtt tcagctgcaa aattgggacg    5838
tggacgacaa gagtgtcgtg ctgcggttgt acatccaccc gatcaccaac gagccgtggg   5898
tcgtggcggc ggatctagcg cgctgcttgg gttacgaaaa gtatcgccaa acgcacacgc   5958
gaatcctcgc cgccttcaag cgaaagctgt cggacctagt tcacaccgaa ccttttttcgg 6018 gtaccgttga atcagaggta gcacgactgg agggtgcacc ggtggagcta tcgtctcgcg   6078
aacgggacat tgtggtggtc aacgagggtg gaatccacca gatgctgatc ggttcacggc   6138
```

```
tgccca atg tgc aaa agt aca agg agc ttg tgt ttg gta aaa ttt tac        6186
       Met Cys Lys Ser Thr Arg Ser Leu Cys Leu Val Lys Phe Tyr
           360             365                 370 cag cgg ccc gtg ccc gag gtg agc tgc aaa ttg gca cca ttg gac agg        6234
Gln Arg Pro Val Pro Glu Val Ser Cys Lys Leu Ala Pro Leu Asp Arg
    375             380                 385 gtg atg gag gtg cag tgg agc cca caa atc aac tac agt caa acg aaa        6282
Val Met Glu Val Gln Trp Ser Pro Gln Ile Asn Tyr Ser Gln Thr Lys
390             395                 400                 405 aga ttt tgg agc tgg agt tgg ccc tgt cgc ggt cca ata gtg aat            6327
Arg Phe Trp Ser Trp Ser Trp Pro Cys Arg Gly Pro Ile Val Asn
                410                 415                 420 tgaaagtggt caagttggaa cagttgcgcg tacaggaatc gtacgagtct aaattgaaaa      6387
ttaccgatat ggagcaccgg cgcatgaagc tcgagtgcaa gctgaagctg atcgagctgg      6447
caatgggtat cggtaaacgg gaccagttga tcgccgacac gtaccgcgat attcaggaaa      6507
tttgtgaagg cctctcaccg cacattgtcc ccgaggtgcc cagctgcaag ctgaactata      6567
tcgcactgta cgaacgtgca gttggagagg gcaaacgggt ggtgcgagtg tgcagaattc      6627
```

<210> SEQ ID NO 114
<211> LENGTH: 143
<212> TYPE: PRT
<213> ORGANISM: mosquito baculovirus

<400> SEQUENCE: 114

```
Leu Ala Val Tyr Gly Arg Pro Glu Val His Asn Thr Cys Leu Ile Thr
1               5                   10                  15

His Ser His His Glu Arg Val Val Ile Val Cys Val Arg Cys Gly Ser
                20                  25                  30

Gln Phe Val Phe Arg Ala Gly His Cys Asn Lys Arg Arg Leu Leu Lys
            35                  40                  45

Pro Leu Val Arg Phe Thr Gly Arg Asn Glu Ala Asn Cys Phe His Met
        50                  55                  60

Asp Ala Phe Thr Glu Thr Phe Leu Arg Gln Arg Val Ile Ile Asn Pro
65                  70                  75                  80

Glu Thr Lys Glu Ile Glu Val Arg Ala Val Cys Ser Asp Gly Val Gly
                85                  90                  95

Tyr Thr Tyr Phe Thr Val Gly Gln Met Pro His Pro Val Thr Glu Arg
                100                 105                 110

Asp Val Ser Gly Gly Ser Ser Asn Lys Ile Pro Ser Arg Ser Arg Gly
            115                 120                 125

Ser Ala Glu Pro Leu Ser Gly Ala Cys Gly Tyr Lys Asn Gln Val
        130                 135                 140
```

<210> SEQ ID NO 115
<211> LENGTH: 216
<212> TYPE: PRT
<213> ORGANISM: mosquito baculovirus

<400> SEQUENCE: 115

```
Leu Phe Asp Thr Thr Met Gln Phe Glu Ile Glu Ile Ser Asn Gly Asn
1               5                   10                  15

Gln Leu Tyr Ser Ser Arg Asn Gln Leu Ile Leu Pro Gly Leu Thr Asp
                20                  25                  30

Val Tyr Tyr His Tyr Val Ser Thr Ser Gly Pro Phe Gly Glu Asp His
            35                  40                  45
```

-continued

```
Pro His Asp Ile Lys Leu His Thr Thr Val His Asn Tyr Asn Pro Asn
    50                  55                  60

Leu Ala Val Phe Val Ile Gln Arg Glu Gly Thr Glu Leu Asn Lys Ile
65                  70                  75                  80

Ala Phe Arg Leu Gln Val Tyr Val Leu Lys Ala Thr Thr Phe Gly Ala
                85                  90                  95

Gly Glu His Ile Ala Glu Val Asn Phe Ile Lys Pro Lys Gly Cys Gly
            100                 105                 110

Asp Gly Lys Arg Ser Val Asp Thr Thr Val Val Glu Pro Asn Glu Pro
        115                 120                 125

Val Asn Lys Arg Ala Arg Thr Pro Ser Pro Ala Pro Val Asp Gln Asp
    130                 135                 140

Leu Pro Glu Pro Lys Pro Glu Pro Glu Ser Ala Ala Glu Pro Gly Pro
145                 150                 155                 160

Glu Leu Pro Asp Met Pro Thr Asp Asp Ala Gln Leu Glu His Glu Pro
                165                 170                 175

Glu Pro Asp Pro Lys Pro Glu Pro Glu Pro Glu Ser Asp Ser Arg Glu
            180                 185                 190

Pro Val Pro Ala Ala Pro Val Val Ala Pro Val Asp Gly His Val Asp
        195                 200                 205

Glu Ser Pro Gln Leu Val Glu Val
    210                 215

<210> SEQ ID NO 116
<211> LENGTH: 61
<212> TYPE: PRT
<213> ORGANISM: mosquito baculovirus

<400> SEQUENCE: 116

Met Cys Lys Ser Thr Arg Ser Leu Cys Leu Val Lys Phe Tyr Gln Arg
 1               5                  10                  15

Pro Val Pro Glu Val Ser Cys Lys Leu Ala Pro Leu Asp Arg Val Met
            20                  25                  30

Glu Val Gln Trp Ser Pro Gln Ile Asn Tyr Ser Gln Thr Lys Arg Phe
        35                  40                  45

Trp Ser Trp Ser Trp Pro Cys Arg Gly Pro Ile Val Asn
    50                  55                  60

<210> SEQ ID NO 117
<211> LENGTH: 7212
<212> TYPE: DNA
<213> ORGANISM: mosquito baculovirus
<220> FEATURE:
<221> NAME/KEY: CDS
<222> LOCATION: (1726)...(3363)
<221> NAME/KEY: CDS
<222> LOCATION: (3384)...(4094)
<221> NAME/KEY: CDS
<222> LOCATION: (5656)...(6351)
<221> NAME/KEY: CDS
<222> LOCATION: (5206)...(5646)
<221> NAME/KEY: CDS
<222> LOCATION: (6354)...(6740)
<221> NAME/KEY: CDS
<222> LOCATION: (406)...(717)
<221> NAME/KEY: CDS
<222> LOCATION: (170)...(385)
<221> NAME/KEY: CDS
<222> LOCATION: (1519)...(1722)

<400> SEQUENCE: 117
ctgcagactc gggctctggt tttggttcgg gcaaatcttg atcgactggg gctggactcg     60
```

```
gcgtacgggc gcgcttgtta accggttcgt ttggttcaac gacggtggtg tcgaccgaac    120 gtttccatc tccgcagcct ttaggtttga taaagttcac ctcggcaat atg ttc acc     178
                                                    Met Phe Thr
                                                     1 ggc gcc gaa tgt ggt cgc ttt aag gac gta cac ttg cag acg aaa agc     226
Gly Ala Glu Cys Gly Arg Phe Lys Asp Val His Leu Gln Thr Lys Ser
     5              10                  15 gat ctt att gag ctc cgt gcc ctc gcg ctg aat cac aaa gac cgc caa     274
Asp Leu Ile Glu Leu Arg Ala Leu Ala Leu Asn His Lys Asp Arg Gln
 20              25                  30                  35 att cgg gtt gta att gtg tac ggt cgt gtg cag ctt gat gtc gtg cgg     322
Ile Arg Val Val Ile Val Tyr Gly Arg Val Gln Leu Asp Val Val Arg
             40                  45                  50 gtg gtc ctc acc aaa ggg tcc act cgt gct tac ata gtg ata gta cac     370
Val Val Leu Thr Lys Gly Ser Thr Arg Ala Tyr Ile Val Ile Val His
                 55                  60                  65 gtc ggt gag ccc ggg taaaattagt tggttgcgcg atg agt aca act ggt tac   423
Val Gly Glu Pro Gly                      Met Ser Thr Thr Gly Tyr
         70                                          75 cgt tgc gga tct caa tct caa act gca ttg tcg tat cga aca aaa agt     471
Arg Cys Gly Ser Gln Ser Gln Thr Ala Leu Ser Tyr Arg Thr Lys Ser
         80                  85                  90 tcc tcg atg ttc ttc gta aaa acg ttc cac aac tcg gga ctg ggg ttg     519
Ser Ser Met Phe Phe Val Lys Thr Phe His Asn Ser Gly Leu Gly Leu
 95                 100                 105                 110 cgc ttt ccg cgt ata ttc tgg gtc ata gat ttt aac gac tta atg tcc     567
Arg Phe Pro Arg Ile Phe Trp Val Ile Asp Phe Asn Asp Leu Met Ser
                115                 120                 125 acc gcc tta tcc tca ccg tcc cgc ttg ata acg gtt ttg cgg tat aga     615
Thr Ala Leu Ser Ser Pro Ser Arg Leu Ile Thr Val Leu Arg Tyr Arg
                    130                 135                 140 aag gac cgt ttg aac tgc tcg att ggg atg cag aag atg tgc cta tcc     663
Lys Asp Arg Leu Asn Cys Ser Ile Gly Met Gln Lys Met Cys Leu Ser
                145                 150                 155 atg acc gtc ccc gta acg cgg ttc gtc agt tta cag acc gcc ata tgg     711
Met Thr Val Pro Val Thr Arg Phe Val Ser Leu Gln Thr Ala Ile Trp
160                 165                 170 tcc ggg tagtacgggc aaatgccaac gctgtggatg attttcgatg cggccatggt     767
Ser Gly
175 tgtgctgagc aaatcgctgt taccaatcag gcaggttacg agcgtgatgg caatcaacac   827 ggccctgtag tagcggtaat ttactatcac ctcgtcgtcc agtgggtagc cgcgcgagac   887 cagtgggtac tcgagatctt caacgaaggg gtgtataatg aggaggtcct gtggtgctag   947 caccgcagat tccgcgctaa cgtacaactc tagcgccgag ttgggcgaaa ttaaatttg   1007 tctatctagc gttctgtata tgcggtcaag ttcatcgtaa acgtggccaa tgtttataac   1067 tctacccca aagctggagc ggaacaggtc caggtcgaac cgcagcacac aattgatctt   1127 gttggacgcg tataaacagg cgtcaactgt acctcggttt ccctgcaca tgcccatcag   1187 ggccacataa tggtgcacca tgttcgagtt caggtacccc atcgagagtt cggtgacgtg   1247 agttttgctg tagtttttga tgaaaatttt acacttgatt tttgtatcca catgcaccgg   1307 acagggttc cgccgaccct cgcgaccggc ttgggatttt gttcgatgaa ccgccgctaa   1367 cgtcacgttc ggtaacaggg tgaggcattt gaccgaccgt gaagtaagtg tatccaactc   1427 catcactgca aactgcgcga acttcaatct ccttcgtctc cggattgatt ataacccttt   1487
```

-continued

```
gccgcagaaa agtctcggta aacgcatcca t atg gaa aca att cgc ctc gtt        1539
                                   Met Glu Thr Ile Arg Leu Val
                                                           180 acg gcc ggt aaa cct tac aag cgg ttt gag cag tcg ccg ttt gtt aca        1587
Thr Ala Gly Lys Pro Tyr Lys Arg Phe Glu Gln Ser Pro Phe Val Thr
    185                 190                 195 atg tcc cgc tct gaa tac gaa ctg cga acc gca cct aac gca aac aat        1635
Met Ser Arg Ser Glu Tyr Glu Leu Arg Thr Ala Pro Asn Ala Asn Asn
200                 205                 210                 215 gac tac tct ttc gtg atg cga atg ggt aat aag aca cgt att gtg aac        1683
Asp Tyr Ser Phe Val Met Arg Met Gly Asn Lys Thr Arg Ile Val Asn
                220                 225                 230 ctc tgg gcg ccc gta cac ggc cag gtt gtt tta tac gac taa atg aat        1731
Leu Trp Ala Pro Val His Gly Gln Val Val Leu Tyr Asp     Met Asn
            235                 240                 245 cga agc tcg aga gcc gag ggt cta cgt gaa gcc ggt ggc gtt aaa ggc        1779
Arg Ser Ser Arg Ala Glu Gly Leu Arg Glu Ala Gly Gly Val Lys Gly
            250                 255                 260 cgc cca aaa tca cgc gcc act aca acc atc aaa gct ggt aga ccg gtg        1827
Arg Pro Lys Ser Arg Ala Thr Thr Thr Ile Lys Ala Gly Arg Pro Val
        265                 270                 275 cgc cca gct cgg cag cga caa gtt gat gaa att tta aac caa gat gaa        1875
Arg Pro Ala Arg Gln Arg Gln Val Asp Glu Ile Leu Asn Gln Asp Glu
    280                 285                 290 aat gac gat gta gca cca cct gta gcc gag ccc cag cta aat ttg gat        1923
Asn Asp Asp Val Ala Pro Pro Val Ala Glu Pro Gln Leu Asn Leu Asp
295                 300                 305                 310 gat aat gtt tgg acc ggt ggt gct acg agt ggt gat caa aat gtg gcc        1971
Asp Asn Val Trp Thr Gly Gly Ala Thr Ser Gly Asp Gln Asn Val Ala
                315                 320                 325 cca ggt tca ccc acg ggt ccc gtg gca atg tcg gtg ata tcg aag cgt        2019
Pro Gly Ser Pro Thr Gly Pro Val Ala Met Ser Val Ile Ser Lys Arg
            330                 335                 340 ctc gtg agc gag tgg cac tcg gac gga gaa ggt gag gat gaa ggt ggg        2067
Leu Val Ser Glu Trp His Ser Asp Gly Glu Gly Glu Asp Glu Gly Gly
            345                 350                 355 cag gat aac gat ccc gag ccc gag tcg gtg gcc aag gtg gac gac ttt        2115
Gln Asp Asn Asp Pro Glu Pro Glu Ser Val Ala Lys Val Asp Asp Phe
        360                 365                 370 tta ttt ccc gag ctc gag gaa gac gga ccg gac tcg gtt ggc gga att        2163
Leu Phe Pro Glu Leu Glu Glu Asp Gly Pro Asp Ser Val Gly Gly Ile
375                 380                 385                 390 ggc aac gtt tct ggt tca gtt ttc gaa gtt gtc ggt ggt ggc ccc gag        2211
Gly Asn Val Ser Gly Ser Val Phe Glu Val Val Gly Gly Gly Pro Glu
                395                 400                 405 ggc gac tat gct gct ggt gag gag gac gaa gta agc aga aat tcg cta        2259
Gly Asp Tyr Ala Ala Gly Glu Glu Asp Glu Val Ser Arg Asn Ser Leu
            410                 415                 420 aac ttc gac atg gcg tcc gag gtg caa agt act gat gcc gct aag gtg        2307
Asn Phe Asp Met Ala Ser Glu Val Gln Ser Thr Asp Ala Ala Lys Val
            425                 430                 435 atg gag ctg ttt aac gcc cta tcc gag gag cag cga aat gtg att cta        2355
Met Glu Leu Phe Asn Ala Leu Ser Glu Glu Gln Arg Asn Val Ile Leu
        440                 445                 450 aac aac ttt ggt gcg gca cca tcc ggt agc gga acc aca ccg cca acc        2403
Asn Asn Phe Gly Ala Ala Pro Ser Gly Ser Gly Thr Thr Pro Pro Thr
455                 460                 465                 470 tcg gct caa ccc gat atg gag gtt gag gat gtt gag act gtg gaa aag        2451
Ser Ala Gln Pro Asp Met Glu Val Glu Asp Val Glu Thr Val Glu Lys
                475                 480                 485
```

```
ccg gag aat tta aac gac att att acg gac cag ttg cgc gat ttc atg    2499
Pro Glu Asn Leu Asn Asp Ile Ile Thr Asp Gln Leu Arg Asp Phe Met
            490                 495                 500 gca cag gag ctg aaa aag gcc gct gaa aac tac gta cca aag tgg ggc    2547
Ala Gln Glu Leu Lys Lys Ala Ala Glu Asn Tyr Val Pro Lys Trp Gly
        505                 510                 515 tca acg gtt ggt gag tcg aaa agt gcg ctc gca att acg gtt gcc gat    2595
Ser Thr Val Gly Glu Ser Lys Ser Ala Leu Ala Ile Thr Val Ala Asp
    520                 525                 530 cgc gtg agc aga tcg ttc atg tac gag ggt cgt att gtc gac tat aac    2643
Arg Val Ser Arg Ser Phe Met Tyr Glu Gly Arg Ile Val Asp Tyr Asn
535                 540                 545                 550 cag gtt gtg cta cac ata ctg gac aat tat gac caa agg ttg gag gag    2691
Gln Val Val Leu His Ile Leu Asp Asn Tyr Asp Gln Arg Leu Glu Glu
                555                 560                 565 ctc ctc tcg ttc cgc acg aaa acc tac ata atc gcc gaa ggt gta ccg    2739
Leu Leu Ser Phe Arg Thr Lys Thr Tyr Ile Ile Ala Glu Gly Val Pro
            570                 575                 580 cac gac tcg aag gtg cac gac tat gtc gac ctg acc cag tat cgg gaa    2787
His Asp Ser Lys Val His Asp Tyr Val Asp Leu Thr Gln Tyr Arg Glu
        585                 590                 595 acc gtg ccg tat tca att gcc ctc aac aac ctg agc cgc ggt gtg gac    2835
Thr Val Pro Tyr Ser Ile Ala Leu Asn Asn Leu Ser Arg Gly Val Asp
    600                 605                 610 cag gcc aac acg ctc cag ctg gcc gag ggg tgc ttg gag cag ctg aat    2883
Gln Ala Asn Thr Leu Gln Leu Ala Glu Gly Cys Leu Glu Gln Leu Asn
615                 620                 625                 630 atg gca aaa att ttc aaa gat ttc aac gaa aac att gtg ccc aac aac    2931
Met Ala Lys Ile Phe Lys Asp Phe Asn Glu Asn Ile Val Pro Asn Asn
                635                 640                 645 ctg cac aag cac aag ccc acc ttc ttc tat gcg aaa att atg aag ctg    2979
Leu His Lys His Lys Pro Thr Phe Phe Tyr Ala Lys Ile Met Lys Leu
            650                 655                 660 ttt gca cga ctg gtg gat agg gtg gac aat gag acg atg act gcg gtc    3027
Phe Ala Arg Leu Val Asp Arg Val Asp Asn Glu Thr Met Thr Ala Val
        665                 670                 675 gag aag cgt ttg ttt cta atg tca caa cgg ttg atc cat tgt atc cca    3075
Glu Lys Arg Leu Phe Leu Met Ser Gln Arg Leu Ile His Cys Ile Pro
    680                 685                 690 ctg gta ata atc ggt cta acg ttc gcc tcc aag tac cgc acc tcg aag    3123
Leu Val Ile Ile Gly Leu Thr Phe Ala Ser Lys Tyr Arg Thr Ser Lys
695                 700                 705                 710 ata gac tgc gaa gct ttg gcc ctg tac gcc gtg aac cat gcg ctg tct    3171
Ile Asp Cys Glu Ala Leu Ala Leu Tyr Ala Val Asn His Ala Leu Ser
                715                 720                 725 gaa aag gtg gat aaa ttg ttc aca ttt gcg gaa gca cag tac ggt gaa    3219
Glu Lys Val Asp Lys Leu Phe Thr Phe Ala Glu Ala Gln Tyr Gly Glu
            730                 735                 740 ccg ctg ctc agc cgc cgt ata cta att gaa gag cag gcg tat ctg tct    3267
Pro Leu Leu Ser Arg Arg Ile Leu Ile Glu Glu Gln Ala Tyr Leu Ser
        745                 750                 755 ttc ggg aac cac ctc gag cag cgc aac cgc gag ctg aat gtg att ctg    3315
Phe Gly Asn His Leu Glu Gln Arg Asn Arg Glu Leu Asn Val Ile Leu
    760                 765                 770 gat acc gta ctc aac gcc gta cga aag acg tac agg gtg tct aga gtt    3363
Asp Thr Val Leu Asn Ala Val Arg Lys Thr Tyr Arg Val Ser Arg Val
775                 780                 785                 790 taagttgaca ccgattaaag atg ggc tgc gac gta acg ttc acc ttg atc cac  3416
                     Met Gly Cys Asp Val Thr Phe Thr Leu Ile His
```

|  |  |  |  |  |  |  |  |  |  |  |  |  |  |  |  |
|---|---|---|---|---|---|---|---|---|---|---|---|---|---|---|---|
|  |  |  |  |  | 795 |  |  |  |  | 800 |  |  |  |  |  |
| gag | gta | tat | tct | gag | gtt | ccc | gtc | gat | gga | aag | cac | gtc | ccg | gtc | gaa |
| Glu | Val | Tyr | Ser | Glu | Val | Pro | Val | Asp | Gly | Lys | His | Val | Pro | Val | Glu |
|  |  |  | 805 |  |  |  |  | 810 |  |  |  |  | 815 |  |  |

3464 tat gac cgg tac aaa atc agg tta ttg aag gag ctg acg cgt ttc ctg   3512
Tyr Asp Arg Tyr Lys Ile Arg Leu Leu Lys Glu Leu Thr Arg Phe Leu
        820             825                 830 tgc ggt gaa acg gat aag gtt gac ggt gcc acg agt gaa gct aaa gcg   3560
Cys Gly Glu Thr Asp Lys Val Asp Gly Ala Thr Ser Glu Ala Lys Ala
835             840                 845 gat tgt ggg ggc aag tac acg gat gaa gag cgc aag ctg ttt ggg ttt   3608
Asp Cys Gly Gly Lys Tyr Thr Asp Glu Glu Arg Lys Leu Phe Gly Phe
850             855                 860                 865 aaa tcg aag cag gtg att gac gat gaa agg ttg tcc agg ctg ctg gag   3656
Lys Ser Lys Gln Val Ile Asp Asp Glu Arg Leu Ser Arg Leu Leu Glu
        870             875                 880 gat aac aag ttg ctg tac tct gcg gtg agt gag cgt gat gcg gcg aaa   3704
Asp Asn Lys Leu Leu Tyr Ser Ala Val Ser Glu Arg Asp Ala Ala Lys
            885             890                 895 cgt gag cgc atg gag cag ctg aag cgg gag gaa atg gag ctc aag agt   3752
Arg Glu Arg Met Glu Gln Leu Lys Arg Glu Glu Met Glu Leu Lys Ser
        900             905                 910 caa acg cga aga ttg cgc aaa ctg aac cag ggt cgt ttg ctg tcc aag   3800
Gln Thr Arg Arg Leu Arg Lys Leu Asn Gln Gly Arg Leu Leu Ser Lys
915             920                 925 tct gaa aac ttt ctt tcg atg gac ccc aag ttg cgc gac aag ttg atc   3848
Ser Glu Asn Phe Leu Ser Met Asp Pro Lys Leu Arg Asp Lys Leu Ile
930             935                 940                 945 gat cac acc gtc ata ttg gaa cca cag tac gac att ttg gcc ctg tcc   3896
Asp His Thr Val Ile Leu Glu Pro Gln Tyr Asp Ile Leu Ala Leu Ser
        950             955                 960 gag tat aac gat ttg gta gcg caa aag gat gcc ctc gag aag tac gaa   3944
Glu Tyr Asn Asp Leu Val Ala Gln Lys Asp Ala Leu Glu Lys Tyr Glu
            965             970                 975 cga atg tcc aga cga tcg ata aag aat ccg tac acc cgc tcc gcc ata   3992
Arg Met Ser Arg Arg Ser Ile Lys Asn Pro Tyr Thr Arg Ser Ala Ile
        980             985                 990 aac atc gtt gag cgc cgt gag ggt gcg tca atg ttc cgt gag aag aag   4040
Asn Ile Val Glu Arg Arg Glu Gly Ala Ser Met Phe Arg Glu Lys Lys
        995                 1000                1005 cgc gaa aac att att gac aac ata cgc ggt atc gac aat agc gaa agt   4088
Arg Glu Asn Ile Ile Asp Asn Ile Arg Gly Ile Asp Asn Ser Glu Ser
1010            1015                1020                1025 gta gcg tgatatattt ttgaaatata aatatataaa ataaataaat agataaataa   4144
Val Ala ataaatgttt ctggttgaaa ttaaccaata tttattatcg ttgtatcaca cgtacccata   4204
gtaattatat atataaaaaa aagtccaatg taatttattg ggccctggaa tactttagcg   4264
gtggaccagt gctatcatcc ggtgcgggtc gctttcgtac gggtgaaatg ggtgcaattt   4324
caccgcgcct ctgcttgtcg tacagttccc aggtcatggt tgggccttct tggaacgctt   4384
tgaggtagac cttgatgtcg gcctgttcga tgggtctgtt gctgcgcaaa tgtccactgg   4444
cctgttgtac aattcggtac gagttgatat agttgtgcag ctggaccatt tcgtacgcta   4504
gtaaattttt aacaaaggcg ttgttcagta cgccggggtt ggcgatgtac tcgtccagct   4564
caacggttgg gattcgcagc aactcgatgg tgcggcccga aatggaacct tcacggcgct   4624
ttagctcctc gagcaccagt aggcggaaga gttgttcgaa ctttaccagt atgacgcccc   4684

-continued

```
gcaacaatag gtagtgtgaa acgcaggttt ggcagcccaa cgaaatgtac atgtttgcca    4744
ccacgttgtg cacaacttgc agtggtgcga gcgccaacat gtcattacgt tgggcaacaa    4804
tttggtcgcc cacctcggcc atgaggtgca tcacgtccca cgagttgtga aaatgttcac    4864
cgtgaatgta gggtagtggg accaccgcaa tggggtccag ctcgcactcc ttggccgcgc    4924
tgttgtagtg ggcaacgaat tcgggcttgc tggacatgta cgccatctgg cggtcctgac    4984
cgcgtttgtt gccgagaatc aaatcgaggt gcagcttggt gcgcttttga tatatggacc    5044
aaaattggcg tacgcgttct tcgctgacca cgatcggtgc gggaggtcgt gccagcagca    5104
tcgatagatt catgaggtag acaatggttg caaactcaac tttggcgagg ttggattcgg    5164
tttcggtggg gctcaacagg ctggtgatca ctaggtaaaa a atg tgc cta ttg agc    5220
                                             Met Cys Leu Leu Ser
                                                             1030 gac tcg cgt tgg cga gtc tgt aag ttt tcc ttc gca atg tcg ttc atc    5268
Asp Ser Arg Trp Arg Val Cys Lys Phe Ser Phe Ala Met Ser Phe Ile
        1035                1040                1045 gtg aaa atc gca ctt acg agc ccg gaa tac ctg aaa gat ttg ctg gta    5316
Val Lys Ile Ala Leu Thr Ser Pro Glu Tyr Leu Lys Asp Leu Leu Val
    1050                1055                1060 aac acg cta gaa tgt gaa ggt gtg gac gca aac att gca gct acg cag    5364
Asn Thr Leu Glu Cys Glu Gly Val Asp Ala Asn Ile Ala Ala Thr Gln
Asn Thr Leu Glu Cys Glu Gly Val Asp Ala Asn Ile Ala Ala Thr Gln
1065                1070                1075                1080 ggt gcg ctg gct atg gcg cgc acg tta aaa att tcc aac gtt cgg tgg    5412
Gly Ala Leu Ala Met Ala Arg Thr Leu Lys Ile Ser Asn Val Arg Trp
                1085                1090                1095 gat gaa ccg ttt aat gag aac cac ggg gtg tac gcg ctg ttg agc tac    5460
Asp Glu Pro Phe Asn Glu Asn His Gly Val Tyr Ala Leu Leu Ser Tyr
        1100                1105                1110 atc gca acg ctg ccc att tac gca aac cac gac caa gtt aag gag ata    5508
Ile Ala Thr Leu Pro Ile Tyr Ala Asn His Asp Gln Val Lys Glu Ile
    1115                1120                1125 gcc gaa gtg gtg cta tgg cca ctt tta agc gcc tgc acg aat cac gat    5556
Ala Glu Val Val Leu Trp Pro Leu Leu Ser Ala Cys Thr Asn His Asp
                1130                1135                1140 att aag ttt gca ctc gcg gca aac tgt agt gcg gag gag aga ttc gta    5604
Ile Lys Phe Ala Leu Ala Ala Asn Cys Ser Ala Glu Glu Arg Phe Val
1145                1150                1155                1160 gcc gaa acg ctg cgt atg gtt ggg ata acg gta ttg gaa gaa             5646
Ala Glu Thr Leu Arg Met Val Gly Ile Thr Val Leu Glu Glu
        1165                1170 taagtcaaa atg ttg ctc gga tca gtc atc atc gtc atc ata ttg ata gtg    5697
         Met Leu Leu Gly Ser Val Ile Ile Val Ile Ile Leu Ile Val
                 1175                1180                1185 gta gta ttt ttg atc tac tat cta ctt ttc gct gcc gct aaa act agc     5745
Val Val Phe Leu Ile Tyr Tyr Leu Leu Phe Ala Ala Ala Lys Thr Ser
    1190                1195                1200 agt agc gac tcg agt tca cct caa cag cca cct aaa ccc gag ccc gga     5793
Ser Ser Asp Ser Ser Ser Pro Gln Gln Pro Pro Lys Pro Glu Pro Gly
1205                1210                1215                1220 ccc aat acc gaa gat ccc ggc gat gag gag gtc gaa gag aat caa acg     5841
Pro Asn Thr Glu Asp Pro Gly Asp Glu Glu Val Glu Glu Asn Gln Thr
        1225                1230                1235 ttc ggt gcg gcc ctc gag ctc acc gac aaa acg ctc atc aac ttg acc     5889
Phe Gly Ala Ala Leu Glu Leu Thr Asp Lys Thr Leu Ile Asn Leu Thr
    1240                1245                1250 aac agt gac ctg gtg gtg ctc aaa acc ccg gct cga aat aca atc caa     5937
Asn Ser Asp Leu Val Val Leu Lys Thr Pro Ala Arg Asn Thr Ile Gln
1255                1260                1265
```

-continued

```
atg gcc gca caa gct gcg ctt caa gtc gaa tcg gaa ctg gtt tgc gtg         5985
Met Ala Ala Gln Ala Ala Leu Gln Val Glu Ser Glu Leu Val Cys Val
    1270            1275                1280 ggc caa gtt tcg ttg ggc tcg aac gac cag gtc gtg ttc cgt aac gca         6033
Gly Gln Val Ser Leu Gly Ser Asn Asp Gln Val Val Phe Arg Asn Ala
1285                1290                1295                1300 cat gtg cac gta acg gcg gtg ccg cta aca tct gga ccc tcg ttc ttc         6081
His Val His Val Thr Ala Val Pro Leu Thr Ser Gly Pro Ser Phe Phe
                1305                1310                1315 tac gct aca cgt tcg gag cac ccg aga ccg gta gcg tgc gaa tcg ggg         6129
Tyr Ala Thr Arg Ser Glu His Pro Arg Pro Val Ala Cys Glu Ser Gly
            1320                1325                1330 tgc aaa atc gtg cgc gat aat gcc cac aag ttg acg ata att ttc tat         6177
Cys Lys Ile Val Arg Asp Asn Ala His Lys Leu Thr Ile Ile Phe Tyr
        1335                1340                1345 ccc gac ttg tcg ccc aac gtg tcc aca tgt ctg gac tgt atc gac ccg         6225
Pro Asp Leu Ser Pro Asn Val Ser Thr Cys Leu Asp Cys Ile Asp Pro
    1350                1355                1360 gaa agc gac cac gac gtg gtc atc gtg ctg agc aag gct cag gcc gac         6273
Glu Ser Asp His Asp Val Val Ile Val Leu Ser Lys Ala Gln Ala Asp
1365                1370                1375                1380 atc gca aca ctt gcc gcg cta atg gcc aga aag ttt ata tat aaa gca         6321
Ile Ala Thr Leu Ala Ala Leu Met Ala Arg Lys Phe Ile Tyr Lys Ala
                1385                1390                1395 ccc cac att ttt acc cac aca ttc gcc caa ta  atg cct ttc cga gtg         6368
Pro His Ile Phe Thr His Thr Phe Ala Gln     Met Pro Phe Arg Val
            1400                1405                1410 aag ttc tac cca cga tcc ctc aag tat ttc gag ctt agc ccg gac tcg         6416
Lys Phe Tyr Pro Arg Ser Leu Lys Tyr Phe Glu Leu Ser Pro Asp Ser
        1415                1420                1425 ctc gag tac aca att tgc tgc gat gac gag tat cac cgg ttg gag acc         6464
Leu Glu Tyr Thr Ile Cys Cys Asp Asp Glu Tyr His Arg Leu Glu Thr
    1430                1435                1440 gag ctg tac agt gac gct gga acg tac gtg tac gag ttc acg gtg gac         6512
Glu Leu Tyr Ser Asp Ala Gly Thr Tyr Val Tyr Glu Phe Thr Val Asp
1445                1450                1455 tcg ggc tgt aaa gtt tgc gac gtt gaa gcg ttt ctg gtc aga ttc atg         6560
Ser Gly Cys Lys Val Cys Asp Val Glu Ala Phe Leu Val Arg Phe Met
1460                1465                1470                1475 ttg aac tcg gaa aag aat att gac ctg tac gct gcg gag gat ttg gag         6608
Leu Asn Ser Glu Lys Asn Ile Asp Leu Tyr Ala Ala Glu Asp Leu Glu
                1480                1485                1490 tat tac ggg tgc gcc cac gat acc aag cat cgc gaa gct gaa aag tac         6656
Tyr Tyr Gly Cys Ala His Asp Thr Lys His Arg Glu Ala Glu Lys Tyr
            1495                1500                1505 aac tct gga ggt gaa tac tac tat acg ccg atg aag cga gtg cca agt         6704
Asn Ser Gly Gly Glu Tyr Tyr Tyr Thr Pro Met Lys Arg Val Pro Ser
        1510                1515                1520 ggc ata gct aga tgt agg att tgt gat aga aaa tct taaccagtaa             6750
Gly Ile Ala Arg Cys Arg Ile Cys Asp Arg Lys Ser
    1525                1530                1535 aataaacgat atatataaaa tttattaaag tgtatttatt ttgaaccgtt gaccgtttaa      6810
ttgtgatact ttctgaactc gggatcgaac acctctggct ctgcaaactc gtcgtcggtc      6870
gtgcaatcgt tttctctgaa ggtgggttgc acgacctcgg cccgcgtcgg tccaccgtca      6930
tcgtcgtcgt cgtcttcttc aaagcagatc tgtatattgt gcattttttt ctccacacga     6990
tgtaggcgca aaagtgtgta gaatacggcg gtgaacattg ccacgctaag gctcagcgct      7050
```

```
attgcgaggg ccgatgtgtc cgagaggcag ggcattttgc tgtcgtgcac cacaattctg    7110
taggttaacc ttttccctgg ccgcgctgag atgttcagct tcatagtcgt cgggccgggc    7170
ttcggtttgg ttaaccaaat gactgtaaaa atactgctgc ag                       7212
```

<210> SEQ ID NO 118
<211> LENGTH: 72
<212> TYPE: PRT
<213> ORGANISM: mosquito baculovirus

<400> SEQUENCE: 118

```
Met Phe Thr Gly Ala Glu Cys Gly Arg Phe Lys Asp Val His Leu Gln
1               5                   10                  15

Thr Lys Ser Asp Leu Ile Glu Leu Arg Ala Leu Ala Leu Asn His Lys
            20                  25                  30

Asp Arg Gln Ile Arg Val Val Ile Val Tyr Gly Arg Val Gln Leu Asp
        35                  40                  45

Val Val Arg Val Val Leu Thr Lys Gly Ser Thr Arg Ala Tyr Ile Val
    50                  55                  60

Ile Val His Val Gly Glu Pro Gly
65                  70
```

<210> SEQ ID NO 119
<211> LENGTH: 104
<212> TYPE: PRT
<213> ORGANISM: mosquito baculovirus

<400> SEQUENCE: 119

```
Met Ser Thr Thr Gly Tyr Arg Cys Gly Ser Gln Ser Gln Thr Ala Leu
1               5                   10                  15

Ser Tyr Arg Thr Lys Ser Ser Ser Met Phe Phe Val Lys Thr Phe His
            20                  25                  30

Asn Ser Gly Leu Gly Leu Arg Phe Pro Arg Ile Phe Trp Val Ile Asp
        35                  40                  45

Phe Asn Asp Leu Met Ser Thr Ala Leu Ser Ser Pro Ser Arg Leu Ile
    50                  55                  60

Thr Val Leu Arg Tyr Arg Lys Asp Arg Leu Asn Cys Ser Ile Gly Met
65                  70                  75                  80

Gln Lys Met Cys Leu Ser Met Thr Val Pro Val Thr Arg Phe Val Ser
                85                  90                  95

Leu Gln Thr Ala Ile Trp Ser Gly
            100
```

<210> SEQ ID NO 120
<211> LENGTH: 68
<212> TYPE: PRT
<213> ORGANISM: mosquito baculovirus

<400> SEQUENCE: 120

```
Met Glu Thr Ile Arg Leu Val Thr Ala Gly Lys Pro Tyr Lys Arg Phe
1               5                   10                  15

Glu Gln Ser Pro Phe Val Thr Met Ser Arg Ser Glu Tyr Glu Leu Arg
            20                  25                  30

Thr Ala Pro Asn Ala Asn Asn Asp Tyr Ser Phe Val Met Arg Met Gly
        35                  40                  45

Asn Lys Thr Arg Ile Val Asn Leu Trp Ala Pro Val His Gly Gln Val
    50                  55                  60

Val Leu Tyr Asp
65
```

-continued

65

<210> SEQ ID NO 121
<211> LENGTH: 546
<212> TYPE: PRT
<213> ORGANISM: mosquito baculovirus

<400> SEQUENCE: 121
```
Met Asn Arg Ser Ser Arg Ala Glu Gly Leu Arg Glu Ala Gly Gly Val
 1               5                  10                  15

Lys Gly Arg Pro Lys Ser Arg Ala Thr Thr Thr Ile Lys Ala Gly Arg
            20                  25                  30

Pro Val Arg Pro Ala Arg Gln Arg Gln Val Asp Glu Ile Leu Asn Gln
        35                  40                  45

Asp Glu Asn Asp Asp Val Ala Pro Pro Val Ala Glu Pro Gln Leu Asn
    50                  55                  60

Leu Asp Asp Asn Val Trp Thr Gly Gly Ala Thr Ser Gly Asp Gln Asn
65                  70                  75                  80

Val Ala Pro Gly Ser Pro Thr Gly Pro Val Ala Met Ser Val Ile Ser
                85                  90                  95

Lys Arg Leu Val Ser Glu Trp His Ser Asp Gly Glu Gly Glu Asp Glu
            100                 105                 110

Gly Gly Gln Asp Asn Asp Pro Glu Pro Glu Ser Val Ala Lys Val Asp
        115                 120                 125

Asp Phe Leu Phe Pro Glu Leu Glu Glu Asp Gly Pro Asp Ser Val Gly
    130                 135                 140

Gly Ile Gly Asn Val Ser Gly Ser Val Phe Glu Val Val Gly Gly Gly
145                 150                 155                 160

Pro Glu Gly Asp Tyr Ala Ala Gly Glu Glu Asp Glu Val Ser Arg Asn
                165                 170                 175

Ser Leu Asn Phe Asp Met Ala Ser Glu Val Gln Ser Thr Asp Ala Ala
            180                 185                 190

Lys Val Met Glu Leu Phe Asn Ala Leu Ser Glu Glu Gln Arg Asn Val
        195                 200                 205

Ile Leu Asn Asn Phe Gly Ala Ala Pro Ser Gly Ser Gly Thr Thr Pro
    210                 215                 220

Pro Thr Ser Ala Gln Pro Asp Met Glu Val Glu Asp Val Glu Thr Val
225                 230                 235                 240

Glu Lys Pro Glu Asn Leu Asn Asp Ile Ile Thr Asp Gln Leu Arg Asp
                245                 250                 255

Phe Met Ala Gln Glu Leu Lys Lys Ala Ala Glu Asn Tyr Val Pro Lys
            260                 265                 270

Trp Gly Ser Thr Val Gly Glu Ser Lys Ser Ala Leu Ala Ile Thr Val
        275                 280                 285

Ala Asp Arg Val Ser Arg Ser Phe Met Tyr Glu Gly Arg Ile Val Asp
    290                 295                 300

Tyr Asn Gln Val Val Leu His Ile Leu Asp Asn Tyr Asp Gln Arg Leu
305                 310                 315                 320

Glu Glu Leu Leu Ser Phe Arg Thr Lys Thr Tyr Ile Ile Ala Glu Gly
                325                 330                 335

Val Pro His Asp Ser Lys Val His Asp Tyr Val Asp Leu Thr Gln Tyr
            340                 345                 350

Arg Glu Thr Val Pro Tyr Ser Ile Ala Leu Asn Asn Leu Ser Arg Gly
        355                 360                 365
```

-continued

```
Val Asp Gln Ala Asn Thr Leu Gln Leu Ala Glu Gly Cys Leu Glu Gln
    370                 375                 380

Leu Asn Met Ala Lys Ile Phe Lys Asp Phe Asn Glu Asn Ile Val Pro
385                 390                 395                 400

Asn Asn Leu His Lys His Lys Pro Thr Phe Phe Tyr Ala Lys Ile Met
                405                 410                 415

Lys Leu Phe Ala Arg Leu Val Asp Arg Val Asp Asn Glu Thr Met Thr
                420                 425                 430

Ala Val Glu Lys Arg Leu Phe Leu Met Ser Gln Arg Leu Ile His Cys
                435                 440                 445

Ile Pro Leu Val Ile Ile Gly Leu Thr Phe Ala Ser Lys Tyr Arg Thr
            450                 455                 460

Ser Lys Ile Asp Cys Glu Ala Leu Ala Leu Tyr Ala Val Asn His Ala
465                 470                 475                 480

Leu Ser Glu Lys Val Asp Lys Leu Phe Thr Phe Ala Glu Ala Gln Tyr
                485                 490                 495

Gly Glu Pro Leu Leu Ser Arg Arg Ile Leu Ile Glu Glu Gln Ala Tyr
                500                 505                 510

Leu Ser Phe Gly Asn His Leu Glu Gln Arg Asn Arg Glu Leu Asn Val
                515                 520                 525

Ile Leu Asp Thr Val Leu Asn Ala Val Arg Lys Thr Tyr Arg Val Ser
            530                 535                 540

Arg Val
545

<210> SEQ ID NO 122
<211> LENGTH: 237
<212> TYPE: PRT
<213> ORGANISM: mosquito baculovirus

<400> SEQUENCE: 122

Met Gly Cys Asp Val Thr Phe Thr Leu Ile His Glu Val Tyr Ser Glu
  1               5                  10                  15

Val Pro Val Asp Gly Lys His Val Pro Val Glu Tyr Asp Arg Tyr Lys
                 20                  25                  30

Ile Arg Leu Leu Lys Glu Leu Thr Arg Phe Leu Cys Gly Glu Thr Asp
             35                  40                  45

Lys Val Asp Gly Ala Thr Ser Glu Ala Lys Ala Asp Cys Gly Gly Lys
 50                  55                  60

Tyr Thr Asp Glu Glu Arg Lys Leu Phe Gly Phe Lys Ser Lys Gln Val
 65                  70                  75                  80

Ile Asp Asp Glu Arg Leu Ser Arg Leu Leu Glu Asp Asn Lys Leu Leu
                 85                  90                  95

Tyr Ser Ala Val Ser Glu Arg Asp Ala Ala Lys Arg Glu Arg Met Glu
                100                 105                 110

Gln Leu Lys Arg Glu Glu Met Glu Leu Lys Ser Gln Thr Arg Arg Leu
            115                 120                 125

Arg Lys Leu Asn Gln Gly Arg Leu Leu Ser Lys Ser Glu Asn Phe Leu
130                 135                 140

Ser Met Asp Pro Lys Leu Arg Asp Lys Leu Ile Asp His Thr Val Ile
145                 150                 155                 160

Leu Glu Pro Gln Tyr Asp Ile Leu Ala Leu Ser Glu Tyr Asn Asp Leu
                165                 170                 175

Val Ala Gln Lys Asp Ala Leu Glu Lys Tyr Glu Arg Met Ser Arg Arg
                180                 185                 190
```

```
Ser Ile Lys Asn Pro Tyr Thr Arg Ser Ala Ile Asn Ile Val Glu Arg
        195                 200                 205

Arg Glu Gly Ala Ser Met Phe Arg Glu Lys Lys Arg Glu Asn Ile Ile
        210                 215                 220

Asp Asn Ile Arg Gly Ile Asp Asn Ser Glu Ser Val Ala
225                 230                 235

<210> SEQ ID NO 123
<211> LENGTH: 147
<212> TYPE: PRT
<213> ORGANISM: mosquito baculovirus

<400> SEQUENCE: 123

Met Cys Leu Leu Ser Asp Ser Arg Trp Arg Val Cys Lys Phe Ser Phe
1               5                   10                  15

Ala Met Ser Phe Ile Val Lys Ile Ala Leu Thr Ser Pro Glu Tyr Leu
            20                  25                  30

Lys Asp Leu Leu Val Asn Thr Leu Glu Cys Glu Gly Val Asp Ala Asn
        35                  40                  45

Ile Ala Ala Thr Gln Gly Ala Leu Ala Met Ala Arg Thr Leu Lys Ile
    50                  55                  60

Ser Asn Val Arg Trp Asp Glu Pro Phe Asn Glu Asn His Gly Val Tyr
65                  70                  75                  80

Ala Leu Leu Ser Tyr Ile Ala Thr Leu Pro Ile Tyr Ala Asn His Asp
                85                  90                  95

Gln Val Lys Glu Ile Ala Glu Val Val Leu Trp Pro Leu Leu Ser Ala
            100                 105                 110

Cys Thr Asn His Asp Ile Lys Phe Ala Leu Ala Ala Asn Cys Ser Ala
        115                 120                 125

Glu Glu Arg Phe Val Ala Glu Thr Leu Arg Met Val Gly Ile Thr Val
    130                 135                 140

Leu Glu Glu
145

<210> SEQ ID NO 124
<211> LENGTH: 232
<212> TYPE: PRT
<213> ORGANISM: mosquito baculovirus

<400> SEQUENCE: 124

Met Leu Leu Gly Ser Val Ile Ile Val Ile Ile Leu Ile Val Val Val
1               5                   10                  15

Phe Leu Ile Tyr Tyr Leu Leu Phe Ala Ala Ala Lys Thr Ser Ser Ser
            20                  25                  30

Asp Ser Ser Pro Gln Gln Pro Lys Pro Glu Pro Gly Pro Asn
        35                  40                  45

Thr Glu Asp Pro Gly Asp Glu Glu Val Glu Glu Asn Gln Thr Phe Gly
    50                  55                  60

Ala Ala Leu Glu Leu Thr Asp Lys Thr Leu Ile Asn Leu Thr Asn Ser
65                  70                  75                  80

Asp Leu Val Val Leu Lys Thr Pro Ala Arg Asn Thr Ile Gln Met Ala
                85                  90                  95

Ala Gln Ala Ala Leu Gln Val Glu Ser Glu Leu Val Cys Val Gly Gln
            100                 105                 110

Val Ser Leu Gly Ser Asn Asp Gln Val Val Phe Arg Asn Ala His Val
        115                 120                 125
```

His Val Thr Ala Val Pro Leu Thr Ser Gly Pro Ser Phe Phe Tyr Ala
130 135 140

Thr Arg Ser Glu His Pro Arg Pro Val Ala Cys Glu Ser Gly Cys Lys
145 150 155 160

Ile Val Arg Asp Asn Ala His Lys Leu Thr Ile Ile Phe Tyr Pro Asp
165 170 175

Leu Ser Pro Asn Val Ser Thr Cys Leu Asp Cys Ile Asp Pro Glu Ser
180 185 190

Asp His Asp Val Val Ile Val Leu Ser Lys Ala Gln Ala Asp Ile Ala
195 200 205

Thr Leu Ala Ala Leu Met Ala Arg Lys Phe Ile Tyr Lys Ala Pro His
210 215 220

Ile Phe Thr His Thr Phe Ala Gln
225 230

<210> SEQ ID NO 125
<211> LENGTH: 129
<212> TYPE: PRT
<213> ORGANISM: mosquito baculovirus

<400> SEQUENCE: 125

Met Pro Phe Arg Val Lys Phe Tyr Pro Arg Ser Leu Lys Tyr Phe Glu
1 5 10 15

Leu Ser Pro Asp Ser Leu Glu Tyr Thr Ile Cys Cys Asp Asp Glu Tyr
20 25 30

His Arg Leu Glu Thr Glu Leu Tyr Ser Asp Ala Gly Thr Tyr Val Tyr
35 40 45

Glu Phe Thr Val Asp Ser Gly Cys Lys Val Cys Asp Val Glu Ala Phe
50 55 60

Leu Val Arg Phe Met Leu Asn Ser Glu Lys Asn Ile Asp Leu Tyr Ala
65 70 75 80

Ala Glu Asp Leu Glu Tyr Tyr Gly Cys Ala His Asp Thr Lys His Arg
85 90 95

Glu Ala Glu Lys Tyr Asn Ser Gly Gly Glu Tyr Tyr Tyr Thr Pro Met
100 105 110

Lys Arg Val Pro Ser Gly Ile Ala Arg Cys Arg Ile Cys Asp Arg Lys
115 120 125

Ser

<210> SEQ ID NO 126
<211> LENGTH: 7212
<212> TYPE: DNA
<213> ORGANISM: mosquito baculovirus
<220> FEATURE:
<221> NAME/KEY: CDS
<222> LOCATION: (708)...(944)
<221> NAME/KEY: CDS
<222> LOCATION: (1197)...(1364)
<221> NAME/KEY: CDS
<222> LOCATION: (2057)...(2242)

<400> SEQUENCE: 126
ctgcagactc gggctctggt tttggttcgg gcaaatcttg atcgactggg gctggactcg 60
gcgtacgggc gcgcttgtta accggttcgt ttggttcaac gacggtggtg tcgaccgaac 120
gttttccatc tccgcagcct ttaggtttga taaagttcac ctcggcaata tgttcaccgg 180
cgccgaatgt ggtcgcttta aggacgtaca cttgcagacg aaaagcgatc ttattgagct 240

```
ccgtgccctc gcgctgaatc acaaagaccg ccaaattcgg gttgtaattg tgtacggtcg    300
tgtgcagctt gatgtcgtgc gggtggtcct caccaaaggg tccactcgtg cttacatagt    360
gatagtacac gtcggtgagc ccgggtaaaa ttagttggtt gcgcgatgag tacaactggt    420
taccgttgcg gatctcaatc tcaaactgca ttgtcgtatc gaacaaaaag ttcctcgatg    480
ttcttcgtaa aaacgttcca caactcggga ctggggttgc gctttccgcg tatattctgg    540
gtcatagatt ttaacgactt aatgtccacc gccttatcct caccgtcccg cttgataacg    600
gttttgcggt atagaaagga ccgtttgaac tgctcgattg ggatgcagaa gatgtgccta    660
tccatgaccg tccccgtaac gcggttcgtc agtttacaga ccgccat atg gtc cgg      716
                                                   Met Val Arg
                                                     1 gta gta cgg gca aat gcc aac gct gtg gat gat ttt cga tgc ggc cat      764
Val Val Arg Ala Asn Ala Asn Ala Val Asp Asp Phe Arg Cys Gly His
    5              10                  15 ggt tgt gct gag caa atc gct gtt acc aat cag gca ggt tac gag cgt      812
Gly Cys Ala Glu Gln Ile Ala Val Thr Asn Gln Ala Gly Tyr Glu Arg
20              25                  30                  35 gat ggc aat caa cac ggc cct gta gta gcg gta att tac tat cac ctc      860
Asp Gly Asn Gln His Gly Pro Val Val Ala Val Ile Tyr Tyr His Leu
                40                  45                  50 gtc gtc cag tgg gta gcc gcg cga gac cag tgg gta ctc gag atc ttc      908
Val Val Gln Trp Val Ala Ala Arg Asp Gln Trp Val Leu Glu Ile Phe
        55                  60                  65 aac gaa ggg gtg tat aat gag gag gtc ctg tgg tgc tagcaccgca           954
Asn Glu Gly Val Tyr Asn Glu Glu Val Leu Trp Cys
70                  75 gattccgcgc taacgtacaa ctctagcgcc gagttgggcg aaattaaaat ttgtctatct   1014
agcgttctgt atatgcggtc aagttcatcg taaacgtggc caatgtttat aactctaccc   1074
ccaaagctgg agcggaacag gtccaggtcg aaccgcagca cacaattgat cttgttggac   1134
gcgtataaac aggcgtcaac tgtacctcgg ttttccctgc acatgcccat cagggccaca   1194 ta atg gtg cac cat gtt cga gtt cag gta ccc cat cga gag ttc ggt      1241
   Met Val His His Val Arg Val Gln Val Pro His Arg Glu Phe Gly
    80                  85                  90 gac gtg agt ttt gct gta gtt ttt gat gaa aat ttt aca ctt gat ttt     1289
Asp Val Ser Phe Ala Val Val Phe Asp Glu Asn Phe Thr Leu Asp Phe
95              100                 105                 110 tgt atc cac atg cac cgg aca ggg gtt ccg ccg acc ctc gcg acc ggc     1337
Cys Ile His Met His Arg Thr Gly Val Pro Pro Thr Leu Ala Thr Gly
                115                 120                 125 ttg gga ttt tgt tcg atg aac cgc cgc taacgtcacg ttcggtaaca           1384
Leu Gly Phe Cys Ser Met Asn Arg Arg
            130                 135 gggtgaggca tttgaccgac cgtgaagtaa gtgtatccaa ctccatcact gcaaactgcg   1444
cgaacttcaa tctccttcgt ctccggattg attataaccc tttgccgcag aaaagtctcg   1504
gtaaacgcat ccatatggaa acaattcgcc tcgttacggc cggtaaacct acaagcggt    1564 ttgagcagtc gccgtttgtt acaatgtccc gctctgaata cgaactgcga accgcaccta   1624
acgcaaacaa tgactactct ttcgtgatgc gaatgggtaa taagcacgt attgtgaacc    1684 tctgggcgcc cgtacacggc caggttgttt tatacgacta aatgaatcga agctcgagag   1744
ccgagggtct acgtgaagcc ggtggcgtta aggccgccc aaaatcacgc gccactacaa    1804
ccatcaaagc tggtagaccg gtgcgccag ctcggcagcg acaagttgat gaaatttaa     1864 accaagatga aaatgacgat gtagcaccac ctgtagccga gccccagcta aatttggatg   1924
```

-continued

```
ataatgtttg gaccggtggt gctacgagtg gtgatcaaaa tgtggcccca ggttcaccca   1984
cgggtcccgt ggcaatgtcg gtgatatcga agcgtctcgt gagcgagtgg cactcggacg   2044
gagaaggtga gg atg aag gtg ggc agg ata acg atc ccg agc ccg agt cgg   2095
            Met Lys Val Gly Arg Ile Thr Ile Pro Ser Pro Ser Arg
                140                 145 tgg cca agg tgg acg act ttt tat ttc ccg agc tcg agg aag acg gac    2143
Trp Pro Arg Trp Thr Thr Phe Tyr Phe Pro Ser Ser Arg Lys Thr Asp
150                 155                 160 cgg act cgg ttg gcg gaa ttg gca acg ttt ctg gtt cag ttt tcg aag    2191
Arg Thr Arg Leu Ala Glu Leu Ala Thr Phe Leu Val Gln Phe Ser Lys
165                 170                 175                 180 ttg tcg gtg gtg gcc ccg agg gcg act atg ctg ctg gtg agg agg acg    2239
Leu Ser Val Val Ala Pro Arg Ala Thr Met Leu Leu Val Arg Arg Thr
                185                 190                 195 aag taagcagaaa ttcgctaaac ttcgacatgg cgtccgaggt gcaaagtact         2292
Lys gatgccgcta aggtgatgga gctgtttaac gccctatccg aggagcagcg aaatgtgatt  2352
ctaaacaact ttggtgcggc accatccggt agcggaacca caccgccaac ctcggctcaa  2412
cccgatatgg aggttgagga tgttgagact gtggaaaagc cggagaattt aaacgacatt  2472
attacggacc agttgcgcga tttcatggca caggagctga aaaaggccgc tgaaaactac  2532
gtaccaaagt ggggctcaac ggttggtgag tcgaaaagtg cgctcgcaat tacggttgcc  2592
gatcgcgtga gcagatcgtt catgtacgag ggtcgtattg tcgactataa ccaggttgtg  2652
ctacacatac tggacaatta tgaccaaagg ttggaggagc tgctctcgtt ccgcacgaaa  2712
acctacataa tcgccgaagg tgtaccgcac gactcgaagg tgcacgacta tgtggacctg  2772
acccagtatc gggaaaccgt gccgtattca attgccctca caacctgag ccgcggtgtg  2832 gaccaggcca acacgctcca gctggccgag gggtgcttgg agcagctgaa tatggcaaaa  2892
attttcaaag atttcaacga aaacattgtg cccaacaacc tgcacaagca caagcccacc  2952
ttcttctatg cgaaaattat gaagctgttt gcacgactgg tggatagggt ggacaatgag  3012
acgatgactg cggtcgagaa gcgtttgttt ctaatgtcac aacggttgat ccattgtatc  3072
ccactggtaa taatcggtct aacgttcgcc tccaagtacc gcacctcgaa gatagactgc  3132
gaagctttgg ccctgtacgc cgtgaaccat gcgctgtctg aaaaggtgga taaattgttc  3192
acatttgcgg aagcacagta cggtgaaccg ctgctcagcc gccgtatact aattgaagag  3252
caggcgtatc tgtctttcgg gaaccacctc gagcagcgca accgcgagct gaatgtgatt  3312
ctggataccg tactcaacgc cgtacgaaag acgtacaggg tgtctagagt ttaagttgac  3372
accgattaaa gatgggctgc gacgtaacgt tcaccttgat ccacgaggta tattctgagg  3432
ttcccgtcga tggaaagcac gtcccggtcg aatatgaccg gtacaaaatc aggttattga  3492
aggagctgac gcgtttcctg tgcggtgaaa cggataaggt tgacggtgcc acgagtgaag  3552
ctaaagcgga ttgtgggggc aagtacacgg atgaagagcg caagctgttt gggtttaaat  3612
cgaagcaggt gattgacgat gaaaggttgt ccaggctgct ggaggataac aagttgctgt  3672
actctgcggt gagtgagcgt gatgcggcga acgtgagcg catggagcag ctgaagcggg  3732
aggaaatgga gctcaagagt caaacgcgaa gattgcgcaa actgaaccag ggtcgtttgc  3792
tgtccaagtc tgaaaacttt ctttcgatgg accccaagtt gcgcgacaag ttgatcgatc  3852
acaccgtcat attggaacca cagtacgaca ttttggcct gtccgagtat aacgatttgg  3912
tagcgcaaaa ggatgccctc gagaagtacg aacgaatgtc cagacgatcg ataaagaatc  3972
```

```
cgtacacccg ctccgccata aacatcgttg agcgccgtga gggtgcgtca atgttccgtg    4032
agaagaagcg cgaaaacatt attgacaaca tacgcggtat cgacaatagc gaaagtgtag    4092
cgtgatatat ttttgaaata taaatatata aaataaataa atagataaat aaataaatgt    4152
ttctggttga aattaaccaa tatttattat cgttgtatca cacgtaccca tagtaattat    4212
atatataaaa aaaagtccaa tgtaatttat tgggccctgg aatactttag cggtggacca    4272
gtgctatcat ccggtgcggg tcgctttcgt acgggtgaaa tgggtgcaat ttcaccgcgc    4332
ctctgcttgt cgtacagttc ccaggtcatg gttgggcctt cttggaacgc tttgaggtag    4392
accttgatgt cggcctgttc gatgggtctg ttgctgcgca aatgtccact ggcctgttgt    4452
acaattcggt acgagttgat atagttgtgc agctggacca tttcgtacgc tagtaaattt    4512
ttaacaaagg cgttgttcag tacgccgggg ttggcgatgt actcgtccag ctcaacggtt    4572
gggattcgca gcaactcgat ggtgcggccc gaaatggaac cttcacgcg ctttagctcc     4632 tcgagcacca gtaggcggaa gagttgttcg aactttacca gtatgacgcc ccgcaacaat    4692
aggtagtgtg aaacgcaggt ttggcagccc aacgaaatgt acatgtttgc caccacgttg    4752
tgcacaactt gcagtggtgc gagcgccaac atgtcattac gttgggcaac aatttggtcg    4812
cccacctcgg ccatgaggtg catcacgtcc cacgagttgt gaaaatgttc accgtgaatg    4872
tagggtagtg ggaccaccgc aatggggtcc agctcgcact ccttggccgc gctgttgtag    4932
tgggcaacga attcgggctt gctggacatg tacgccatct ggcggtcctg accgcgtttg    4992
ttgccgagaa tcaaatcgag gtgcagcttg gtgcgctttt gatatatgga ccaaaattgg    5052
cgtacgcgtt cttcgctgac cacgatcggt gcgggaggtc gtgccagcag catcgataga    5112
ttcatgaggt agacaatggt tgcaaactca actttggcga ggttggattc ggtttcggtg    5172
gggctcaaca ggctggtgat cactaggtaa aaaatgtgcc tattgagcga ctcgcgttgg    5232
cgagtctgta agttttcctt cgcaatgtcg ttcatcgtga aaatcgcact tacgagcccg    5292
gaatacctga aagatttgct ggtaaacacg ctagaatgtg aaggtgtgga cgcaaacatt    5352
gcagctacgc agggtgcgct ggctatggcg cgcacgttaa aaatttccaa cgttcggtgg    5412
gatgaaccgt ttaatgagaa ccacggggtg tacgcgctgt tgagctacat cgcaacgctg    5472
cccatttacg caaaccacga ccaagttaag gagatagccg aagtggtgct atggccactt    5532
ttaagcgcct gcacgaatca cgatattaag tttgcactcg cggcaaactg tagtgcggag    5592
gagagattcg tagccgaaac gctgcgtatg gttgggataa cggtattgga agaataagtc    5652
aaaatgttgc tcggatcagt catcatcgtc atcatattga tagtggtagt attttttgatc    5712 tactatctac ttttcgctgc cgctaaaact agcagtagcg actcgagttc acctcaacag    5772
ccacctaaac ccgagcccgg acccaatacc gaagatcccg gcgatgagga ggtcgaagag    5832
aatcaaacgt tcggtgcggc cctcgagctc accgacaaaa cgctcatcaa cttgaccaac    5892
agtgacctgg tggtgctcaa aaccccggct cgaaatacaa tccaaatggc cgcacaagct    5952
gcgcttcaag tcgaatcgga actggtttgc gtgggccaag tttcgttggg ctcgaacgac    6012
caggtcgtgt tccgtaacgc acatgtgcac gtaacggcgg tgccgctaac atctggaccc    6072
tcgttcttct acgctacacg ttcggagcac ccgagaccgg tagcgtgcga atcggggtgc    6132
aaaatcgtgc gcgataatgc ccacaagttg acgataattt tctatcccga cttgtcgccc    6192
aacgtgtcca catgtctgga ctgtatcgac ccggaaagcg accacgacgt ggtcatcgtg    6252
ctgagcaagg ctcaggccga catcgcaaca cttgccgcgc taatggccag aaagtttata    6312
```

-continued

```
tataaagcac cccacatttt tacccacaca ttcgcccaat aatgcctttc cgagtgaagt    6372
tctacccacg atccctcaag tatttcgagc ttagcccgga ctcgctcgag tacacaattt    6432
gctgcgatga cgagtatcac cggttggaga ccgagctgta cagtgacgct ggaacgtacg    6492
tgtacgagtt cacggtggac tcgggctgta agtttgcga cgttgaagcg tttctggtca    6552
gattcatgtt gaactcggaa aagaatattg acctgtacgc tgcggaggat ttggagtatt    6612
acgggtgcgc ccacgatacc aagcatcgcg aagctgaaaa gtacaactct ggaggtgaat    6672
actactatac gccgatgaag cgagtgccaa gtggcatagc tagatgtagg atttgtgata    6732
gaaaatctta accagtaaaa taacgatat atataaaatt tattaaagtg tatttatttt    6792
gaaccgttga ccgtttaatt gtgatacttt ctgaactcgg gatcgaacac ctctggctct    6852
gcaaactcgt cgtcggtcgt gcaatcgttt tctctgaagg tgggttgcac gacctcggcc    6912
cgcgtcggtc caccgtcatc gtcgtcgtcg tcttcttcaa agcagatctg tatattgtgc    6972
acatttttct ccacacgatg taggcgcaaa agtgtgtaga atacgcggt gaacattgcc    7032 acgctaaggc tcagcgctat tgcgagggcc gatgtgtccg agaggcaggg catttgctg    7092 tcgtgcacca caattctgta ggttaacctt ttccctggcc gcgctgagat gttcagcttc    7152
atagtcgtcg ggccgggctt cggtttggtt aaccaaatga ctgtaaaaat actgctgcag    7212
```

<210> SEQ ID NO 127
<211> LENGTH: 79
<212> TYPE: PRT
<213> ORGANISM: mosquito baculovirus

<400> SEQUENCE: 127

```
Met Val Arg Val Val Arg Ala Asn Ala Asn Ala Val Asp Asp Phe Arg
  1               5                  10                  15

Cys Gly His Gly Cys Ala Glu Gln Ile Ala Val Thr Asn Gln Ala Gly
             20                  25                  30

Tyr Glu Arg Asp Gly Asn Gln His Gly Pro Val Val Ala Val Ile Tyr
         35                  40                  45

Tyr His Leu Val Val Gln Trp Val Ala Ala Arg Asp Gln Trp Val Leu
     50                  55                  60

Glu Ile Phe Asn Glu Gly Val Tyr Asn Glu Glu Val Leu Trp Cys
 65                  70                  75
```

<210> SEQ ID NO 128
<211> LENGTH: 56
<212> TYPE: PRT
<213> ORGANISM: mosquito baculovirus

<400> SEQUENCE: 128

```
Met Val His His Val Arg Val Gln Val Pro His Arg Glu Phe Gly Asp
  1               5                  10                  15

Val Ser Phe Ala Val Val Phe Asp Glu Asn Phe Thr Leu Asp Phe Cys
             20                  25                  30

Ile His Met His Arg Thr Gly Val Pro Pro Thr Leu Ala Thr Gly Leu
         35                  40                  45

Gly Phe Cys Ser Met Asn Arg Arg
     50                  55
```

<210> SEQ ID NO 129
<211> LENGTH: 62
<212> TYPE: PRT
<213> ORGANISM: mosquito baculovirus

```
<400> SEQUENCE: 129

Met Lys Val Gly Arg Ile Thr Ile Pro Ser Pro Ser Arg Trp Pro Arg
 1               5                  10                  15

Trp Thr Thr Phe Tyr Phe Pro Ser Ser Arg Lys Thr Asp Arg Thr Arg
             20                  25                  30

Leu Ala Glu Leu Ala Thr Phe Leu Val Gln Phe Ser Lys Leu Ser Val
         35                  40                  45

Val Ala Pro Arg Ala Thr Met Leu Leu Val Arg Arg Thr Lys
         50                  55                  60

<210> SEQ ID NO 130
<211> LENGTH: 7212
<212> TYPE: DNA
<213> ORGANISM: mosquito baculovirus
<220> FEATURE:
<221> NAME/KEY: CDS
<222> LOCATION: (1862)...(2971)
<221> NAME/KEY: CDS
<222> LOCATION: (5783)...(6769)
<221> NAME/KEY: CDS
<222> LOCATION: (3498)...(3854)
<221> NAME/KEY: CDS
<222> LOCATION: (59)...(403)
<221> NAME/KEY: CDS
<222> LOCATION: (1177)...(1449)
<221> NAME/KEY: CDS
<222> LOCATION: (3150)...(3359)

<400> SEQUENCE: 130
ctgcagcagt atttttacag tcatttggtt aaccaaaccg aagcccggcc cgacgact        58 atg aag ctg aac atc tca gcg cgg cca ggg aaa agg tta acc tac aga     106
Met Lys Leu Asn Ile Ser Ala Arg Pro Gly Lys Arg Leu Thr Tyr Arg
 1               5                  10                  15 att gtg gtg cac gac agc aaa atg ccc tgc ctc tcg gac aca tcg gcc     154
Ile Val Val His Asp Ser Lys Met Pro Cys Leu Ser Asp Thr Ser Ala
             20                  25                  30 ctc gca ata gcg ctg agc ctt agc gtg gca atg ttc acc gcc gta ttc     202
Leu Ala Ile Ala Leu Ser Leu Ser Val Ala Met Phe Thr Ala Val Phe
         35                  40                  45 tac aca ctt ttg cgc cta cat cgt gtg gag aaa aat gtg cac aat ata     250
Tyr Thr Leu Leu Arg Leu His Arg Val Glu Lys Asn Val His Asn Ile
     50                  55                  60 cag atc tgc ttt gaa gaa gac gac gac gac gat gac ggt gga ccg acg     298
Gln Ile Cys Phe Glu Glu Asp Asp Asp Asp Asp Asp Gly Gly Pro Thr
 65                  70                  75                  80 cgg gcc gag gtc gtg caa ccc acc ttc aga gaa aac gat tgc acg acc     346
Arg Ala Glu Val Val Gln Pro Thr Phe Arg Glu Asn Asp Cys Thr Thr
                 85                  90                  95 gac gac gag ttt gca gag cca gag gtg ttc gat ccc gag ttc aga aag     394
Asp Asp Glu Phe Ala Glu Pro Glu Val Phe Asp Pro Glu Phe Arg Lys
            100                 105                 110 tat cac aat taaacggtca acggttcaaa ataaatacac tttaataaat                443
Tyr His Asn
        115 tttatatata tcgtttattt tactggttaa gattttctat cacaaatcct acatctagct       503 atgccacttg gcactcgctt catcggcgta tagtagtatt cacctccaga gttgtacttt       563 tcagcttcgc gatgcttggt atcgtgggcg caccgtaat actccaaatc ctccgcagcg        623 tacaggtcaa tattctttc cgagttcaac atgaatctga ccagaaacgc ttcaacgtcg        683 caaactttac agcccgagtc caccgtgaac tcgtacacgt acgttccagc gtcactgtac       743
```

-continued

```
agctcggtct ccaaccggtg atactcgtca tcgcagcaaa ttgtgtactc gagcgagtcc      803
gggctaagct cgaaatactt gagggatcgt gggtagaact tcactcggaa aggcattatt      863
gggcgaatgt gtgggtaaaa atgtggggtg ctttatatat aaactttctg gccattagcg      923
cggcaagtgt tgcgatgtcg gcctgagcct tgctcagcac gatgaccacg tcgtggtcgc      983
tttccgggtc gatacagtcc agacatgtgg acacgttggg cgacaagtcg ggatagaaaa     1043
ttatcgtcaa cttgtgggca ttatcgcgca cgattttgca ccccgattcg cacgctaccg     1103
gtctcgggtg ctccgaacgt gtagcgtaga agaacgaggg tccagatgtt agcggcaccg     1163
ccgttacgtg cac atg tgc gtt acg gaa cac gac ctg gtc gtt cga gcc        1212
            Met Cys Val Thr Glu His Asp Leu Val Val Arg Ala
                120                 125 caa cga aac ttg gcc cac gca aac cag ttc cga ttc gac ttg aag cgc       1260
Gln Arg Asn Leu Ala His Ala Asn Gln Phe Arg Phe Asp Leu Lys Arg
    130                 135                 140 agc ttg tgc ggc cat ttg gat tgt att tcg agc cgg ggt ttt gag cac       1308
Ser Leu Cys Gly His Leu Asp Cys Ile Ser Ser Arg Gly Phe Glu His
145                 150                 155 cac cag gtc act gtt ggt caa gtt gat gag cgt ttt gtc ggt gag ctc       1356
His Gln Val Thr Val Gly Gln Val Asp Glu Arg Phe Val Gly Glu Leu
160                 165                 170                 175 gag ggc cgc acc gaa cgt ttg att ctc ttc gac ctc ctc atc gcc ggg       1404
Glu Gly Arg Thr Glu Arg Leu Ile Leu Phe Asp Leu Leu Ile Ala Gly
                180                 185                 190 atc ttc ggt att ggg tcc ggg ctc ggg ttt agg tgg ctg ttg agg           1449
Ile Phe Gly Ile Gly Ser Gly Leu Gly Phe Arg Trp Leu Leu Arg
    195                 200                 205 tgaactcgag tcgctactgc tagttttagc ggcagcgaaa agtagatagt agatcaaaaa     1509
tactaccact atcaatatga tgacgatgat gactgatccg agcaacattt tgacttattc     1569
ttccaatacc gttatcccaa ccatacgcag cgtttcggct acgaatctct cctccgcact     1629
acagtttgcc gcgagtgcaa acttaatatc gtgattcgtg caggcgctta aaagtggcca     1689
tagcaccact tcggctatct ccttaacttg gtcgtggttt gcgtaaatgg gcagcgttgc     1749
gatgtagctc aacagcgcgt acaccccgtg gttctcatta aacggttcat cccaccgaac     1809
gttggaaatt tttaacgtgc gcgccatagc cagcgcaccc tgcgtagctg ca atg ttt    1867
                                                         Met Phe gcg tcc aca cct tca cat tct agc gtg ttt acc agc aaa tct ttc agg       1915
Ala Ser Thr Pro Ser His Ser Ser Val Phe Thr Ser Lys Ser Phe Arg
    210                 215                 220 tat tcc ggg ctc gta agt gcg att ttc acg atg aac gac att gcg aag       1963
Tyr Ser Gly Leu Val Ser Ala Ile Phe Thr Met Asn Asp Ile Ala Lys
225                 230                 235                 240 gaa aac tta cag act cgc caa cgc gag tcg ctc aat agg cac att ttt       2011
Glu Asn Leu Gln Thr Arg Gln Arg Glu Ser Leu Asn Arg His Ile Phe
                245                 250                 255 tac cta gtg atc acc agc ctg ttg agc ccc acc gaa acc gaa tcc aac       2059
Tyr Leu Val Ile Thr Ser Leu Leu Ser Pro Thr Glu Thr Glu Ser Asn
            260                 265                 270 ctc gcc aaa gtt gag ttt gca acc att gtc tac ctc atg aat cta tcg       2107
Leu Ala Lys Val Glu Phe Ala Thr Ile Val Tyr Leu Met Asn Leu Ser
        275                 280                 285 atg ctg ctg gca cga cct ccc gca ccg atc gtg gtc agc gaa gaa cgc       2155
Met Leu Leu Ala Arg Pro Pro Ala Pro Ile Val Val Ser Glu Glu Arg
    290                 295                 300 gta cgc caa ttt tgg tcc ata tat caa aag cgc acc aag ctg cac ctc       2203
Val Arg Gln Phe Trp Ser Ile Tyr Gln Lys Arg Thr Lys Leu His Leu
```

```
                305                  310                  315                  320
gat ttg att ctc ggc aac aaa cgc ggt cag gac cgc cag atg gcg tac           2251
Asp Leu Ile Leu Gly Asn Lys Arg Gly Gln Asp Arg Gln Met Ala Tyr
                        325                  330                  335 atg tcc agc aag ccc gaa ttc gtt gcc cac tac aac agc gcg gcc aag           2299
Met Ser Ser Lys Pro Glu Phe Val Ala His Tyr Asn Ser Ala Ala Lys
                        340                  345                  350 gag tgc gag ctg gac ccc att gcg gtg gtc cca cta ccc tac att cac           2347
Glu Cys Glu Leu Asp Pro Ile Ala Val Val Pro Leu Pro Tyr Ile His
                        355                  360                  365 ggt gaa cat ttt cac aac tcg tgg gac gtg atg cac ctc atg gcc gag           2395
Gly Glu His Phe His Asn Ser Trp Asp Val Met His Leu Met Ala Glu
                        370                  375                  380 gtg ggc gac caa att gtt gcc caa cgt aat gac atg ttg gcg ctc gca           2443
Val Gly Asp Gln Ile Val Ala Gln Arg Asn Asp Met Leu Ala Leu Ala
385                  390                  395                  400 cca ctg caa gtt gtg cac aac gtg gtg gca aac atg tac att tcg ttg           2491
Pro Leu Gln Val Val His Asn Val Val Ala Asn Met Tyr Ile Ser Leu
                        405                  410                  415 ggc tgc caa acc tgc gtt tca cac tac cta ttg ttg cgg ggc gtc ata           2539
Gly Cys Gln Thr Cys Val Ser His Tyr Leu Leu Leu Arg Gly Val Ile
                        420                  425                  430 ctg gta aag ttc gaa caa ctc ttc cgc cta ctg gtg ctc gag gag cta           2587
Leu Val Lys Phe Glu Gln Leu Phe Arg Leu Leu Val Leu Glu Glu Leu
                        435                  440                  445 aag cgc cgt gaa ggt tcc att tcg ggc cgc acc atc gag ttg ctg cga           2635
Lys Arg Arg Glu Gly Ser Ile Ser Gly Arg Thr Ile Glu Leu Leu Arg
        450                  455                  460 atc cca acc gtt gag ctg gac gag tac atc gcc aac ccc ggc gta ctg           2683
Ile Pro Thr Val Glu Leu Asp Glu Tyr Ile Ala Asn Pro Gly Val Leu
465                  470                  475                  480 aac aac gcc ttt gtt aaa aat tta cta gcg tac gaa atg gtc cag ctg           2731
Asn Asn Ala Phe Val Lys Asn Leu Leu Ala Tyr Glu Met Val Gln Leu
                        485                  490                  495 cac aac tat atc aac tcg tac cga att gta caa cag gcc agt gga cat           2779
His Asn Tyr Ile Asn Ser Tyr Arg Ile Val Gln Gln Ala Ser Gly His
                        500                  505                  510 ttg cgc agc aac aga ccc atc gaa cag gcc gac atc aag gtc tac ctc           2827
Leu Arg Ser Asn Arg Pro Ile Glu Gln Ala Asp Ile Lys Val Tyr Leu
        515                  520                  525 aaa gcg ttc caa gaa ggc cca acc atg acc tgg gaa ctg tac gac aag           2875
Lys Ala Phe Gln Glu Gly Pro Thr Met Thr Trp Glu Leu Tyr Asp Lys
        530                  535                  540 cag agg cgc ggt gaa att gca ccc att tca ccc gta cga aag cga ccc           2923
Gln Arg Arg Gly Glu Ile Ala Pro Ile Ser Pro Val Arg Lys Arg Pro
545                  550                  555                  560 gca ccg gat gat agc act ggt cca ccg cta aag tat tcc agg gcc caa           2971
Ala Pro Asp Asp Ser Thr Gly Pro Pro Leu Lys Tyr Ser Arg Ala Gln
                        565                  570                  575 taaattacat tggactttt ttttatatata taattactat gggtacgtgt gatacaacga         3031
taataaatat tggttaattt caaccagaaa catttattta tttatctatt tatttatttt         3091
atatatttat atttcaaaaa tatatcacgc tacactttcg ctattgtcga taccgcgt          3149 atg ttg tca ata atg ttt tcg cgc ttc ttc tca cgg aac att gac gca           3197
Met Leu Ser Ile Met Phe Ser Arg Phe Phe Ser Arg Asn Ile Asp Ala
                        580                  585                  590 ccc tca cgg cgc tca acg atg ttt atg gcg gag cgg gtg tac gga ttc           3245
Pro Ser Arg Arg Ser Thr Met Phe Met Ala Glu Arg Val Tyr Gly Phe
                        595                  600                  605
```

```
ttt atc gat cgt ctg gac att cgt tcg tac ttc tcg agg gca tcc ttt     3293
Phe Ile Asp Arg Leu Asp Ile Arg Ser Tyr Phe Ser Arg Ala Ser Phe
    610                 615                 620 tgc gct acc aaa tcg tta tac tcg gac agg gcc aaa atg tcg tac tgt     3341
Cys Ala Thr Lys Ser Leu Tyr Ser Asp Arg Ala Lys Met Ser Tyr Cys
625                 630                 635                 640 ggt tcc aat atg acg gtg tgatcgatca acttgtcgcg caactgggg             3389
Gly Ser Asn Met Thr Val
                645 tccatcgaaa gaaagttttc agacttggac agcaaacgac cctggttcag tttgcgcaat   3449 cttcgcgttt gactcttgag ctccatttcc tcccgcttca gctgctcc atg cgc tca    3506
                                                    Met Arg Ser cgt ttc gcc gca tca cgc tca ctc acc gca gag tac agc aac ttg tta     3554
Arg Phe Ala Ala Ser Arg Ser Leu Thr Ala Glu Tyr Ser Asn Leu Leu
650                 655                 660                 665 tcc tcc agc agc ctg gac aac ctt tcg tca atc acc tgc ttc gat         3602
Ser Ser Ser Ser Leu Asp Asn Leu Ser Ser Ile Thr Cys Phe Asp
                670                 675                 680 tta aac cca aac agc ttg cgc tct tca tcc gtg tac ttg ccc cca caa     3650
Leu Asn Pro Asn Ser Leu Arg Ser Ser Ser Val Tyr Leu Pro Pro Gln
                685                 690                 695 tcc gct tta gct tca ctc gtg gca ccg tca acc tta tcc gtt tca ccg     3698
Ser Ala Leu Ala Ser Leu Val Ala Pro Ser Thr Leu Ser Val Ser Pro
    700                 705                 710 cac agg aaa cgc gtc agc tcc ttc aat aac ctg att ttg tac cgg tca     3746
His Arg Lys Arg Val Ser Ser Phe Asn Asn Leu Ile Leu Tyr Arg Ser
715                 720                 725 tat tcg acc ggg acg tgc ttt cca tcg acg gga acc tca gaa tat acc     3794
Tyr Ser Thr Gly Thr Cys Phe Pro Ser Thr Gly Thr Ser Glu Tyr Thr
730                 735                 740                 745 tcg tgg atc aag gtg aac gtt acg tcg cag ccc atc ttt aat cgg tgt     3842
Ser Trp Ile Lys Val Asn Val Thr Ser Gln Pro Ile Phe Asn Arg Cys
                750                 755                 760 caa ctt aaa ctc tagacaccct gtacgtcttt cgtacggcgt tgagtacggt         3894
Gln Leu Lys Leu
            765 atccagaatc acattcagct cgcggttgcg ctgctcgagg tggttcccga aagacagata   3954 cgcctgctct tcaattagta tacggcggct gagcagcggt tcaccgtact gtgcttccgc   4014 aaatgtgaac aatttatcca cctttcaga cagcgcatgg ttcacggcgt acagggccaa    4074 agcttcgcag tctatcttcg aggtgcggta cttggaggcg aacgttagac cgattattac   4134 cagtgggata caatggatca accgttgtga cattagaaac aaacgcttct cgaccgcagt   4194 catcgtctca ttgtccaccc tatccaccag tcgtgcaaac agcttcataa ttttcgcata   4254 gaagaaggtg ggcttgtgct tgtgcaggtt gttgggcaca atgttttcgt tgaaatcttt   4314 gaaaattttt gccatattca gctgctccaa gcacccctcg gccagctgga gcgtgttggc   4374 ctggtccaca ccgcggctca ggttgttgag ggcaattgaa tacggcacgg tttcccgata   4434 ctgggtcagg tccacatagt cgtgcacctt cgagtcgtgc ggtacacctt cggcgattat   4494 gtaggttttc gtgcggaacg agagcagctc ctccaacctt tggtcataat tgtccagtat   4554 gtgtagcaca acctggttat agtcgacaat acgaccctcg tacatgaacg atctgctcac   4614 gcgatcggca accgtaattg cgagcgcact tttcgactca ccaaccgttg agccccactt   4674 tggtacgtag ttttcagcgg ccttttcag ctcctgtgcc atgaaatcgc gcaactggtc    4734 cgtaataatg tcgtttaaat tctccggctt ttccacagtc tcaacatcct caacctccat   4794
```

```
atcgggttga gccgaggttg gcggtgtggt tccgctaccg gatggtgccg caccaaagtt    4854
gtttagaatc acatttcgct gctcctcgga tagggcgtta aacagctcca tcaccttagc    4914
ggcatcagta ctttgcacct cggacgccat gtcgaagttt agcgaatttc tgcttacttc    4974
gtcctcctca ccagcagcat agtcgccctc ggggccacca ccgacaactt cgaaaactga    5034
accagaaacg ttgccaattc cgccaaccga gtccggtccg tcttcctcga gctcgggaaa    5094 taaaagtcg  tccaccttgg ccaccgactc gggctcggga tcgttatcct gcccaccttc    5154
atcctcacct tctccgtccg agtgccactc gctcacgaga cgcttcgata tcaccgacat    5214
tgccacggga cccgtgggtg aacctggggc cacattttga tcaccactcg tagcaccacc    5274
ggtccaaaca ttatcatcca aatttagctg gggctcggct acaggtggtg ctacatcgtc    5334
attttcatct tggtttaaaa tttcatcaac ttgtcgctgc cgagctgggc gcaccggtct    5394
accagctttg atggttgtag tggcgcgtga ttttgggcgg cctttaacgc caccggcttc    5454
acgtagaccc tcggctctcg agcttcgatt catttagtcg tataaaacaa cctggccgtg    5514
tacgggcgcc cagaggttca caatacgtgt cttattaccc attcgcatca cgaaagagta    5574
gtcattgttt gcgttaggtg cggttcgcag ttcgtattca gagcgggaca ttgtaacaaa    5634
cggcgactgc tcaaaccgct tgtaaggttt accggccgta acgaggcgaa ttgtttccat    5694
atggatgcgt ttaccgagac ttttctgcgg caaagggtta taatcaatcc ggagacgaag    5754
gagattgaag ttcgcgcagt ttgcagtg atg gag ttg gat aca ctt act tca       5806
                                Met Glu Leu Asp Thr Leu Thr Ser
                                                        770 cgg tcg gtc aaa tgc ctc acc ctg tta ccg aac gtg acg tta gcg gcg       5854
Arg Ser Val Lys Cys Leu Thr Leu Leu Pro Asn Val Thr Leu Ala Ala
    775                 780                 785 gtt cat cga aca aaa tcc caa gcc ggt cgc gag ggt cgg cgg aac ccc       5902
Val His Arg Thr Lys Ser Gln Ala Gly Arg Glu Gly Arg Arg Asn Pro
790                 795                 800                 805 tgt ccg gtg cat gtg gat aca aaa atc aag tgt aaa att ttc atc aaa       5950
Cys Pro Val His Val Asp Thr Lys Ile Lys Cys Lys Ile Phe Ile Lys
                810                 815                 820 aac tac agc aaa act cac gtc acc gaa ctc tcg atg ggg tac ctg aac       5998
Asn Tyr Ser Lys Thr His Val Thr Glu Leu Ser Met Gly Tyr Leu Asn
            825                 830                 835 tcg aac atg gtg cac cat tat gtg gcc ctg atg ggc atg tgc agg gaa       6046
Ser Asn Met Val His His Tyr Val Ala Leu Met Gly Met Cys Arg Glu
        840                 845                 850 aac cga ggt aca gtt gac gcc tgt tta tac gcg tcc aac aag atc aat       6094
Asn Arg Gly Thr Val Asp Ala Cys Leu Tyr Ala Ser Asn Lys Ile Asn
    855                 860                 865 tgt gtg ctg cgg ttc gac ctg gac ctg ttc cgc tcc agc ttt ggg ggt       6142
Cys Val Leu Arg Phe Asp Leu Asp Leu Phe Arg Ser Ser Phe Gly Gly
870                 875                 880                 885 aga gtt ata aac att ggc cac gtt tac gat gaa ctt gac cgc ata tac       6190
Arg Val Ile Asn Ile Gly His Val Tyr Asp Glu Leu Asp Arg Ile Tyr
                890                 895                 900 aga acg cta gat aga caa att tta att tcg ccc aac tcg gcg cta gag       6238
Arg Thr Leu Asp Arg Gln Ile Leu Ile Ser Pro Asn Ser Ala Leu Glu
            905                 910                 915 ttg tac gtt agc gcg gaa tct gcg gtg cta gca cca cag gac ctc ctc       6286
Leu Tyr Val Ser Ala Glu Ser Ala Val Leu Ala Pro Gln Asp Leu Leu
        920                 925                 930 att ata cac ccc ttc gtt gaa gat ctc gag tac cca ctg gtc tcg cgc       6334
Ile Ile His Pro Phe Val Glu Asp Leu Glu Tyr Pro Leu Val Ser Arg
```

-continued

| | | | | | | | | | | | | | | | |
|---|---|---|---|---|---|---|---|---|---|---|---|---|---|---|---|
| ggc | tac | cca | ctg | gac | gac | gag | gtg | ata | gta | aat | tac | cgc | tac | tac | agg | 6382
| Gly | Tyr | Pro | Leu | Asp | Asp | Glu | Val | Ile | Val | Asn | Tyr | Arg | Tyr | Tyr | Arg |
| 950 | | | | | 955 | | | | 960 | | | | | 965 | |

```
ggc tac cca ctg gac gac gag gtg ata gta aat tac cgc tac tac agg      6382
Gly Tyr Pro Leu Asp Asp Glu Val Ile Val Asn Tyr Arg Tyr Tyr Arg
950             955             960             965 gcc gtg ttg att gcc atc acg ctc gta acc tgc ctg att ggt aac agc      6430
Ala Val Leu Ile Ala Ile Thr Leu Val Thr Cys Leu Ile Gly Asn Ser
            970             975             980 gat ttg ctc agc aca acc atg gcc gca tcg aaa atc atc cac agc gtt      6478
Asp Leu Leu Ser Thr Thr Met Ala Ala Ser Lys Ile Ile His Ser Val
        985             990             995 ggc att tgc ccg tac tac ccg gac cat atg gcg gtc tgt aaa ctg acg      6526
Gly Ile Cys Pro Tyr Tyr Pro Asp His Met Ala Val Cys Lys Leu Thr
    1000            1005            1010 aac cgc gtt acg ggg acg gtc atg gat agg cac atc ttc tgc atc cca      6574
Asn Arg Val Thr Gly Thr Val Met Asp Arg His Ile Phe Cys Ile Pro
1015            1020            1025 atc gag cag ttc aaa cgg tcc ttt cta tac cgc aaa acc gtt atc aag      6622
Ile Glu Gln Phe Lys Arg Ser Phe Leu Tyr Arg Lys Thr Val Ile Lys
1030            1035            1040            1045 cgg gac ggt gag gat aag gcg gtg gac att aag tcg tta aaa tct atg      6670
Arg Asp Gly Glu Asp Lys Ala Val Asp Ile Lys Ser Leu Lys Ser Met
            1050            1055            1060 acc cag aat ata cgc gga aag cgc aac ccc agt ccc gag ttg tgg aac      6718
Thr Gln Asn Ile Arg Gly Lys Arg Asn Pro Ser Pro Glu Leu Trp Asn
            1065            1070            1075 gtt ttt acg aag aac atc gag gaa ctt ttt gtt cga tac gac aat gca      6766
Val Phe Thr Lys Asn Ile Glu Glu Leu Phe Val Arg Tyr Asp Asn Ala
        1080            1085            1090 gtt tgagattgag atccgcaacg gtaaccagtt gtactcatcg cgcaaccaac            6819
Val taatttacc cgggctcacc gacgtgtact atcactatgt aagcacgagt ggacccttg       6879 gtgaggacca cccgcacgac atcaagctgc acacgaccgt acacaattac aacccgaatt     6939
tggcggtctt tgtgattcag cgcgagggca cggagctcaa taagatcgct tttcgtctgc     6999
aagtgtacgt ccttaaagcg accacattcg gcgccggtga acatattgcc gaggtgaact     7059
ttatcaaacc taaaggctgc ggagatggaa aacgttcggt cgacaccacc gtcgttgaac     7119
caaacgaacc ggttaacaag cgcgcccgta cgccgagtcc agccccagtc gatcaagatt     7179
tgcccgaacc aaaaccagag cccgagtctg cag                                  7212
```

<210> SEQ ID NO 131
<211> LENGTH: 115
<212> TYPE: PRT
<213> ORGANISM: mosquito baculovirus

<400> SEQUENCE

-continued

```
                85                  90                  95

Asp Asp Glu Phe Ala Glu Pro Glu Val Phe Asp Pro Glu Phe Arg Lys
            100                 105                 110

Tyr His Asn
        115

<210> SEQ ID NO 132
<211> LENGTH: 91
<212> TYPE: PRT
<213> ORGANISM: mosquito baculovirus

<400> SEQUENCE: 132

Met Cys Val Thr Glu His Asp Leu Val Val Arg Ala Gln Arg Asn Leu
 1               5                  10                  15

Ala His Ala Asn Gln Phe Arg Phe Asp Leu Lys Arg Ser Leu Cys Gly
            20                  25                  30

His Leu Asp Cys Ile Ser Ser Arg Gly Phe Glu His His Gln Val Thr
        35                  40                  45

Val Gly Gln Val Asp Glu Arg Phe Val Gly Glu Leu Glu Gly Arg Thr
    50                  55                  60

Glu Arg Leu Ile Leu Phe Asp Leu Leu Ile Ala Gly Ile Phe Gly Ile
65                  70                  75                  80

Gly Ser Gly Leu Gly Phe Arg Trp Leu Leu Arg
                85                  90

<210> SEQ ID NO 133
<211> LENGTH: 370
<212> TYPE: PRT
<213> ORGANISM: mosquito baculovirus

<400> SEQUENCE: 133

Met Phe Ala Ser Thr Pro Ser His Ser Ser Val Phe Thr Ser Lys Ser
 1               5                  10                  15

Phe Arg Tyr Ser Gly Leu Val Ser Ala Ile Phe Thr Met Asn Asp Ile
            20                  25                  30

Ala Lys Glu Asn Leu Gln Thr Arg Gln Arg Glu Ser Leu Asn Arg His
        35                  40                  45

Ile Phe Tyr Leu Val Ile Thr Ser Leu Leu Ser Pro Thr Glu Thr Glu
    50                  55                  60

Ser Asn Leu Ala Lys Val Glu Phe Ala Thr Ile Val Tyr Leu Met Asn
65                  70                  75                  80

Leu Ser Met Leu Leu Ala Arg Pro Pro Ala Pro Ile Val Val Ser Glu
                85                  90                  95

Glu Arg Val Arg Gln Phe Trp Ser Ile Tyr Gln Lys Arg Thr Lys Leu
            100                 105                 110

His Leu Asp Leu Ile Leu Gly Asn Lys Arg Gly Gln Asp Arg Gln Met
        115                 120                 125

Ala Tyr Met Ser Ser Lys Pro Glu Phe Val Ala His Tyr Asn Ser Ala
    130                 135                 140

Ala Lys Glu Cys Glu Leu Asp Pro Ile Ala Val Val Pro Leu Pro Tyr
145                 150                 155                 160

Ile His Gly Glu His Phe His Asn Ser Trp Asp Val Met His Leu Met
                165                 170                 175

Ala Glu Val Gly Asp Gln Ile Val Ala Gln Arg Asn Asp Met Leu Ala
            180                 185                 190

Leu Ala Pro Leu Gln Val Val His Asn Val Val Ala Asn Met Tyr Ile
```

-continued

```
        195                 200                 205

Ser Leu Gly Cys Gln Thr Cys Val Ser His Tyr Leu Leu Leu Arg Gly
    210                 215                 220

Val Ile Leu Val Lys Phe Glu Gln Leu Phe Arg Leu Leu Val Leu Glu
225                 230                 235                 240

Glu Leu Lys Arg Arg Glu Gly Ser Ile Ser Gly Arg Thr Ile Glu Leu
                245                 250                 255

Leu Arg Ile Pro Thr Val Glu Leu Asp Glu Tyr Ile Ala Asn Pro Gly
            260                 265                 270

Val Leu Asn Asn Ala Phe Val Lys Asn Leu Leu Ala Tyr Glu Met Val
        275                 280                 285

Gln Leu His Asn Tyr Ile Asn Ser Tyr Arg Ile Val Gln Gln Ala Ser
    290                 295                 300

Gly His Leu Arg Ser Asn Arg Pro Ile Glu Gln Ala Asp Ile Lys Val
305                 310                 315                 320

Tyr Leu Lys Ala Phe Gln Glu Gly Pro Thr Met Thr Trp Glu Leu Tyr
                325                 330                 335

Asp Lys Gln Arg Arg Gly Glu Ile Ala Pro Ile Ser Pro Val Arg Lys
            340                 345                 350

Arg Pro Ala Pro Asp Asp Ser Thr Gly Pro Pro Leu Lys Tyr Ser Arg
        355                 360                 365

Ala Gln
    370

<210> SEQ ID NO 134
<211> LENGTH: 70
<212> TYPE: PRT
<213> ORGANISM: mosquito baculovirus

<400> SEQUENCE: 134

Met Leu Ser Ile Met Phe Ser Arg Phe Phe Ser Arg Asn Ile Asp Ala
 1               5                  10                  15

Pro Ser Arg Arg Ser Thr Met Phe Met Ala Glu Arg Val Tyr Gly Phe
            20                  25                  30

Phe Ile Asp Arg Leu Asp Ile Arg Ser Tyr Phe Ser Arg Ala Ser Phe
        35                  40                  45

Cys Ala Thr Lys Ser Leu Tyr Ser Asp Arg Ala Lys Met Ser Tyr Cys
    50                  55                  60

Gly Ser Asn Met Thr Val
65                  70

<210> SEQ ID NO 135
<211> LENGTH: 119
<212> TYPE: PRT
<213> ORGANISM: mosquito baculovirus

<400> SEQUENCE: 135

Met Arg Ser Arg Phe Ala Ala Ser Arg Ser Leu Thr Ala Glu Tyr Ser
 1               5                  10                  15

Asn Leu Leu Ser Ser Ser Ser Leu Asp Asn Leu Ser Ser Ser Ile Thr
            20                  25                  30

Cys Phe Asp Leu Asn Pro Asn Ser Leu Arg Ser Ser Ser Val Tyr Leu
        35                  40                  45

Pro Pro Gln Ser Ala Leu Ala Ser Leu Val Ala Pro Ser Thr Leu Ser
    50                  55                  60

Val Ser Pro His Arg Lys Arg Val Ser Ser Phe Asn Asn Leu Ile Leu
```

```
65                  70                  75                  80
Tyr Arg Ser Tyr Ser Thr Gly Thr Cys Phe Pro Ser Thr Gly Thr Ser
                85                  90                  95
Glu Tyr Thr Ser Trp Ile Lys Val Asn Val Thr Ser Gln Pro Ile Phe
            100                 105                 110
Asn Arg Cys Gln Leu Lys Leu
        115

<210> SEQ ID NO 136
<211> LENGTH: 329
<212> TYPE: PRT
<213> ORGANISM: mosquito baculovirus

<400> SEQUENCE: 136

Met Glu Leu Asp Thr Leu Thr Ser Arg Ser Val Lys Cys Leu Thr Leu
 1               5                  10                  15
Leu Pro Asn Val Thr Leu Ala Ala Val His Arg Thr Lys Ser Gln Ala
             20                  25                  30
Gly Arg Glu Gly Arg Arg Asn Pro Cys Pro Val His Val Asp Thr Lys
         35                  40                  45
Ile Lys Cys Lys Ile Phe Ile Lys Asn Tyr Ser Lys Thr His Val Thr
 50                  55                  60
Glu Leu Ser Met Gly Tyr Leu Asn Ser Asn Met Val His His Tyr Val
65                   70                  75                  80
Ala Leu Met Gly Met Cys Arg Glu Asn Arg Gly Thr Val Asp Ala Cys
                85                  90                  95
Leu Tyr Ala Ser Asn Lys Ile Asn Cys Val Leu Arg Phe Asp Leu Asp
            100                 105                 110
Leu Phe Arg Ser Ser Phe Gly Gly Arg Val Ile Asn Ile Gly His Val
        115                 120                 125
Tyr Asp Glu Leu Asp Arg Ile Tyr Arg Thr Leu Asp Arg Gln Ile Leu
    130                 135                 140
Ile Ser Pro Asn Ser Ala Leu Glu Leu Tyr Val Ser Ala Glu Ser Ala
145                 150                 155                 160
Val Leu Ala Pro Gln Asp Leu Leu Ile Ile His Pro Phe Val Glu Asp
                165                 170                 175
Leu Glu Tyr Pro Leu Val Ser Arg Gly Tyr Pro Leu Asp Asp Glu Val
            180                 185                 190
Ile Val Asn Tyr Arg Tyr Arg Ala Val Leu Ile Ala Ile Thr Leu
        195                 200                 205
Val Thr Cys Leu Ile Gly Asn Ser Asp Leu Leu Ser Thr Thr Met Ala
    210                 215                 220
Ala Ser Lys Ile Ile His Ser Val Gly Ile Cys Pro Tyr Tyr Pro Asp
225                 230                 235                 240
His Met Ala Val Cys Lys Leu Thr Asn Arg Val Thr Gly Thr Val Met
                245                 250                 255
Asp Arg His Ile Phe Cys Ile Pro Ile Glu Gln Phe Lys Arg Ser Phe
            260                 265                 270
Leu Tyr Arg Lys Thr Val Ile Lys Arg Asp Gly Glu Asp Lys Ala Val
        275                 280                 285
Asp Ile Lys Ser Leu Lys Ser Met Thr Gln Asn Ile Arg Gly Lys Arg
    290                 295                 300
Asn Pro Ser Pro Glu Leu Trp Asn Val Phe Thr Lys Asn Ile Glu Glu
305                 310                 315                 320
```

```
Leu Phe Val Arg Tyr Asp Asn Ala Val
            325

<210> SEQ ID NO 137
<211> LENGTH: 7212
<212> TYPE: DNA
<213> ORGANISM: mosquito baculovirus
<220> FEATURE:
<221> NAME/KEY: CDS
<222> LOCATION: (575)...(946)
<221> NAME/KEY: CDS
<222> LOCATION: (5695)...(5934)
<221> NAME/KEY: CDS
<222> LOCATION: (237)...(470)
<221> NAME/KEY: CDS
<222> LOCATION: (1)...(174)
<221> NAME/KEY: CDS
<222> LOCATION: (4295)...(4450)
<221> NAME/KEY: CDS
<222> LOCATION: (1149)...(1301)
<221> NAME/KEY: CDS
<222> LOCATION: (6747)...(7209)

<400> SEQUENCE: 137 ctg cag cag tat ttt tac agt cat ttg gtt aac caa acc gaa gcc cgg      48
Leu Gln Gln Tyr Phe Tyr Ser His Leu Val Asn Gln Thr Glu Ala Arg
  1               5                  10                  15 ccc gac gac tat gaa gct gaa cat ctc agc gcg gcc agg gaa aag gtt      96
Pro Asp Asp Tyr Glu Ala Glu His Leu Ser Ala Ala Arg Glu Lys Val
             20                  25                  30 aac cta cag aat tgt ggt gca cga cag caa aat gcc ctg cct ctc gga     144
Asn Leu Gln Asn Cys Gly Ala Arg Gln Gln Asn Ala Leu Pro Leu Gly
         35                  40                  45 cac atc ggc cct cgc aat agc gct gag cct tagcgtggca atgttcaccg       194
His Ile Gly Pro Arg Asn Ser Ala Glu Pro
     50                  55 ccgtattcta cacacttttg cgcctacatc gtgtggagaa aa atg tgc aca ata      248
                                             Met Cys Thr Ile
                                                          60 tac aga tct gct ttg aag aag acg acg acg acg atg acg gtg gac cga    296
Tyr Arg Ser Ala Leu Lys Lys Thr Thr Thr Thr Met Thr Val Asp Arg
             65                  70                  75 cgc ggg ccg agg tcg tgc aac cca cct tca gag aaa acg att gca cga    344
Arg Gly Pro Arg Ser Cys Asn Pro Pro Ser Glu Lys Thr Ile Ala Arg
         80                  85                  90 ccg acg acg agt ttg cag agc cag agg tgt tcg atc ccg agt cag aa      392
Pro Thr Thr Ser Leu Gln Ser Gln Arg Cys Ser Ile Pro Ser Ser Glu
 95                 100                 105                 110 agt atc aca att aaa cgg tca acg gtt caa aat aaa tac act tta ata    440
Ser Ile Thr Ile Lys Arg Ser Thr Val Gln Asn Lys Tyr Thr Leu Ile
                115                 120                 125 aat ttt ata tat atc gtt tat ttt act ggt taagattttc tatcacaaat      490
Asn Phe Ile Tyr Ile Val Tyr Phe Thr Gly
            130                 135 cctacatcta gctatgccac ttggcactcg cttcatcggc gtatagtagt attcacctcc   550
agagttgtac ttttcagctt cgcg atg ctt ggt atc gtg ggc gca ccc gta      601
                          Met Leu Gly Ile Val Gly Ala Pro Val
                                  140                 145 ata ctc caa atc ctc cgc agc gta cag gtc aat att ctt ttc cga gtt    649
Ile Leu Gln Ile Leu Arg Ser Val Gln Val Asn Ile Leu Phe Arg Val
            150                 155                 160 caa cat gaa tct gac cag aaa cgc ttc aac gtc gca aac ttt aca gcc    697
Gln His Glu Ser Asp Gln Lys Arg Phe Asn Val Ala Asn Phe Thr Ala
            165                 170                 175
```

-continued

```
cga gtc cac cgt gaa ctc gta cac gta cgt tcc agc gtc act gta cag      745
Arg Val His Arg Glu Leu Val His Val Arg Ser Ser Val Thr Val Gln
            180                 185                 190 ctc ggt ctc caa ccg gtg ata ctc gtc atc gca gca aat tgt gta ctc      793
Leu Gly Leu Gln Pro Val Ile Leu Val Ile Ala Ala Asn Cys Val Leu
        195                 200                 205 gag cga gtc cgg gct aag ctc gaa ata ctt gag gga tcg tgg gta gaa      841
Glu Arg Val Arg Ala Lys Leu Glu Ile Leu Glu Gly Ser Trp Val Glu
210                 215                 220                 225 ctt cac tcg gaa agg cat tat tgg gcg aat gtg tgg gta aaa atg tgg      889
Leu His Ser Glu Arg His Tyr Trp Ala Asn Val Trp Val Lys Met Trp
                230                 235                 240 ggt gct tta tat ata aac ttt ctg gcc att agc gcg gca agt gtt gcg      937
Gly Ala Leu Tyr Ile Asn Phe Leu Ala Ile Ser Ala Ala Ser Val Ala
            245                 250                 255 atg tcg gcc tgagccttgc tcagcacgat gaccacgtcg tggtcgcttt              986
Met Ser Ala
        260 ccgggtcgat acagtccaga catgtggaca cgttgggcga caagtcggga tagaaaatta   1046 tcgtcaactt gtgggcatta tcgcgcacga ttttgcaccc cgattcgcac gctaccggtc   1106 tcgggtgctc cgaacgtgta gcgtagaaga acgagggtcc ag atg tta gcg gca      1160
                                             Met Leu Ala Ala ccg ccg tta cgt gca cat gtg cgt tac gga aca cga cct ggt cgt tcg    1208
Pro Pro Leu Arg Ala His Val Arg Tyr Gly Thr Arg Pro Gly Arg Ser
265                 270                 275                 280 agc cca acg aaa ctt ggc cca cgc aaa cca gtt ccg att cga ctt gaa    1256
Ser Pro Thr Lys Leu Gly Pro Arg Lys Pro Val Pro Ile Arg Leu Glu
                285                 290                 295 gcg cag ctt gtg cgg cca ttt gga ttg tat ttc gag ccg ggg ttt        1301
Ala Gln Leu Val Arg Pro Phe Gly Leu Tyr Phe Glu Pro Gly Phe
            300                 305                 310 tgagcaccac caggtcactg ttggtcaagt tgatgagcgt tttgtcggtg agctcgaggg   1361
ccgcaccgaa cgtttgattc tcttcgacct cctcatcgcc gggatcttcg gtattgggtc   1421
cgggctcggg tttaggtggc tgttgaggtg aactcgagtc gctactgcta gttttagcgg   1481
cagcgaaaag tagatagtag atcaaaaata ctaccactat caatatgatg acgatgatga   1541
ctgatccgag caacattttg acttattctt ccaataccgt tatcccaacc atacgcagcg   1601
tttcggctac gaatctctcc tccgcactac agtttgccgc gagtgcaaac ttaatatcgt   1661
gattcgtgca ggcgcttaaa agtggccata gcaccacttc ggctatctcc ttaacttggt   1721
cgtggtttgc gtaaatgggc agcgttgcga tgtagctcaa cagcgcgtac accccgtggt   1781
tctcattaaa cggttcatcc caccgaacgt tggaaatttt taacgtgcgc gccatagcca   1841
gcgcaccctg cgtagctgca atgtttgcgt ccacaccttc acattctagc gtgtttacca   1901
gcaaatcttt caggtattcc gggctcgtaa gtgcgatttt cacgatgaac gacattgcga   1961
aggaaaactt acagactcgc caacgcgagt cgctcaatag gcacatttttt tacctagtga   2021 tcaccagcct gttgagcccc accgaaaccg aatccaacct cgccaaagtt gagtttgcaa   2081
ccattgtcta cctcatgaat ctatcgatgc tgctggcacg acctcccgca ccgatcgtgg   2141
tcagcgaaga acgcgtacgc caattttggt ccatatatca aaagcgcacc aagctgcacc   2201
tcgatttgat tctcggcaac aaacgcggtc aggaccgcca gatggcgtac atgtccagca   2261
agcccgaatt cgttgcccac tacaacgcg cggccaagga gtgcgagctg acccccattg   2321
cggtggtccc actaccctac attcacggtg aacattttca caactcgtgg gacgtgatgc   2381
```

-continued

```
acctcatggc cgaggtgggc gaccaaattg ttgcccaacg taatgacatg ttggcgctcg    2441
caccactgca agttgtgcac aacgtggtgg caaacatgta catttcgttg ggctgccaaa    2501
cctgcgtttc acactaccta ttgttgcggg gcgtcatact ggtaaagttc gaacaactct    2561
tccgcctact ggtgctcgag gagctaaagc gccgtgaagg ttccatttcg ggccgcacca    2621
tcgagttgct gcgaatccca accgttgagc tggacgagta catcgccaac cccggcgtac    2681
tgaacaacgc ctttgttaaa aatttactag cgtacgaaat ggtccagctg cacaactata    2741
tcaactcgta ccgaattgta caacaggcca gtggacattt gcgcagcaac agacccatcg    2801
aacaggccga catcaaggtc tacctcaaag cgttccaaga aggcccaacc atgacctggg    2861
aactgtacga caagcagagg cgcggtgaaa ttgcacccat ttcacccgta cgaaagcgac    2921
ccgcaccgga tgatagcact ggtccaccgc taaagtattc cagggcccaa taaattacat    2981
tggacttttt tttatatata taattactat gggtacgtgt gatacaacga taataaatat    3041
tggttaattt caaccagaaa catttattta tttatctatt tatttatttt atatatttat    3101
atttcaaaaa tatatcacgc tacactttcg ctattgtcga taccgcgtat gttgtcaata    3161
atgttttcgc gcttcttctc acggaacatt gacgcaccct cacggcgctc aacgatgttt    3221
atggcggagc gggtgtacgg attctttatc gatcgtctgg acattcgttc gtacttctcg    3281
agggcatcct tttgcgctac caaatcgtta tactcggaca gggccaaaat gtcgtactgt    3341
ggttccaata tgacggtgtg atcgatcaac ttgtcgcgca acttgggtc catcgaaaga     3401
aagttttcag acttggacag caaacgaccc tggttcagtt tgcgcaatct tcgcgtttga    3461
ctcttgagct ccatttcctc ccgcttcagc tgctccatgc gctcacgttt cgccgcatca    3521
cgctcactca ccgcagagta cagcaacttg ttatcctcca gcagcctgga caacctttca    3581
tcgtcaatca cctgcttcga tttaaaccca aacagcttgc gctcttcatc cgtgtacttg    3641
cccccacaat ccgctttagc ttcactcgtg gcaccgtcaa ccttatccgt ttcaccgcac    3701
aggaaacgcg tcagctcctt caataacctg attttgtacc ggtcatattc gaccgggacg    3761
tgctttccat cgacgggaac ctcagaatat acctcgtgga tcaaggtgaa cgttacgtcg    3821
cagcccatct ttaatcggtg tcaacttaaa ctctagacac cctgtacgtc tttcgtacgg    3881
cgttgagtac ggtatccaga atcacattca gctcgcggtt gcgctgctcg aggtggttcc    3941
cgaaagacag atacgcctgc tcttcaatta gtataccggcg gctgagcagc ggttcaccgt    4001
actgtgcttc cgcaaatgtg aacaatttat ccaccttttc agacagcgca tggttcacgg    4061
cgtacagggc caaagcttcg cagtctatct tcgaggtgcg gtacttggag gcgaacgtta    4121
gaccgattat taccagtggg atacaatgga tcaaccgttg tgcattaga aacaaacgct     4181
tctcgaccgc agtcatcgtc tcattgtcca ccctatccac cagtcgtgca aacagcttca    4241
taattttcgc atagaagaag gtgggcttgt gcttgtgcag gttgttgggc aca atg       4297
                                                               Met
```

| | | | | | | | | | | | | | | | | |
|---|---|---|---|---|---|---|---|---|---|---|---|---|---|---|---|---|
| ttt | tcg | ttg | aaa | tct | ttg | aaa | att | ttt | gcc | ata | ttc | agc | tgc | tcc | aag |   4345 |
| Phe | Ser | Leu | Lys | Ser | Leu | Lys | Ile | Phe | Ala | Ile | Phe | Ser | Cys | Ser | Lys | |
|     | 315 |     |     |     |     | 320 |     |     |     |     | 325 |     |     |     |     | |
| cac | ccc | tcg | gcc | agc | tgg | agc | gtg | ttg | gcc | tgg | tcc | aca | ccg | cgg | ctc |   4393 |
| His | Pro | Ser | Ala | Ser | Trp | Ser | Val | Leu | Ala | Trp | Ser | Thr | Pro | Arg | Leu | |
|     | 330 |     |     |     |     | 335 |     |     |     |     | 340 |     |     |     |     | |
| agg | ttg | ttg | agg | gca | att | gaa | tac | ggc | acg | gtt | tcc | cga | tac | tgg | gtc |   4441 |
| Arg | Leu | Leu | Arg | Ala | Ile | Glu | Tyr | Gly | Thr | Val | Ser | Arg | Tyr | Trp | Val | |
| 345 |     |     |     |     | 350 |     |     |     |     | 355 |     |     |     |     | 360 | |

```
agg tcc aca tagtcgtgca ccttcgagtc gtgcggtaca ccttcggcga              4490
```

-continued

```
Arg Ser Thr ttatgtaggt tttcgtgcgg aacgagagca gctcctccaa cctttggtca taattgtcca      4550
gtatgtgtag cacaacctgg ttatagtcga caatacgacc ctcgtacatg aacgatctgc      4610
tcacgcgatc ggcaaccgta attgcgagcg cacttttcga ctcaccaacc gttgagcccc      4670
actttggtac gtagttttca gcggcctttt tcagctcctg tgccatgaaa tcgcgcaact      4730
ggtccgtaat aatgtcgttt aaattctccg gcttttccac agtctcaaca tcctcaacct      4790
ccatatcggg ttgagccgag gttggcggtg tggttccgct accggatggt gccgcaccaa      4850
agttgtttag aatcacattt cgctgctcct cggatagggc gttaaacagc tccatcacct      4910
tagcggcatc agtactttgc acctcggacg ccatgtcgaa gtttagcgaa tttctgctta      4970
cttcgtcctc ctcaccagca gcatagtcgc cctcggggcc accaccgaca acttcgaaaa      5030
ctgaaccaga aacgttgcca attccgccaa ccgagtccgg tccgtcttcc tcgagctcgg      5090
gaaataaaaa gtcgtccacc ttggccaccg actcgggctc gggatcgtta tcctgcccac      5150
cttcatcctc accttctccg tccgagtgcc actcgctcac gagacgcttc gatatcaccg      5210
acattgccac gggacccgtg ggtgaacctg gggccacatt ttgatcacca ctcgtagcac      5270
caccggtcca aacattatca tccaaattta gctggggctc ggctacaggt ggtgctacat      5330
cgtcattttc atcttggttt aaaatttcat caacttgtcg ctgccgagct gggcgcaccg      5390
gtctaccagc tttgatggtt gtagtggcgc gtgattttgg gcggccttta acgccaccgg      5450
cttcacgtag accctcggct ctcgagcttc gattcattta gtcgtataaa acaacctggc      5510
cgtgtacggg cgcccagagg ttcacaatac gtgtcttatt acccattcgc atcacgaaag      5570
agtagtcatt gtttgcgtta ggtgcggttc gcagttcgta ttcagagcgg gacattgtaa      5630
caaacggcga ctgctcaaac cgcttgtaag gtttaccggc cgtaacgagg cgaattgttt      5690 ccat atg gat gcg ttt acc gag act ttt ctg cgg caa agg gtt ata atc       5739
     Met Asp Ala Phe Thr Glu Thr Phe Leu Arg Gln Arg Val Ile Ile
         365                 370                 375 aat ccg gag acg aag gag att gaa gtt cgc gca gtt tgc agt gat gga        5787
Asn Pro Glu Thr Lys Glu Ile Glu Val Arg Ala Val Cys Ser Asp Gly
380                 385                 390 gtt gga tac act tac ttc acg gtc ggt caa atg cct cac cct gtt acc        5835
Val Gly Tyr Thr Tyr Phe Thr Val Gly Gln Met Pro His Pro Val Thr
395                 400                 405                 410 gaa cgt gac gtt agc ggc ggt tca tcg aac aaa atc cca agc cgg tcg        5883
Glu Arg Asp Val Ser Gly Gly Ser Ser Asn Lys Ile Pro Ser Arg Ser
                415                 420                 425 cga ggg tcg gcg gaa ccc ctg tcc ggt gca tgt gga tac aaa aat caa        5931
Arg Gly Ser Ala Glu Pro Leu Ser Gly Ala Cys Gly Tyr Lys Asn Gln
            430                 435                 440 gtg taaaattttc atcaaaaact acagcaaaac tcacgtcacc gaactctcga             5984
Val tggggtacct gaactcgaac atggtgcacc attatgtggc cctgatgggc atgtgcaggg      6044
aaaaccgagg tacagttgac gcctgtttat acgcgtccaa caagatcaat tgtgtgctgc      6104
ggttcgacct ggacctgttc cgctccagct ttgggggtag agttataaac attggccacg      6164
tttacgatga acttgaccgc atatacagaa cgctagatag acaaatttta atttcgccca      6224
actcggcgct agagttgtac gttagcgcgg aatctgcggt gctagcacca caggacctcc      6284
tcattataca ccccttcgtt gaagatctcg agtacccact ggtctcgcgc ggctaccac       6344 tggacgacga ggtgatagta aattaccgct actacagggc cgtgttgatt gccatcacgc      6404
```

-continued

```
tcgtaacctg cctgattggt aacagcgatt tgctcagcac aaccatggcc gcatcgaaaa   6464
tcatccacag cgttggcatt tgcccgtact acccggacca tatggcggtc tgtaaactga   6524
cgaaccgcgt tacggggacg gtcatggata ggcacatctt ctgcatccca atcgagcagt   6584
tcaaacggtc ctttctatac cgcaaaaccg ttatcaagcg ggacggtgag gataaggcgg   6644
tggacattaa gtcgttaaaa tctatgaccc agaatatacg cggaaagcgc aaccccagtc   6704
ccgagttgtg gaacgttttt acgaagaaca tcgaggaact tt ttg ttc gat acg      6758
                                               Leu Phe Asp Thr
                                                   445 aca atg cag ttt gag att gag atc cgc aac ggt aac cag ttg tac tca     6806
Thr Met Gln Phe Glu Ile Glu Ile Arg Asn Gly Asn Gln Leu Tyr Ser
        450                 455                 460 tcg cgc aac caa cta att tta ccc ggg ctc acc gac gtg tac tat cac     6854
Ser Arg Asn Gln Leu Ile Leu Pro Gly Leu Thr Asp Val Tyr Tyr His
    465                 470                 475 tat gta agc acg agt gga ccc ttt ggt gag gac cac ccg cac gac atc     6902
Tyr Val Ser Thr Ser Gly Pro Phe Gly Glu Asp His Pro His Asp Ile
480                 485                 490                 495 aag ctg cac acg acc gta cac aat tac aac ccg aat ttg gcg gtc ttt     6950
Lys Leu His Thr Thr Val His Asn Tyr Asn Pro Asn Leu Ala Val Phe
                500                 505                 510 gtg att cag cgc gag ggc acg gag ctc aat aag atc gct ttt cgt ctg     6998
Val Ile Gln Arg Glu Gly Thr Glu Leu Asn Lys Ile Ala Phe Arg Leu
            515                 520                 525 caa gtg tac gtc ctt aaa gcg acc aca ttc ggc gcc ggt gaa cat att     7046
Gln Val Tyr Val Leu Lys Ala Thr Thr Phe Gly Ala Gly Glu His Ile
        530                 535                 540 gcc gag gtg aac ttt atc aaa cct aaa ggc tgc gga gat gga aaa cgt     7094
Ala Glu Val Asn Phe Ile Lys Pro Lys Gly Cys Gly Asp Gly Lys Arg
    545                 550                 555 tcg gtc gac acc acc gtc gtt gaa cca aac gaa ccg gtt aac aag cgc     7142
Ser Val Asp Thr Thr Val Val Glu Pro Asn Glu Pro Val Asn Lys Arg
560                 565                 570                 575 gcc cgt acg ccg agt cca gcc cca gtc gat caa gat ttg ccc gaa cca     7190
Ala Arg Thr Pro Ser Pro Ala Pro Val Asp Gln Asp Leu Pro Glu Pro
                580                 585                 590 aaa cca gag ccc gag tct g cag                                       7212
Lys Pro Glu Pro Glu Ser
            595

<210> SEQ ID NO 138
<211> LENGTH: 58
<212> TYPE: PRT
<213> ORGANISM: mosquito baculovirus

<400> SEQUENCE: 138

Leu Gln Gln Tyr Phe Tyr Ser His Leu Val Asn Gln Thr Glu Ala Arg
 1               5                  10                  15

Pro Asp Asp Tyr Glu Ala Glu His Leu Ser Ala Ala Arg Glu Lys Val
            20                  25                  30

Asn Leu Gln Asn Cys Gly Ala Arg Gln Gln Asn Ala Leu Pro Leu Gly
        35                  40                  45

His Ile Gly Pro Arg Asn Ser Ala Glu Pro
    50                  55

<210> SEQ ID NO 139
<211> LENGTH: 78
<212> TYPE: PRT
<213> ORGANISM: mosquito baculovirus
```

-continued

```
<400> SEQUENCE: 139

Met Cys Thr Ile Tyr Arg Ser Ala Leu Lys Lys Thr Thr Thr Met
1               5                   10                  15

Thr Val Asp Arg Arg Gly Pro Arg Ser Cys Asn Pro Pro Ser Glu Lys
                20                  25                  30

Thr Ile Ala Arg Pro Thr Thr Ser Leu Gln Ser Gln Arg Cys Ser Ile
            35                  40                  45

Pro Ser Ser Glu Ser Ile Thr Ile Lys Arg Ser Thr Val Gln Asn Lys
        50                  55                  60

Tyr Thr Leu Ile Asn Phe Ile Tyr Ile Val Tyr Phe Thr Gly
65                  70                  75

<210> SEQ ID NO 140
<211> LENGTH: 124
<212> TYPE: PRT
<213> ORGANISM: mosquito baculovirus

<400> SEQUENCE: 140

Met Leu Gly Ile Val Gly Ala Pro Val Ile Leu Gln Ile Leu Arg Ser
1               5                   10                  15

Val Gln Val Asn Ile Leu Phe Arg Val Gln His Glu Ser Asp Gln Lys
                20                  25                  30

Arg Phe Asn Val Ala Asn Phe Thr Ala Arg Val His Arg Glu Leu Val
            35                  40                  45

His Val Arg Ser Ser Val Thr Val Gln Leu Gly Leu Gln Pro Val Ile
        50                  55                  60

Leu Val Ile Ala Ala Asn Cys Val Leu Glu Arg Val Arg Ala Lys Leu
65                  70                  75                  80

Glu Ile Leu Glu Gly Ser Trp Val Glu Leu His Ser Glu Arg His Tyr
                85                  90                  95

Trp Ala Asn Val Trp Val Lys Met Trp Gly Ala Leu Tyr Ile Asn Phe
            100                 105                 110

Leu Ala Ile Ser Ala Ala Ser Val Ala Met Ser Ala
        115                 120

<210> SEQ ID NO 141
<211> LENGTH: 51
<212> TYPE: PRT
<213> ORGANISM: mosquito baculovirus

<400> SEQUENCE: 141

Met Leu Ala Ala Pro Pro Leu Arg Ala His Val Arg Tyr Gly Thr Arg
1               5                   10                  15

Pro Gly Arg Ser Ser Pro Thr Lys Leu Gly Pro Arg Lys Pro Val Pro
                20                  25                  30

Ile Arg Leu Glu Ala Gln Leu Val Arg Pro Phe Gly Leu Tyr Phe Glu
            35                  40                  45

Pro Gly Phe
        50

<210> SEQ ID NO 142
<211> LENGTH: 52
<212> TYPE: PRT
<213> ORGANISM: mosquito baculovirus

<400> SEQUENCE: 142

Met Phe Ser Leu Lys Ser Leu Lys Ile Phe Ala Ile Phe Ser Cys Ser
```

```
           1               5                  10                 15
Lys His Pro Ser Ala Ser Trp Ser Val Leu Ala Trp Ser Thr Pro Arg
                    20              25                 30

Leu Arg Leu Arg Ala Ile Glu Tyr Gly Thr Val Ser Arg Tyr Trp
         35              40                 45

Val Arg Ser Thr
         50
```

```
<210> SEQ ID NO 143
<211> LENGTH: 80
<212> TYPE: PRT
<213> ORGANISM: mosquito baculovirus

<400> SEQUENCE: 143

Met Asp Ala Phe Thr Glu Thr Phe Leu Arg Gln Arg Val Ile Ile Asn
 1               5                  10                 15

Pro Glu Thr Lys Glu Ile Glu Val Arg Ala Val Cys Ser Asp Gly Val
                20                  25                 30

Gly Tyr Thr Tyr Phe Thr Val Gly Gln Met Pro His Pro Val Thr Glu
             35                  40                  45

Arg Asp Val Ser Gly Ser Ser Asn Lys Ile Pro Ser Arg Ser Arg
         50                  55                  60

Gly Ser Ala Glu Pro Leu Ser Gly Ala Cys Gly Tyr Lys Asn Gln Val
65                   70                  75                  80

<210> SEQ ID NO 144
<211> LENGTH: 154
<212> TYPE: PRT
<213> ORGANISM: mosquito baculovirus

<400> SEQUENCE: 144

Leu Phe Asp Thr Thr Met Gln Phe Glu Ile Glu Ile Arg Asn Gly Asn
 1               5                  10                 15

Gln Leu Tyr Ser Ser Arg Asn Gln Leu Ile Leu Pro Gly Leu Thr Asp
                20                  25                 30

Val Tyr Tyr His Tyr Val Ser Thr Ser Gly Pro Phe Gly Glu Asp His
             35                  40                  45

Pro His Asp Ile Lys Leu His Thr Thr Val His Asn Tyr Asn Pro Asn
         50                  55                  60

Leu Ala Val Phe Val Ile Gln Arg Glu Gly Thr Glu Leu Asn Lys Ile
65                   70                  75                  80

Ala Phe Arg Leu Gln Val Tyr Val Leu Lys Ala Thr Phe Gly Ala
                 85                  90                  95

Gly Glu His Ile Ala Glu Val Asn Phe Ile Lys Pro Lys Gly Cys Gly
            100                  105                 110

Asp Gly Lys Arg Ser Val Asp Thr Thr Val Val Glu Pro Asn Glu Pro
        115                  120                 125

Val Asn Lys Arg Ala Arg Thr Pro Ser Pro Ala Pro Val Asp Gln Asp
    130                  135                 140

Leu Pro Glu Pro Lys Pro Glu Pro Glu Ser
145                  150

<210> SEQ ID NO 145
<211> LENGTH: 3997
<212> TYPE: DNA
<213> ORGANISM: mosquito baculovirus

<400> SEQUENCE: 145
```

```
ctgcagcgat agtttccatg aactcatcaa gctgaaacct accatttgcc ttggctcccg      60
ccagtagttc ctgccggaag tcgtggaaga aatcttcgcc ggtttgctcc attactctcc     120
tccgaagaca gcggccccgt cgcactcgta ttgagcaatc gtttccaatt tgatgtcgta     180
ggctaccttg gcaatacctg tcggcaattg cgatcgcatg aggcgcggaa aatcatcggc     240
gacccgatag ctgcgcacgt cgctgacgac aaaacgcggt tcatcgtagt cagggagcgg     300
cgcgtagccg tgtgcaacca acttctggtc aaaggcctca acggcctctg ccttgtcgag     360
ctgcgcctgg acgcggtgag caagctcgtt gagcgagcgg gcacctaccg catcagccag     420
attgctcagc cggtacacgc gcaggaacag tgcgtcgttc agggattcga gctggtcttc     480
cgaagaaatg cggatgctgc tccgttcggc gcccgagagc gatttgacct cgacagccgt     540
gttaccgaag atgaaatcct gatgtgaccg ttccggacca agccaggctt caacgacggc     600
attgctcggc atttcccgat cgatcagttc cgtcagaaag acgatttcgg cgaagaggcc     660
tcgaacatct tcggcggaca gatgctgact tcggcccgag aggaaactct tccaacgacg     720
gatgtgcgcc aacgagactg ccagagagcc ggccgaatcg gtggcgtact ccaacgcgaa     780
tgcaagggta cggcacagtc cctcgaaaag atcgcgatca acctgtcttt caagagcgag     840
gactaggtgt tgctgcccct gatctccggc acgaagatca catcgacac cgttcactgt     900
gaccgcgttc ttccggtact gggctgtgtg gtcgccgtga agctccacaa tgaacaggca     960
ggcaccgctg gcatcgcgtc ccagaaaaca gggtacggcc gttttcaccg caacctggcg    1020
gacattgaag tccgtgccag gaacggcgat ttcgtcccat ggcgaggttt caggcatcgt    1080
agtcctcctc ctcgtcagga tcgtccacat agccctgcat ctgctgaagc cagaccttgt    1140
tgacgagaca ttgatggtcg tcgagtagtc cccgtaaggg aagctcatgc caaaggcagc    1200
gatcggcccc gtcacggcat cgcccttggg ttccagactg tgaatcatga ggagggtct     1260
gttcctcacc atccggtaat gtgtgtcgga taccgccccc gagccgtcgt cgtcgccagc    1320
gaccgttctg gcctcagcgc gttgctcgtc gctgagcccg agtttctcgt caccacgcga    1380
agcaactctg tccttgttca ggcgccacgc agtgccgttc ggctgatccc tcccgacgac    1440
acgcacctga ttcctcaacg tgaatgggcg ttcgccaccc gacccacctg agggagaaat    1500
cagcagaaca tccgcaagcg gacgcttcgt cgcgatccgt tcgagatagc tcaccacatc    1560
cgatttctgc cccgcaaagg tcgaatgaca ttcgaatcga gtgagaaaat cgtcgatcac    1620
ctcgacgggc acgtctctga agatgacgcc tttcttggtg gactcctccg gccgtccgcc    1680
gaatccactt cgccagcgat cggcgatcag ctcaaagttc ttggcattca cgtcggggc     1740
ggtggagacg atgtaacttt cacggagtcg cccactgaaa ctctgttcga ccgtgacctc    1800
ttggccggat ctcatcttgt tcgcggccgt gatcagcagg ctgtccggat gcgagcggac    1860
ataaagccca aagtcctttg gactgaggcg atcgcgccgc atgcgcttga cctgctgcac    1920
aagttcttcg gcggcttcgg cgatgtggga gtaccagttg atcgaatcgc gagaaagatg    1980
gacacggcag agatcctcga agcccggccg gtagccgaac cagcgaccca tctgcatgag    2040
ggtgtcgtac atcttcgtgt tgcggtacat gtagctgacg gtcaatccct cgatggttaa    2100
acctcgcgac aggctcaggc caccgaccgc gaccgccgtc agcccgatgc cttccttctc    2160
gtaccgggtg tagtcgagca cctcgtcact cttgctgttg atgacataga ggtgaagatg    2220
ctcgaagacg ccactgaggg cagccttcac ctcagcccat gtgactccaa cgtcggcgta    2280
ttcggcatcg aaggcctcct tcaggccttg catgtacatg tttcttgacg aaacgtcctc    2340
```

-continued

```
cggcatcgcg tagttggcga gaaccgcttc cctgatcttc ttctccctga ggctcaggaa   2400
gtcgcgcaca gccttctgta tcggcacaaa gcgcgacaca ttgaccatca tcgagcaatg   2460
cttgctggcc tgtccgcgca ggttccggat ggcgcgtgca atgatgaact cgtcgagtgc   2520
gcgatggagg ctggcaggca gctcatggac aggatcatcg cgtttgtgcg agtagggaat   2580
gagatcctcg caatcatcga tcggcctgat gatcgattcg ctggtcgcct cattcaggaa   2640
taccttctcc gcaccgaaat aggtggtggg cgcatccagg caatagatga agtcgcgagg   2700
gaaaagctct tcctgcacat catcgccata ggcatctgga ttgatgaaga tgttggcgaa   2760
cggggttgcc gtatatccga cgtagcatga cttcgcgaat agacccagga tgcggcgaat   2820
catggcattc gttcgggtcg ggtcgagatc ctccttgttc gtgttgatgg atgcgttgtc   2880
ggcttcgtcg tcgatcagca gcatgggtac atcggagatg cggtcttctc cttcggcgtt   2940
cagcgccttc agccatttgt gcaacgcggt gagcgtcgtg acgttcttct tgatgatcag   3000
gatgatcggc ttgctgaagt cgttgatctt ccagccactc ttggctgctg tattcttgtt   3060
gaagtcctcg ttgatgttgg tgagcgttgc cggatgcgga tatcccgaaa cgagaccgac   3120
gccgatgttg cggcgatcct cggggtcact cgatcggccg atgaaggcct cgtcgattcg   3180
ctgctgtgtc tgcctgcgca ggttgttgtg aatgccagcg atgacgacga tgaacttgta   3240
gcccgcatcg gctgcacgtg ctatcagacc cgtgtagttg gccgtcttcc ccgactgcac   3300
atggccgatg accaagccac ggcggttcca gctcgtgcct tcgctcagtg gatcctgaag   3360
gtgaccaaga atgcgagtgg tcacatcgct cagcgactgg accatctgcg gaggccagcc   3420
ctcgttgcga aggaattcct cgtatgcact ggcataggtc caagtgacgt cctcgcgctt   3480
gtgaacccat tgatcgtcat gcttcgcatt gacatcaacc aatgaaattc ctgctcccat   3540
gcgggtcaca accgattcca tagcttcggt gacaatgttg cggaggtctc ccgcatagcc   3600
gaagattgca gcaatctgtc ttgccttttc ctccacctga tcgcgcgtcg gcgtttccgc   3660
catgttggca aggcccgaga tgagcgcgtt ggcaatgttt cgttcttccg tgatggctgt   3720
aatgctcatg caaaggcctc gttgatgaat ttttcggcca gatccatctg gccatcgaag   3780
agatgcgtgg agcgcacgat ctgaagaaaa gctttcgcat cgcccggccc gtcgccgtac   3840
agcacttggc gcaggctact caggcgctcc atggtctggc tttcatccac cgatcgttga   3900
ttgatctcgc gcgggtgagt cgagtagtcg gaatagatca tctcgaccgg cagtgaggca   3960
gcaaccgaat caagcagcgt gcgcagcagg tctgcag                            3997
```

<210> SEQ ID NO 146
<211> LENGTH: 3997
<212> TYPE: DNA
<213> ORGANISM: mosquito baculovirus

<400> SEQUENCE: 146

```
ctgcagacct gctgcgcacg ctgcttgatt cggttgctgc ctcactgccg gtcgagatga     60
tctattccga ctactcgact cacccgcgcg agatcaatca acgatcggtg gatgaaagcc    120
agaccatgga gcgcctgagt agcctgcgcc aagtgctgta cggcgacggg ccgggcgatg    180
cgaaagcttt tcttcagatc gtgcgctcca cgcatctctt cgatggccag atggatctgg    240
ccgaaaaatt catcaacgag gcctttgcat gagcattaca gccatcacgg aagaacgaaa    300
cattgccaac gcgctcatct cgggccttgc caacatggcg gaaacgccga cgcgcgatca    360
ggtggaggaa aaggcaagac agattgctgc aatcttcggc tatgcgggag acctccgcaa    420
cattgtcacc gaagctatgg aatcggttgt gacccgcatg ggagcaggaa tttcattggt    480

```
tgatgtcaat gcgaagcatg acgatcaatg ggttcacaag cgcgaggacg tcacttggac    540
ctatgccagt gcatacgagg aattccttcg caacgagggc tggcctccgc agatggtcca    600
gtcgctgagc gatgtgacca ctcgcattct tggtcacctt caggatccac tgagcgaagg    660
cacgagctgg aaccgccgtg gcttggtcat cggccatgtg cagtcgggga agacggccaa    720
ctacacgggt ctgatagcac gtgcagccga tgcgggctac aagttcatcg tcgtcatcgc    780
tggcattcac aacaacctgc gcaggcagac acagcagcga atcgacgagg ccttcatcgg    840
ccgatcgagt gaccccgagg atcgccgcaa catcggcgtc ggtctcgttt cgggatatcc    900
gcatccggca acgctcacca acatcaacga ggacttcaac aagaatacag cagccaagag    960
tggctggaag atcaacgact tcagcaagcc gatcatcctg atcatcaaga gaacgtcac    1020
gacgctcacc gcgttgcaca aatggctgaa ggcgctgaac gccgaaggag aagaccgcat    1080
ctccgatgta cccatgctgc tgatcgacga cgaagccgac aacgcatcca tcaacacgaa    1140
caaggaggat ctcgacccga cccgaacgaa tgccatgatt cgccgcatcc tgggtctatt    1200
cgcgaagtca tgctacgtcg gatatacggc aaccccgttc gccaacatct tcatcaatcc    1260
agatgcctat ggcgatgatg tgcaggaaga gcttttccct cgcgacttca tctattgcct    1320
ggatgcgccc accacctatt tcggtgcgga aaggtattc ctgaatgagg cgaccagcga    1380
atcgatcatc aggccgatcg atgattgcga ggatctcatt ccctactcgc acaaacgcga    1440
tgatcctgtc catgagctgc ctgccagcct ccatcgcgca ctcgacgagt tcatcattgc    1500
acgcgccatc cggaacctgc gcggacaggc cagcaagcat tgctcgatga tggtcaatgt    1560
gtcgcgcttt gtgccgatac agaaggctgt gcgcgacttc ctgagcctca gggagaagaa    1620
gatcagggaa gcggttctcg ccaactacgc gatgccggag gacgtttcgt caagaaacat    1680
gtacatgcaa ggcctgaagg aggccttcga tgccgaatac gccgacgttg gagtcacatg    1740
ggctgaggtg aaggctgccc tcagtggcgt cttcgagcat cttcacctct atgtcatcaa    1800
cagcaagagt gacgaggtgc tcgactacac ccggtacgag aaggaaggca tcgggctgac    1860
ggcggtcgcg gtcggtggcc tgagcctgtc gcgaggttta accatcgagg gattgaccgt    1920
cagctacatg taccgcaaca cgaagatgta cgacaccctc atgcagatgg tcgctggtt    1980
cggctaccgg ccgggcttcg aggatctctg ccgtgtccat ctttctcgcg attcgatcaa    2040
ctggtactcc cacatcgccg aagccgccga agaacttgtg cagcaggtca agcgcatgcg    2100
gcgcgatcgc ctcagtccaa aggactttgg gctttatgtc cgctcgcatc cggacagcct    2160
gctgatcacg gccgcgaaca agatgagatc cggccaagag gtcacggtcg aacagagttt    2220
cagtgggcga ctccgtgaaa gttacatcgt ctccaccgcc cccgacgtga atgccaagaa    2280
ctttgagctg atcgccgatc gctggcgaag tggattcggc ggacggccgg aggagtccac    2340
caagaaaggc gtcatcttca gagacgtgcc cgtcgaggtg atcgacgatt ttctcactcg    2400
attcgaatgt cattcgacct ttgcggggca gaaatcggat gtggtgagct atctcgaacg    2460
gatcgcgacg aagcgtccgc ttgcggatgt tctgctgatt tctccctcag gtgggtcggg    2520
tggcgaacgc ccattcacgt tgaggaatca ggtgcgtgtc gtcggagggg atcagccgaa    2580
cggcactgcg tggcgcctga acaaggacag agttgcttcg cgtggtgacg agaaactcgg    2640
gctcagcgac gagcaacgcg ctgaggccag aacggtcgct ggcgacgacg acggctcggg    2700
ggcggtatcc gacacacatt accggatggt gaggaacaga cccctcctca tgattcacag    2760
tctggaaccc aagggcgatg ccgtgacggg gccgatcgct gcctttggca tgagcttccc    2820
```

-continued

```
ttacggggac tactcgacga ccatcaatgt ctcgtcaaca aggtctggct tcagcagatg    2880
cagggctatg tggacgatcc tgacgaggag gaggactacg atgcctgaaa cctcgccatg    2940
ggacgaaatc gccgttcctg gcacggactt caatgtccgc caggttgcgg tgaaaacggc    3000
cgtaccctgt ttctggggac gcgatgccag cggtgcctgc ctgttcattg tggagcttca    3060
cggcgaccac acagcccagt accggaagaa cgcggtcaca gtgaacggtg tcgatgtcga    3120
tcttcgtgcc ggagatcagg ggcagcaaca cctagtcctc gctcttgaaa gacaggttga    3180
tcgcgatctt ttcgagggac tgtgccgtac ccttgcattc gcgttggagt acgccaccga    3240
ttcggccggc tctctggcag tctcgttggc gcacatccgt cgttggaaga gtttcctctc    3300
gggccgaagt cagcatctgt ccgccgaaga tgttcgaggc ctcttcgccg aaatcgtctt    3360
tctgacggaa ctgatcgatc gggaaatgcc gagcaatgcc gtcgttgaag cctggcttgg    3420
tccggaacgg tcacatcagg atttcatctt cggtaacacg gctgtcgagg tcaaatcgct    3480
ctcgggcgcc gaacggagca gcatccgcat ttcttcggaa gaccagctcg aatccctgaa    3540
cgacgcactg ttcctgcgcg tgtaccggct gagcaatctg gctgatgcgg taggtgcccg    3600
ctcgctcaac gagcttgtca ccgccgtcca ggcgcagctc gacaaggcag aggccgttga    3660
ggcctttgac cagaagttgg ttgcacacgc tacgcgccg ctccctgact acgatgaacc    3720
gcgttttgtc gtcagcgacg tgcgcagcta tcgggtcgcc gatgattttc cgcgcctcat    3780
gcgatcgcaa ttgccgacag gtattgccaa ggtagcctac gacatcaaat tggaaacgat    3840
tgctcaatac gagtgcgacg gggccgctgt cttcggagga gagtaatgga gcaaaccggc    3900
gaagatttct tccacgactt ccggcaggaa ctactggcgg gagccaaggc aaatggtagg    3960
tttcagcttg atgagttcat ggaaactatc gctgcag                             3997
```

<210> SEQ ID NO 147
<211> LENGTH: 705
<212> TYPE: DNA
<213> ORGANISM: mosquito baculovirus

<400> SEQUENCE: 147

```
atgagtgaat tcatcgagac cgtacactac aacaccgacc cgatccggtc gagctatggc     60
atttgtgggc tgcacacccg cgggaaccgg ggctgccgag agtgggtgat tgatatcgat    120
ttgaaaactg acgaccccga gttggccaac tttgtgctca acgtgtccgt ggtcacctca    180
atgttcttct tcggtaccga aaacattaaa gttaccaca cgggcaacga cggcatccac    240
atttggctca acccggccaa cttcccggtg gactcgagcg ccgaattgcg cggattctac    300
ctcgccgcca tgcagctacc caaaggtgag gaggaactac acgagctggt gcggaccacc    360
gagtgcaggt tgttttgcga cgccgactgc tgcggaatcg attgcaagcc caagatgcgc    420
atcatcgaca ccccacccaa tcccacgaaa ccgatttcgt ttgccgagtg ctttgtgcgc    480
gctctctgct gcaacgaaac ctatatgaac gaaatgacat cgattatacg caacaaccgg    540
gacgtggtga gcaccgtcac cgacgtgtgg agactctttt ggccgcccat agatgcgggc    600
ctgtttcaat cgccagctag actctgccgt gcacccctca gttaccactt gaagggcggt    660
cggctttcgc gtcgtattga cttggatgaa tattttaaaa atgat                    705
```

<210> SEQ ID NO 148
<211> LENGTH: 1032
<212> TYPE: DNA
<213> ORGANISM: mosquito baculovirus

<400> SEQUENCE: 148

-continued

```
atgcgcctcg aagatgaacc gagcctcgag gaccagatga ttgattttat aaacaataac      60
ccactaatat cgagcctgct ggtttcagcg ggtttcgatt tcataaacga cggtttccgc     120
gccctcatga agaaggccat ggtgcggtac atcccgatgc tgcaagccgc cgcaatacgg     180
ttcggtgaag gcttgacacg taaaatggtc tcggaggcgt ttcgtgtgct catgtttagc     240
cgcataaacc agatggccgt gcagctgacc ggcgctctag cgaaggcaat tgcacgcttt     300
ggtgcgatgg ccagttcggt gattggaatc gtgttgatat ttttcgtcgc agccgatata     360
attctcatgt tctgggaccc gtacggttac agcaacatgt ttccgcccga gtttctgggc     420
gatttgacgc tcaactttct gtcggcgttt ttcgagcaaa cgggtacgcg aaacgtaatc     480
gaaatgatac cccaagcgta cgactctatg gtgaaaggtg gtgaggagga tggactctac     540
ctaacatttg ccgccctaca atacgtgagc catatggagg tgaactcgga cgggcagttg     600
ttgctgctac gaaacagtaa cccaatcaag caggaggaac ttgagccgca caacctcacg     660
gtggccctct tcggcgctat aaacctgcag agttatgagg atcttaagcg gcatatggcc     720
agcgccaacc gggccttcgg tatagacccc gaaacgttgc agcaagtggc cccgtggaga     780
gatagacccg ggacagtaat ttcagctggc gtcctagttg cgcttgtggt cgttttgacc     840
gggagtcaac ttttcagcac aaaagcgccc gatctagcta cggtggtgct cattgtaatt     900
ctggtggcca tagtgataat cgtgctacaa ctcgaccgta taacacccct ggcccgactt     960
gccatcgtaa agcatgaaga gaacgagaaa aatcgcgtcg gccaacgctt cgccggactg    1020
cttagacgtg ct                                                         1032
```

BACULOVIRUSES, INSECTICIDAL COMPOSITIONS, AND METHODS FOR CONTROL OF INVERTEBRATES

FIELD OF THE INVENTION

The invention relates to the fields of insect control using baculoviruses and control of baculoviral infections in invertebrates.

BACKGROUND OF THE INVENTION

Historically, mosquito control operations have primarily used chemical pesticides or the bacterium *Bacillus thuringiensis israelensis* (Bti) for control of larval mosquitoes. Chemical larvicides are rapidly losing market share due to safety issues and the expense of treating large aquatic habitats, where the larvae are produced. While Bti is effective and safe, it is quickly inactivated in the environment, and works poorly in polluted water habitats.

The other major biocontrol for insects is viruses, and the Baculoviridae family of viruses, commonly called baculoviruses, has been widely studied and developed commercially for certain insects. Baculoviruses are composed of large, double-stranded, circular DNA molecules that are packaged in rod-shaped capsids. The Baculoviridae includes the Nucleopolyhedroviruses and the Granuloviruses subgroups (see Granados R R and B A Federici, Eds. 1986 *The Biology of Baculoviruses*, Vol. 1. Boca Raton, Fla.: CRC Press; Volkman, L E et al. 1995. *Baculoviruses*. In: Virus Taxonomy. Sixth Report of the International Committee on Taxonomy of Viruses. Murphy, F A et al. Eds Springer Verlag Wien).

Insect control using baculoviruses is an attractive approach, because baculoviruses only infect invertebrates, and they can generally be produced in sufficiently high numbers for commercial use. The viruses are produced naturally in two forms: "occluded" and "non-occluded". The occluded form, in which the DNA genome is surrounded by crystalline proteins (forming a structure called the inclusion or occlusion body), is the form in which the virus is spread naturally from one insect to another. It is also the form that makes a good insecticide formulation, since it is stable in the environment and in commercial packaging, and it can be mixed more readily with other pesticide formulations.

Despite the many advantages of baculoviruses for insect control, one commercial disadvantage is that a single baculovirus species has a fairly narrow host range, so a given baculovirus cannot be used for broad spectrum insect control. One of the best studied baculoviruses, *Autographa californica* nuclear polyhedrosis virus (AcNPV), is considered to have a fairly broad host range for a baculovirus, since it is known to infect over thirty species of Lepidoptera. The celery looper multiple embedded virus described by Hostetter and Puttler (U.S. Pat. No. 4,911,913) also is considered to have broad insecticidal activity within the Lepidoptera.

Thus, to develop an effective baculoviral control strategy for mosquitoes, there is a need to identify a viral strain that will infect as many mosquito species as possible. The first documented report of a mosquito pathogenic virus was made in 1963 with the discovery of a "cytoplasmic polyhedrosis virus" from *Culex tarsalis* in California (Kellen et al., 1963, J. Insect Pathol. 5:98–103), but this virus was later shown to be a densonucleosis virus, from the family Parvoviridae (Federici, B A 1985, "Viral Pathogens". IN Biological Control of Mosquitoes, H C Chapman, Ed., Bull. No. 6, American Mosquito Control Association, Inc., pp. 62–74).

Additional viruses pathogenic to mosquitoes have been reported from many different mosquito hosts, primarily by researchers in the U.S., Europe and Russia (Federici, 1985; ibid.; Goettel, M S 1985 Agr. Forestry Bull. 8:41–44). The first report of a baculovirus from a mosquito host was from *Aedes sollicitans* collected in Louisiana (Clark, T B, H C Chapman, and T Fukuda, 1969, J. Invert. Pathol. 14(2) ;284–286). Natural infections with NPVs have been reported from about ten mosquito species representing the genera Aedes, Anopheles, Culex, Psorophora, Uranotaenia and Wyeomyia (Federici, ibid.). Such infections were identified as being NPV infections based only on electron microscopic observations of the shape and size of occlusion bodies in collected larvae and on histopathological and cytopathological observations on infected larvae (Federici and Lowe 1972 Invert. Pathol. 20:14–21; Federici, B A 1980 Virology 100: 1–9; Stiles and Paschke 1980 J. Invertebr.Pathol. 35: 58–64). The AesoNPV characterized by these researchers produces spindle-shaped occlusion bodies 5–20 microns in length. H. Chapman (1974, Ann Rev Entomol 19:33–59) characterized an NPV infection in *Culex quinquefasciatus* in which the occlusion bodies are globular and from 1–5 microns in diameter. A viral disease of *Culex tarsalis*, characterized by tetragonal inclusion bodies, was described by W. R. Kellen et al. (1963, J. Insect Pathol. 5:98–103). While this virus was lost upon culturing, Clark and Chapman concluded it was the same virus that infected *Culex salinarius* (1969, J. Invert. Pathol 13:312), a virus that did not infect *Culex peccator* or *Culex quinquefasciatus*.

This area of mosquito pathology has received very little attention since these preliminary, initial reports 25–30 years ago, despite the tremendous advancements made with other insect baculoviruses for use as biopesticides and expression vectors (Adams, J R and J T McClintock, 1991, pp. 87–204 In: *Atlas of Invertebrate Viruses*, Adams and Bonami, Eds., Boca Raton: CRC Press; Possee, R D 1997, Curr. Opin. Biotechnol. 8: 569–572; and Possee, R D et al. 1997 Pestic. Sci. 51: 462–470), and no NPV has been purified or isolated from mosquitoes to allow molecular studies for unequivocal identification. A major reason for the inactivity in this area has centered on the inability to reliably transmit mosquito baculoviruses to their original and alternate hosts (Federici, 1985). There are numerous factors that can affect the infectivity of a baculovirus for an insect host, including chemical, physical and/or biological factors.

Much effort has been directed at developing methods and protocols to enhance the storage and stability of baculoviruses (usually in occluded form), for use in field applications. Factors that either reduce or enhance infectivity have been identified as components of storage mixtures, formulations, or crops on which baculoviral applications are to be made. For example, several proteins have been shown to enhance baculoviral infections. Enhancin, a metalloproteinase, has been isolated from an armyworm (*Trichoplusia ni*) granulosis virus (GV), and it can enhance the activity of baculoviruses by digesting certain peritrophic membrane proteins (Corsaro et al. 1993. In "Parasites and Pathogens of Insects", Beckage, N E et al., Eds., Volume 2: pp. 127–145, Academic Press, San Diego; Lepore L S. et al. 1996 J. Invertebr. Pathol. 68(2): 131–140; Wang P and R R Granados 1997, Proc. Natl. Acad. Sci. USA 94(13): 6977–6982; Wang, P. et al. 1997 J. Gen. Virol. 78: 3081–3089). A virus enhancing protein has also been detected in the spheroid, spindle and virion of an entomopoxvirus (Wijonarko A and T Hukuhara 1998, J. Invertebr. Pathol. 72(1): 82–86). Chitinase has also been shown to enhance infectivity of the gypsy moth NPV (Shapiro M et al.

1987, J. Econ. Entomol. 80(6): 1113–1116). Several acids, including boric and sorbic, have been shown to enhance infectivity of lepidopterous baculoviruses (Morales L et al. 1997, Ann. Soc. Entomol. Bras. 26(1): 115–120; Shapiro M and R A Bell 1982, Ann. Entomol. Soc. Am 75(3):346–349), while tannic acids have been shown to inhibit NPV infectivity (Keating et al. 1989, J. Invertebr. Pathol. 54(2):165–174; Young et al. 1995, Biological Control 5(2): 145–150).

Studies investigating the effects of various plant constituents on the infectivity of baculoviruses found that most of these actually inhibit infectivity (Elleman C J and Entwistle P F 1985, Ann. Appl. Biol 106(1): 83–92, 93–100; Felton G W and S S Duffey 1990, J. Chem. Ecol 16(4): 1221–1236; Hoover K et al. 1998 J. Chem. Ecol. 24(2): 253–271; Keating, S T et al., 1990 J. Invertebr. Pathol. 56(3): 317–326).

In addition to the use of naturally occurring baculoviruses as insect control agents, it is possible to improve the insecticidal capabilities of such baculoviruses by engineering the virus so that it is more aggressive in killing its host, which is not typically the goal of a natural viral infection. By improving the rate of killing, the engineered baculoviruses limit the feeding and consequently damage caused to crops. Since farmers tend to apply insecticides only when damage becomes visible, it is important that the insecticide act swiftly. For example, Miller and O'Reilly have described a mechanism of improving the $LT_{50}$ (the time needed to kill 50% of the insect population) by deleting a gene which causes the production of an enzyme that inactivates insect molting hormones, ecdysteroid UDP-glucosyl transferase (EGT) (U.S. Pat. No. 5,352,451). The expression of the baculovirus EGT gene in wild-type baculoviruses prevents the insect larva from molting or pupating, allowing more time for the virus to propagate itself in the larval stage. Inactivation of the baculovirus EGT gene allows molting and pupation of the infected larva to proceed, which results in a shorter larval stage and less damage to crops. As another example, Hammock et al. (U.S. Pat. No. 5,674,485) have shown that juvenile hormone esterase can also be used in recombinant baculoviral insecticides to improve the $LT_{50}$.

Several authors have described techniques and methods for engineering insect toxin protein genes into the baculoviral genome, providing for exposure of the insect to not only an infectious virus particle but additionally to a debilitating toxic molecule, such as polypeptide toxins produced by scorpions, wasps, mites, or spiders. Tomalski et al., U.S. Pat. No. 5,266,317, issued Nov. 30, 1993, describe the use of recombinant baculoviruses that express an insect-specific paralytic neurotoxin of an insect predacious mite. Additionally, insect-selective toxins have been identified in venoms from snails, spiders, and a number of other arthropods (see review by Zlotkin, 1985, In Comprehensive Insect Physiology, Biochemistry, and Pharmacology, Vol. 10, Chapter 15, pp. 499–541). The use of more than one toxin gene in a recombinant baculovirus has also been described, to maximize the insect-killing rate and to minimize the chance for resistance to develop (U.S. Pat. No. 5,756,340 Hammock, et al.).

There remains a need to identify methods for effective transmission of baculoviruses to mosquitoes in the environment. There also remains a need to provide improved baculovirus compositions for enhanced transmission of baculoviruses to insects in the environment.

SUMMARY OF INVENTION

This invention provides an insecticidal composition comprising (a) a baculovirus effective for producing a lethal or debilitating infection in an insect; and (b) at least 1 mM of a divalent cation selected from the group consisting of: magnesium, cobalt, strontium and nickel is disclosed. Also provided are methods for controlling insect pests comprising the step of applying an insect-controlling amount of the composition to a habitat for the insect pests.

This invention further provides novel, isolated mosquito-infecting baculoviruses having at least one of the following characteristics: (a) nuclear occlusion bodies, globular in shape, diameter approximately 400 nm, each containing between 1–8 rod-shaped virions, approximately 200×40 nm; (b) nuclear occlusion bodies with no surrounding membrane and with a density of approximately 1.14–1.18 g/ml which agglutinate upon freezing; and (c) infectious in *Culex quinquefasciatus* and *Culex nigripalpus*. The novel mosquito baculoviruses of this invention can also be characterized by nucleic acid sequences provided herein, as well as by polypeptides encoded by the nucleic acid sequences. Methods for the in vitro propagation of mosquito baculoviruses comprising infecting a culture of mosquito cells with the mosquito baculovirus, growing the cells in culture medium containing at least 1 mM of a divalent cation selected from the group consisting of: magnesium, cobalt, strontium and nickel and a chelator or binder that selectively reduces the effective calcium ion concentration below 1 mM until inclusion bodies are detected in the cells, and harvesting the virus from the cells, are also provided.

Other aspects of the invention comprise isolated nucleic acids of the novel mosquito baculoviruses, isolated nucleic acids encoding polypeptides of the novel mosquito baculovirus, and cells containing these nucleic acids.

Also provided are methods for controlling baculovirus infections in invertebrates comprising administering to invertebrates calcium, iron or copper ions to provide an effective concentration of at least 1 mM.

DETAILED DESCRIPTION OF THE INVENTION

Definitions

"Baculovirus" means a member of the family Baculoviridae, whether currently known or described in the future.

"CuniNPV" means a novel baculovirus that infects *Culex nigripalpus*.

"Insect-antagonistic gene" means any gene, the product (which may be anti-sense nucleic acid or a polypeptide) of which interferes with the growth, development, or reproduction of an insect. Examples of insect-antagonistic genes include toxins, insect hormones, insect hormone mimics, and sterilization peptides.

Detailed Description

Described herein is the discovery of improved insecticidal compositions for the control of insects using viruses of the Baculoviridae. The invention described herein includes a baculovirus-based insecticidal composition comprising (a) a baculovirus effective for producing a lethal or debilitating infection in an insect, and (b) at least 1 mM of a divalent cation selected from the group consisting of: magnesium, cobalt, strontium and nickel. In a preferred embodiment, the composition further comprises an insecticidal composition-suitable carrier. The baculovirus of the invention is any virus of the family Baculoviridae, previously known or hereafter isolated and described. As currently classified, the Baculoviridae consists of double-stranded, circular, closed DNA viral genomes (between approximately 80 and 230 kilobases) that are typically packaged in rod-shaped capsids, with a general size range of approximately 30–60 nanometers by 250–300 nanometers (Miller, L 1996 "Insect Viruses" In Fundamental Virology, 3$^{rd}$ Ed., Fields B N et al eds., Lippincott-Raven Publ., Philadelphia, Pa. USA). The existing genera and species in the Baculoviridae are listed in Virus Taxonomy—6$^{th}$ Report of the International Committee on Taxonomy of Viruses, Murphy F A et al. eds., Springer Verlag, Wien, 1995, pp 104–111. Baculoviruses are currently known to infect insects of the Lepidoptera, Coleopterra, Hymenoptera and Diptera, including but not limited to *Autographa californica, Heliothis zea, Heliothis armigera, Syngrapha falcifera, Spodoptera frugiperda,* and *Thichoplusia ni* (a complete list of hosts for known baculoviruses is provided in the Virus Taxonomy reference cited above). New members of the Baculoviridae are continually being discovered, and the compositions and methods of this invention are fully applicable to baculoviruses discovered in the future.

A lethal or debilitating infection in an insect is an infection in the larval stage which prevents the majority of adults from emerging, or in the cases where the adult emerges, in which the adult reproductive capacity is statistically significantly diminished. The divalent cation to be included in the composition can be $Mg^{++}$. Alternatively, $Co^{++}$, $Sr^{++}$ or $Ni^{++}$ can be used. In a preferred embodiment in a liquid formulation, at least 5 mM $Mg^{++}$ is used. No upper limit of the divalent cation, e.g. $Mg^{++}$ need be specified so long as the amount used is not toxic. For example, between 5 and 40 mM $Mg^{++}$ can be used. Alternatively, a combination of divalent ions comprising $Mg^{++}$ and one or more of the ions $Co^{++}$, $Sr^{++}$ or $Ni^{++}$, giving a total divalent concentration of at least 1 mM and preferably at least 5 mM, can be used. When used in a non-liquid formulation, the amount of divalent cation should be calculated on a weight/weight basis, i.e. 5 mM $MgCl_2$ would be approximately 1 g $MgCl_2$ per kg or liter of the formulation.

In a specific embodiment, the baculovirus-based insecticidal composition further comprises a chelator or binder that selectively reduces the effective calcium ion concentration below approximately 1 mM. In specific embodiments, the chelator or binder reduces the effective calcium ion concentration below approximately 0.5 mM or below 0.1 mM.

In another embodiment, the invention is a mosquito larvacidal composition comprising (a) a baculovirus effective for producing a lethal or debilitating infection in mosquito larvae; and (b) at least 1 mM of a divalent cation selected from the group consisting of: magnesium, cobalt, strontium and nickel. In a preferred embodiment, the composition further comprises a larvacidal composition-suitable carrier.

In preferred embodiments, the mosquito larvacidal composition comprises a baculovirus selected from the group of nuclear polyhedrosis viruses that infect Culex, Aedes, Anopheles, Psorophoia, Uranotaenia, and Wyeomyia mosquito species. In specific embodiments, the baculovirus can be AesoNPV or the novel baculovirus CuniNPV further described hereinbelow. In a specific embodiment, the composition is a preparation of air-dried, baculovirus-infected mosquito larvae that are processed into a powder containing at least 1 mM of a divalent cation selected from the group consisting of: magnesium, cobalt, strontium and nickel.

In other embodiments, the mosquito larvacidal composition further comprises a chelator or binder that selectively reduces the effective calcium ion concentration below approximately 1 mM. In specific embodiments, the chelator or binder reduces the effective calcium ion concentration below approximately 0.5 mM or below 0.1 mM.

Given the effectiveness of divalent cations, particularly $Mg^{++}$, in combination with the novel mosquito baculovirus of this invention, in enhancing baculovirus infectivity of mosquitos, it is possible to use this combination to enhance the infectivity of other agents, e.g. bacteria or other viruses, in mosquitos. Thus, in another embodiment, the mosquito larvacidal composition comprises (a) a microorganism or virus capable of producing a lethal or debilitating infection in mosquito larvae; (b) a mosquito baculovirus; and (c) at least 1 mM of a divalent cation selected from the group consisting of: magnesium, cobalt, strontium and nickel. In specific embodiments, the microorganism can be a bacterium or a fungus, the virus can be any mosquito-infecting virus, and the mosquito baculovirus is CuniNPV (as described herein). In a further embodiment, the composition further comprises a larvacidal composition-suitable carrier. In other embodiments, the mosquito larvacidal composition further comprises a chelator or binder that selectively reduces the effective calcium ion concentration below approximately 1 mM. In specific embodiments, the chelator or binder reduces the effective calcium ion concentration below approximately 0.5 mM or below 0.1 mM.

Generally, the insecticidal or larvacidal compositions can be in the form of: wettable powders, dispersible granular formulations, granules, suspensions, emulsions, solutions for aerosols, baits and other conventional insecticide preparations. Carriers for insecticidal compositions are well-known in the art and one of skill in the art can choose an appropriate carrier based on the application site and the target insect. Examples of techniques for the formulation of baculoviruses as insecticidal compositions are described in Rhodes D J (1993, "Formulation of Biological Control Agents" In Exploitation of Microorganisms; Jones D G ed., Chapman & Hall, London, pp. 411–429) and references cited therein. The insecticidal composition-suitable carrier can be a solid or liquid diluent or carrier. The diluent or carrier can be a liquid, such as water, alcohol, hydrocarbons or other organic solvents, or a mineral, animal or vegetable oil, or a solid, such as a powder, e.g. talc, clay, silicate or corn cob grits. Wetting agents, coating agents, agents to promote physical flexibility, UV protectants, dispersants and sticking agents can also be added to the insecticidal compositions of the present invention. Similarly, nutrients may be added to increase feeding behavior and/or to attract insects. Flow agents, for example, clay-based flow agents, may be added to minimize caking of the wettable powders or other dry preparations during storage. Alternatively, the insecticidal or larvacidal composition can be microencapsulated using plant lignins or other suitable microencapsulating materials as the carrier.

In any insecticidal or larvacidal composition of the invention, the baculovirus can be a recombinant baculovirus that has been engineered to express one or more insect-antagonistic genes. The insect-antagonistic gene can be any gene that interferes with the growth, development or reproduction of the insect. Such an engineered baculovirus is more aggressive in killing its host. By improving the rate of killing, such engineered baculoviruses may limit the number of subsequent generations of the insect that are produced, limit the opportunity for disease-causing viruses vectored by the insect to increase in number, and limit the potential for insects to develop resistance to the gene. In specific embodiments, the insect-antagonistic gene is selected from the group consisting of: scorpion toxins, straw itch-mite toxin, spider toxins, snail toxins, insect hormones, insect hormone mimics, sterilization peptides. However, it is recognized that it may not always be advantageous to improve the rate of killing of the insect. For example, in the case of mosquito larvae, a slower kill rate may be advantageous because it maintains competition for nutrients and space against noninfected larvae.

Recombinant baculoviruses can be made using techniques well-established in the art. Generally, the recombinant baculovirus may be prepared by cloning a gene encoding the insect-antagonistic gene into a baculovirus transfer vector at a restriction site downstream of a promoter capable of directing expression of the insect-antagonistic gene in insect cells, and co-transfecting cells susceptible to baculovirus infection with the recombinant transfer vector and an intact wild-type baculovirus DNA. Homologous recombination occurs, resulting in a recombinant baculovirus harbouring the chimeric gene operably linked to a promoter (U.S. Pat. No. 5,166,317). The recombinant baculovirus may or may not contain an expressible polyhedrin gene. When an expressible polyhedrin gene is provided, the occluded form of the virus is produced. Alternatively, those of routine skill in the art can construct recombinant, occluded baculoviruses by coinfection of cells with a helper virus which supplies polyhedrin gene function. The construction of a stable, occluded recombinant nuclear polyhedrosis virus which has a functional polyhedrin gene and which, in insect cells infected therewith, expresses an insect-antagonistic gene which is secreted by the cells, the insect-antagonistic gene product being expressed with a signal peptide such that the insect-antagonistic gene product is secreted from the insect cells is described in U.S. Pat. No. 5,770,192.

The present invention also provides methods for controlling insect pests comprising the step of applying an insect-controlling amount of the insecticidal compositions of this invention to a habitat for the insect pest. The insect-controlling amount is the amount sufficient to interfere with the growth, development and/or reproduction of the insect. The insect controlling amount can readily be determined experimentally by a person of ordinary skill in the art using bioassays and other information available in the art, examples of which are described herein.

Also disclosed and claimed herein are specific methods for controlling mosquitoes comprising the step of applying a mosquito-controlling amount of a mosquito larvacidal composition to a habitat of mosquitoes. The amount to be applied can be in a liquid or non-liquid formulation. The formulation is chosen to maximize exposure of the target mosquito population to the larvacidal composition by conventional application methods. Since mosquito larvae are filter feeders, the method of delivery is by ingestion. Delivery can be enhanced by the addition of feeding stimulants. In a preferred embodiment, the virus and sufficient $Mg^{++}$ are microencapsulated for delivery together to the mosquito gut. Encapsulation methods are well-documented in the art. Encapsulation of baculoviral-based insecticides helps to maintain activity by protecting the virus from harmful environmental conditions. Starch, flour and gluten have been studied extensively as materials to encapsulate insecticides. Such encapsulated insecticides can be applied as granular or sprayable formulations. Shasha et al. (U.S. Pat. No. 5,750,467) describe dispersible encapsulations or adjuvants that use plant lignins to deliver insecticides, such as baculoviruses. Lebo, Jr. et al. (U.S. Pat. No. 5,552,149) describe methods for microencapsulation such as pesticides that employ lignosulfonates, especially to provide protection from ultraviolet rays. The mosquito-controlling amount is the amount sufficient to interfere with the growth, development and/or reproduction of the mosquito larvae. In a specific embodiment, the habitat to which the larvacidal composition is applied is a mosquito breeding area, e.g. a body of water. In a specific embodiment, the mosquitoes to be controlled are members of the Culicidae.

The invention herein described further comprises a newly isolated mosquito-infecting baculovirus, hereinafter referred to as a CuniNPV, that is characterized by one or more of the following:

(a) nuclear occlusion bodies, globular in shape, diameter approximately 400 nm (e.g. ±10 nm), each containing between 1–8 rod-shaped virions, approximately 200× 40 nm;

(b) nuclear occlusion bodies, with no surrounding membrane, with a density of approximately 1.14–1.18 g/ml which agglutinate upon freezing, and (c) infectious in *Culex quinquefasciatus* and *Culex nigripalpus*.

The isolated mosquito-infecting baculovirus can be further characterized by the presence of major occlusion body proteins, sized as 29.7 kDa and 97 kDa on SDS-PAGE.

Alternatively, the novel mosquito-infecting baculovirus of this invention can be characterized as a baculovirus which contains nucleic acid that shares at least 60% identity with the sequence of one or more nucleic acids selected from the group of sequences set forth as SEQ ID NO:1; SEQ ID NO:4; SEQ ID NO:10; SEQ ID NO:19; SEQ ID NO:38; SEQ ID NO:42; SEQ ID NO:44; SEQ ID NO:46; SEQ ID NO:48; SEQ ID NO:50; SEQ ID NO:53; SEQ ID NO:61; SEQ ID NO:66; SEQ ID NO:70; SEQ ID NO:72; SEQ ID NO:74; SEQ ID NO:76; SEQ ID NO:80; SEQ ID NO:83; SEQ ID NO:87; SEQ ID NO:94; SEQ ID NO:106; SEQ ID NO:117; SEQ ID NO:130; SEQ ID NO:145, and SEQ ID NO:146. In preferred embodiments, the novel mosquito-infecting baculovirus of this invention can be characterized as a baculovirus which contains nucleic acid that shares at least 70%, 80% or 90% identity with the sequence of one or more nucleic acids selected from the group of sequences set forth as SEQ ID NO:1; SEQ ID NO:4; SEQ ID NO:10; SEQ ID NO:19; SEQ ID NO:38; SEQ ID NO:42; SEQ ID NO:44; SEQ ID NO:46; SEQ ID NO:48; SEQ ID NO:50; SEQ ID NO:53; SEQ ID NO:61; SEQ ID NO:66; SEQ ID NO:70; SEQ ID NO:72; SEQ ID NO:74; SEQ ID NO:76; SEQ ID NO:80; SEQ ID NO:83; SEQ ID NO:87; SEQ ID NO:94; SEQ ID NO:106; SEQ ID NO:117; SEQ ID NO:130; SEQ ID NO:145, and SEQ ID NO:146. In specific embodiments, mosquito-infecting baculoviruses of this invention comprise a nucleic acid sequence with at least 75%, 77%, 79%, 81%, 83%, 85%, 87%, 89%, 91%, 93%, 95%, 97% or 99% identity to a nucleic acid selected from the group of sequences set forth as SEQ ID NO:147 and SEQ ID NO:148.

An example of a CuniNPV has been deposited with the American Type Culture Collection (10801 University Boulevard, P.O. Box 1549, Manassas, Va. 20108) under the Budapest Treaty on the International Recognition of the Deposit of Microorganism for the Purposes of Patent Procedure, on Feb. 3, 1999 as accession number VR-2639. The genome sequence of VR-2639 is deposited in GenBank under Accession Number AF403738.

An isolated mosquito-infecting baculovirus is one which has been either purified from infected mosquito larvae, cloned through plaque purification in mosquito cell culture, or otherwise prepared from a single viral isolate. A method for isolating the novel baculoviruses of this invention from infected mosquito larvae is described in the Examples.

Additional mosquito-infecting baculoviruses of this invention can be identified by probing viral DNA isolated from diseased mosquito larvae, obtained as herein described. One method for detection is the use of polymerase chain reaction amplification. Polymerase chain reaction (PCR) amplification can be used to detect other mosquito-infecting baculoviruses of this invention by amplifying baculoviral specific DNA sequences. Repeated cycles of denaturation, primer annealing and extension carried out with polymerase, e.g., a heat stable enzyme Taq polymerase, lead to exponential increases in the concentration of desired DNA sequences. Using the nucleic acid sequences of a mosquito baculovirus as disclosed herein, synthetic oligonucleotides, or "primers", can be prepared which are complementary to the ends of sequences which are to be amplified. The sample DNA, obtained from mosquito larval populations, can be denatured at high temperatures (e.g., 95° C.) and then reannealed in the presence of a large molar excess of the primers. The primers, oriented with their 3' ends pointing towards each other, hybridize to opposite strands of the target sequence and prime enzymatic extension along the nucleic acid template in the presence of the four deoxyribonucleotide triphosphates. The end product is then denatured again for another cycle. After this three-step cycle has been repeated several times, amplification of a DNA segment by more than one million-fold can be achieved.

Primers chosen for the PCR amplification should be at least approximately 10 nucleotides in length and amplifying a product at least approximately 30 nucleotides in length. The length and G+C content of the primers are used to determine the melting temperature ($T_m$) according to formulas known in the art. The $T_m$ establishes the temperature at which primer annealing to the sample DNA is performed. For primers shorter than 20 nucleotides, an estimate of $T_m$ can be calculated as $T_m$=4(G+C)+2(A+T), while for longer primers, an estimate of the $T_m$ requires the use of the nearest neighbor calculation, which takes into account thermodynamic parameters and is embedded in most available computer programs for designing PCR primers (see, e.g. Dieffenbach, C S et al. 1995 General concepts for PCR primer design. IN: PCR Primer, A Laboratory Manual; Dieffenbach and Dveksler, eds., Cold Spring Harbor Laboratory Press, Plainview, N.Y.).

Detection of the amplified product can be by any of several standard methods, such as electrophoresis on an agarose or polyacrylamide gel and ethidium bromide staining to visualize the nucleic acids on the gel. Once the presence of a baculovirus in the sample has been detected, the novel mosquito-infecting baculovirus can be isolated and purified according to methods described herein.

The novel mosquito-infecting baculoviruses of the present invention can be propagated and produced by repeatedly infecting mosquito larvae and harvesting the larvae. Alternatively, the novel mosquito-infecting baculoviruses of the present invention can be propagated by introducing the baculovirus to a cultured mosquito cell, growing the mosquito cells for a period until inclusion bodies are detected inside the cells and then harvesting the baculovirus from the cells. Methods for culturing mosquito cells have been described (see, e.g. Kurtti and Munderloh 1984 Adv. Cell Cult. 3:259–302; Oelofsen, M J et al. 1990 J. Med. Entomol. 27:939–944; Charpentier, G et al. 1995 J. Med. Entomol. 32:793–800). In a specific embodiment, the mosquito cell culture medium for propagating the virus contains at least 1 mM divalent cation and less than 1 mM, $Ca^{++}$. In a preferred embodiment, the mosquito cell culture medium contains at least 5 mM $Mg^{++}$ and less than 1 mM, and preferably less than 0.5 or 0.1 mM, $Ca^{++}$.

Mosquito-infecting baculoviruses of this invention with significant homology, i.e. sequence identity, to one or more nucleic acids selected from the group of sequences set forth as SEQ ID NO:1; SEQ ID NO:4; SEQ ID NO:10; SEQ ID NO:19; SEQ ID NO:38; SEQ ID NO:42; SEQ ID NO:44; SEQ ID NO:46; SEQ ID NO:48; SEQ ID NO:50; SEQ ID NO:53; SEQ ID NO:61; SEQ ID NO:66; SEQ ID NO:70; SEQ ID NO:72; SEQ ID NO:74; SEQ ID NO:76; SEQ ID NO:80; SEQ ID NO:83; SEQ ID NO:87; SEQ ID NO:94; SEQ ID NO:106; SEQ ID NO:117; SEQ ID NO:130; SEQ ID NO:145, and SEQ ID NO:146 can readily be obtained by screening collected mosquito larvae suspected of being infected with a probe comprising one or more nucleic acid sequences contained in SEQ ID NO:1; SEQ ID NO:4; SEQ ID NO:10; SEQ ID NO:19; SEQ ID NO:38; SEQ ID NO:42; SEQ ID NO:44; SEQ ID NO:46; SEQ ID NO:48; SEQ ID NO:50; SEQ ID NO:53; SEQ ID NO:61; SEQ ID NO:66; SEQ ID NO:70; SEQ ID NO:72; SEQ ID NO:74; SEQ ID NO:76; SEQ ID NO:80; SEQ ID NO:83; SEQ ID NO:87; SEQ ID NO:94; SEQ ID NO:106; SEQ ID NO:117; SEQ ID NO:130; SEQ ID NO:145, and SEQ ID NO:146, or a unique fragment thereof. Nucleic acid samples from collected mosquito larvae that specifically hybridize with such a probe under relatively high-stringency conditions (e.g. low salt conditions and/or high temperatures of hybridization) can be processed for the isolation of a mosquito-infecting baculovirus of this invention according to the procedures described herein.

As is known in the art, annealing reactions (between primers or probes and the sample DNA or RNA) are affected by the concentration, sequence complexity, base composition and length of the primer/probe; the concentration of monovalent cations; the presence of hybrid destabilizing agents (e.g. formamide); and the incubation temperature. The following formula relates many of these parameters to the $T_m$ (the temperature at which half of the DNA molecules have dissociated into single strands): $T_m$=81.5° C.+16.6 log M+41 (mole fraction of G+C)−(500/L)−0.62 (% formamide), where M is the molar concentration of monovalent cations and L is the molecular length of the probe DNA in bases. Increasing the salt concentration from 100 mM to 1 M increases the $T_m$ by 16° C. Annealing temperatures that are 25° C. below the $T_m$ of the native DNA usually provide the maximum rate of hybridization. For example, for genomic DNAs, the annealing temperature is typically 65° C. in aqueous solvents containing 250 mM $Na^+$. Adding formamide to a final concentration of 50% lowers the annealing temperature to 42° C. In general, the higher the probe concentration, the more rapid the annealing reaction. However, the competing reaction of probe strands reannealing to each other will also occur more rapidly. For this reason, probe concentrations need to be kept relatively low (≦10 ng/ml hybridization solution). Alternatively, single-stranded probes can be used.

Stringency, or the degree to which mismatches are permitted in the binding of two single strands, is a critical parameter in all annealing reactions and is affected by salt concentration and annealing temperature. The $T_m$ of a duplex decreases by approximately 1° C. for each 1% of mismatched base pairs, except for short DNA (15–30 bases, for which each mismatch can reduce the Tm by 5° C. (Wolff. R and Gemmill. R 1997 Purify and analyzing genomic DNA IN: Genome Analysis—A Laboratory Manual, Vol. 1; Birren, B et al., eds., Cold Spring Harbor Laboratory Press, Plainview, N.Y.). The higher the salt concentration, the greater the number of mismatches that can be tolerated at a given temperature. The final stringency of the reaction can then be readily adjusted by using a series of post-hybridization washes of increasing stringency. The specific hybridization signal should be assessed by autoradiography between these washes and compared with the background.

Several standard hybridization conditions have been developed on the basis of the considerations above. Stringent hybridization can be performed in an aqueous hybridization solution containing 2×SSC at 65° C. General methods for optimizing and performing hybridizations are set forth in Sambrook et al., "Molecular Cloning, a Laboratory Manual," Cold Spring Harbor Laboratory Press (1989). Any viruses so isolated can be confirmed to be a mosquito-infecting baculovirus of this invention by performing the biochemical/molecular, microscopic and infectivity characterizations described herein.

The novel baculoviruses of this invention can be engineered to express an insect-antagonistic gene under the control of a baculoviral promoter in amounts sufficient to produce a debilitating effect in the mosquito, for example paralysis or premature molting.

In one embodiment, a recombinant mosquito baculovirus can be constructed by inserting the promoter/insect-antagonistic gene at a location in the mosquito baculovirus genome that is a nonessential region for viral replication and propagation, by methods known to those skilled in the art. For example, the baculoviral genes identified as EGT, p10, DA26, ETL, p94 and orf603 have been shown previously to be good sites for insertion of an engineered promoter/insect-antagonistic gene construct. The egt gene in baculoviruses is typically located adjacent to the late expression factor 1 (lef-1) gene (SEQ ID NO:147, also present at nucleotides 2630–3334 in SEQ ID NO:13). The p10 gene is typically located immediately upstream of and in opposite orientation to the p74 gene (SEQ ID NO:148; also present at nucleotides 222–1253 in SEQ ID NO:66).

In a specific embodiment, the promoter/insect-antagonistic gene is inserted into the non-essential gene locus, by first constructing a transplacement, or transfer, plasmid which contains the desired promoter/insect-antagonistic gene flanked by CuniNPV non-essential gene sequences, and all the elements necessary for autonomous replication in bacteria, such as *E. coli*. Such plasmids are then cotransfectecd into insect cells or larvae with the transplacement plasmid and wild type CuniNPV, thus allowing the allelic replacement of the non-essential gene of CuniNPV with the desired promoter/insect-antagonistic gene constuct. The desired recombinant CuniNPV is isolated after selection on the basis of its non-essential gene function-negative phenotype and screening for the proper allelic replacement events by restriction endonuclease analysis and Southern hybridization. (Miller et al. (1987) "Biotechnology in Invertebrate Pathology and Cell Culture" pp. 295–303; Miller et al. (1986) in Genetic Engineering. Principles and Methods, Vol. 8, eds. J. Setlow and A. Hollaender, Plenum Press, New York, pp.277–298; U.S. Pat. No. 5,266,317).

The present invention also provides methods for controlling baculovirus infections in invertebrates such as beneficial insects and members of the Crustacea, e.g. shrimp species such as *Penaeus duorarum* and *Penaeus aztecus*. The baculovirus known as "Baculovirus penaei", commonly known as "BP" and designated as PvSNPV (Francki, R. I. B., Fauquet, C. M., Knudson, D. L. and Brown, F. (Eds.) 1991 "Classification and Nomenclature of Viruses," 5$^{th}$ Report of the International Committee on Taxonomy of Viruses; Springer-Verlag, New York) is known to infect at least 14 species of penaeid shrimp and can can cause serious epizootics with high mortality of larval and postlarval stages in some of those species (Lightner, D V and Redman R M 1991 Host, geographic range and diagnosis procedures for the penaeid virus diseases of concern to shrimp culturists in the Americas; In "Frontiers in Shrimp research"; P. Deloach, W. J. Dougherty, and M. A. Davidson. eds., pp. 177–196; Elsevier, Amsterdam). BP is responsible for annual economic losses in cultured penaeid shrimp in the Americas and Hawaii due to mass mortalities that occur in the hatchery phase of production (Stuck, K C and Overstreet R M 1994 J Invertebr. Pathol 64:18–25). BP also commonly infects a substantial number of wild brown shrimp, *P. aztecus*, from the northern Gulf of Mexico (Overstreet, R M 1994 "BP in Penaeid Shrimps" In USMSFP 10$^{th}$ Anniversary Review, Gulf Coast Research Laboratory Special Publ. No. 1:97–106). The method disclosed herein comprises administering to the invertebrate an amount of calcium, iron or copper ions that is effective in reducing or eliminating baculoviral infections. In specific embodiments, the effective calcium, iron or copper ion concentration is 1 mM, 5 mM or 10 mM. In a specific embodiment, calcium, iron or copper ions are added to the water in which shrimp are living or being farmed to give an effective concentration of at least 1 mM.

The invention also provides an isolated nucleic acid comprising the nucleotide sequence set forth in SEQ ID NO:1; SEQ ID NO:4; SEQ ID NO:10; SEQ ID NO:19; SEQ ID NO:38; SEQ ID NO:42; SEQ ID NO:44; SEQ ID NO:46; SEQ ID NO:48; SEQ ID NO:50; SEQ ID NO:53; SEQ ID NO:61; SEQ ID NO:66; SEQ ID NO:70; SEQ ID NO:72; SEQ ID NO:74; SEQ ID NO:76; SEQ ID NO:80; SEQ ID NO:83; SEQ ID NO:87; SEQ ID NO:94; SEQ ID NO:106; SEQ ID NO:117; SEQ ID NO:130; SEQ ID NO:145, and SEQ ID NO:146, as well as allelic variants, homologs or unique fragments thereof. To be unique, the fragment must be of sufficient size to distinguish it from other known nucleic acid sequences, most readily determined by comparing any nucleic acid fragment to the nucleotide sequences of nucleic acids in computer databases of such sequences, such as GenBank. Such comparative searches are standard in the art. The fragment may code for a polypeptide, e.g. SEQ ID NO:147 or SEQ ID NO:148, or it may be a primer or probe sequence. Typically, a unique fragment useful as a primer or probe will be at least about 20 to about 25 nucleotides in length, depending upon the specific nucleotide content of the sequence. Additionally, fragments can be, for example, at least about 30, 40, 50, 75, 100, 200 or 500 nucleotides in length. The nucleic acids can be single or double stranded, and can be DNA or RNA, depending upon the purpose for which it is intended.

The present invention additionally provides an isolated nucleic acid that hybridizes under stringent conditions with a nucleic acid selected from the group of sequences set forth in SEQ ID NO:1; SEQ ID NO:4; SEQ ID NO:10; SEQ ID NO:19; SEQ ID NO:38; SEQ ID NO:42; SEQ ID NO:44; SEQ ID NO:46; SEQ ID NO:48; SEQ ID NO:50; SEQ ID NO:53; SEQ ID NO:61; SEQ ID NO:66; SEQ ID NO:70; SEQ ID NO:72; SEQ ID NO:74; SEQ ID NO:76; SEQ ID NO:80; SEQ ID NO:83; SEQ ID NO:87; SEQ ID NO:94; SEQ ID NO:106; SEQ ID NO:117; SEQ ID NO:130; SEQ ID NO:145, SEQ ID NO:146, SEQ ID NO:147, and SEQ ID NO:148. In a specific embodiment, stringent conditions would include an aqueous hybridization solution comprising the nucleic acid probe and 0.07 M $NaH_2PO_4$, 0.18 M $Na_2HPO_4$, 0.001 M EDTA, 7% SDS, 1% BSA at 65° C., followed by posthybridization washes as follows: 2×SSC/0.1%SDS at room temperature for 5 minutes, followed by two washes in 0.1×SSC/0.1%SDS at 65° C. for 20 minutes each. Such hybridizing nucleic acids can be fragments of the complementary strands for the referenced sequences or can be primers or probes that can identify the referenced sequences.

In a specific embodiment, the invention provides an isolated nucleic acid encoding a polypeptide comprising the amino acid sequence set forth in SEQ ID NO:2, SEQ ID NO:3, SEQ ID NO:5, SEQ ID NO:6, SEQ ID NO:7, SEQ ID NO:8, SEQ ID NO:9, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:29, SEQ ID NO:30, or SEQ ID NO:31, SEQ ID NO:32, SEQ ID NO:34, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:52, SEQ ID NO:54, SEQ ID NO:55, SEQ ID NO:57, SEQ ID NO:58, SEQ ID NO:60, SEQ ID NO:62, SEQ ID NO:64, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:82, SEQ ID NO:84, SEQ ID NO:85, SEQ ID NO:86, SEQ ID NO:88, SEQ ID NO:89, SEQ ID NO:91, SEQ ID NO:93, SEQ ID NO:95, SEQ ID NO:96, SEQ ID NO:97, SEQ ID NO:98, SEQ ID NO:99, SEQ ID NO:10, SEQ ID NO:102, SEQ ID NO:103, SEQ ID NO:104, SEQ ID NO:105, SEQ ID NO:107, SEQ ID NO:108, SEQ ID NO:109, SEQ ID NO:110, SEQ ID NO:111, SEQ ID NO:112, SEQ ID NO:114, SEQ ID NO:115, SEQ ID NO:116, SEQ ID NO:118, SEQ ID NO:119, SEQ ID NO:120, SEQ ID NO:121, SEQ ID NO:122, SEQ ID NO:123, SEQ ID NO:124, SEQ ID NO:125, SEQ ID NO:127, SEQ ID NO:128, SEQ ID NO:129, SEQ ID NO:131, SEQ ID NO:132, SEQ ID NO:33, SEQ ID NO:134, SEQ ID NO:135, SEQ ID NO:136, SEQ ID NO:138, SEQ ID NO:139, SEQ ID NO:140, SEQ ID NO:141, SEQ ID NO:142, SEQ ID NO:143, or SEQ ID NO:144. Homologies of these amino acid sequences to sequences in the computer databases are presented in Tables 11 and 12. Table 11 presents a comparison of these CuniNPV amino acid sequences with known Lepidopteran baculovirus amino acid sequences. Table 12 presents non-baculoviral sequence matches to the CuniNPV amino acid sequences in the databases. The analyses presented in both tables were done using BLASTP 2.0.8 (Altschul, S F et al 1997 Nucleic Acids Res. 25:3389–3402).

The present invention additionally provides a purified polypeptide or protein encoded by a nucleic acid of this invention. Purified means substantially free from the naturally occurring materials with which the polynucleotide or polypeptide is normally associated in nature. The purified protein need not be homogeneous, but must be sufficiently free of contaminants to be useful in research or commercial applications, for example, for use in detecting or preparing antibodies to the protein, or in screening libraries of molecules for those molecules that interact with the protein. Greater levels of purity can be obtained using methods derived from well known protocols. The polypeptide or protein can be readily obtained by any of several means. For example, the nucleotide sequence encoding the polypeptide can be translated and then the corresponding polypeptide, or any portion thereof, can be synthesized mechanically by standard methods. Additionally, the nucleic acids encoding the polypeptide can be expressed or synthesized, an antibody specific for the resulting polypeptide can be raised by standard methods (see, e.g., Harlow and Lane, *Antibodies: A Laboratory Manual*, Cold Spring Harbor Laboratory, Cold Spring Harbor, N.Y. 1988), and the polypeptide can be isolated from infected mosquito larvae or cells by selective binding with the antibody. Such polypeptides can be purified to the extent desired by standard methods of protein purification (see, e.g., Sambrook et al., *Molecular Cloning: A Laboratory Manual*, 2nd Ed., Cold Spring Harbor Laboratory, Cold Spring Harbor, N.Y., 1989). The antibodies so produced can be used as diagnostic tools for the presence of the virus.

As will be appreciated by those skilled in the art, the invention also includes those polypeptides having slight variations in amino acid sequences or other properties. Amino acid substitutions can be selected by known parameters to be neutral (see. e.g., Robinson W E Jr. and Mitchell W M., AIDS 4:S151–S162(1990)). Such variations may arise naturally as allelic variations (e.g., due to genetic polymorphism) or may be produced by human intervention (e.g., by mutagenesis of cloned DNA sequences). Such as induced point, deletion, insertion and substitution mutants. Minor changes in amino acid sequence are generally preferred, such as conservative amino acid replacements, small internal deletions or insertions, and additions or deletions at the ends of the molecules. Substitutions may be designed based on, for example, the model of Dayhoff, el al. (in *Atlas of Protein Sequence and Structure* 1978, Nat'l Biomed. Res. Found., Washington, D.C.). These modifications can result in changes in the amino acid sequence, provide silent mutations, modify a restriction site, or provide other specific mutations. Likewise, such amino acid changes result in a different nucleic acid encoding the polypeptides and proteins. Thus, alternative nucleic acids are also contemplated by such modifications.

The present invention also provides cells containing a nucleic acid of the invention. A cell containing a nucleic acid encoding a polypeptide typically can replicate the DNA and, further, typically can express the encoded polypeptide. The cell can be a prokaryotic cell, particularly for the purpose of producing quantities of the nucleic acid, or a eukaryotic cell, particularly an insect cell. The cell is preferably an insect cell for the purpose of expressing the encoded polypeptide so that the resultant produced polypeptide has insect cell-determined protein processing modifications.

Throughout this application, various publications are referenced. The disclosures of these publications in their entireties are hereby incorporated by reference into this application in order to more fully describe the state of the art to which this invention pertains.

EXAMPLES

Example 1

Methods

A. Field Collections

Mosquito larvae were collected from a man-made settling pond of swine effluent located in Gainesville, Fla. The pond was approximately 30 square meters and surrounded by elderberry trees (*Sambucus canadensis*) with pennywort (*Hydrocotyl ranunculoides*) and duckweed (Lemna spp.) along the margins. Samples were collected once or twice a week during the peak mosquito breeding periods and at least once a month during the off season.

Larvae were concentrated at the field site by straining 50–60 liters of field water through 60 mesh sieves at the site and placing the collected larvae in 15–30 liters of field water. In the laboratory, larvae were again strained through a series of 10, 18, 35 and 80 mesh sieves (2.0, 1.0, 0.5, 0.13 mm openings respectively) and the contents of each sieve washed into 300–800 ml of water. Third and fourth instar larvae were retained by the 35 and 18 mesh sieves while the first and second instar larvae were found in the 80 mesh sieve. The total volume of water and larvae was measured from the 18 and 35 mesh sieves and after agitation, a sample of 10 to 100 ml removed, measured and the number of larvae counted. Larvae from the sample were examined for signs of infection and for species identification. The total number of larvae, the proportion of each species and the percentage infection was estimated from the samples of the two sieves. If a significant number of larvae were retained in the 10 mesh sieve, a sample was taken from it and included in the estimates. The estimate of the total number of larvae collected from the 35 mesh or larger was used as an indicator of the larval population.

B. Water Analysis and Characterization

Samples of the field water were prepared for chemical analysis by several methods. Water strained through 400 mesh (38 micron openings) was centrifuged it 4,800 g for 10 min and the supernatant frozen. In addition, 10 ml samples of the supernatant and unfiltered water were digested in 1 N $HNO_3$ by heating a 1:1 mixture of water: 1 N $HNO_3$ to just below the boiling point until the volume had been reduced to 1–2 ml. The residue was reconstituted in 1 N $HNO_3$ and held at room temperature. In addition, unfiltered water was filtered through a Whatman No. 41 filter and stored frozen. Water samples were submitted for elemental analysis to the University of Florida Analytical Research Laboratory (Room 631 Wallace Building, University of Florida, Gainesville, Fla.). Cation concentrations were obtained using ICAP argon plasma (Thermo-Jerrell-Ash Corp, 27 East Forge Parkway, Franklin, Mass. 02038). The conductivity of the field water was 1.8±0.4 mmhos and the pH averaged 7.8±0.03 (n=92). A sample of field water was analyzed to determine the content of 20 cations. Potassium, sodium, magnesium, and calcium accounted for 90% of the cations with potassium having the highest concentration. Additional water samples were evaluated for these predominant cations, and the average concentrations are summarized in Table 4.

C. Electron Microscopy

Infected larvae were prepared for ultrastructural examination by fixing dissected guts in 2.5% glutaraldehyde for 2 hr, postfixing in 2% osmium tetroxide, dehydrating in ethanol series and embedding in epon-araldite. Thin sections, stained in uranyl acetate land lead citrate, were photographed at 75 kV. Suspensions of virions, released by alkaline treatment, were negatively stained in 1% PTA on coated grids and photographed at 75 kV.

D. Laboratory Bioassay

Groups of 100 *Culex quinquefasciatus* larvae, 3 or 4 days old, were exposed in 4 oz plastic cups in 100 ml of water with 2 ml of 2% alfalfa and potbelly pig chow mixture (2:1). In paired tests, virus from eight infected larvae were homogenized and added to the field water while the other cup had no virus added. Larvae were exposed in one of the following: field water strained through 400 mesh sieves, field water supernatant, field water pellet, or deionized water. Different salt mixtures were made up, each one using all but one of the following: 1.8 mM MgCl, 0.5 mM $CaCl_2$, 6.0 mM KCl, 1.8 mM NaCl and 3 mM $NH_4Cl$. Additionally, in paired tests, larvae were exposed in containers with and without the addition of 10 mM $MgCl_2$, and with and without virus. Additional treatments included alkali pretreatment of the virus prior to exposure (Federici B A and Lowe, 1972 *J. Invertebr. Pathol.* 20:14–21) and the addition of the optical brightener Calcofluor M2R (Shapiro and Robertson, 1990, *J. Econ. Entomol.* 85: 1120–1124). After 48 hrs, the larvae were removed and examined for signs of infection. Only those larvae with hypertrophied nuclei either in the midgut or the gastric caecae were scored as positive.

E. Isolation of CuniNPV and Molecular Characterization

Density gradient centrifugation of homogenized infected larvae on a continuous Ludox HS40 gradient (DuPont), commonly used to isolate microsporidia, was adapted to efficiently purify occlusion bodies (Undeen, A H and J V ávra, 1997, Research methods for entomopathogenic Protozoa, In: Manual of Techniques in Insect Pathology, L. A. Lacey (Ed.), 117–151, San Diego: Academic Press). After centrifugation was completed, the band containing the inclusion bodies was washed in 0.001N NaOH, pH 10.0 to efficiently remove all of the silica. Washing only in deionized water leaves traces of silica that can crystallize and interfere with later manipulations of the inclusion bodies. DNA was extracted using standard protocols. Pulsed field gel electrophoresis and restriction digests with Eco RI, BamHI, and PstI were conducted to determine the genome size.

F. Sequencing of CuniNPV

Viral DNA with digested with a restriction enzyme (HindIII, PstI, or EcoRI), and the fragments were cloned into pUC19 (shotgun cloning). To clone larger fragments, digested viral DNA was electrophoresed, and the band(s) of interest were eluted from the gel. Sequencing of purified fragments was done at the University of FLorida DNA Sequencing Core Laboratory (Gainesville, Fla.) using the Taq DyeDeoxy Terminator protocols developed by Applied Biosystems (Perkin-Elmer Corp., Foster City, Calif.) and fluorescence-labeled dideoxynucleotides and primers. Oligo primers were designed using OLIGO 4.0 (National BioSciences, Inc., Plymouth, Minn.) and synthesized at the DNA Synthesis Core Laboratory (University of FLorida, Gainesville, Fla.). The labeled extension products were analyzed on an Applied BioSystems Model 373A or 377 DNA sequencer Perkin Elmer Corp., Foster City. Calif.). Nucleotide sequences were aligned and assembled using programs in the Sequencher 3.0 software package (Gene Codes Corp., An Arbor, Minn.).

G. Mosquito Susceptibility to CuniNPV

CuniNPV produced in *Culex quinquefasciatus* and purified on a Ludox HS40 continuous gradient was used for all tests. Mosquito larvae of various species were obtained from laboratory-reared stock or from field isolations. Larvae were 48 hours old at the time of the bioassays. Groups of 100 healthy larvae were counted into cups with 100 ml of 10 mM $MgCl_2$. For each test, one group was exposed to 10 larval equivalents of CuniNPV and one group was not exposed to the virus, thus serving as a control. To test the susceptibility of the predacious mosquito, *Toxorhynchites ambionensis*, 20 second instar larvae were set up individually in well plates with 10 mM $MgCl_2$ and fed 3 live *Cx. quinquefasciatus* larvae infected with NPV. Similar groups of *Tx. ambionensis* were fed healthy *Cx. quinquefasciatus* larvae and served as a control. One hundred healthy *Cx. quinquefasciatus* larvae, exposed at the same time as the test species, served as positive controls to verify the infectivity of the virus being tested. After 48 hours, all larvae were examined for presence of infection and mortality was calculated. In tests where the positive control gave infection levels lower than 80%, the data was discarded.

Example 2

Host Range of the NPV

Collections of *Cx. nigripalpus* made at different times during the year showed that the presence of four species of Culex varies over the year. *Culex nigripalpus* were present during the warmer months while *Culex quinquefasciatus* were present in cooler months and during the winter. *Culex salinarius* and *Culex restuans* were also present during the winter. A few *Anopheles crucians* were found in the summer and *Culiseta inornata* were present occasionally in the cooler months.

Table 1 compares the CuniNPV infection rate in the four Culex species collected. *Culex nigripalpus* was the most common mosquito and infected larvae were present in 90% of the collections. The average infection rate was 20.1±2.3% with a maximum rate of 60%. The next most frequently collected mosquito was *Cx. quinquefasciatus*, which was present in 49% of the collections. The average infection rate was 7.8±2.0% and the maximum infection rate was 20%. Infected *Cx. salinarius* were present in 34% of the collections with an average infection rate of 11.5±4.6% and a maximum rate of 30%. *Culex restuans* were present in 6% of the collections and no CuniNPV infected *Cx. restuans* were observed.

Larvae infected with a cytoplasmic polyhedrosis virus were collected in January through March in 1997 and 1998. *Culex restuans, Cx. quinquefasciatus,* and *Cx. salinarius* were all infected with the CPV. The highest CPV infection rate was 18%. *Culex nigripalpus* was not present during this time period.

During September to October 1996, the population of *Cx. nigripalpus* was extremely high with collections of 4,300 to 42,000 larvae and the NPV infection rate was as high as 31%. The populations of Culex species fluctuates throughout the year. During March through December 1997, the largest collection was 24,000 larvae consisting of *Cx. salinarius* and *Cx. restuans. Culex nigripalpus* was the predominant mosquito by June through October 1997. For an eight week period from July to September 1997, NPV infected larvae were found in all of the species collections. Table 2 compares the average number of larvae collected and the percentage infection rate for two epizootic periods in 1996 and 1997. In 1997, the population was significantly reduced and the percentage of CuniNPV infected larvae was higher than the 1996 period.

Example 3

Laboratory Transmission

Colony *Cx. quinquesfasciatus* were infected when exposed in field water at a rate ranging from 6–20%, but when insects were exposed in deionized water, the infection rate dropped to between 0 and 3%. Alkali pretreatment and the use of optical brighteners were ineffective in increasing the infection rate in deionized water. Table 3 compares the infection rates from the field samples and assays with colony *Cx. quinquefasciatus* in field water with and without virus. Statistical comparison by a student t-test shows that the difference between infection rates in field water with (35.4% ave.) or without virus (10.7% ave) is significant. In contrast, the infection rate of the virus in deionized water averaged less than 1%. These experiments demonstrate that there is/are additional factor/activator(s) present in the field water that is/are necessary to obtain higher rates of infection of larvae by the virus.

To identify such factors, a correlation analysis between the percentage infection in colony mosquitoes exposed to different samples of field water to which virus is added, and the four cations individually, expressed either as a concentration or as a percentage of the total cation content in the field water is presented in Table 4. There is a negative correlation between the percentage infection and either total water conductivity, K, Na or Ca, while there is a positive correlation with Mg. Alternatively, when the infection percentage is correlated with each cation expressed as a percentage of the principle cations (e.g. Mg/(K+Na+Mg+Ca), only Mg has a significant correlation.

Table 5 summarizes the results from the bioassay of larvae exposed to virus in salt mixtures. Compared to the negative results routinely obtained with deionized water, the addition of a salt mixture significantly improves the infectivity of the virus (which can also be termed the susceptibility of larvae). Further analysis shows that the only salt that enhanced infectivity on its own is $MgSO_4$, while the infectivity in a salt mixture that does not include $CaCl_2$ was more than doubled. These $Ca^{++}$-lacking mixtures, which contain 1.8 mM $Mg^{++}$, have some infectivity, while there is no infectivity in mixtures without any $Mg^{++}$.

Results of infectivity studies using other divalent cations show that several other cations are potential activators, while a few inhibit infection. Table 6 presents data on additional cations, including barium, cobalt, nickel and strontium, which significantly improve the infectivity of the virus. Table 7 demonstrates that copper and iron, in addition to calcium, inhibit infection when added with $Mg^{++}$. Manganese was neutral in its effect. Tin and zinc were too toxic to determine their effect on infectivity.

Example 5

Mosquito Host Range and Morphology of Infection

A. Mosquito Host Range

The CuniNPV infected only species of Culex including *Cx. nigripalpus, Cx. quinquefasciatus* and *Cx. salinarius* (Table 8). The only other Culex species tested, *Cx. restuans*, was not susceptible using laboratory-reared insects.

B. Symptomatology

Gross morphology. Larvae of *Cx quinquefasciatus* and *Cx. nigripalpus* exposed to CuniNPV are typically stunted in development when compared to unexposed individuals. The first signs of infection are observed 24–28 hours post-exposure in cells of the gastric caecae and posterior midgut epithelium. The nuclei of the infected cells are hypertrophied and appeared opaque to white in color due to the proliferation of occlusion bodies within the nuclei. Nuclei of cells in the anterior midgut are rarely infected. Within 48 hours post-exposure many infected nuclei of the gastric caecae and posterior midgut are filled with occlusion bodies. Death of the larvae usually occurs within 72–96 hours.

Fine Morphology. Occlusion bodies of CuniNPV are restricted to nuclei of the midgut epithelium and gastric caecae. Occlusion bodies are globular in shape with a diameter of approximately 300 nm, and they do not have a membrane surrounding them, as is typical for other baculoviruses. Each occlusion body contains up to about 8 rod-shaped virions. The rod-shaped virions were approximately 200×40 nm and composed of a nucleocapsid, intermediate layer and an outer envelope.

Example 6

Biochemical/Molecular Characterization of CuniNPV

The occlusion bodies have a density of 1.14–1.18 g/ml and are sensitive to agglutination upon freezing. Based on pulse field gel electrophoresis and restriction digests with Eco RI. BamHI, and PstI, the genome size of CuniNPV is approximately 70–75 kb. Sequences obtained from a CuniNPV were analyzed for the presence of open reading frames (orf), i.e. sequences coding for polypeptides, and the identified orfs were compared to known sequences in publicly available computer databases to identify homologies. Table 11 presents homologies between the novel orfs from the mosquito-infecting baculoviruses of this invention and known polypeptides from Lepidopteran baculoviruses. Table 12 presents the "best matches", i.e. the highest homologies, between the novel orfs from the mosquito-infecting baculoviruses of this invention and known polypeptides in the database.

mosquitoes are ground into a powder, and $MgCl_2$ is mixed into the powder, in an amount sufficient to promote infection. If additional inert carrier is needed, corn cob grits can be added.

Another formulation involves the preparation of a microencapsulated baculovirus preparation using lignin and magnesium, according to methods described in U.S. Pat. No. 5,750,467. The following formulations were tested:

Formulation 1: 6 g lignin, 0.6 g Mg carbonate, 0.066 g virus

Formulation 2: 6 g lignin, 0.06 g Mg, 0.066 g virus

Formulation 3: 6 g lignin, 6 g Mg, 0.6 g Ca, 0.072 g virus

Formulation 4: 6 g lignin, 6 g Mg, 0.6 g Ca, 0.126 g virus

Formulation 5: 6 g lignin, 0.6 g Mg, 0.066 g virus

Formulation 6: 6 g lignin, 0.06 g Mg, 0.06 g. virus

Example 9

Improved Transmission of AesoNPV

A mosquito baculovirus originally isolated in Louisiana from *Aedes sollicitans* (AesoNPV) was tested against a variety of mosquitoes. As shown in Tables 9 and 10, $MgCl_2$ enhances infectivity approximately 4-fold for *Aedes triseriatus*. In tests with *Aedes aegypti*, usually a poor host for this virus, a 7-fold increase in infectivity was obtained. Also, it was possible to infect a Culex species with a baculovirus from an Aedes host for the first time by using $Mg^{++}$.

TABLE 1

Average infection rate of Culex spp. from collections during October 1996 through January 1998 (79 total collections).

|  | Cx. nigripalpus | Cx. quinquefasciatus | Cx. salinarius | Cx. restuans |
| --- | --- | --- | --- | --- |
| Present | 10/96–1/97 4/97–12/97 | 10/96–5/97 9/97–1/98 | 1/97–3/97 1/98 | 1/97–3/97 1/98 |
| No. collections with infected larvae in sample | 45 | 11 | 8 | 0 |
| No. collections with specified species in samples | 71 | 39 | 27 | 5 |
| Average percentage infection (positive collections only) | 20.1 ± 2.3 | 7.8 ± 2.0 | 11.5 ± 4.6 | 0 |
| Max infection rate | 60 | 20 | 30 | 0 |
| Average field infect rate (positive only) | 15.6 ± 1.9 | 9.9 ± 2.4 | 9.3 ± 1.3 | 7.7 ± 1.9 |

Example 7
Production of CuniNPV 2500 3-day old *Culex nigripalpus* or *Cx. quinquefasciatus* larvae are exposed to 100 larval equivalents of CuniNPV in 3 liters of 14 mM $MgSO_4$. This yields 100% infection, and Virus is harvested at 48 hour post-exposure. Large numbers of trays can be produced quickly to provide large amounts of virus.

Example 8
Formulations for Insecticidal Compositions

Compositions suitable for applying to mosquito habitats can be made from air-dried, infected mosquitoes. The dried

TABLE 2

Comparison of two epizootic periods of nuclear polyhedrosis virus in *Culex nigripalpus*.

|  | Culex Population Index | NPV Infection Rate |
| --- | --- | --- |
| 8/28/96–10/21/96 (N = 8) | | |
| Average ± SE | 15,000 ± 4,300 | 10.6 ± 3.7% |
| Minimum | 4,300 | 1.4% |

TABLE 2-continued

Comparison of two epizootic periods of nuclear polyhedrosis virus in *Culex nigripalpus*.

|  | Culex Population Index | NPV Infection Rate |
|---|---|---|
| Maximum | 42,000 | 31.1% |
| 7/10/97–9/2/97 (N = 8) | | |
| Average " SE | 4,000 ± 1,000 | 28.9 ± 4.6% |
| Minimum | 1,700 | 11.6% |
| Maximum | 9,700 | 48.0% |

TABLE 3

Infection rate of Culex spp. collected in the field and colony *Culex quinquefasciatus* exposed in field water with and without virus added.

| | Field Infection Rate of Culex spp. | Colony *Culex quinquefasciatus* | | | |
|---|---|---|---|---|---|
| | | Field Water | Field Water + Virus | Dionized Water + Virus | 10 mM $MgCl_2$ |
| N | 61 | 61 | 57 | 22 | 68 |
| Average ± SE | 10.7 ± 1.7% | 8.9 ± 1.6% | 35.4 ± 3.1% | 0.5 ± 0.2% | 68.1 ± 3.5% |
| Maximum | 48.0% | 50.0% | 94.8% | 3.0% | 100% |
| Paired Differences Assay in Field Water- Field Infection Rate | | −1.5 ± 1.2%* | | | |
| Assays in Field Water plus virus- Field Water | | | 25.8 ± 2.9%[A] | | |

*Not significantly different from zero.
[A]Significantly different from zero.

TABLE 4

Concentration of principle cations and the correlation coefficient and probability of > |R| of percentage infection with cation content of field water and the conductivity of the samples.

| | Concentration (mM) | | % of Principle Cations | | |
|---|---|---|---|---|---|
| | Mean ± SE N = 22 | R (sign from slope) | Prob > |R| | R (sign from slope) | Prob > |R| |
| K | 10.7 ± 0.5 | −0.28 | 0.19 | −0.37 | 0.10 |
| Na | 3.2 ± 0.2 | −0.31 | 0.18 | −0.37 | 0.10 |
| Mg | 1.9 ± 0.1 | 0.01 | 0.96 | 0.46 | 0.03 |
| Ca | 0.8 ± 0.05 | −0.15 | 0.52 | 0.1 | 0.68 |
| Conductivity (mmhos) | 2.0 ± .06 | −0.33 | 0.14 | | |

TABLE 5

Percentage infection in colony *Culex quinquefasciatus* in salt mixtures of 6.0 mM KCl, 1.8 mM NaCl, 0.5 mM $CaCl_2$ and 1.8 mM $MgCl_2$.

| | % Infection | |
|---|---|---|
| Media | Salt Mixture without Component | Component Alone |
| Complete Salt Mixture | 13.6% | |
| $CaCl_2$ | 19.9% | 0.0% |
| $MgCl_2$ or $MgSO_4$ | 0.0% | 10.9% |
| KCl | 8.6% | 0.0% |
| NaCL | 3.0% | 0.0% |

TABLE 5-continued

Percentage infection in colony *Culex quinquefasciatus* in salt mixtures of 6.0 mM KCl, 1.8 mM NaCl, 0.5 mM $CaCl_2$ and 1.8 mM $MgCl_2$.

| | % Infection | |
|---|---|---|
| Media | Salt Mixture without Component | Component Alone |
| Deionized Water | | 0.0% |

TABLE 6

Activation potential of cations tested with NPV against *Culex quinquesfasciatus*.
Activation by Various Cations
Activators:

| Cation | Dose Range (mM) | % Infection Range |
|---|---|---|
| Ba | 1.25–10.0 | 5.5–12.5 |
| Co | 0.1–0.63 | 17.3–35.9 |
| Mg | 2.0–40.0 | 18.1–100.0 |
| Ni | 0.05–0.2 | 11.3–95.5 |

TABLE 6-continued

Activation potential of cations tested with NPV against *Culex quinquesfasciatus*.
Activation by Various Cations
Activators:

| Cation | Dose Range (mM) | % Infection Range |
|---|---|---|
| Sr | 1.25–10.0 | 8.5–81.4 |

TABLE 7

Inhibition by various Cations

| Cation | Inhibitor |
|---|---|
| Ca | Inhibitor |
| Cu | Inhibitor |
| Fe | Inhibitor |
| Mn | not |
| Sn | maybe |
| Zn | maybe |

TABLE 8

Results of NPV Bioassays against mosquito larvae

| Mosquito Species Tested | Number of Tests | % Mortality* | % Infection |
|---|---|---|---|
| *Aedes aegypti* | 4 | 0 | 0 |
| *A. albopictus* | 3 | 0 | 0 |
| *A. triseriatus* | 3 | 0 | 0 |
| *A. taeniorhynchus* | 3 | 0 | 0 |
| *Anopheles albimanus* | 4 | 7.9 ± 1.4 | 0 |
| *A. quadramaculatus* | 4 | 0 | 0 |
| *Culex nigripalpus*** | 2 | 9.0 ± 1.0 | 42.9 ± 7.1 |
| *C. quinquefasciatus* | 7 | 5.0 ± 1.7 | 88.2 ± 2.9 |
| *C. restuans*** | 1 | 2.1 | 0 |
| *C. salinarius*** | 2 | 0 | 32.9 ± 9.8 |
| *Culesita melanura* | 2 | 0 | 0 |
| *Toxorynchites ambionensis* | 1 | 0 | 0 |

*Abbot-corrected Mortality
**Egg rafts collected from the field and reared in the laboratory

TABLE 9

Different mosquito species exposed to 3–5 larval equivalents of NPV from *Aedes sollicitans* in the presence of MgCl$_2$

| Species Tested | N | % Mortality* | % Infection |
|---|---|---|---|
| *Ae. triseriatus* | 900 | 12.1 | 77.3 |
| *Ur. iowii* | 55 | 5.6 | 77.0 |
| *Cx. nigripalpus* | 200 | 27.7 | 38.0 |
| *Ae. aegypti* | 500 | 9.3 | 26.9 |
| *Ae. albopictus* | 100 | 3.1 | — |
| *Ae. taeniorhynchus* | 100 | — | — |
| *Cx. quinquefasciatus* | 100 | — | — |

*Abbott corrected

TABLE 10

Magnesium Dose Response Test

| Mosquito Species | N | [MgCl$_2$] mM | Viral Dosage (LE) | % Mortality | % Infection |
|---|---|---|---|---|---|
| *Ae. triseriatus* | 100 | 10 | 0 | 26 | — |
| *Ae. triseriatus* | 100 | 2.5 | 5 | 27 | 98.6 |
| *Ae. triseriatus* | 100 | 5 | 5 | 22 | 100.0 |
| *Ae. triseriatus* | 100 | 10 | 5 | 19 | 100.0 |
| *Ae. triseriatus* | 100 | 0 | 5 | 21 | 26.6 |
| *Ae. aegypti* | 100 | 10 | 0 | 98 | — |
| *Ae. aegypti* | 100 | 10 | 5 | 81 | 28.4 |
| *Ae. aegypti* | 100 | 0 | 5 | 93 | 4.3 |

TABLE 11

| SEQ ID NO | Full Length (nt) | ORF | Position (length, a) | Homology to Lepidopteran Baculovirus Amino Acid Sequences (length, aa) | AA Identities | AA Positives | E Value |
|---|---|---|---|---|---|---|---|
| 10 | 6621 | 1 | 2630–3337 (235) | LdNPV LEF-1 (234) | 48/197 (24%) | 80/197 (40%) | 1e-08 |
| | | | | BmNPV LEF-1 (270) | 52/200 (26%) | 83/200 (41%) | 4e-08 |
| | | | | CfNPV LEF-1 (251) | 56/202 (27%) | 82/202 (39%) | 2e-07 |
| | | | | OpNPV LEF-1 (243) | 54/200 (27%) | 80/200 (40%) | 3e-07 |
| | | | | AcNPV LEF-1 (266) | 51/200 (25%) | 81/200 (40%) | 6e-07 |
| | | | | CfNPV LEF-1 (246) | 52/203 (25%) | 79/203 (38%) | 4e-06 |
| 10 | 6621 | 2 | 1887–2498 (203) | AcNPV 1 23.0 kd protein in HE65-PK2 intergenic region (204) | 65/200 (32%) | 107/200 (53%) | 1e-26 |
| | | | | OpNPV hypothetical 22.1 kd protein (orf115) (205) | 66/204 (32%) | 106/204 (51%) | 2e-26 |
| | | | | BmNPV-AcMNPV orf115 (204) | 64/203 (31%) | 105/203 (51%) | 4e-26 |
| | | | | LdNPV unknown (203) | 55/156 (35%) | 86/156 (54%) | 3e-25 |
| | | | | XnGV-AcNPV orf115 homolog (61) | 18/54 (33%) | 30/54 (55%) | 0.001 |
| | | | | LdNPV unknown (530) | 51/215 (23%) | 78/215 (35%) | 1.1 |
| 44 | 1018 | 1 | 85–969 (294) | OpNPV ODV-E56 (374) | 90/253 (35%) | 133/253 (52%) | 8e-26 |
| | | | | CfNPV ODV-E56 (37) | 88/248 (35%) | 126/248 (50%) | 1e-25 |
| | | | | LdNPV envelope protein (356) | 94/290 (32%) | 145/290 (49%) | 3e-25 |
| | | | | CpGV ODV-E56 (355) | 85/279 (30%) | 144/279 (51%) | 9e-25 |
| | | | | AcNPV ODV-E56 (376) | 76/249 (30%) | 124/249 (49%) | 1e-21 |
| | | | | BmNPV ODV-E56 (= AcNPV orf148) (375) | 73/251 (29%) | 127/251 (50%) | 1e-20 |
| | | | | HzNPV ODV-E56 (= AcNPV orf148 homolog) (175) | 59/168 (35%) | 88/168 (52%) | 2e-18 |
| | | | | XnGV envelope protein homolog (190) | 35/129 (27%) | 63/129 (48%) | 6e-05 |

TABLE 11-continued

| SEQ ID NO | Full Length (nt) | ORF | Position (length, a) | Homology to Lepidopteran Baculovirus Amino Acid Sequences (length, aa) | AA Identities | AA Positives | E Value |
|---|---|---|---|---|---|---|---|
| 66 | 2227 | 1 | 222–1256 (344) | LdNPV envelope protein p74 (672) | 101/318 (31%) | 166/318 (51%) | 3e-38 |
| | | | | CfNPV p74 protein (645) | 76/212 (35%) | 121/212 (56%) | 8e-35 |
| | | | | OpNPV p74 protein (644) | 75/212 (35%) | 121/212 (56%) | 8e-35 |
| | | | | AcNPV p74 protein (645) | 78/248 (31%) | 133/248 (53%) | 3e-34 |
| | | | | SlNPV (*Spodoptero lituta*) p74 protein (657) | 90/307 (29%) | 160/307 (51%) | 4e-34 |
| | | | | BmNPV p74 (= AcNPV orf138) (645) | 73/208 (35%) | 119/208 (57%) | 6e-34 |
| | | | | SlNPV (*S. littoralis*) p74 protein (657) | 72/210 (34%) | 122/210 (57%) | 3e-32 |
| | | | | LsNPV p74 (366) | 68/204 (33%) | 120/204 (58%) | 1e-30 |
| | | | | BsNPV unknown protein (196) | 53/190 (27%) | 93/190 (48%) | 3e-12 |
| 66 | 2227 | 2 | 1195–2226 (343) | LdNPV unknown protein (390) | 44/165 (26%) | 71/165 (42%) | 0.007 |
| 72 | 827 | 1 | 256–696 (146) | OpNPV LEF-4 (457) | 25/88 (28%) | 37/88 (41%) | 0.37 |
| 83 | 3198 | 1 | 2–2782 (926) | MbNPV DNA polymerase (628) | 152/607 (25%) | 274/607 (45%) | 3e-45 |
| | | | | SlNPV (*S. litura*) DNA polymerase (603) | 166/662 (25%) | 284/662 (42%) | 8e-44 |
| | | | | HzNPV DNA-directed DNA polymerase (1020) | 175/709 (24%) | 309/709 (42%) | 4e-41 |
| | | | | SeNPV DNA polymerase (636) | 151/608 (24%) | 267/608 (43%) | 5e-41 |
| | | | | HaNPV DNA polymerase (623) | 155/604 (25%) | 269/604 (43%) | 1e-39 |
| | | | | LdNPV DNA polymerase (1014) | 146/622 (23%) | 269/622 (42%) | 1e-39 |
| | | | | XnGV DNA polymerase (1098) | 207/873 (23%) | 361/873 (40%) | 1e-38 |
| | | | | AcNPV DNA polymerase (984) | 185/788 (23%) | 339/788 (42%) | 8e-38 |
| | | | | BsNPV DNA polymerase (674) | 169/624 (27%) | 282/624 (45%) | 1e-37 |
| | | | | LdNPV DNA polymerase (1013) | 149/615 (24%) | 269/615 (43%) | 3e-37 |
| | | | | BmNPV DNA polymerase (988) | 181/759 (23%) | 325/759 (41%) | 7e-37 |
| | | | | OaNPV DNA polymerase (658) | 151/627 (24%) | 262/627 (41%) | 2e-30 |
| | | | | OpNPV DNA polymerase (985) | 171/782 (21%) | 310/782 (38%) | 6e-30 |
| | | | | CfNPV DNA polymerase (990) | 170/779 (21%) | 306/779 (38%) | 9e-28 |
| 94 | 6627 | 3 | 2122–3111 (329) | AcNPV viral capsid associated protein (42.1 kDa protein in LEF8-FP intergenic region) (365) | 73/294 (24%) | 123/294 (41%) | 2e-05 |
| | | | | BmNPV VP1054 = AcMNPV orf54 (365) | 71/294 (24%) | 124/294 (42%) | 2e-05 |
| | | | | LdNPV LdOrf-57 peptide (332) | 58/224 (25%) | 87/224 (37%) | 0.003 |
| | | | | OpNPV hypothetical 42.5 kDa protein (ORF58) (378) | 22/78 (28%) | 41/78 (52%) | 0.034 |
| 94 | 6627 | 7 | 5920–6516 (198) | AcNPV 33 kd early protein homolog (P33), (259) | 33/133 (24%) | 62/133 (45%) | 3e-05 |
| | | | | BmNPV AcNPV orf92 (259) | 31/133 (23%) | 62/133 (46%) | 5e-05 |
| | | | | OpNPV 33 kd early protein (P33) (282) | 42/154 (27%) | 72/154 (46%) | 3e-04 |
| | | | | LdNPV unknown (251) | 43/171 (25%) | 67/171 (39%) | 0.003 |
| | | | | XnGV AcNPV orf92 homolog (115) | 18/51 (35%) | 28/51 (54%) | 0.98 |
| 117 | 7212 | 2 | 4239–5351 (370) | AcNPV 33 kDa early protein homolog, AcORF-92 peptide (259) | 36/140 (25%) | 65/140 (45%) | 3e-07 |
| | | | | BmNPV AcMNPV orf92 (259) | 34/140 (24%) | 65/140 (46%) | 6e-07 |
| | | | | OpNPV 33 kDa early protein (282) | 45/161 (27%) | 75/161 (45%) | 4e-06 |
| | | | | LdOrf-92 peptide (251) | 52/198 (26%) | 78/198 (39%) | 1e-05 |
| | | | | XnGV AcNPV ORF92 homolog (115) | 21/58 (36%) | 32/58 (53%) | 0.013 |
| | | | | LdNPV envelope protein (676) | 24/91 (26%) | 44/91 (47%) | 1.3 |
| 117 | 7212 | 3 | 441–1430 (329) | AcNPV hypothetical 42.1 kd protein in LEF8-FP intergenic region (365) | 73/294 (24%) | 123/294 (41%) | 2e-05 |
| | | | | BmNPV VP1054 (= AcNPV orf54) (365) | 71/294 (24%) | 124/294 (42%) | 2e-05 |
| | | | | LdNPV LdOrf57 peptide (332) | 58/224 (25%) | 87/224 (37%) | 0.003 |
| | | | | OpNPV hypothetical 42.5 kd protein (orf58) (378) | 22/78 (28%) | 41/78 (52%) | 0.034 |

TABLE 12

| SEQ ID NO | Length (nt) | ORF | Position SEQ (length, aa) | Best Match (length, aa) | aa Identities | aa Positive | E Value |
|---|---|---|---|---|---|---|---|
| 1 | 2446 | 1 | 8–1399 (463) | Human papillomavirus type 12 early protein (494) | 31/113 (27%) | 46/113 (40%) | 0.96 |
| | | 2 | 1522–2250 (242) | Fowlpox virus hypothetical protein 8 (154) | 19/74 (25%) | 32/74 (42%) | 1.8 |
| | | 3 | 226–627 (133) | *Caenorhabditis elegans* predicted using gene finder (360) | 22/79 (27%) | 35/79 (43%) | 0.43 |
| | | 4 | 2–208 (68) | Putative transposase Y4UI, Rhizobuim sp. transposase homologue (514) | 20/54 (38%) | 27/52 (%1%) | 2.3 |
| | | 5 | 1–195 (64) | *Pseudomonas stutzeri* polyhydroxybutyrate depolymerase (576) | 14/41 (34%) | 19/41 (46%) | 6.7 |
| | | 6 | 1954–2124 (56) | — | — | — | — |
| | | 7 | 963–1124 (53) | Chain A, structure of diferric mare lactoferrin at 2.62a resolution (689) | 13/44 (29%) | 21/44 (47%) | 9.1 |
| 10 | 6621 | 1 | 2630–3337 (235) | LdNPV late expression factor (LEF) 1 (234) | 48/197 (24%) | 80/197 (40%) | 1e-8 |
| | | 2 | 1887–2498 | AcNPV (orf 115), hypothetical 23.0 kd protein in HE65-PK2 | 56/155 (36%) | 88/155 (56%) | 1e-25 |

TABLE 12-continued

| SEQ ID NO | Length (nt) | ORF SEQ | Position (length, aa) | Best Match (length, aa) | aa Identities | aa Positive | E Value |
|---|---|---|---|---|---|---|---|
| | | | (203) | intergenic region (204) | | | |
| | | 3 | 4813–5388 (191) | *Saccharomyces cerevisiae* protein kinase 1 (1063) | 16/48 (33%) | 25/48 (51%) | 1.7 |
| | | 4 | 11–544 (177) | *Coprinus cinereus* pheromone receptor (518) | 15/51 (29%) | 25/51 (48%) | 2.7 |
| | | 5 | 3601–4125 (174) | human, peptide, T-cell receptor alpha chain, TCR alpha (TLC RB129) (129) | 26/117 (22%) | 50/117 (42%) | 4.5 |
| | | 6 | 5333–5851 (172) | *Xenopus laevis* membrane anchored metalloprotease; disintegrin; cysteine-rich protein (706) | 23/79 (29%) | 37/79 (46%) | 2.5 |
| | | 7 | 4076–4423 (118) | *Bacillus subtilis* methionyl-tRNA synthetase (664) | 14/36 (38%) | 17/36 (46%) | 4.5 |
| | | 8 | 1278–1631 (117) | *Sacchatomyces cerevisiae* probable membrane protein YPR049c-yeast(1178) | 25/67 (37%) | 34/67 (50%) | 0.4 |
| | | 9 | 1444–1791 (115) | *Prunus dulcis* extensin (278) | 13/33 (39%) | 17/33 (51%) | 1.4 |
| | | 10 | 534–860 (108) | *Dictyostelium discoideum* spore coat protein SP87 (677) | 24/81 (29%) | 33/81 (40%) | 0.87 |
| | | 11 | 901–1224 (107) | *Gallus gallus* slow myosin heavy chain 2 (761) | 20/67 (29%) | 39/67 (57%) | 0.042 |
| | | 12 | 3977–4288 (103) | mouse neural cell adhesion molecule long domain form precursor(1115) | 20/64 (31% | 31/64 (48%) | 3.2 |
| | | 13 | 5892–6191 (99) | *Glycine max* guanine nucleotide regulatory protein (211) | 20/76 (26%) | 27/76 (35%) | 2.1 |
| | | 14 | 4458–4742 (94) | human glutamate decarboxylase (EC 4.1.1.15) (593) | 21/55 (38%) | 24/55 (43%) | 5.3 |
| | | 15 | 1640–1885 (81) | — | — | — | — |
| | | 16 | 2243–2476 (77) | envelope surface glycoprotein SU-feline leukemia virus (strain Sarma) (404) | 17/59 (28%) | 25/59 (41%) | 5.9 |
| | | 17 | 6432–6623 (65) | Hepatitis G virus polyprotein (2842) | 14/35 (40%) | 18/35 (51%) | 8.7 |
| | | 18 | 965–1156 (63) | *Lotus japonicus* rac GTPase activating protein 1 (493) | 18/52 (34%) | 23/52 (43%) | 1.0 |
| | | 19 | 4404–4592 (62) | *Drosophila melanogaster* probable transcriptional regulator dre4 (1059) | 16/56 (28%) | 28/56 (49%) | 1.3 |
| | | 20 | 3865–4044 (59) | — | — | — | — |
| | | 21 | 1371–2541 (56) | *Saccharomyces cerevisiae* Sds3 protein-hypothetical (327) | 12/25 (48%) | 13/25 (52%) | 6.9 |
| | | 22 | 2683–2835 (50) | *Oncorhynchus mykiss* retinoblastoma 1 (910) | 12/40 (30%) | 24/40 (60%) | 3.1 |
| 38 | 1300 | 1 | 2–1299 (432) | *Methanococcus jannaschii* P115 homolog (1169) | 78/349 (22%) | 153/349 (43%) | 7e-9 |
| | | 2 | 539–919 (126) | *Escherichia coli* putative O-antigen transporter (415) | 24/81 (29%) | 39/81 (47%) | 3.6 |
| | | 3 | 858–1211 (117) | *Schizosaccharomyces pombe* hypothetical 41.0 kDa protein C1F8.06 in chromosome 1 (385) | 28/89 (31%) | 42/89 (46%) | 1.3 |
| 44 | 1018 | 1 | 85–969 (294) | OpNPV occlusion derived virus envelope protein E56 (ODV-E56) (374) | 70/199 (35%) | 103/199 (51%) | 7e-19 |
| | | 2 | 133–336 (67) | *Rhodococcus* sp. transposase (754) | 16/39 (41%) | 23/39 (58%) | 2.9 |
| 48 | 1076 | 1 | 1–1074 (357) | *Arabidopsis thaliana*, similar to Homo copine I (644) | 33/144 (22%) | 64/144 (43%) | 2.1 |
| | | 2 | 180–362 (60) | *Pyrococcus horikoshii* long hypothetical protein (102) | 13/27 (48%) | 18/27 (66%) | 8.9 |
| | | 3 | 1–153 (50) | *Danio rerio* LIM-domain binding factor 4; LDB4 (374) | 15/41 (36%) | 24/41 (57%) | 4.1 |
| 53 | 1656 | 1 | 242–1528 (428) | *Klebsiella pneumoniae* citrate carrier protein (444) | 157/411 (38%) | 231/411 (56%) | 8e-78 |
| | | 2 | 434–1655 (407) | — | — | — | — |
| | | 3 | 867–1430 (187) | Homo sapiens KIAA0324 (1288) | 47/187 (25%) | 71/187 (37%) | 0.19 |
| | | 4 | 894–1187 (97) | *Drosophila melanogaster* hoemotic protein spalt-major (1355) | 26/90 (28%) | 38/90 (41%) | 0.42 |
| | | 5 | 1440–1655 (72) | Chilo iridescent virus putative small basic protein (57) | 17/30 (56%) | 20/30 (66%) | 0.53 |
| | | 6 | 1180–1341 (53) | *Streptomyces coelicolor* hypothetical protein in PRJL 5' region (ORF 1) (256) | 19/47 (40%) | 25/47 (52%) | 1.1 |
| | | 7 | 94–255 (53) | *Mycobacterium tuberculosis* hypothetical protein Rv1232c (435) | 16/43 (37%) | 20/43 (46%) | 0.8 |
| | | 8 | 64–219 (51) | *Mycobacterium tuberculosis* hypothetical 36.6 kDa protein CY338.11C precursor (1289) | 18/47 (38%) | 24/47 (50%) | 1.8 |
| 66 | 2227 | 1 | 222–1256 | LdNPV envelope protein p74 (672) | 101/318 (31%) | 166/318 (51%) | 3e-38 |

TABLE 12-continued

| SEQ ID NO | Length (nt) | ORF SEQ | Position (length, aa) | Best Match (length, aa) | aa Identities | aa Positive | E Value |
|---|---|---|---|---|---|---|---|
| | | 2 | 1195–2226 (344) | LdNPV unknown (390) | 44/165 (26%) | 71/165 (42%) | 0.007 |
| | | 3 | 116–589 (343) | — | — | — | — |
| 72 | 827 | 1 | 256–696 (157) | OpNPV late expression factor 4 (LEF-4) (457) | 25/88 (28%) | 37/88 (41%) | 0.38 |
| | | 2 | 264–614 (146) | *Toxoplasma gondii* micronemal protein MIC2 (769) | 30/95 (31%) | 41/95 (42%) | 0.35 |
| 76 | 692 | 1 | 27–691 (221) | — | — | — | — |
| | | 2 | 324–691 (122) | — | — | — | — |
| | | 3 | 3–164 (53) | — | — | — | — |
| | | 4 | 13–168 (51) | — | — | — | — |
| 83 | 3198 | 1 | 1–2771 (923) | MbNPV DNA polymerase (628) | 148/607 (24%) | 270/607 (44%) | 1e-40 |
| | | 2 | 2520–3208 (229) | *Bos taurus* beta-1 integrin subunit (773) | 28/108 (25%) | 55/108 (50%) | 0.026 |
| | | 3 | 742–1059 (105) | *Photorhabdus luminescens* insecticidal toxin complex protein TcbA (2504) | 16/45 (35%) | 23/45 (50%) | 3.9 |
| | | 4 | 2305–2532 (75) | — | — | — | — |
| | | 5 | 2958–3182 (74) | — | — | — | — |
| | | 6 | 1837–2001 (54) | *Bacillus subtilis* ATP synthase (subunit i) (127) | 12/28 (42%) | 19/28 (67%) | 5.3 |
| 94 | 6627 | 1 | 3407–5047 (546) | *Rattus norvegicus* alpha actinin (892) | 39/149 (26%) | 69/149 (46%) | 0.078 |
| | | 2 | 1–1231 (410) | *Lactococcus lactis* phage BK5-T ORF266; putative (266) | 39/176 (22%) | 78/176 (44%) | 9e-05 |
| | | 3 | 2122–3111 (329) | AcNPV viral capsid associated protein (hypothetical 42.1 kDa protein in LEF8-FP intergenic region) (365) | 73/294 (24%) | 123/294 (41%) | 2e-05 |
| | | 4 | 5065–5778 (237) | *Echinococcus granulosus* antigen II/3 (559) | 43/162 (26%) | 79/162 (48%) | 0.009 |
| | | 5 | 5037–5744 (235) | *Schizosaccharomyces pombe* serine-rich protein (534) | 46/188 (24%) | 82/188 (43%) | 0.012 |
| | | 6 | 1497–2132 (211) | *Populus balsamifera* subsp. *trichocarpa* laccase (437) | 37/127 (29%) | 54/127 (42%) | 0.51 |
| | | 7 | 5920–6516 (198) | AcNPV 33 kDa early protein homolog (P33) AcOrf-92 peptide (259) | 32/133 (24%) | 56/133 (42%) | 4e-04 |
| | | 8 | 1530–2069 (179) | *Mus musculus* GABA-B1a receptor (960) | 16/59 (27%) | 29/59 (49%) | 8.7 |
| | | 9 | 1505–1810 (101) | *Homo sapiens* S6 kinase-related kinase (482) | 24/68 (35%) | 32/68 (46%) | 0.14 |
| | | 10 | 2957–3199 (80) | *Serratia odorifera* outer membrane protein II (243) | 11/26 (42%) | 18/26 (68%) | 6.8 |
| | | 11 | 2195–2401 (80) | *Schizosaccharomyces pombe* conserved hypothetical protein (634) | 14/27 (51%) | 18/27 (65%) | 1.7 |
| | | 12 | 2389–2628 (79) | *Homo sapiens* Na+-dependent purine specific transporter (658) | 12/26 (46%) | 18/26 (69%) | 3.0 |
| | | 13 | 1–240 (79) | *Homo sapiens* insulin-like growth factor binding protein precursor (258) | 28/87 (32%) | 33/87 (37%) | 7.1 |
| | | 14 | 402–629 (75) | *Saccharomyces cerevisiae* probable membrane protein YLR194c-yeast (254) | 15/43 (34%) | 23/43 (52%) | 0.15 |
| 94 | | 15 | 3200–3406 (68) | *Trypanosoma brucei* protease precursor (450) | 12/32 (37%) | 17/32 (52%) | 5.0 |
| | | 16 | 3738–3926 (62) | — | — | — | — |
| | | 17 | 289–483 (61) | — | — | — | — |
| | | 18 | 2878–3048 (56) | *Homo sapiens* lutropin/choriogonadotropin receptor (685) | 12/37 (32%) | 20/37 (53%) | 6.9 |
| | | 19 | 4441–4599 (52) | Rabbit hemorrhagic disease virus, capsid structural protein VP60 (579) | 9/21 (42%) | 15/21 (70%) | 7.0 |
| 117 | 6682 | 1 | 1726–3366 (546) | *Rattus norvegicus* alpha actinin (892) | 39/149 (26%) | 69/149 (46%) | 0.1 |
| | | 2 | 4239–5351 (370) | AcNPV 33 kDa early protein homolog (P33), AcORF-92 peptide (259) | 36/140 (25%) | 65/140 (45%) | 5e-06 |
| | | 3 | 441–1430 (329) | AcNPV hypothetical 42.1 kDa protein in PROTEIN IN LEF8-FP intergenic region, viral capsid associated protein (365) | 73/294 (24%) | 123/294 (41%) | 2e-05 |
| | | 4 | 3384–4097 (237) | *Arabidopsis thaliana* putative protein (577) | 28/83 (33%) | 42/83 (49%) | 0.012 |

TABLE 12-continued

| SEQ ID NO | Length (nt) | ORF SEQ | Position (length, aa) | Best Match (length, aa) | aa Identities | aa Positive | E Value |
|---|---|---|---|---|---|---|---|
| | | 5 | 5656–6354 (232) | *Cricetulus griseus* DNA repair protein XRCC1 (633) | 17/41 (41%) | 25/41 (60%) | 0.32 |
| | | 6 | 1–466 (155) | *Pneumocystis carinii* KEXIN (671) | 16/34 (47%) | 19/34 (55%) | 0.064 |
| | | 7 | 5206–5649 (147) | *Arabidopsis thaliana* acetolactate synthase (670) | 25/72 (34%) | 34/72 (46%) | 2.6 |
| | | 8 | 6354–6743 (129) | Human papillomavirus type 12E7 protein (103) | 17/52 (32%) | 27/52 (51%) | 1.0 |
| | | 9 | 62–64–6638 (124) | *Eschenchia coli* Exodeoxyribonuclease VIII (EC 3.1.11.-) (Exo VIII), (797) | 20/77 (25%) | 36/77 (45%) | 0.9 |
| | | 10 | 3356–3715 (119) | *Saccharomyces cerevisiae* a-agglutinin core subunit, ORF YNR044w (725) | 32/94 (34%) | 42/94 (44%) | 024 |
| | | 11 | 6807-7154 (115) | *Mus musculus* sodium channel 25 (309) | 15/58 (25%) | 26/58 (43%) | 1 |
| | | 12 | 406–720 (104) | *Schizosaccharomyces pombe* conserved hypothetical protein (634) | 14/27 (51%) | 18/27 (65%) | 2.5 |
| | | 13 | 5761–6036 (91) | *Escherichia coli* hypothetical 77K protein (spoT 3' region) (685) | 13/33 (39%) | 21/33 (63%) | 8.7 |
| | | 14 | 1276–1518 (80) | *Serratia odorifera* outer membrane protein II (243) | 11/26 (42%) | 18/26 (68%) | 6.8 |
| | | 15 | 708–947 (79) | Homo sapiens Na+ dependent purine specific transporter (658) | 12/26 (46%) | 18/26 (69%) | 3.0 |
| | | 16 | 6740–6976 (78) | Human papillomavirus type 2a, probable E4 protein (132) | 14/47 (29%) | 26/47 (54%) | 0.89 |
| 117 | | 17 | 170–388 (72) | *Candida albicans* DNA-directed DNA polymerase III (EC 2.7.7.7) (1038) | 17/55 (30%) | 30/55 (53%) | 6.5 |
| | | 18 | 3851–4063 (70) | *Schizosaccharomyces pombe* hypothetical protein (962) | 16/67 (23%) | 32/67 (46%) | 1.7 |
| | | 19 | 1519–1725 (68) | *Trypanosoma brucei* protease precursor(450) | 12/32 (37%) | 17/32 (52%) | 5.0 |
| | | 20 | 2057–2254 (62) | — | — | — | — |
| | | 21 | 7036–7211 (58) | — | | | |
| | | 22 | 197–1367 (56) | Homo sapiens lutropin/choriogonadotropin receptor (685) | 12/37 (32%) | 20/37 (53%) | 6.9 |
| | | 23 | 2760—2918 (52) | — | — | — | — |
| | | 24 | 5909–6064 (51) | Homo sapiens KIAA0306 (1451) | 17/49 (34%) | 24/49 (48%) | 3.1 |

We claim:

1. A method for the in vitro propagation of a mosquito baculovirus comprising infecting a culture of mosquito cells with a baculovirus, growing the cells in culture medium containing at least 1 mM of a divalent cation selected from the group consisting of: magnesium, cobalt, strontium, and nickel; and a chelator binder that selectively reduces the effective calcium ion concentration below about 1 mM until inclusion bodies are detected in the cells, and harvesting the virus from the cells.

2. The baculovirus of claim 1, wherein the baculovirus has been engineered to express an insect-antagonistic gene.

3. The baculovirus of claim 2, wherein the insect-antagonistic gene is selected from the group consisting of: toxins, insect hormones, insect hormone mimics, and sterilization peptides.

4. An isolated mosquito-infecting baculovirus having the following characteristics:

(a) nuclear occlusion bodies, globular in shape, diameter approximately 400 nm, each containing between about 1–8 rod-shaped virions, approximately 200×40 nm;

(b) nuclear occlusion bodies with no surrounding membrane and with a denisty of approximately 1.14–1.18 g/ml which agglutinate upon freezing; and (c) infectious in *Culex quinquefaciatus* and *Culex nigripalpus.*

5. The baculovirus of claim 4, wherein the baculovirus has been engineered to express an insect-antagonistic gene.

6. The baculovirus of claim 5, wherein the insect-antagonistic gene is selected from the group consisting of: toxins, insect hormones, insect hormone mimics, and sterilization peptides.

7. A method for controlling mosquitos comprising the step of applying a mosquito-controlling amount of the baculovirus of claim 4 to a habitat.

8. The method of claim 7 wherein said habitat is a mosquito breeding area.

9. The method of claim 7, wherein the mosquitos are members of Culicidae.

10. An insecticidal composition consisting essentially of:

(a) a baculovirus effective for producing a lethal or debilitating infection in an insect; and (b) at least about 1 mM of a divalent cation selected from the group consisting of: magnesium, cobalt, strontium, and nickel.

11. The composition of claim 10, further comprising an insecticidal composition-suitable carrier.

12. The composition of claim 10, wherein the divalent cation is magnesium.

13. The composition of claim 12 wherein the concentration of magnesium is at least about 5 mM.

14. The insecticidal composition of claim 13, wherein the composition is a mosquito larvacidal composition.

15. The composition of claim 14, wherein the baculovirus is CuniNPV.

16. The composition of claim 14, wherein the baculovirus is selected from the group consisting of nuclear polyhedrosis viruses that infect Culex, Aedes, Anopheles, Psorophora, Uranotaenia, and Wyeomyia mosquito species.

17. A method for controlling mosquitos comprising the step of applying a mosquito-controlling amount of the composition of claim 10 to a habitat for said mosquito.

18. The method of claim 17, wherein the mosquitos are members of Culicidae.

19. The method of claim 17, wherein said habitat is a mosquito breeding area.

20. An insecticidal composition comprising:

(a) a baculovirus effective for producing a lethal or debilitating infection in an insect;

(b) at least about 1 mM of a divalent cation selected from the group consisting of: magnesium, cobalt, strontium, and nickel; and (c) a chelator or binder that selectively reduces the effective calcium concentration below about 1 mM.

21. The composition of claim 20, further comprising an insecticidal composition-suitable carrier.

22. The composition of claim 20 wherein the divalent cation is magnesium.

23. The composition of claim 22 wherein the concentration of magnesium is at least about 5 mM.

24. The composition of claim 23, wherein the composition is a mosquito larvacidal composition.

25. The composition of claim 24, wherein the baculovirus is CuniNPV.

26. The composition of claim 24, wherein the baculovirus is selected from the group consisting of nuclear polyhedrosis viruses that infect Culex, Aedes, Anopheles, Psorophora, Uranotaenia, and Wyeomyia mosquito species.

27. An isolated nucleic acid comprising a nucleotide sequence set forth in SEQ ID NO: 83.

28. A cell containing a nucleic acid of claim 27.

29. The cell of claim 28 wherein the cell is from an insect.

* * * * *